US011225474B2

(12) United States Patent
Chilov et al.

(10) Patent No.: US 11,225,474 B2
(45) Date of Patent: Jan. 18, 2022

(54) CRYSTALLINE SALT FORMS OF 3-(1,2,4-TRIAZOLO[4,3-A]PYRIDINE-3-YLETHYNYL)-4-METHYL-N-(4-((4-METHYLPIPERAZIN-1-YL)METHYL)-3-TRIFLUOROMETHYLPHENYL)BENZAMIDE FOR MEDICAL APPLICATION

(71) Applicant: LIMITED LIABILITY COMPANY <<FUSION PHARMA>>, Moscow (RU)

(72) Inventors: Germes G. Chilov, Krasnodar (RU); Ilya Yurievich Titov, Moscow (RU)

(73) Assignee: LIMITED LIABILITY COMPANY «FUSION PHARMA»

( * ) Notice: Subject to any disclaimer, the term of this patent is extended or adjusted under 35 U.S.C. 154(b) by 0 days.

(21) Appl. No.: 16/094,790

(22) PCT Filed: Apr. 18, 2017

(86) PCT No.: PCT/RU2017/050025
§ 371 (c)(1),
(2) Date: Oct. 18, 2018

(87) PCT Pub. No.: WO2017/184032
PCT Pub. Date: Oct. 26, 2017

(65) Prior Publication Data
US 2020/0325131 A1    Oct. 15, 2020

(30) Foreign Application Priority Data
Apr. 18, 2016    (RU) .................. RU2016114904

(51) Int. Cl.
*C07D 471/04*    (2006.01)
*A61P 35/00*    (2006.01)

(52) U.S. Cl.
CPC ............ *C07D 471/04* (2013.01); *A61P 35/00* (2018.01); *C07B 2200/13* (2013.01)

(58) Field of Classification Search
CPC .... C07D 471/04; A61P 35/00; C07B 2200/13
See application file for complete search history.

(56) References Cited

FOREIGN PATENT DOCUMENTS

| EP | 2927232 | 10/2015 |
|----|---------|---------|
| RU | 2477723 | 3/2013 |
| WO | WO 2012/173521 | 12/2012 |
| WO | WO 2013/170774 | 11/2013 |
| WO | WO 2015/108490 | 7/2015 |
| WO | WO 2017/184032 | 10/2017 |

OTHER PUBLICATIONS

Mian et al., "PF-114, a potent and selective inhibitor of native and mutated BCR/ABL is active against Philadelphia chromosome-positive (Ph+) leukemias harboring the T3151 mutation," Leukemia, 2015, 29(5):1104-1114.
PCT International Search Report International Appln. No. PCT/RU 2017/050025, dated Aug. 31, 2017, 2 pages.

*Primary Examiner* — Alicia L Otton
(74) *Attorney, Agent, or Firm* — Fish & Richardson P.C.

(57) ABSTRACT

The invention relates to the organic chemistry, pharmacology and medicine, and concerns the prevention and treatment of human and animal diseases associated with the disruption of the activity of various kinases, in particular Abl kinase, for example diseases such as leukemia, acute myelogenous leukemia, chronic myelogenous leukemia, acute lymphocytic leukemia, breast cancer, non-small cell lung cancer, gastrointestinal stromal tumors, ovarian cancer, lymphoma, using a new salt form of 3-(1,2,4-triazolo[4,3-a]pyridine-3-ylethynyl)-4-methyl-N-(4-((4-methylpiperazin-1-yl)methyl)-3-trifluoromethylphenyl)benzamide. The salt of this compound with methanesulfonic acid,

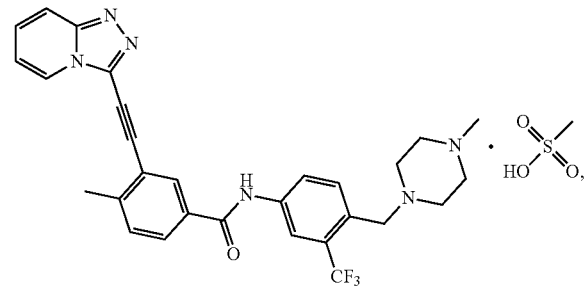

or its hydrate, solvate, as well as polymorphic modifications that have the ability to inhibit the activity of kinases, in particular Abl kinases. The present invention also relates to pharmaceutical compositions comprising a therapeutically effective amount of a salt of the invention, to a method for preparing a crystalline salt of the invention, as well as to a method for treating oncological diseases in a subject.

41 Claims, 65 Drawing Sheets

| ID | Mass, Mg | Solvent | Solvent amount, ml | Counterion (in EtOH) | Counterion Equivalent | Counterion solvent amount, ml | Temperature, °C | Precip Acid addition (+/-) | Precip after cooling to RT (+/-) | Isolation | Yield, mg | XRPD |
|---|---|---|---|---|---|---|---|---|---|---|---|---|
| HAL-G-196-1 | 101,13 | EtOH | 4,5 | HCl | 1,05 | 0,405 | 60 | - | + | Filter | 61, 4 | Cryst, I |
| HAL-G-196-2 | 100,02 | THF | 2,0 | HCl | 1,05 | 0,405 | 60 | - | + | Filter | 71, 6 | Cryst, I |
| HAL-G-196-3 | 101,18 | Acetone | 10,0 | HCl | 1,05 | 0,405 | 50 | - | - | - | - | - |
| HAL-G-196-4 | 102,64 | EtOH | 4,5 | $H_2SO_4$ | 1,05 | 0,405 | 60 | + | + | Filter | 44, 7 | Semi-cryst |
| HAL-G-196-5 | 102,04 | THF | 2,0 | $H_2SO_4$ | 1,05 | 0,405 | 60 | + | Oil | Evap | - | Semi-cryst |
| HAL-G-196-6 | 103,78 | Acetone | 10,0 | $H_2SO_4$ | 1,05 | 0,410 | 50 | + | + | Filter | 96, 8 | Semi-cryst |
| HAL-G-196-7 | 101,08 | EtOH | 4,5 | HBr | 1,05 | 0,405 | 60 | - | + | Filter | 92, 6 | Cryst, I |
| HAL-G-196-8 | 104,11 | THF | 2,0 | HBr | 1,05 | 0,415 | 60 | + | + | Filter | 92, 2 | Cryst, II |
| HAL-G-196-9 | 100,66 | Acetone | 10,0 | HBr | 1,05 | 0,405 | 50 | + | + | Filter | 78, 5 | Cryst, II |
| HAL-G-196-10 | 98,76 | EtOH | 4,5 | Citric | 1,05 | 0,395 | 60 | - | + | Filter | 56, 2 | Amorph. |
| HAL-G-196-11 | 103,18 | THF | 2,0 | Citric | 1,05 | 0,410 | 60 | + | + | Filter | 88, 0 | Amorph. |
| HAL-G-196-12 | 101,25 | Acetone | 10,0 | Citric | 1,05 | 0,405 | 50 | + | + | Filter | 97, 6 | Amorph. |
| HAL-G-196-13 | 101,22 | EtOH | 4,5 | Phosphoric | 1,05 | 0,400 | 60 | + | + | Filter | 100, 5 | Cryst, I |
| HAL-G-196-14 | 98,30 | THF | 2,0 | Phosphoric | 1,05 | 0,400 | 60 | - | Oil | Evap | - | Amorph. |
| HAL-G-196-15 | 98,33 | Acetone | 10,0 | L-tartaric | 1,05 | 0,805 | 50 | + | + | Filter | 58, 2 | Semi-cryst |
| HAL-G-196-16 | 99,41 | EtOH | 4,5 | L-tartaric | 1,05 | 0,805 | 60 | - | + | Filter | 82, 7 | Semi-cryst |
| HAL-G-196-17 | 101,54 | THF | 2,0 | L-tartaric | 1,05 | 0,805 | 60 | + | + | Filter | 99, 5 | Amorph. |
| HAL-G-196-18 | 101,47 | Acetone | 10,0 | MSA | 1,05 | 0,400 | 50 | + | + | Filter | 100, 1 | - |
| HAL-G-196-19 | 99,13 | EtOH | 4,5 | | 1,05 | | 60 | - | - | - | - | - |

FIG. 1

| | | | | | | | | | | | |
|---|---|---|---|---|---|---|---|---|---|---|---|
| HAL-G-196-20 | 99,45 | THF | 2,0 | MSA | 1,05 | 0,400 | 60 | - | + | Filter | 73,5 | Cryst |
| HAL-G-196-21 | 99,77 | Acetone | 10,0 | MSA | 1,05 | 0,400 | 50 | - | + | Filter | 106,1 | Cryst |
| HAL-G-196-22 | 99,60 | EtOH | 4,5 | p-TSA | 1,05 | 0,400 | 60 | - | - | - | - | - |
| HAL-G-196-23 | 100,46 | THF | 2,0 | p-TSA | 1,05 | 0,400 | 60 | - | - | - | - | - |
| HAL-G-196-24 | 96,57 | Acetone | 10,0 | p-TSA | 1,05 | 0,400 | 50 | - | + | Filter | 89,9 | Cryst |
| HAL-G-196-25 | 102,50 | EtOH | 4,5 | D-malic | 1,05 | 0,405 | 60 | - | + | Filter | 145,8 | Cryst |
| HAL-G-196-26 | 99,24 | THF | 2,0 | D-malic | 1,05 | 0,405 | 60 | - | - | - | - | - |
| HAL-G-196-27 | 100,49 | Acetone | 10,0 | D-malic | 1,05 | 0,405 | 50 | - | - | - | - | - |
| HAL-G-196-28 | 102,39 | EtOH | 4,5 | Fumaric | 1,05 | 0,805 | 60 | - | + | Filter | 111,0 | Cryst |
| HAL-G-196-29 | 101,18 | THF | 2,0 | Fumaric | 1,05 | 0,805 | 60 | - | + | Filter | 77,6 | Cryst |
| HAL-G-196-30 | 97,25 | Acetone | 10,0 | Fumaric | 1,05 | 0,805 | 50 | - | + | Filter | 75,1 | Cryst |
| HAL-G-196-31 | 102,31 | EtOH | 4,5 | BSA | 1,05 | 0,410 | 60 | - | - | - | - | - |
| HAL-G-196-32 | 103,74 | THF | 2,0 | BSA | 1,05 | 0,410 | 60 | - | - | - | - | - |
| HAL-G-196-33 | 99,01 | Acetone | 10,0 | BSA | 1,05 | 0,410 | 50 | - | - | - | - | - |
| HAL-G-196-34 | 99,10 | EtOH | 4,5 | L-lactic | 1,05 | 0,410 | 60 | - | - | - | - | - |
| HAL-G-196-35 | 101,45 | THF | 2,0 | L-lactic | 1,05 | 0,410 | 60 | - | - | - | - | - |
| HAL-G-196-36 | 102,09 | Acetone | 10,0 | L-lactic | 1,05 | 0,410 | 50 | - | - | - | - | - |

FIG. 1 (Continued)

| ID | Counterion (in EtOH) | MTBE, ml | Temp, °C | Precip after MTBE Addition/Cooling | Isolation | Yield, mg | XRPD |
|---|---|---|---|---|---|---|---|
| HAL-G-196-3 | HCl | 2.0 | RT | + | Filter | 61.9 | Semi-cryst, II |
| HAL-G-196-19 | MSA | 2.0 | RT | + | Filter | 83.2 | Cryst |
| HAL-G-196-22 | p-TSA | 2.5 | RT | Oil | Evap | - | - |
| HAL-G-196-23 | p-TSA | <0.5 | RT | + | Filter | 77.8 | Cryst. |
| HAL-G-196-26 | D-malic | <0.5 | RT | Oil | Evap | - | Semi-cryst |
| HAL-G-196-27 | D-malic | 2.0 | RT | + | Filter | 53.8 | Amorph. |
| HAL-G-196-31 | BSA | 1.0 | RT | Oil | Evap | - | - |
| HAL-G-196-32 | BSA | <0.5 | RT | Oil | Evap | - | - |
| HAL-G-196-33 | BSA | 2.0 | RT | Oil | Evap | - | - |
| HAL-G-196-34 | L-lactic | 2.0 | RT | - | Evap | - | - |
| HAL-G-196-35 | L-lactic | 2.0 | RT | Oil | Evap | - | - |
| HAL-G-196-36 | L-lactic | 5.0 | RT | Oil | Evap | - | - |

FIG. 2

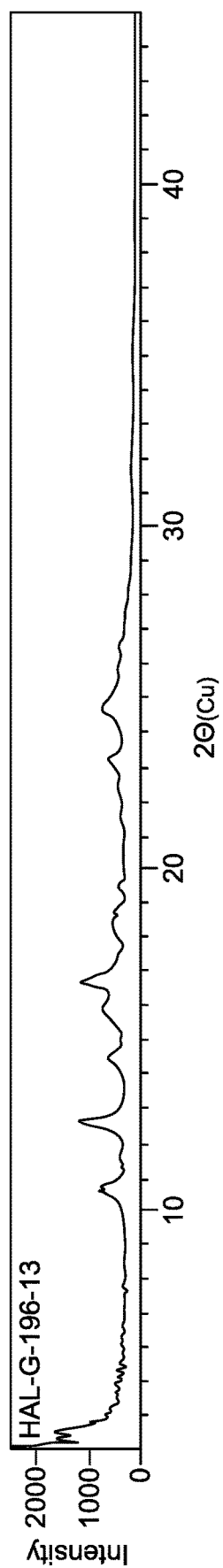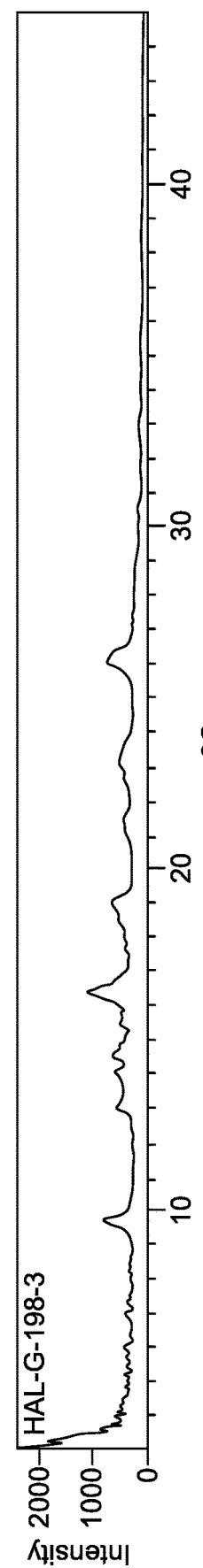
FIG. 21A
FIG. 21B

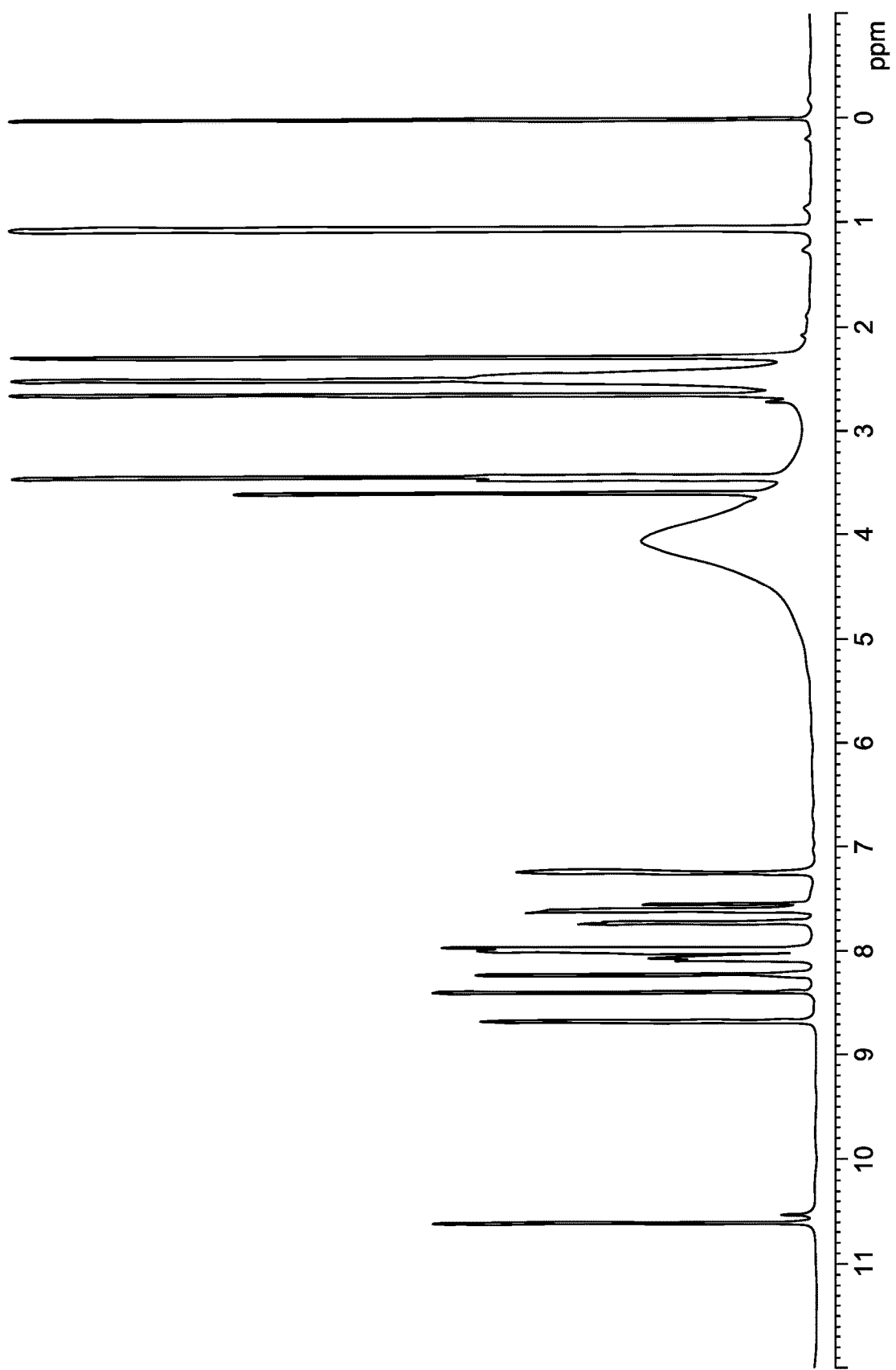

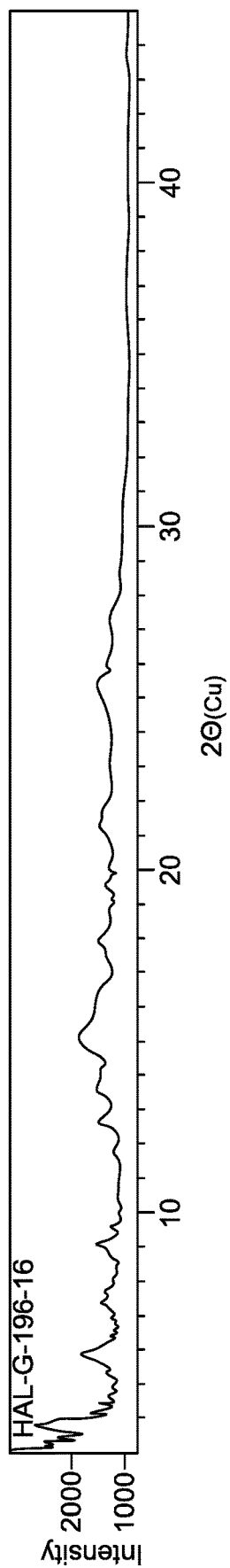
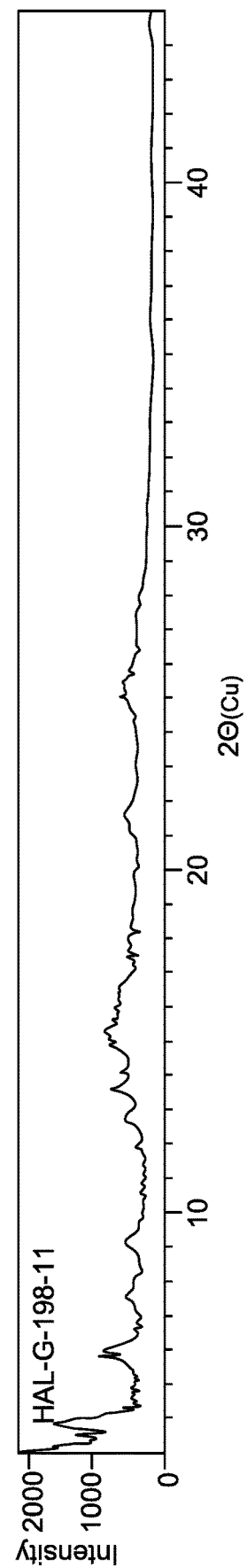
FIG. 25A
FIG. 25B

CRYSTALLINE SALT FORMS OF 3-(1,2,4-TRIAZOLO[4,3-A]PYRIDINE-3-YLETHYNYL)-4-METHYL-N-(4-((4-METHYLPIPERAZIN-1-YL)METHYL)-3-TRIFLUOROMETHYLPHENYL)BENZAMIDE FOR MEDICAL APPLICATION

CROSS-REFERENCE TO RELATED APPLICATIONS

This application is the National Phase under 35 U.S.C. § 371 of PCT International Application Number PCT/RU2017/050025, filed Apr. 18, 2017 (published as WO2017184032) which claims the benefit of Russian Patent Application Number 2016114904, filed Apr. 18, 2016, each of which is incorporated herein by reference in its entirety.

TECHNICAL FIELD

This disclosure relates to the chemistry of organic compounds, pharmacology, and medicine, in particular to compound salt forms, as well as to their crystalline (polymorph) forms possessing improved physicochemical properties and high efficacy and safety as compared with the free base of this compound.

BACKGROUND

For the purpose of drug production, it is important to have the pharmaceutical substance in a form that is convenient for its treatment and handling. This is important not only from the point of view of creating a commercially viable production process, but also from the point of view of the subsequent production of the pharmaceuticals containing this active substance. In addition, there are very essential factors such as chemical stability of active ingredients, stability of their solid forms, and their stability during storage. Pharmaceutical substances and medicinal compositions containing these substances should possess the ability to be stored for acceptable periods of time without significant changes of the physicochemical characteristics of their active substances, such as chemical composition, density, hygroscopicity, and solubility. In this respect, the use of amorphous forms of substances as drugs is generally undesirable. For example, amorphous forms possess unstable physicochemical properties, such as solubility, hygroscopicity, friability, caking, etc. Thus, it is desirable to have a drug as its crystalline and stabile form(s) to produce commercially viable and pharmaceutically acceptable medicinal compositions.

Solid substances including pharmaceutically active compounds frequently can exist in more than one crystalline form; and this phenomenon is known as polymorphism. Polymorphism occurs when a compound can crystallize as multiple, different, solid phases which differ from each other in their crystal packing. Usually polymorphous modifications (polymorphs) have different physical characteristics including solubility and physical and/or chemical stability. Different solid salt forms of one and the same medicinal substance and, furthermore, different polymorphs of one and the same solid salt form can differ in the rate of releasing drug substance, as well as in the stability of the solid state of salt form as well as in their suitability for production of pharmaceutical medicines.

Selection of a suitable salt form for production of the corresponding pharmaceutical substance is an important event of the preclinical phase of drug development. Changing the salt form of active drug substance is one way of modifying the chemical and biological characteristics of the substance without modifying the chemical structure of the substance itself. The choice of specific salt form can deeply influence the physicochemical properties of this drug (for example, the rate of dissolution, solubility, stability, and hygroscopicity). Replacing one salt form of the drug substance by another salt form can change the drug's therapeutic efficacy and/or safety which are especially important considerations for large-scale production of the optimal drug composition. Nevertheless, there is no reliable way to accurately predict the effect of changing the salt form of the active drug substance on its safety and/or its biological activity. Moreover, even studying the physicochemical properties of different salt forms of the active drug substance cannot allow one to unambiguously identify the salt forms possessing the desired pharmacokinetic properties, efficacy, and safety. Briefly, there is no reliable way to predict the influence of specific salt types on behavior of the original compound in pharmaceutical medicines (Berge et al., Pharmaceutical Salts, Journal Pharm. Sci., 1977, Vol. 66, No. 1; Verbeeck et al. Generic substitution: The use of medicinal products containing different salts and implications for safety and efficacy European Journal Pharm. Sci., 28, 2006, 1-6).

Pharmacokinetic parameters are among the most important characteristics defining suitability of a solid salt form (or a particular polymorphous modification) for the use as a pharmaceutical medicine. The average daily and maximal concentrations of a drug in the blood of humans and animals can vary substantially, depending on the composition of the salt form and its polymorphic modification. As a rule, the drug substance salt forms that possess higher solubility in water are those that provide the higher maximal drug concentrations in blood and tissues of humans and animals. Since higher maximal drug concentrations in blood of animals correlate, as a rule, with the increases in toxic effects caused by the drug, changing the salt form of a drug substance can lead to the changes in the drug safety profile.

Solid salt forms are usually preferable for oral medications since these salt forms particularly tend to display the most desirable physical characteristics. In the case of basic drug substances, the salt forms can be obtained by reaction with suitable acids. As mentioned above, different acids vary in their influence on the properties of the corresponding salt forms (such as stability during storage, easy process of production and purification, pharmacokinetic parameters, etc.) and such properties cannot be predicted with satisfactory accuracy. For example, some salts are solid substances at ambient temperature, whereas the other salts are liquids, viscous oils, or resins. Moreover, some salt forms are resistant to influence of heat and light under extreme conditions while the other salt forms are easily decomposed under much softer conditions. Additional uncertainty appears when the drug molecule possesses more than one basic site, giving rise to potentially multiple salt forms with a given acid. Thus, development of a suitable salt form of a basic drug substance for used in a pharmaceutical composition is an extremely important process which is far from being always predictable.

Protein kinases represent an important protein family that participates in regulation of key cellular processes. The impaired activity of protein kinases can lead to different diseases. A potential approach to therapy of the diseases associated with impaired protein kinase activity is the use of low-molecular weight chemical compounds to inhibit kinase activity. Examples of such inhibitors approved for use in clinical practice include: Imatinib, Nilotinib, Dasatinib, Sunitinib, Sorafenib, Lapatinib, Gefitinib, Erlotinib, and Crizotinib. Many protein kinase inhibitor drug candidates are currently at the stage of clinical trials or at the stage of preclinical development.

BCR-ABL is a fusion protein, a product of hybrid gene BCR-ABL1, formed as a result of reciprocal translocation between chromosomes 9 and 22 (the Philadelphia chromosome). BCR-ABL is the constitutively active tyrosine kinase that is responsible for oncogenic cell transformation (i.e., an oncoprotein). The permanent activity of this tyrosine kinase makes a cell capable of dividing without influence of growth factors and causes excessive proliferation. BCR-ABL is a key pathogenic factor causing development of most cases of chronic myeloid leukemia and 20-50% cases of adult acute B-cell lymphoblastic leukemia. Thus, inhibiting the kinase activity of the BCR-ABL hybrid protein is a prospective strategy for fighting different oncological diseases and, in particular, chronic myeloid leukemia.

International patent application PCT/RU2012/000423 (WO/2012/173521), describes derivatives of 1,2,4-triazolo [4,3-a]pyridine, which are efficient and selective inhibitors of Abl kinase and its mutant forms, as well as of the other therapeutically significant kinases. The compounds described included 3-(1,2,4-triazolo[4,3-a]pyridine-3-yl-ethynyl)-4-methyl-N-(4-((4-methylpiperazin-1-yl)methyl)-3-trifluoromethyl-phenyl)benzamide.

Through in vitro and in vivo studies, it has been shown that the compounds disclosed in WO/2012/173521 have potential as drugs for treating oncological diseases, in particular, acute lymphoblastic leukemia, chronic myeloid leukemia, hepatocellular carcinoma, non-small cell lung cancer, and gastrointestinal stromal tumors in humans and animals.

SUMMARY

The present disclosure provides salt of methanesulfonic acid and 3-(1,2,4-triazolo[4,3-a]pyridine-3-ylethynyl)-4-methyl-N-(4-((4-methylpiperazin-1-yl)methyl)-3-trifluoromethylphenyl)benzamide.

In some embodiments, the salt is 3-(1,2,4-triazolo[4,3-a] pyridine-3-ylethynyl)-4-methyl-N-(4-((4-methylpiperazin-1-yl)methyl)-3-trifluoromethylphenyl)benzamide mono methanesulfonic acid salt.

In some embodiments, the salt is crystalline 3-(1,2,4-triazolo[4,3-a]pyridine-3-ylethynyl)-4-methyl-N-(4-((4-methylpiperazin-1-yl)methyl)-3-trifluoromethylphenyl)benzamide mono methanesulfonic acid salt.

In some embodiments, the salt is characterized by an X-ray powder pattern obtained at 25±5° C. using CuKα1 radiation substantially as shown in FIG. 29.

In some embodiments, the salt is characterized by a DSC curve having an endothermic transition at 220° C.

In some embodiments, the salt is 3-(1,2,4-triazolo[4,3-a] pyridine-3-ylethynyl)-4-methyl-N-(4-((4-methylpiperazin-1-yl)methyl)-3-trifluoromethylphenyl)benzamide mono methanesulfonic acid salt, polymorphous modification I.

In some embodiments, the salt comprises monoclinic crystals of space group $P2_1/n$.

In some embodiments, the salt comprises monoclinic crystals having unit cell parameters determined by powder X-ray diffraction at 25±5° C. using CuKα1 radiation of a=51.46±0.05 Å; b=7.81±0.05 Å; c=7.63±0.05 Å; and β=108.9±0.1°.

In some embodiments, the salt comprises monoclinic crystals having a unit cell parameter determined by powder X-ray diffraction at 25±5° C. using CuKα1 radiation of V=2898.9±0.5 Å$^3$.

In some embodiments, the salt is characterized by an X-ray powder pattern obtained at 25±5° C. using CuKα1 radiation having peaks with diffraction angle values (2θ) that include at least one peak, at least two peaks, at least three peaks, or at least two, three or four peaks with a relative intensity of about 20% or greater selected from 16.9, 17.2, 17.4, 18.7 and/or 20.8.

In some embodiments, the salt is characterized by an X-ray powder pattern obtained at 25±5° C. using CuKα1 radiation having peaks with diffraction angle values (2θ) of 16.9, 17.2, 17.4, 18.7 and/or 20.8, each with a relative intensity of about 20% or greater.

In some embodiments, the salt is characterized by an X-ray powder pattern obtained at 25±5° C. using CuKα1 radiation having a peak with a diffraction angle value (2θ) of 18.7 as the peak with highest relative intensity.

In some embodiments, the salt is characterized by an X-ray powder pattern obtained at 25±5° C. using CuKα1 radiation having at least three, four, five, six, seven eight, nine or ten peaks with diffraction angle values (2θ) selected from: 7.2, 11.8, 12.5, 13.4, 14.5, 16.2, 16.9, 17.2, 17.4, 18.7, 20.8, 21.4, 23.2, 24.1, 24.5, 25.4 and 27.1.

In some embodiments, the salt is characterized by an X-ray powder pattern obtained at 25±5° C. using CuKα1 radiation having peaks with the following diffraction angle values (2θ) as characteristic peaks: 7.2, 11.8, 12.5, 13.4, 14.5, 16.2, 16.9, 17.2, 17.4, 18.7, 20.8, 21.4, 23.2, 24.1, 24.5, 25.4, and 27.1.

In some embodiments, the salt is characterized by an X-ray powder pattern obtained at 25±5° C. using CuKα1 radiation having at least four, five, six seven or eight peaks with diffraction angle values (2θ) selected from: 11.8; 14.5; 16.2; 16.9; 17.2; 17.4; 18.7; 20.8; and 23.0.

In some embodiments, the salt is characterized by an X-ray powder pattern obtained at 25±5° C. using CuKα1 radiation having peaks with the following diffraction angle values (2θ) as characteristic peaks: 11.8; 14.5; 16.2; 16.9; 17.2; 17.4; 18.7; 20.8; and 23.0.

In some embodiments, the salt is characterized by an X-ray powder pattern obtained at 25±5° C. using CuKα1 radiation having at least three, four, five or six peaks (or at least 4, at least 5, at least 6 peaks) with diffraction angle values (2θ) selected from: 14.5; 16.9; 17.2; 17.4; 18.7; and 20.8.

In some embodiments, the salt is characterized by an X-ray powder pattern obtained at 25±5° C. using CuKα1 radiation having peaks with the following diffraction angle values (2θ) as characteristic peaks: 14.5; 16.9; 17.2; 17.4; 18.7; and 20.8.

In some embodiments, the salt is characterized by an X-ray powder pattern obtained at 25±5° C. using CuKα1 radiation substantially as shown in FIG. 49(a).

In some embodiments, the salt is characterized by an X-ray powder pattern obtained at 25±5° C. using CuKα1 radiation substantially as shown in Table 6.

In some embodiments, the salt is 3-(1,2,4-triazolo[4,3-a] pyridine-3-ylethynyl)-4-methyl-N-(4-((4-methylpiperazin-1-yl)methyl)-3-trifluoromethylphenyl)benzamide mono methanesulfonic acid salt, polymorphous modification II.

In some embodiments, the salt comprises monoclinic crystals of space group P21/c.

In some embodiments, the salt comprises monoclinic crystals having unit cell parameters determined by powder X-ray diffraction at 25±5° C. using CuKα1 radiation of a=13.77±0.05 Å; b=8.09±0.05 Å and c=30.83±0.05 Å, and β=117.8±0.1.

In some embodiments, the salt comprises monoclinic crystals having a unit cell parameter determined by powder X-ray diffraction at 25±5° C. using CuKα1 radiation of V=3036.36±0.5 Å3.

In some embodiments, the salt is characterized by an X-ray powder pattern obtained at 25±5° C. using CuKα1 radiation having peaks with diffraction angle values (2θ) that include at least three, four, five or six peaks with a relative intensity of about 20% or greater selected from 11.9; 14.7; 17.2; 17.4; 17.6; 19.7; 21.2; 22.0 and 22.6.

In some embodiments, the salt is characterized by an X-ray powder pattern obtained at 25±5° C. using CuKα1 radiation having a peak with a diffraction angle value (2θ) selected from 17.6 or 21.2 as the peak with highest relative intensity.

In some embodiments, the salt is characterized by an X-ray powder pattern obtained at 25±5° C. using CuKα1 radiation having at least three, four, five, six, seven or eight peaks with diffraction angle values (2θ) selected from: 7.3, 11.8, 14.6, 17.2, 17.4, 17.6, 19.7, 21.2, 22.0, 22.6 and 26.1.

In some embodiments, the salt is characterized by an X-ray powder pattern obtained at 25±5° C. using CuKα1 radiation having peaks with diffraction angle values (2θ) selected from: 7.3, 11.8, 14.6, 17.2, 17.4, 17.6, 19.7, 21.2, 22.0, 22.6 and 26.1.

In some embodiments, the salt is characterized by an X-ray powder pattern obtained at 25±5° C. using CuKα1 radiation having at least three peaks (e.g., at least 4, 5, or 6) with the following diffraction angle values (2θ) as characteristic peaks: 17.4; 17.6; 19.4; 19.7; 21.2; 22.0; 22.6 and 25.9.

There is also provided a method of preparing crystalline 3-(1,2,4-triazolo[4,3-a]pyridine-3-ylethynyl)-4-methyl-N-(4-((4-methylpiperazin-1-yl)methyl)-3-trifluoromethylphenyl)benzamide mono methanesulfonic acid salt comprising:

(1) reacting 3-(1,2,4-triazolo[4,3-a]pyridine-3-ylethynyl)-4-methyl-N-(4-((4-methylpiperazin-1-yl)methyl)-3-trifluoromethylphenyl)benzamide and methanesulfonic acid to form 3-(1,2,4-triazolo[4,3-a]pyridine-3-ylethynyl)-4-methyl-N-(4-((4-methylpiperazin-1-yl)methyl)-3-trifluoromethylphenyl)benzamide mono methanesulfonate salt; and (2) cooling a solution of 3-(1,2,4-triazolo[4,3-a]pyridine-3-ylethynyl)-4-methyl-N-(4-((4-methylpiperazin-1-yl)methyl)-3-trifluoromethylphenyl)benzamide mono methanesulfonate salt dissolved in acetone and ethanol (about 5:1 v/v) to a temperature of about 10° C. to form the crystalline salt.

In addition, there is provided crystalline 3-(1,2,4-triazolo[4,3-a]pyridine-3-ylethynyl)-4-methyl-N-(4-((4-methylpiperazin-1-yl)methyl)-3-trifluoromethylphenyl)benzamide mono methanesulfonate salt prepared or obtainable by such a method.

Further provided is a method of preparing crystalline 3-(1,2,4-triazolo[4,3-a]pyridine-3-ylethynyl)-4-methyl-N-(4-((4-methylpiperazin-1-yl)methyl)-3-trifluoromethylphenyl)benzamide mono methanesulfonic acid salt comprising:

(1) reacting 3-(1,2,4-triazolo[4,3-a]pyridine-3-ylethynyl)-4-methyl-N-(4-((4-methylpiperazin-1-yl)methyl)-3-trifluoromethylphenyl)benzamide and methanesulfonic acid to form 3-(1,2,4-triazolo[4,3-a]pyridine-3-ylethynyl)-4-methyl-N-(4-((4-methylpiperazin-1-yl)methyl)-3-trifluoromethylphenyl)benzamide mono methanesulfonate salt; and (2) concentrating a solution of 3-(1,2,4-triazolo[4,3-a]pyridine-3-ylethynyl)-4-methyl-N-(4-((4-methylpiperazin-1-yl)methyl)-3-trifluoromethylphenyl)benzamide mono methanesulfonate salt dissolved in acetone and ethanol (about 5:1 v/v) and then cooling the solution to a temperature of about 20-25° C. to form the crystalline salt.

Also provided is crystalline 3-(1,2,4-triazolo[4,3-a]pyridine-3-ylethynyl)-4-methyl-N-(4-((4-methylpiperazin-1-yl)methyl)-3-trifluoromethylphenyl)benzamide mono methanesulfonate salt prepared or obtainable by such a method.

In some embodiments, the salt as described above is substantially isolated. In some embodiments, at least 80%, at least 90%, at least 95%, at least 97%, at least 98%, or at least 99% of the 3-(1,2,4-triazolo[4,3-a]pyridine-3-ylethynyl)-4-methyl-N-(4-((4-methylpiperazin-1-yl)methyl)-3-trifluoromethylphenyl)benzamide is present as a monomethanesulfonate salt in a form as defined above, or any of the embodiments thereof.

Also provided is composition comprising the salt as defined above, or any of the embodiments thereof, and at least one pharmaceutically acceptable carrier or excipient.

Further provided is a method of treating oncological disease in a subject in need of such treatment, the method comprising administering to the subject an effective amount of the salt as defined above, or any of the embodiments thereof, a composition containing such a salt.

In some embodiments, the oncological disease is acute lymphoblastic leukemia, chronic myeloid leukemia, hepatocellular carcinoma, non-small cell lung cancer, or gastrointestinal stromal tumor.

BRIEF DESCRIPTION OF THE FIGURES

FIG. 1. Crystallization of salts of 3-(1,2,4-triazolo[4,3-a]pyridine-3-ylethynyl)-4-methyl-N-(4-((4-methylpiperazin-1-yl)methyl)-3-trifluoromethylphenyl)benzamide at a scale of 100 mg.

FIG. 2. Crystallization of salts of 3-(1,2,4-triazolo[4,3-a]pyridine-3-ylethynyl)-4-methyl-N-(4-((4-methylpiperazin-1-yl)methyl)-3-trifluoromethylphenyl)benzamide at a scale of 100 mg after adding methyl tert-butyl ether.

FIG. 3A shows the results for HAL-G-194-1 (polymorphous modification I); FIG. 3B shows the results for HAL-G-194-2 (polymorphous modification II).

FIG. 5A shows the results for HAL-G-194-1 (polymorphous modification I); FIG. 5B shows the results for HAL-G-194-2 (polymorphous modification II).

FIG. 9A shows the results for HAL-G-194-1 (free base, polymorphous modification I); FIG. 9B shows the results for HAL-G-196-2 (HCl salt, polymorphous modification I); FIG. 9C shows the results for HAL-G-196-3 (HCl salt, polymorphous modification II).

FIG. 10A shows the results for HAL-G-196-2 (polymorphous modification I); FIG. 10B shows the results for HAL-G-196-3 (polymorphous modification II).

FIG. 12A shows the results for HAL-G-196-2 (polymorphous modification I); FIG. 12B shows the results for HAL-G-194-3 (polymorphous modification II).

FIG. 17A shows the results for HAL-G-196-7 (polymorphous modification I); FIG. 17B shows the results for HAL-G-196-8 (polymorphous modification II).

FIG. 18A shows the results for HAL-G-196-7 (polymorphous modification I); FIG. 18B shows the results for HAL-G-196-8 (polymorphous modification II).

FIG. 19A shows the results for HAL-G-196-7 (polymorphous modification I); FIG. 19B shows the results for HAL-G-196-8 (polymorphous modification II).

FIG. 21A-21B. X-ray powder diffraction patterns of the salt of phosphoric acid and free base 3-(1,2,4-triazolo[4,3-a]pyridine-3-ylethynyl)-4-methyl-N-(4-((4-methylpiperazin-1-yl)methyl)-3-trifluoromethylphenyl)benzamide. FIG. 21A shows the results for HAL-G-196-13; FIG. 21B shows the results for HAL-G-198-3 (after desolvation of HAL-G-196-13);

FIG. 22. $^1$H nuclear magnetic resonance spectrum of a sample of the salt of phosphoric acid and 3-(1,2,4-triazolo[4,3-a]pyridine-3-ylethynyl)-4-methyl-N-(4-((4-methylpiperazin-1-yl)methyl)-3-trifluoromethylphenyl)benzamide (sample—HAL-G-196-13).

FIGS. 25A-25B. X-ray powder diffraction patterns of the salt of tartaric acid and free base 3-(1,2,4-triazolo[4,3-a]pyridine-3-ylethynyl)-4-methyl-N-(4-((4-methylpiperazin-1-yl)methyl)-3-trifluoromethylphenyl)benzamide. FIG. 25A shows the results for HAL-G-196-16; FIG. 25B shows the results for HAL-G-198-1 (after desolvation of HAL-G-196-16).

FIG. 29A shows the results for HAL-G-196-19; FIG. 29B shows the results for HAL-G-196-20; FIG. 29C shows the results for HAL-G-196-21.

Figure 32:
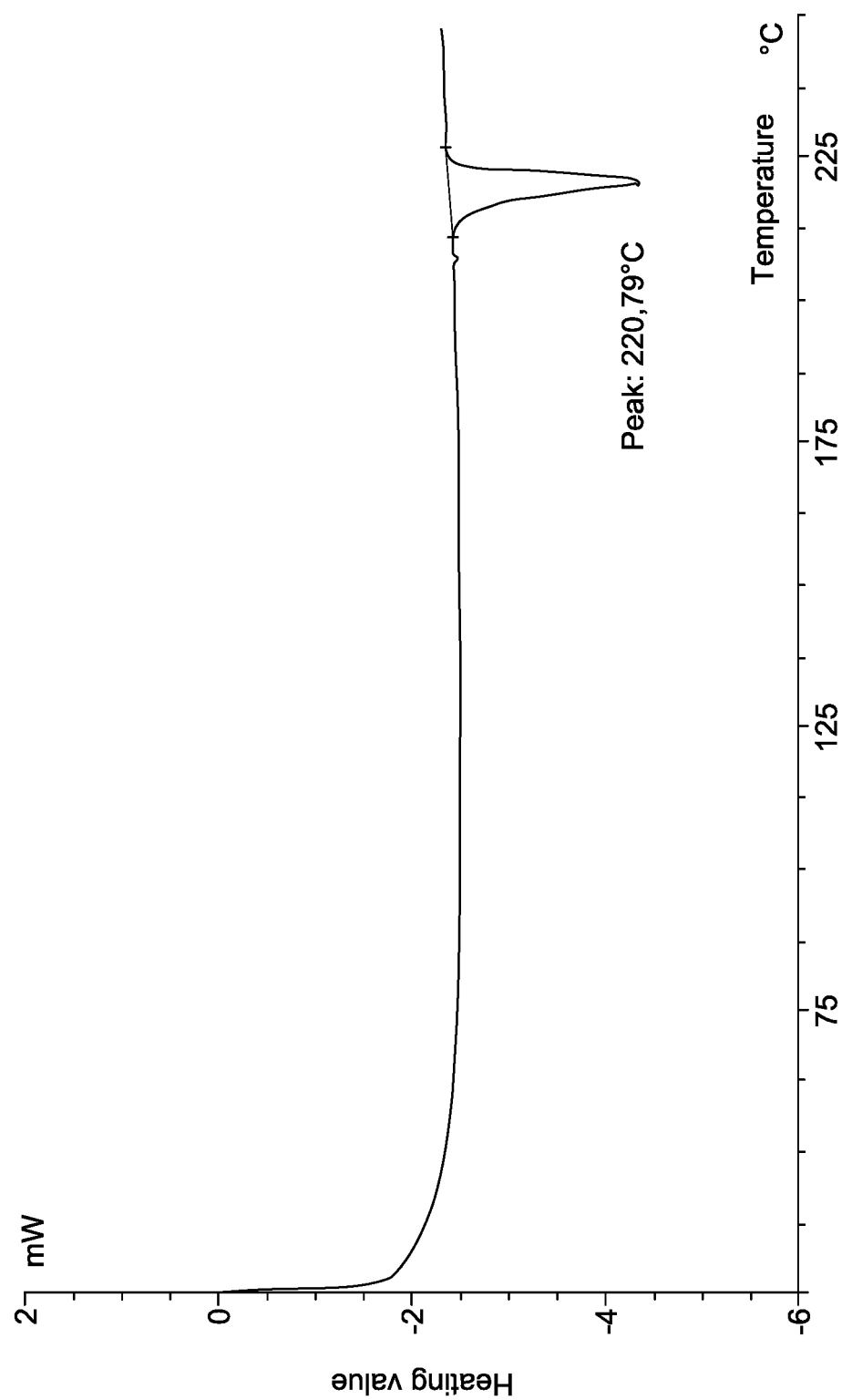

FIG. 32. DSC curve of a sample of the salt of methanesulfonic acid and 3-(1,2,4-triazolo[4,3-a]pyridine-3-ylethynyl)-4-methyl-N-(4-((4-methylpiperazin-1-yl)methyl)-3-trifluoromethylphenyl)benzamide (sample—HAL-G-196-21).

Figure 33A:
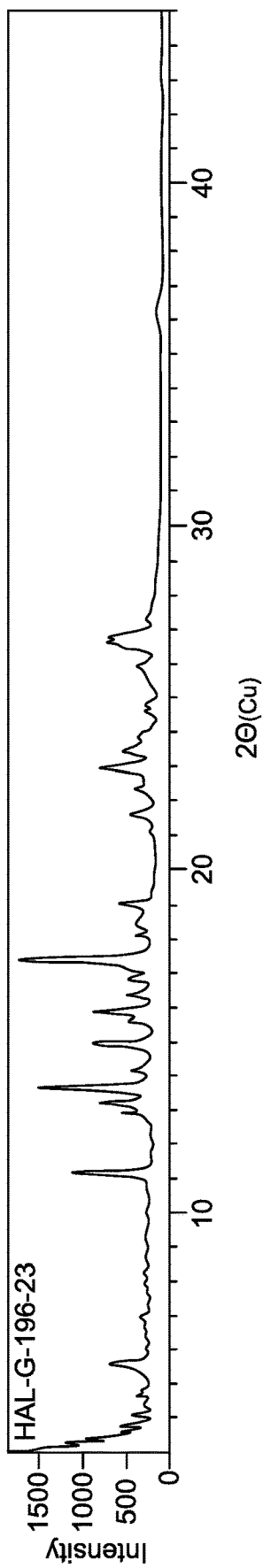
Figure 33B:
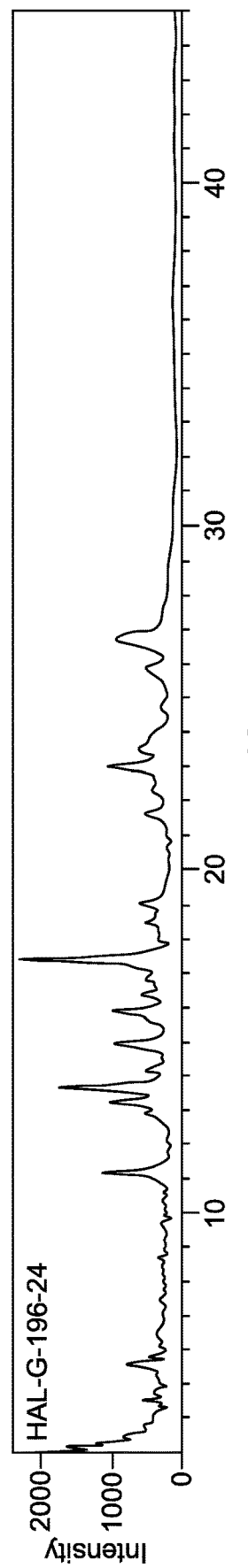

FIGS. 33A-33B. X-ray powder diffraction patterns of the salt of 4-methylbenzenesulfonic acid and 3-(1,2,4-triazolo[4,3-a]pyridine-3-ylethynyl)-4-methyl-N-(4-((4-methylpiperazin-1-yl)methyl)-3-trifluoromethylphenyl)benzamide. FIG. 33A shows the results for HAL-G-196-23; FIG. 33B shows the results for HAL-G-196-24.

Figure 34:
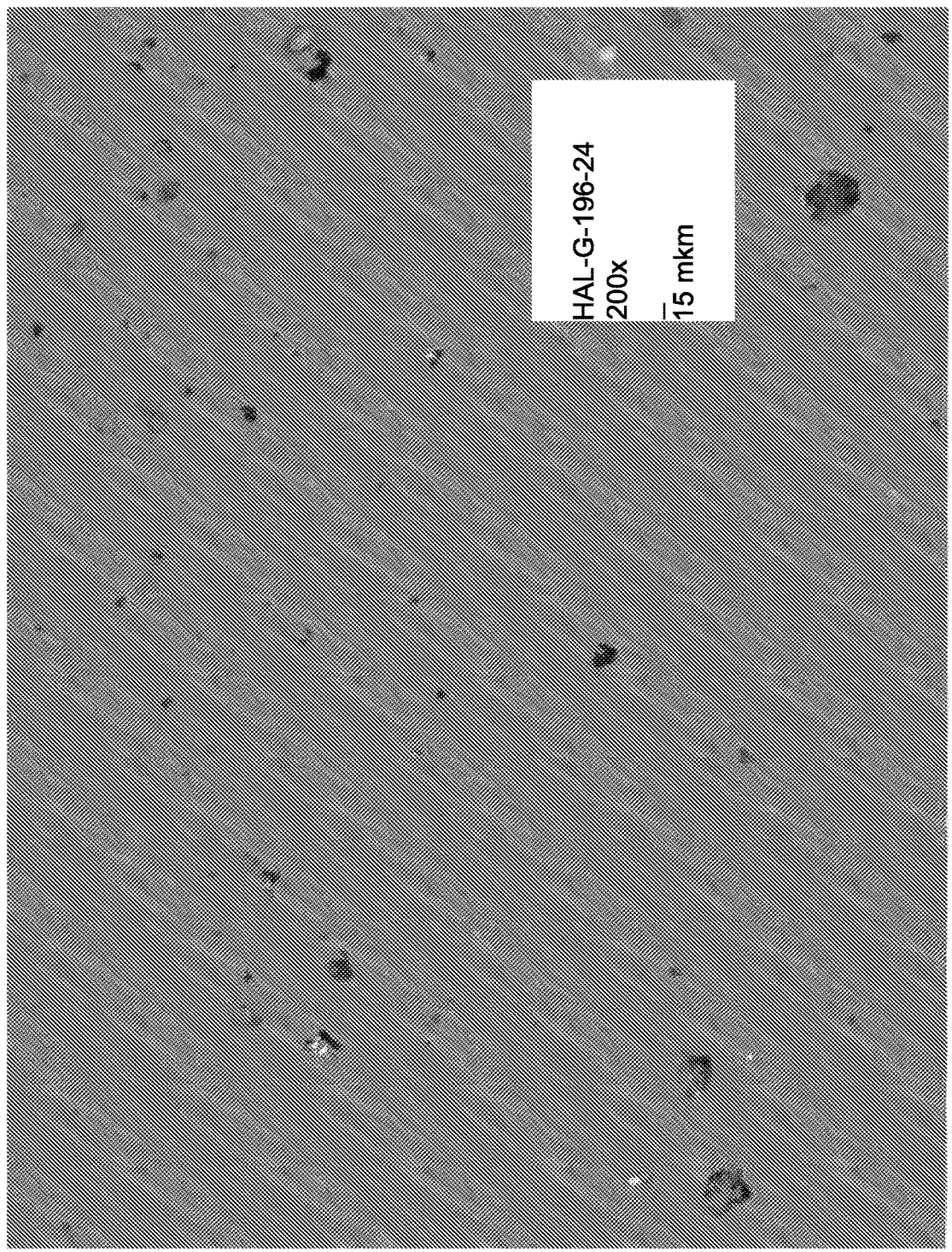

FIG. 34. Photograph of crystals of the salt of 4-methylbenzenesulfonic acid and 3-(1,2,4-triazolo[4,3-a]pyridine-3-ylethynyl)-4-methyl-N-(4-((4-methylpiperazin-1-yl)methyl)-3-trifluoromethylphenyl)benzamide (sample—HAL-G-196-24) obtained by polarization microscopy.

Figure 35:
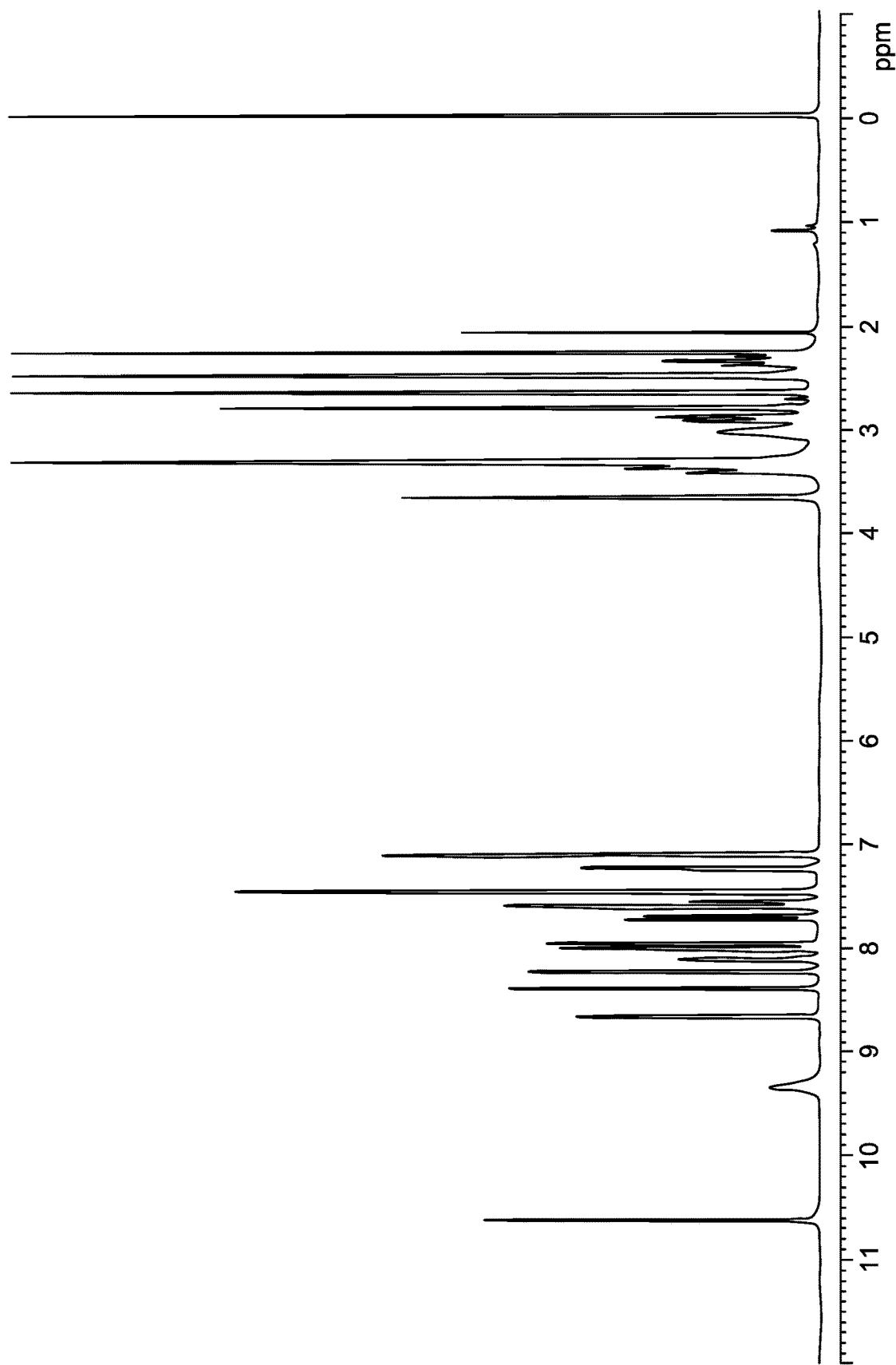

FIG. 35. $^1$H nuclear magnetic resonance spectrum of a sample of the salt of 4-methylbenzenesulfonic acid and 3-(1,2,4-triazolo[4,3-a]pyridine-3-ylethynyl)-4-methyl-N-(4-((4-methylpiperazin-1-yl)methyl)-3-trifluoromethylphenyl)benzamide (sample—HAL-G-196-24).

Figure 36:
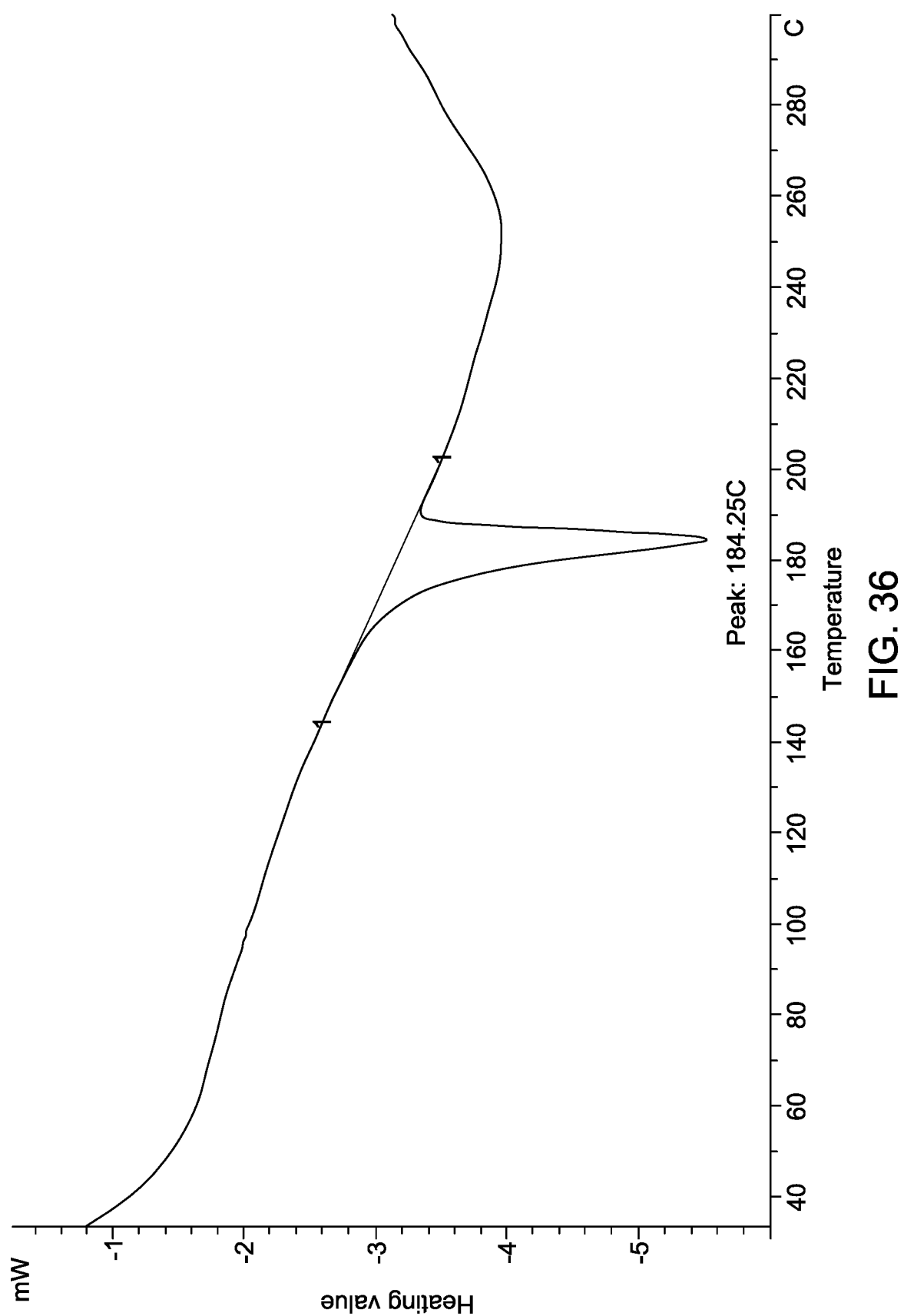

FIG. 36. DSC curve of a sample of the salt of 4-methylbenzenesulfonic acid and 3-(1,2,4-triazolo[4,3-a]pyridine-3-ylethynyl)-4-methyl-N-(4-((4-methylpiperazin-1-yl)methyl)-3-trifluoromethylphenyl)benzamide (sample—HAL-G-196-24).

Figure 37:
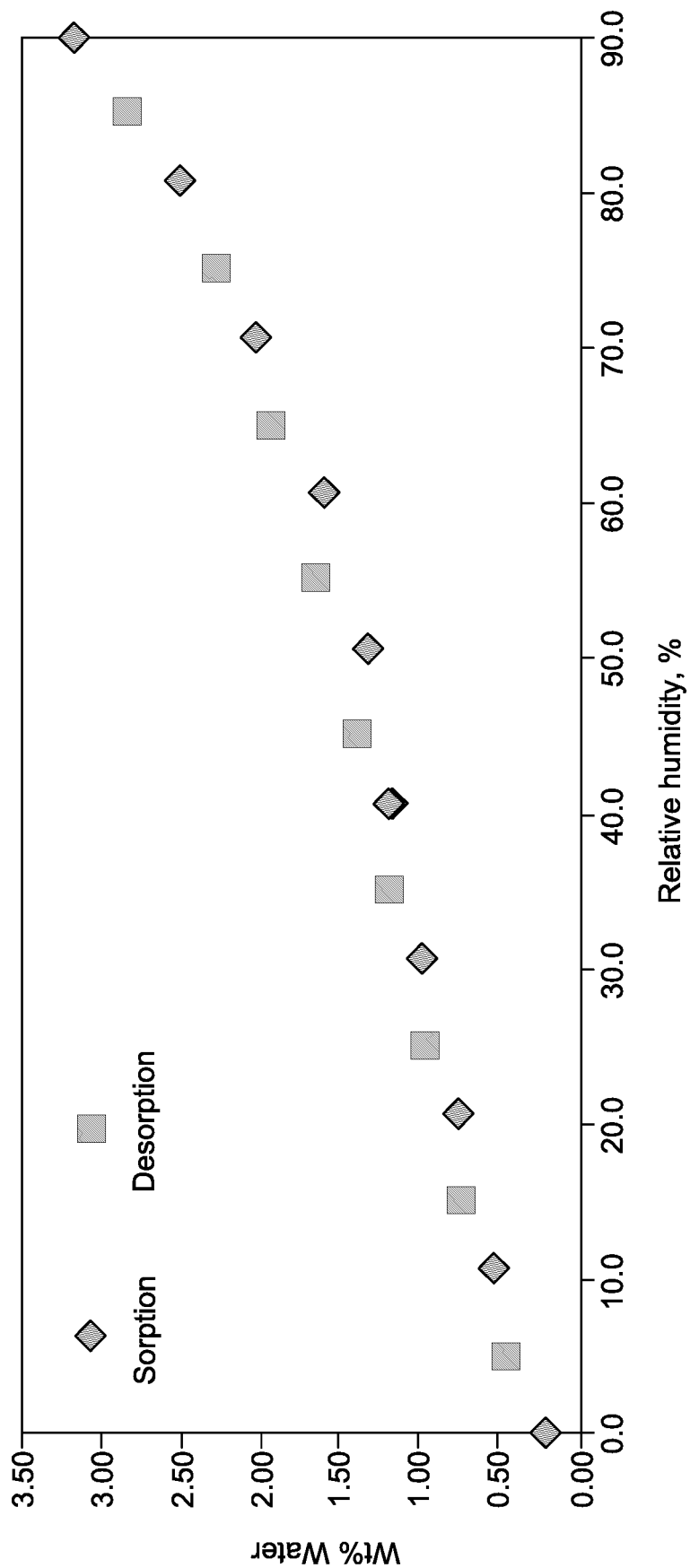

FIG. 37. Plot showing the hygroscopicity of a sample of the salt of 4-methylbenzenesulfonic acid and 3-(1,2,4-triazolo[4,3-a]pyridine-3-ylethynyl)-4-methyl-N-(4-((4-methylpiperazin-1-yl)methyl)-3-trifluoromethylphenyl)benzamide (sample—HAL-G-196-24) analyzed by gravimetric moisture absorption.

Figure 38A:
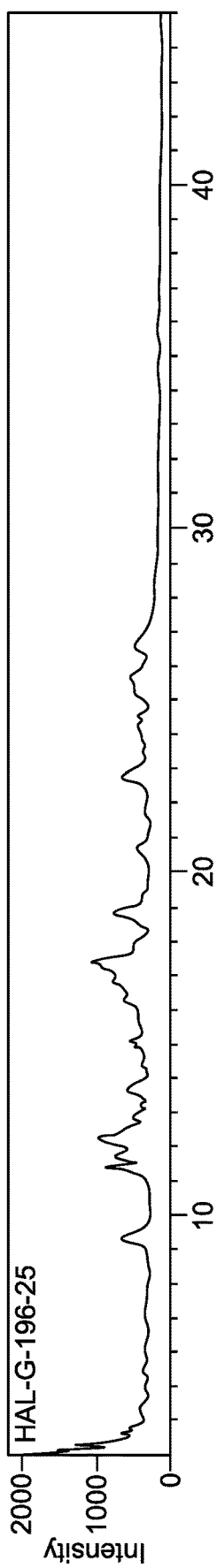
Figure 38B:
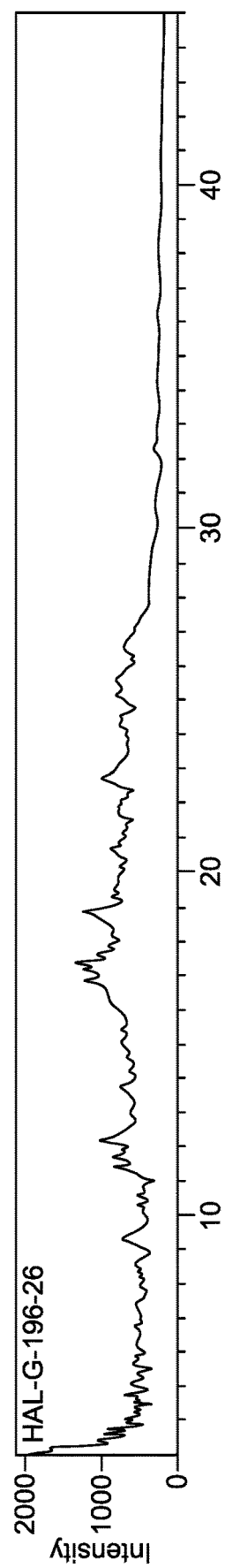

FIGS. 38A-38B. X-ray powder diffraction patterns of the salt of malic acid and free base 3-(1,2,4-triazolo[4,3-a]pyridine-3-ylethynyl)-4-methyl-N-(4-((4-methylpiperazin-1-yl)methyl)-3-trifluoromethylphenyl)benzamide. FIG. 38A shows the results for HAL-G-196-25; FIG. 38B shows the results for HAL-G-198-26.

Figure 39:
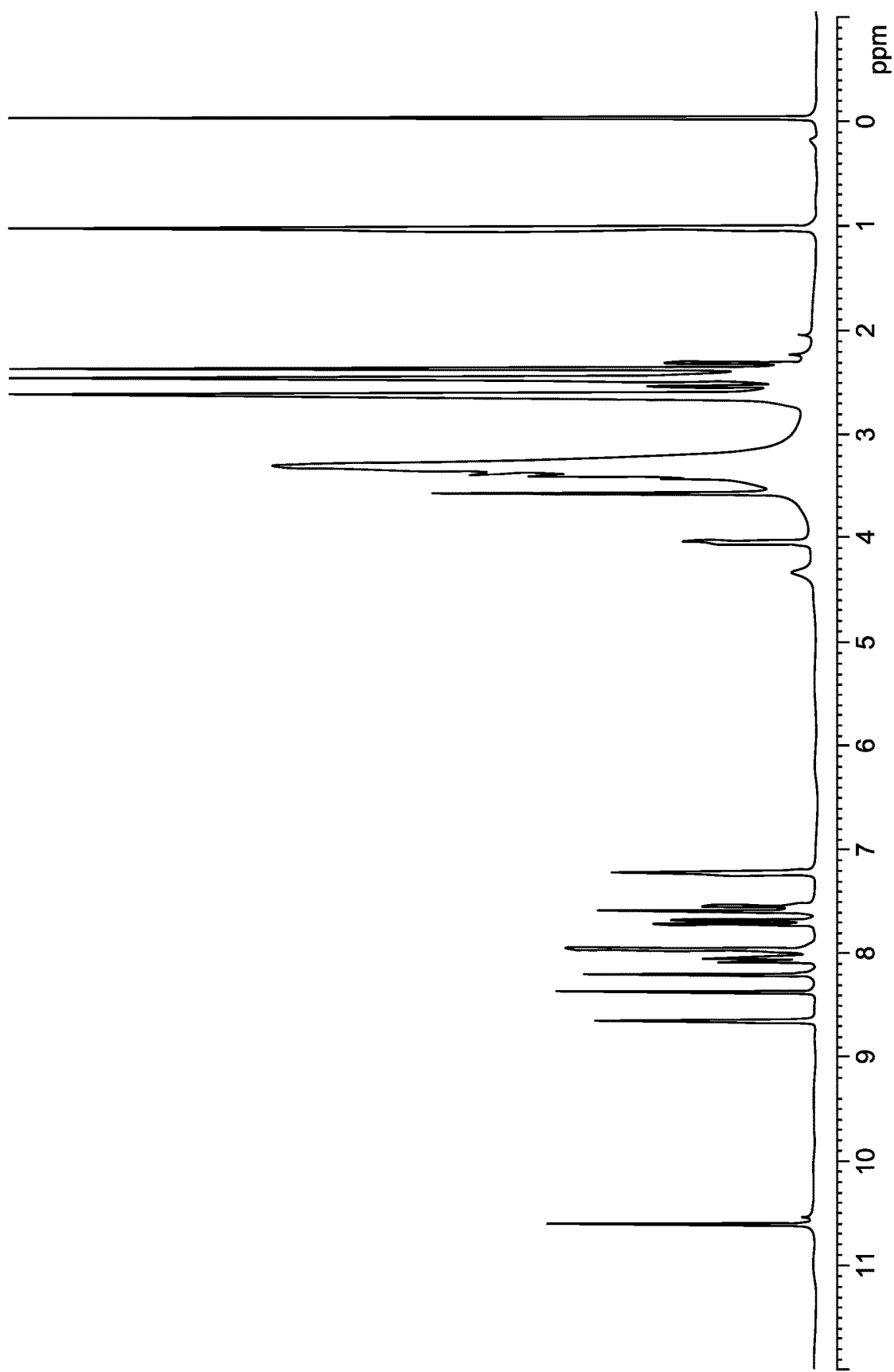

FIG. 39. $^1$H nuclear magnetic resonance spectrum of a sample of the salt of malic acid and 3-(1,2,4-triazolo[4,3-a]pyridine-3-ylethynyl)-4-methyl-N-(4-((4-methylpiperazin-1-yl)methyl)-3-trifluoromethylphenyl)benzamide (sample—HAL-G-196-25).

Figure 40:
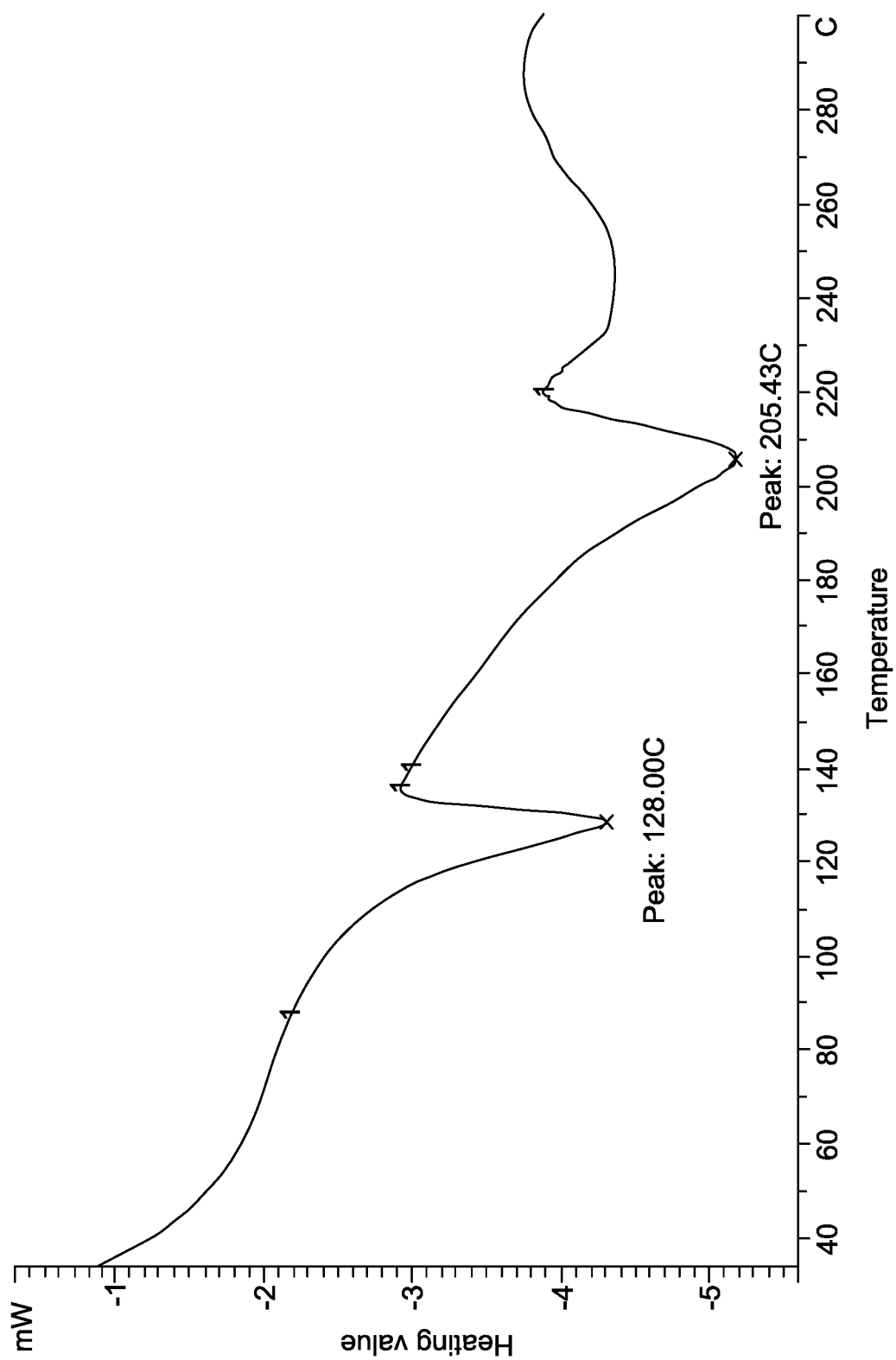

FIG. 40. DSC of a sample of the salt of malic acid and 3-(1,2,4-triazolo[4,3-a]pyridine-3-ylethynyl)-4-methyl-N-(4-((4-methylpiperazin-1-yl)methyl)-3-trifluoromethylphenyl)benzamide (sample—HAL-G-196-25).

Figure 41:
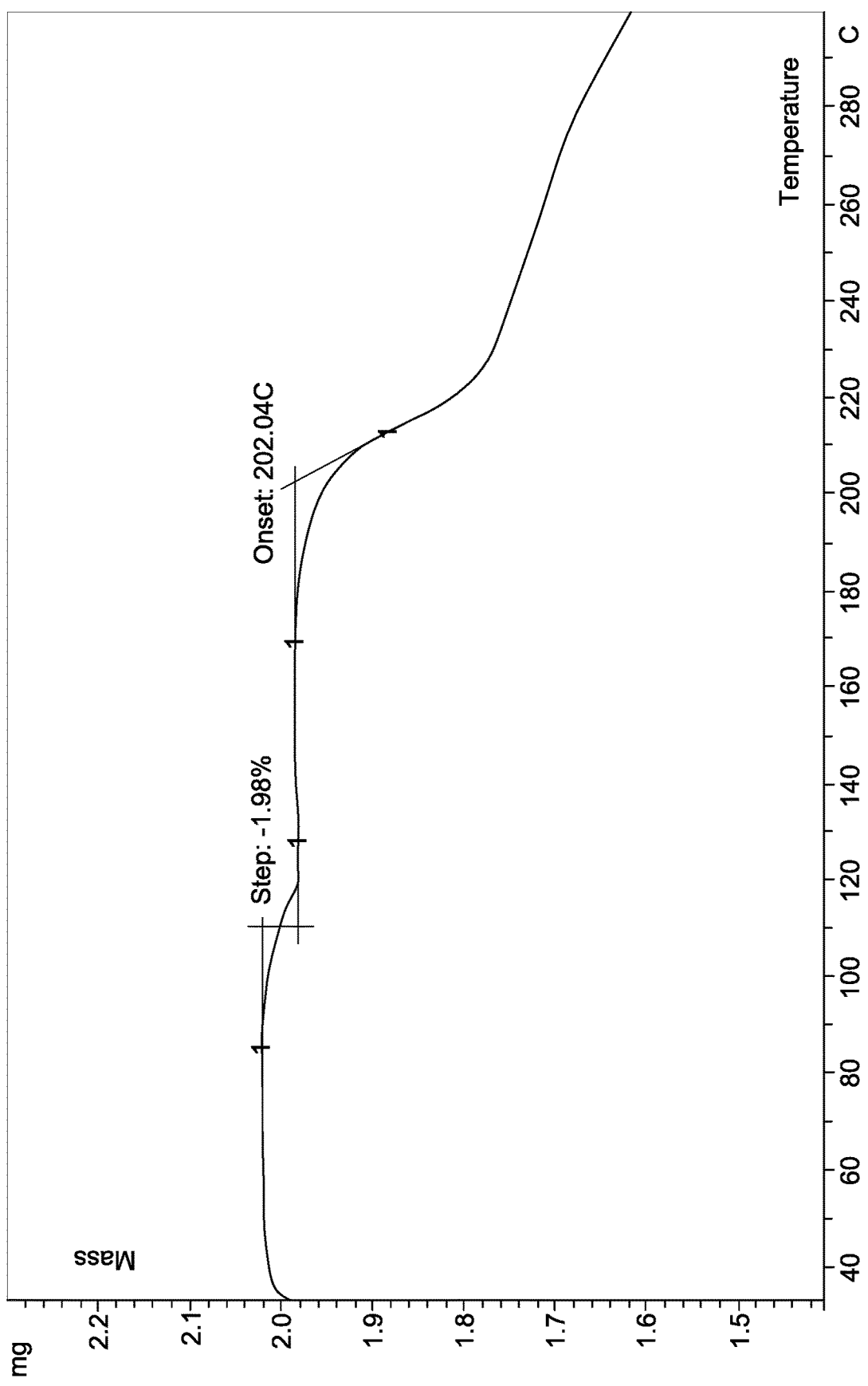

FIG. 41. The TGA curve (thermogravimetric analysis) of the sample of the salt of malic acid and 3-(1,2,4-triazolo[4,3-a]pyridine-3-ylethynyl)-4-methyl-N-(4-((4-methylpiperazin-1-yl)methyl)-3-trifluoromethylphenyl)benzamide (sample—HAL-G-196-25).

Figure 42A:
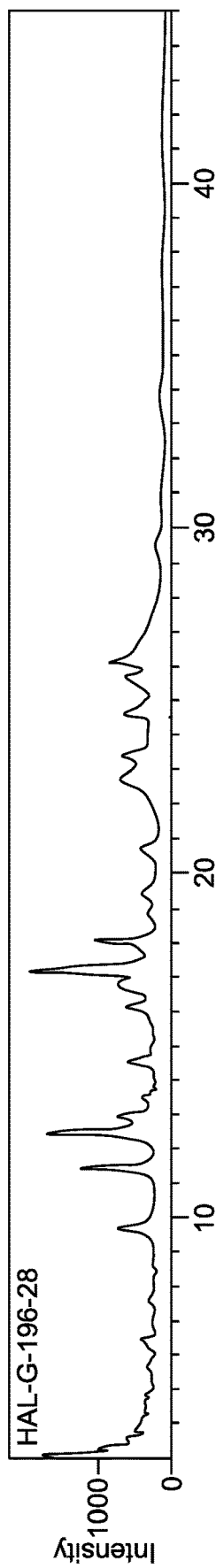
Figure 42B:
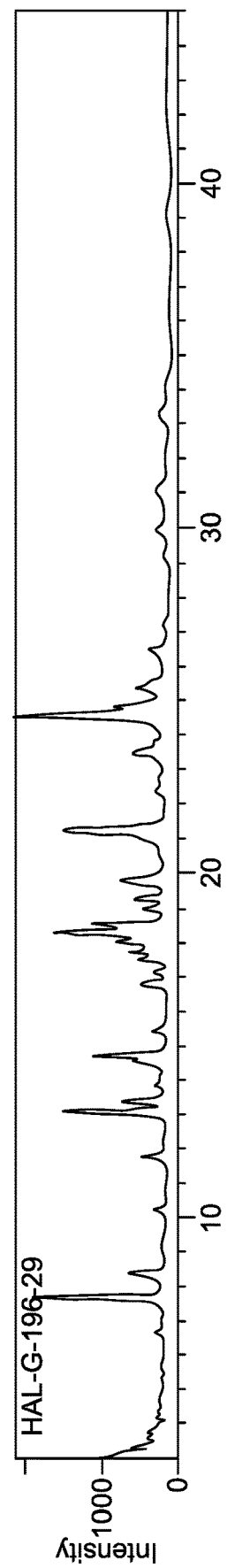

FIGS. 42A-42B. The X-ray powder diffraction patterns of the salt of fumaric acid and free base 3-(1,2,4-triazolo[4,3-a]pyridine-3-ylethynyl)-4-methyl-N-(4-((4-methylpiperazin-1-yl)methyl)-3-trifluoromethylphenyl)benzamide. FIG. 42A shows the results for HAL-G-196-28; FIG. 42B shows the results for HAL-G-198-29.

Figure 43:
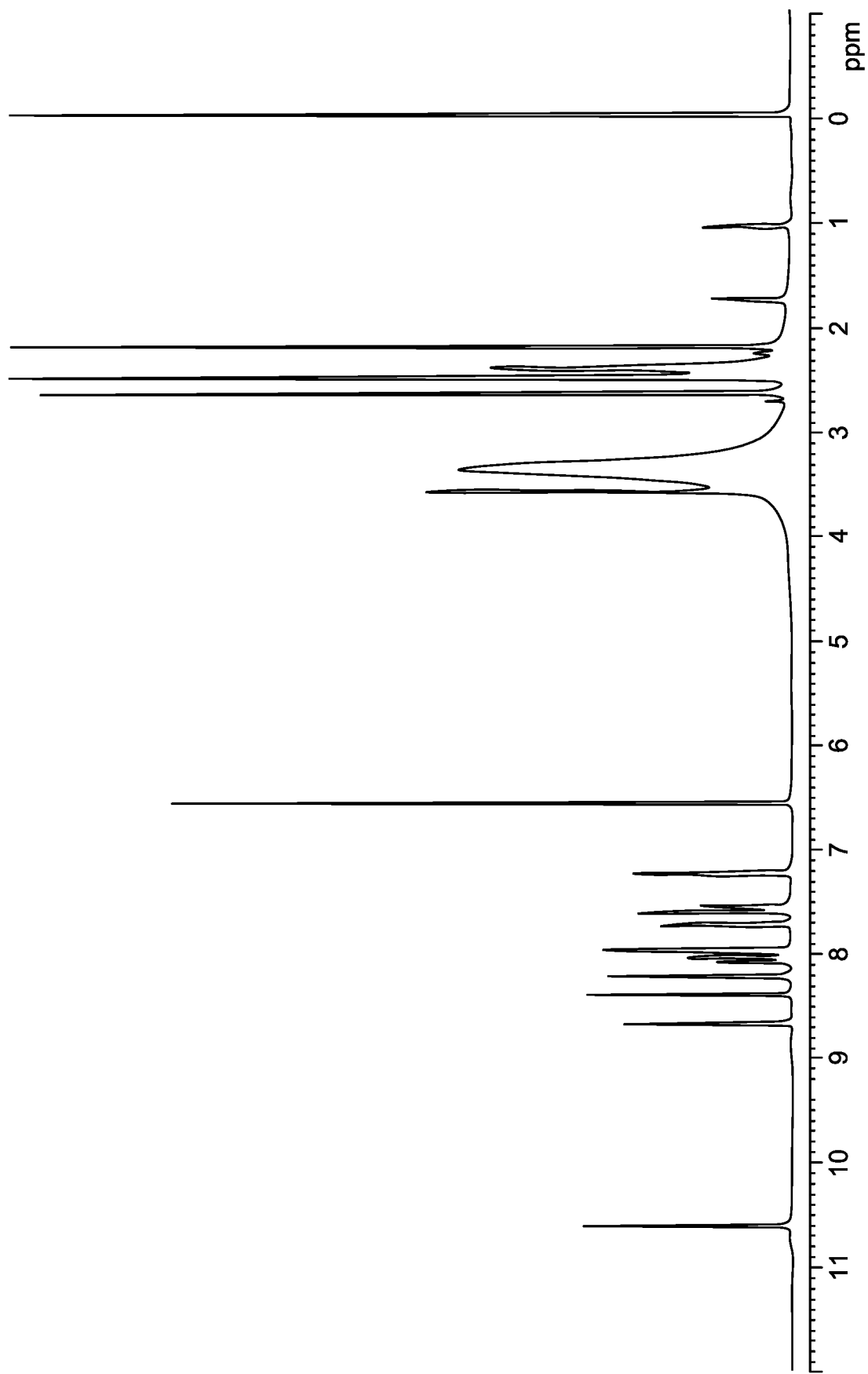

FIG. 43. $^1$H nuclear magnetic resonance spectrum of a sample of the salt of fumaric acid and 3-(1,2,4-triazolo[4,3-a]pyridine-3-ylethynyl)-4-methyl-N-(4-((4-methylpiperazin-1-yl)methyl)-3-trifluoromethylphenyl)benzamide (sample—HAL-G-196-29).

Figure 44A:
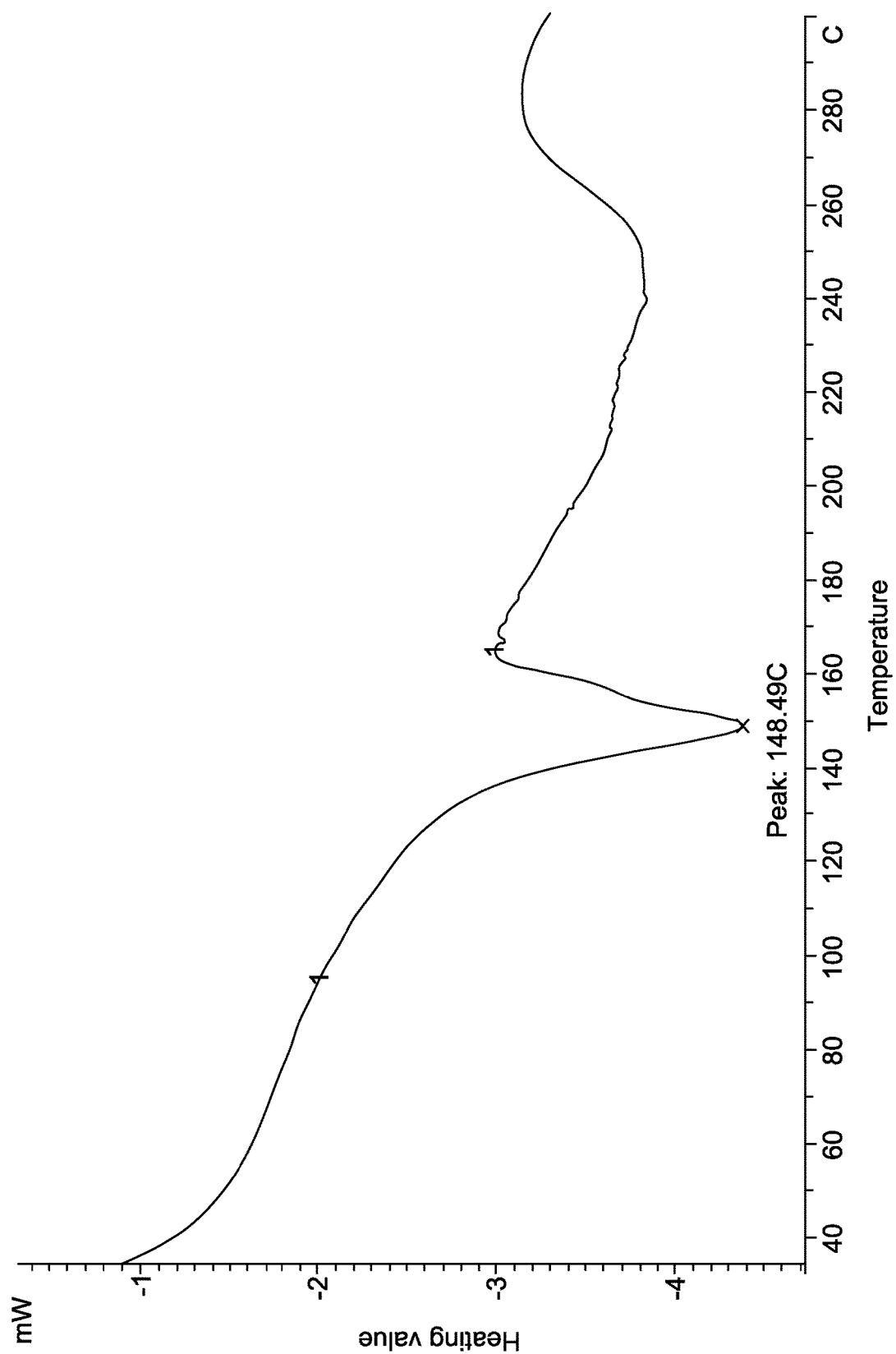
Figure 44B:
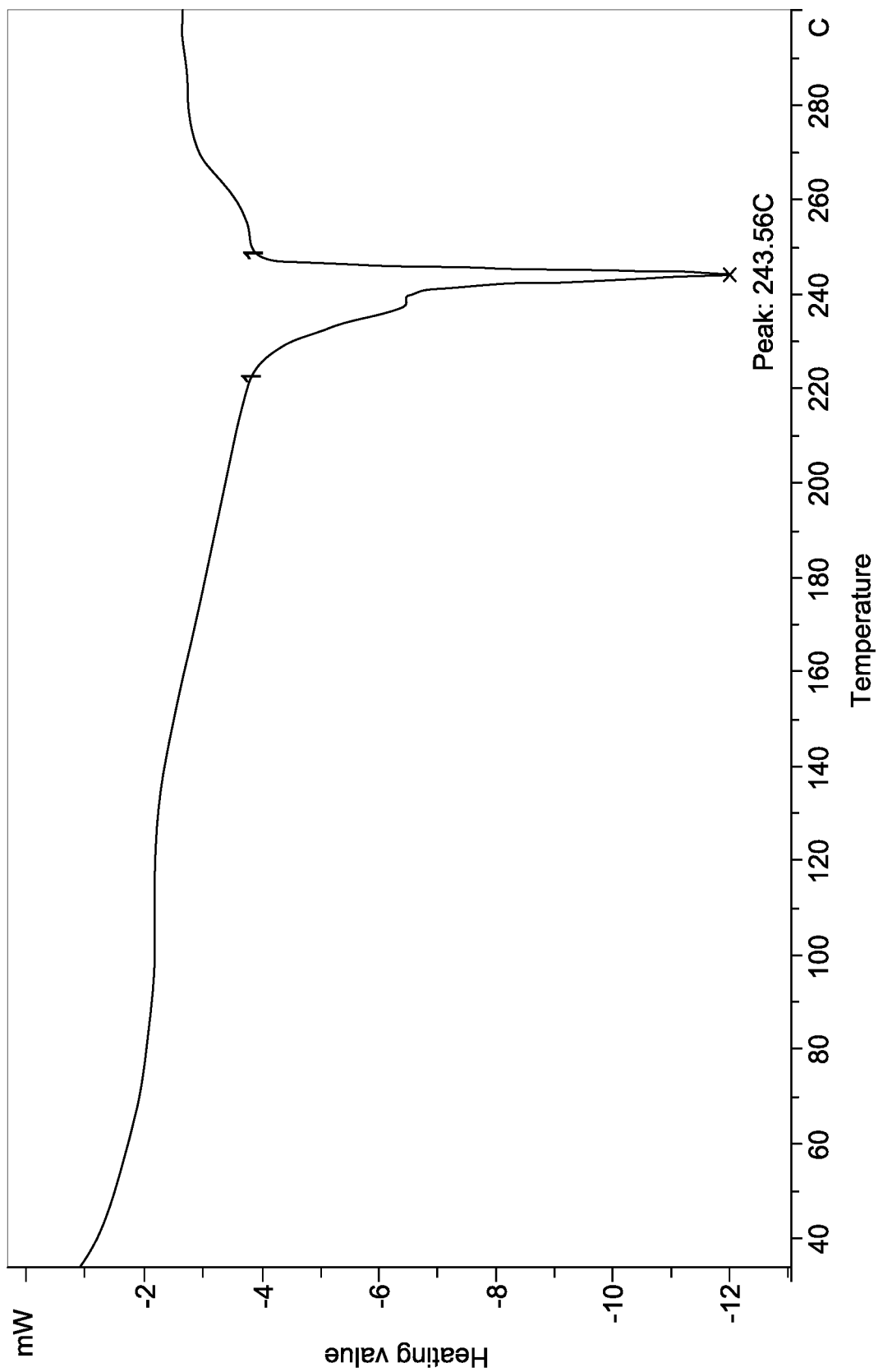

FIGS. 44A-44B. DSC curve of samples of the salt of fumaric acid and 3-(1,2,4-triazolo[4,3-a]pyridine-3-ylethynyl)-4-methyl-N-(4-((4-methylpiperazin-1-yl)methyl)-3-trifluoromethylphenyl)benzamide. FIG. 44A shows the results for HAL-G-196-28; FIG. 44B shows the results for HAL-G-198-29.

Figure 45A:
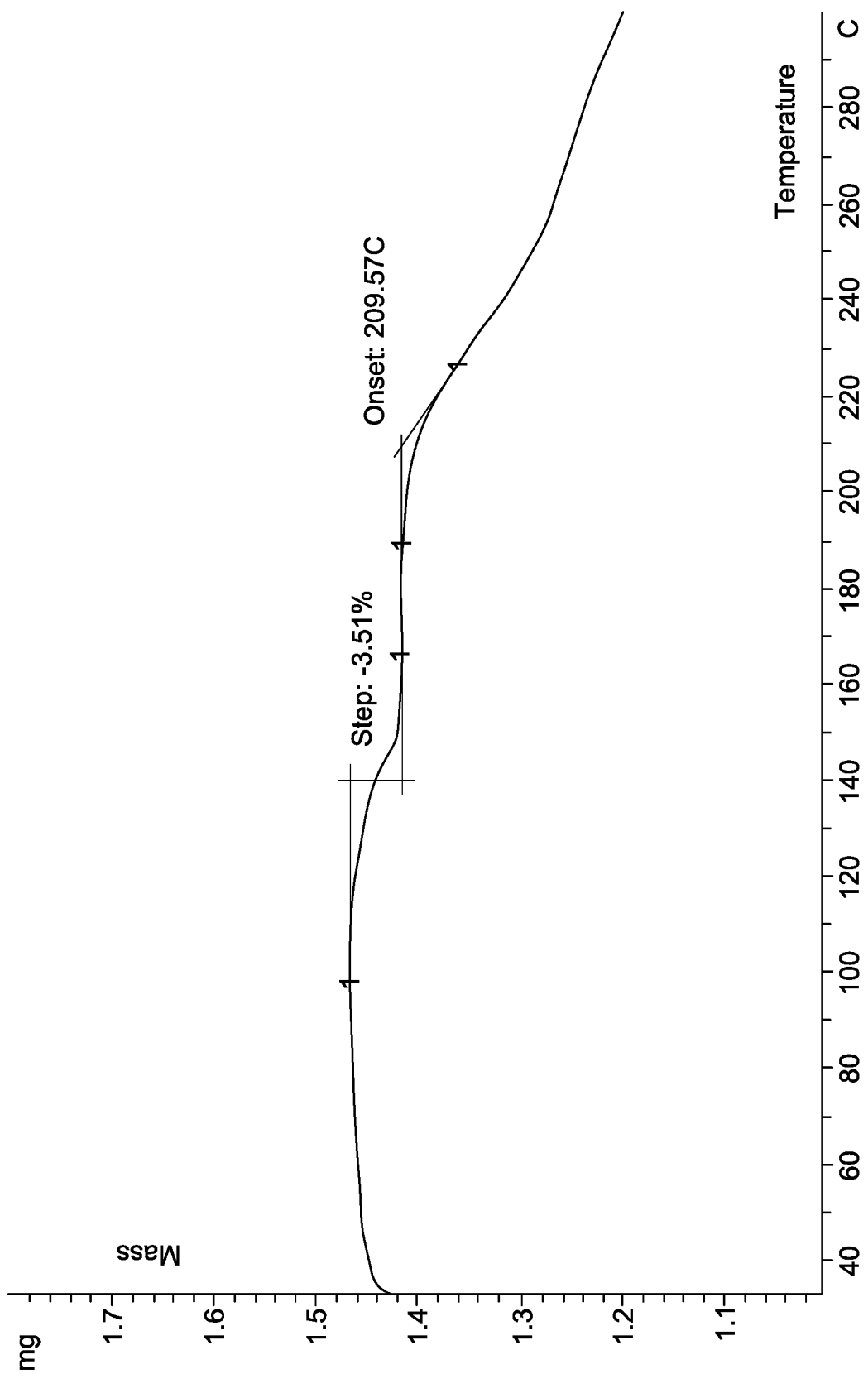
Figure 45B:
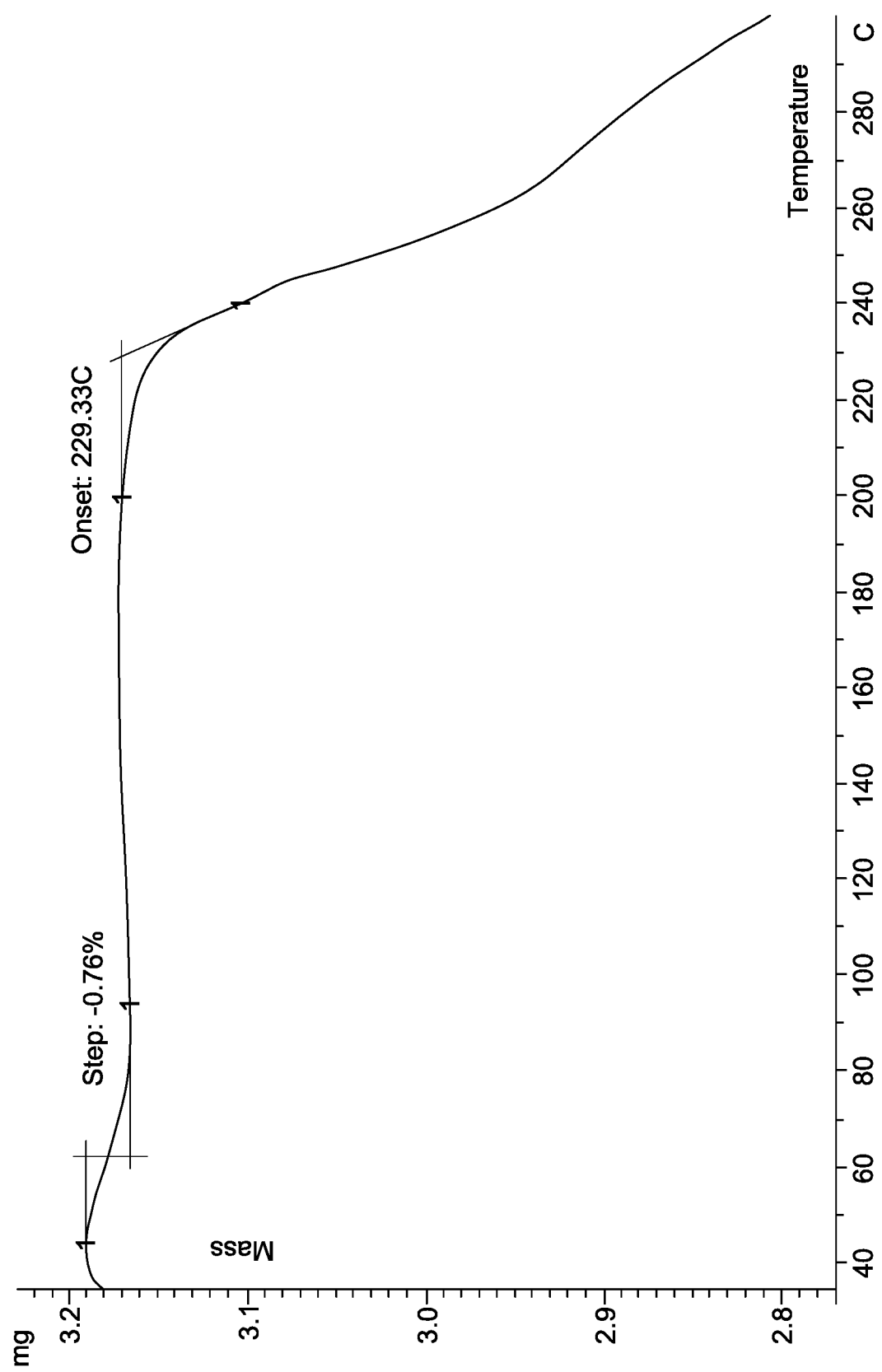

FIGS. 45A-45B. TGA curve of samples of the salt of fumaric acid and 3-(1,2,4-triazolo[4,3-a]pyridine-3-ylethynyl)-4-methyl-N-(4-((4-methylpiperazin-1-yl)methyl)-3-trifluoromethylphenyl)benzamide. FIG. 45A shows the results HAL-G-196-28; FIG. 45B shows the results for HAL-G-198-29.

Figure 46:
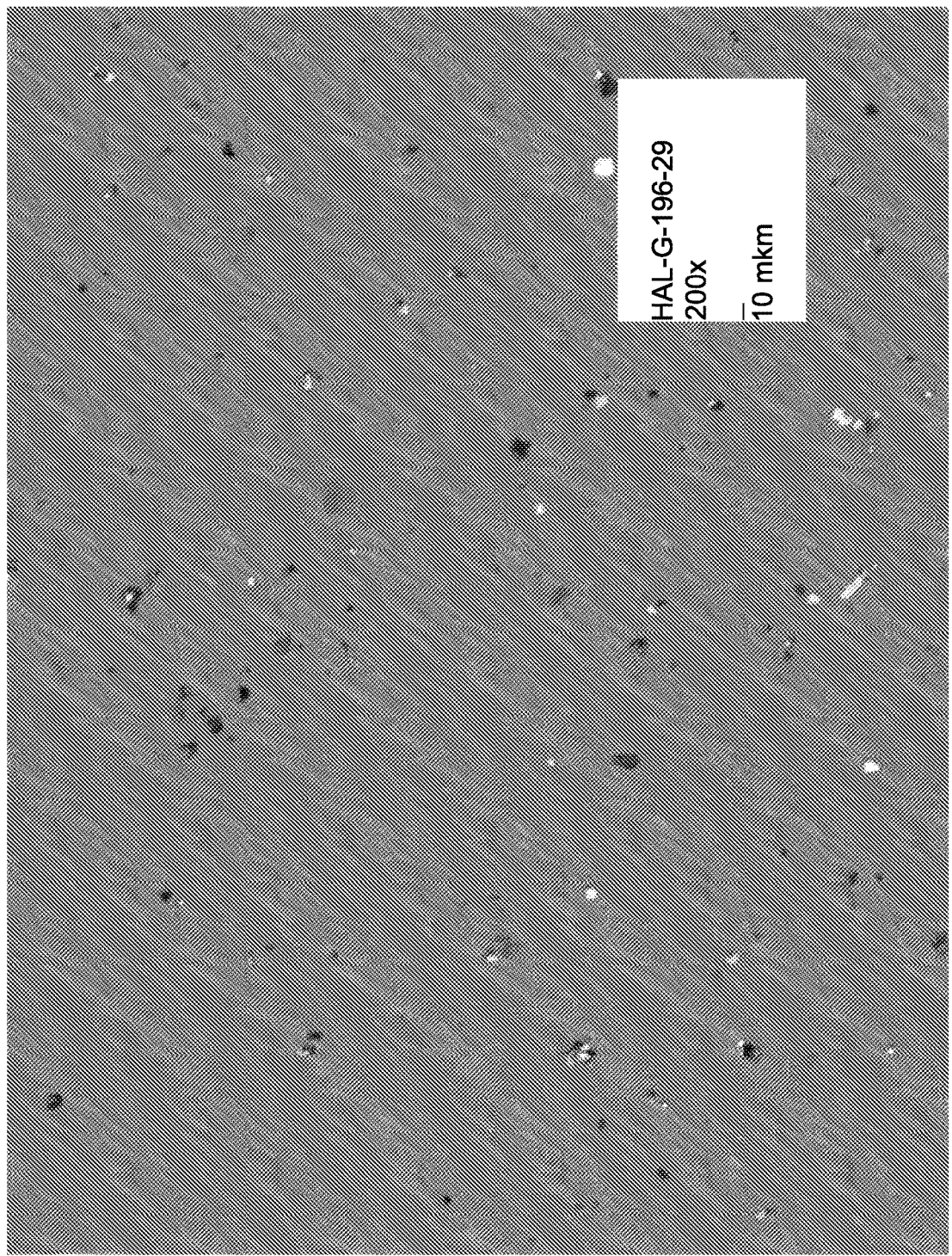

FIG. 46. Photographs of crystals of the salt of fumaric acid and 3-(1,2,4-triazolo[4,3-a]pyridine-3-ylethynyl)-4-methyl-N-(4-((4-methylpiperazin-1-yl)methyl)-3-trifluoromethylphenyl)benzamide (sample—HAL-G-196-29) obtained by polarization microscopy.

Figure 47A:
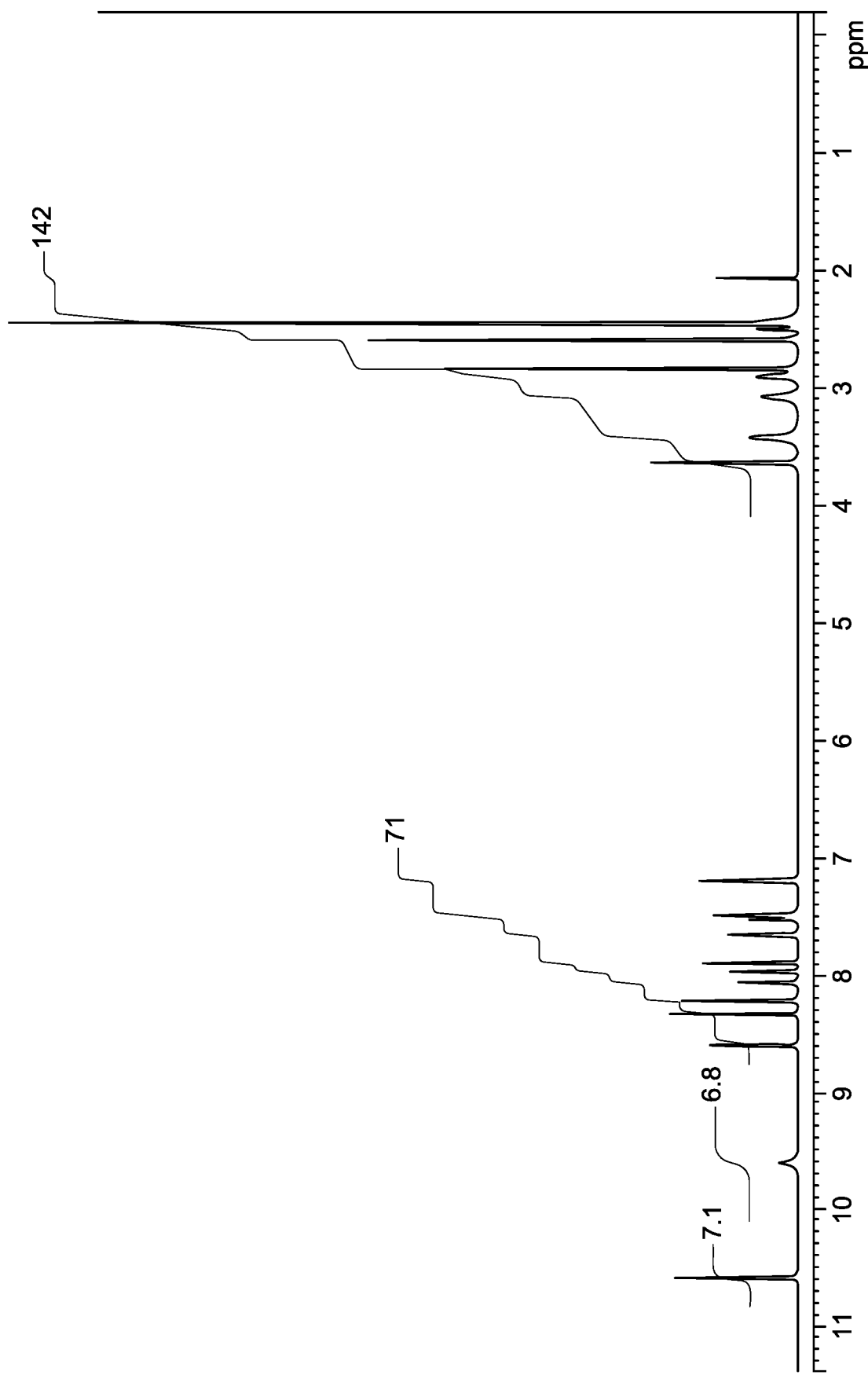
Figure 47B:
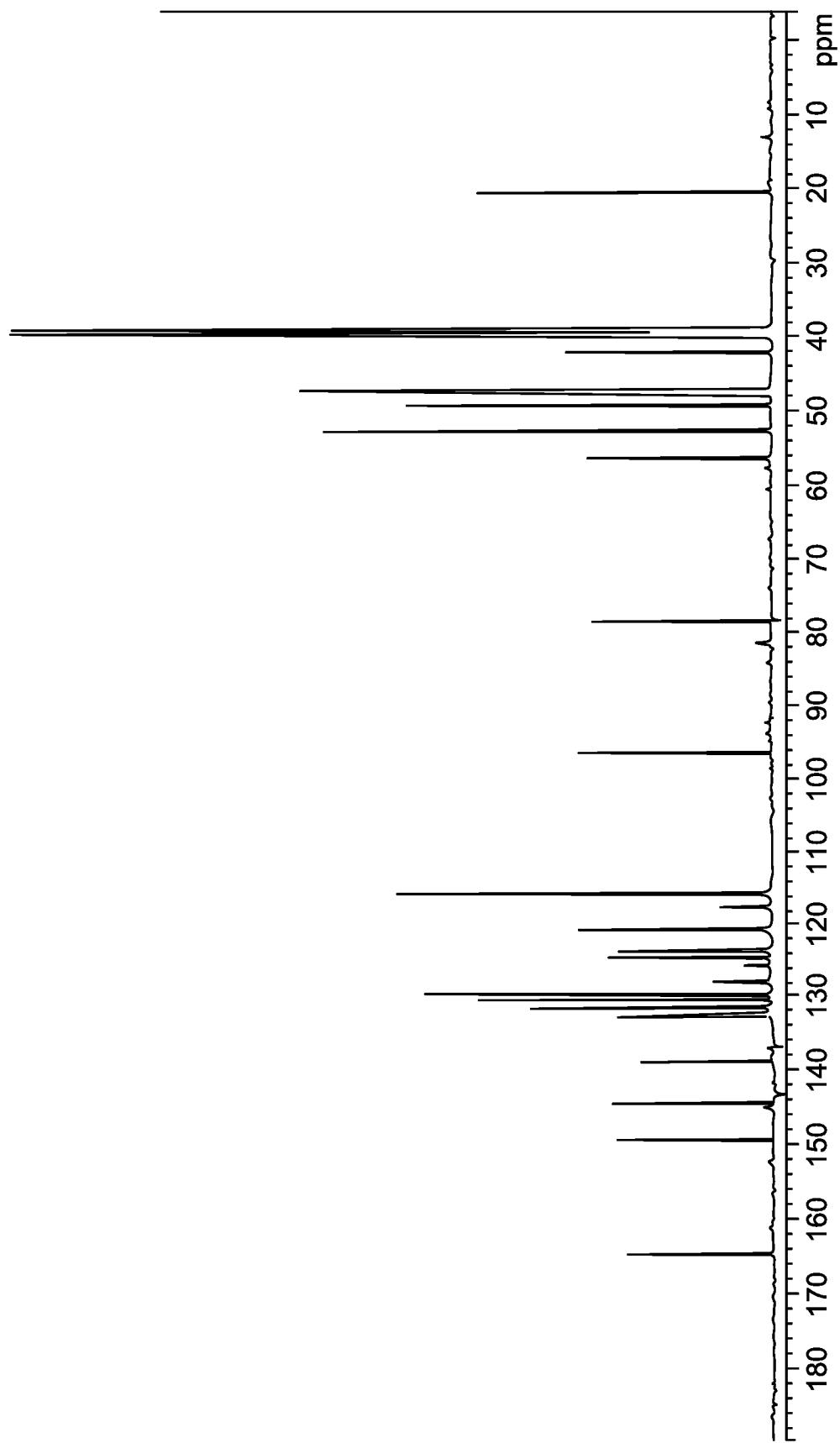

FIGS. 47A-47B. $^1$H and $^{13}$C nuclear magnetic resonance spectra of a sample of the salt of methanesulfonic acid and 3-(1,2,4-triazolo[4,3-a]pyridine-3-ylethynyl)-4-methyl-N-(4-((4-methylpiperazin-1-yl)methyl)-3-trifluoromethylphenyl)benzamide (polymorphous modification I): FIG. 47A shows the results of $^1$H-NMR spectrum (BrukerDRX500, 13400, 500.13 MHz, DMSO-d6); FIG. 47B shows the results of $^{13}$C-NMR spectrum (BrukerDRX500, 125.76 MHz, DMSO-d6).

Figure 48A:
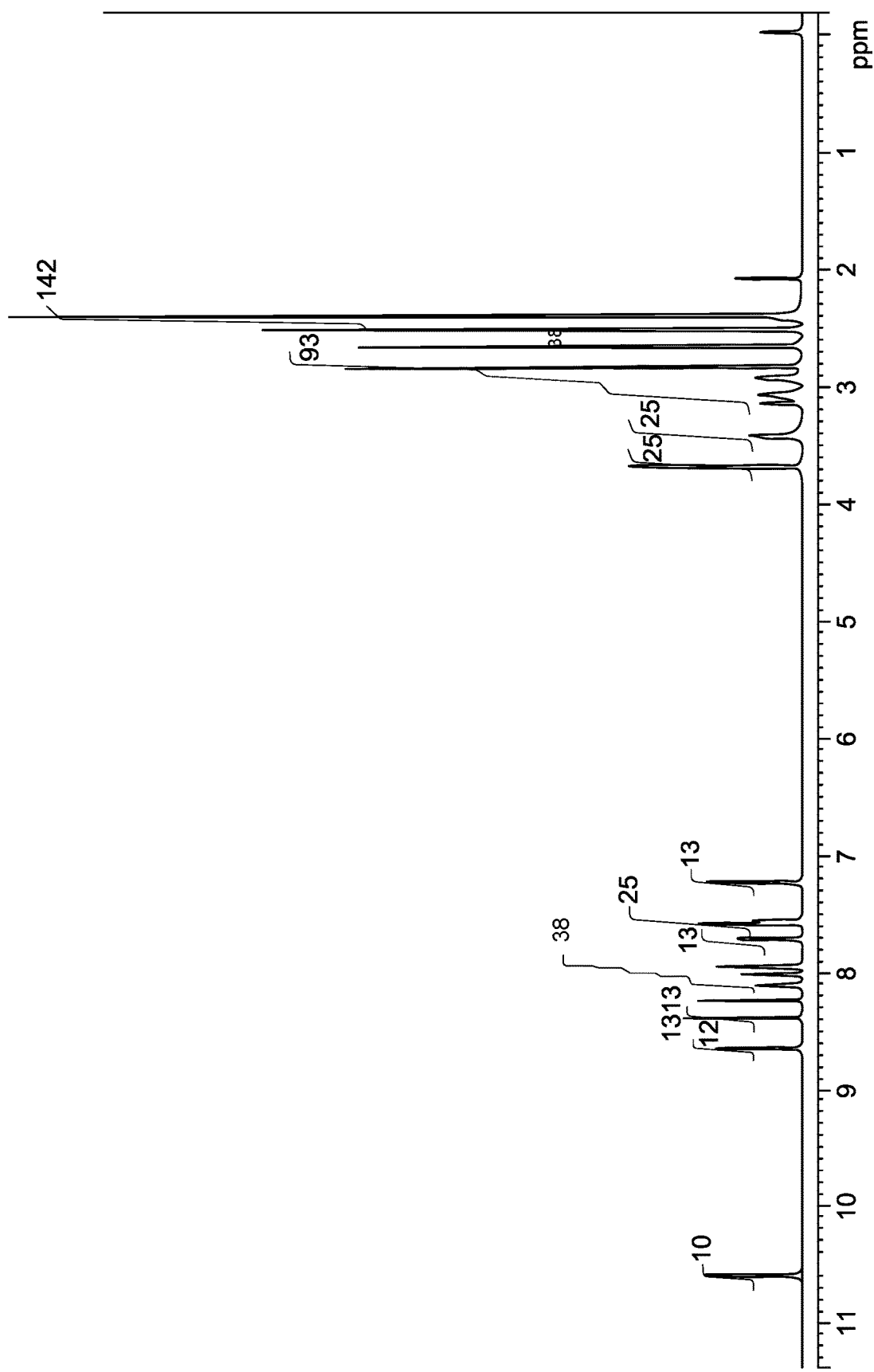
Figure 48B:
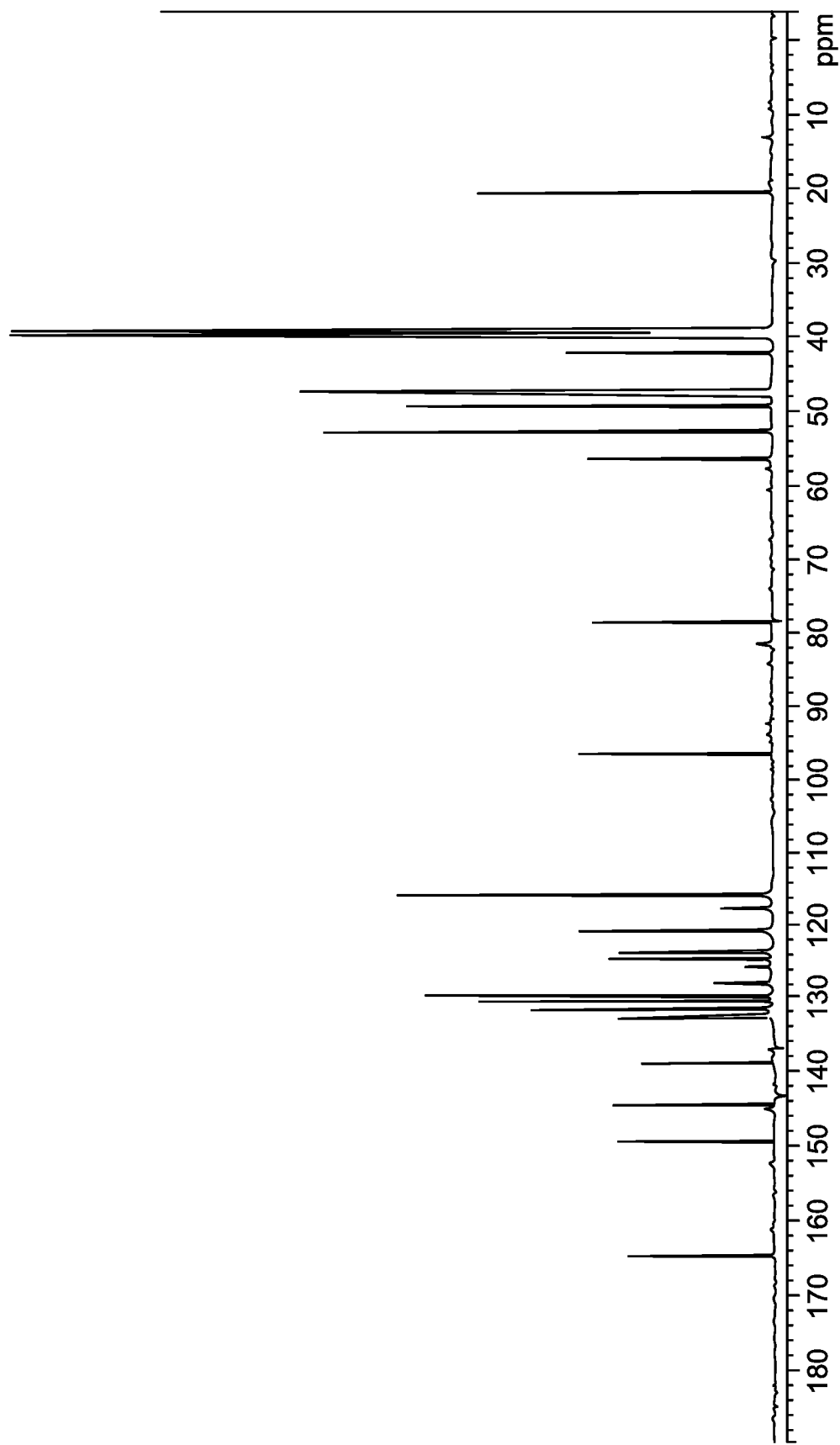

FIGS. 48A-48B. $^1$H and $^{13}$C nuclear magnetic resonance spectra of a sample of the salt of methanesulfonic acid and 3-(1,2,4-triazolo[4,3-a]pyridine-3-ylethynyl)-4-methyl-N-(4-((4-methylpiperazin-1-yl)methyl)-3-trifluoromethylphenyl)benzamide (polymorphous modification II): FIG. 48A shows the results of $^1$H-NMR spectrum (BrukerDRX500, 13, 500.13 MHz, DMSO-d6); FIG. 48B shows the results of $^{13}$C-NMR spectrum (BrukerDRX500, 13, 125.76 MHz, DMSO-d6).

Figure 49A:
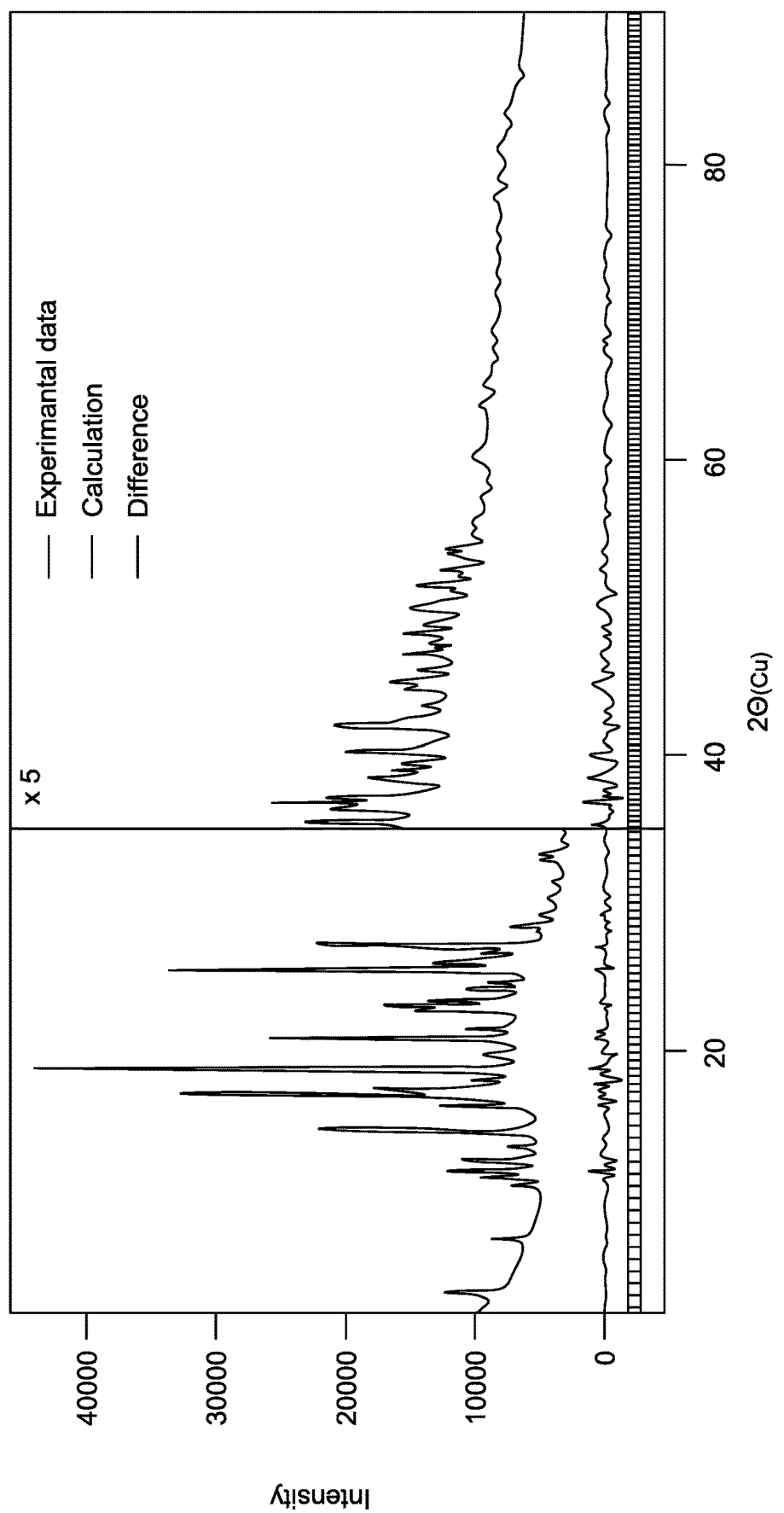
Figure 49B:
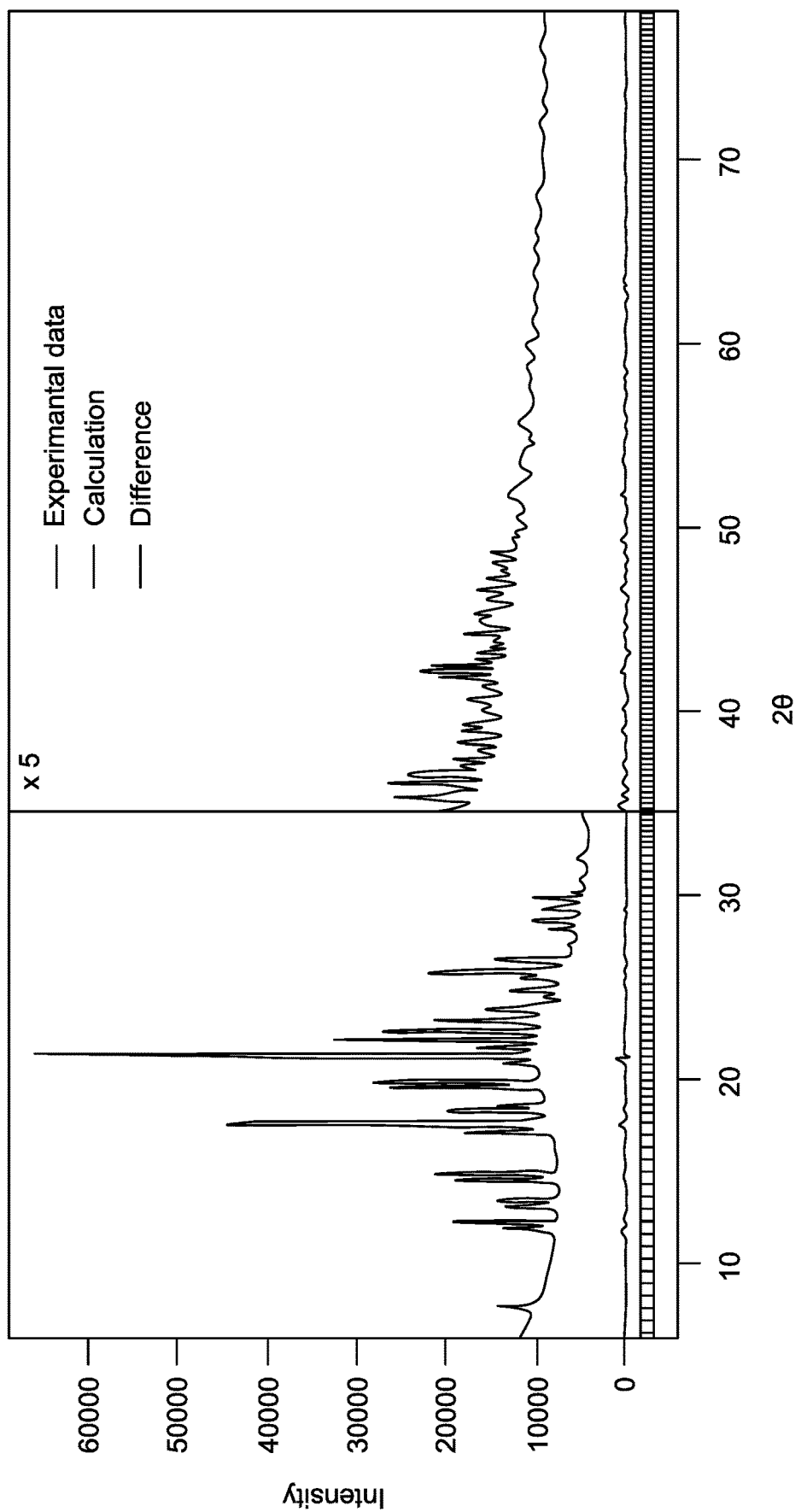

FIGS. 49A-49B. X-ray powder diffraction patterns of the salt of methanesulfonic acid and 3-(1,2,4-triazolo[4,3-a]pyridine-3-ylethynyl)-4-methyl-N-(4-((4-methylpiperazin-1-yl)methyl)-3-trifluoromethylphenyl)benzamide. FIG. 49A shows the results for Polymorphous modification I; FIG. 49B shows the results for Polymorphous modification II.

Figure 50A:
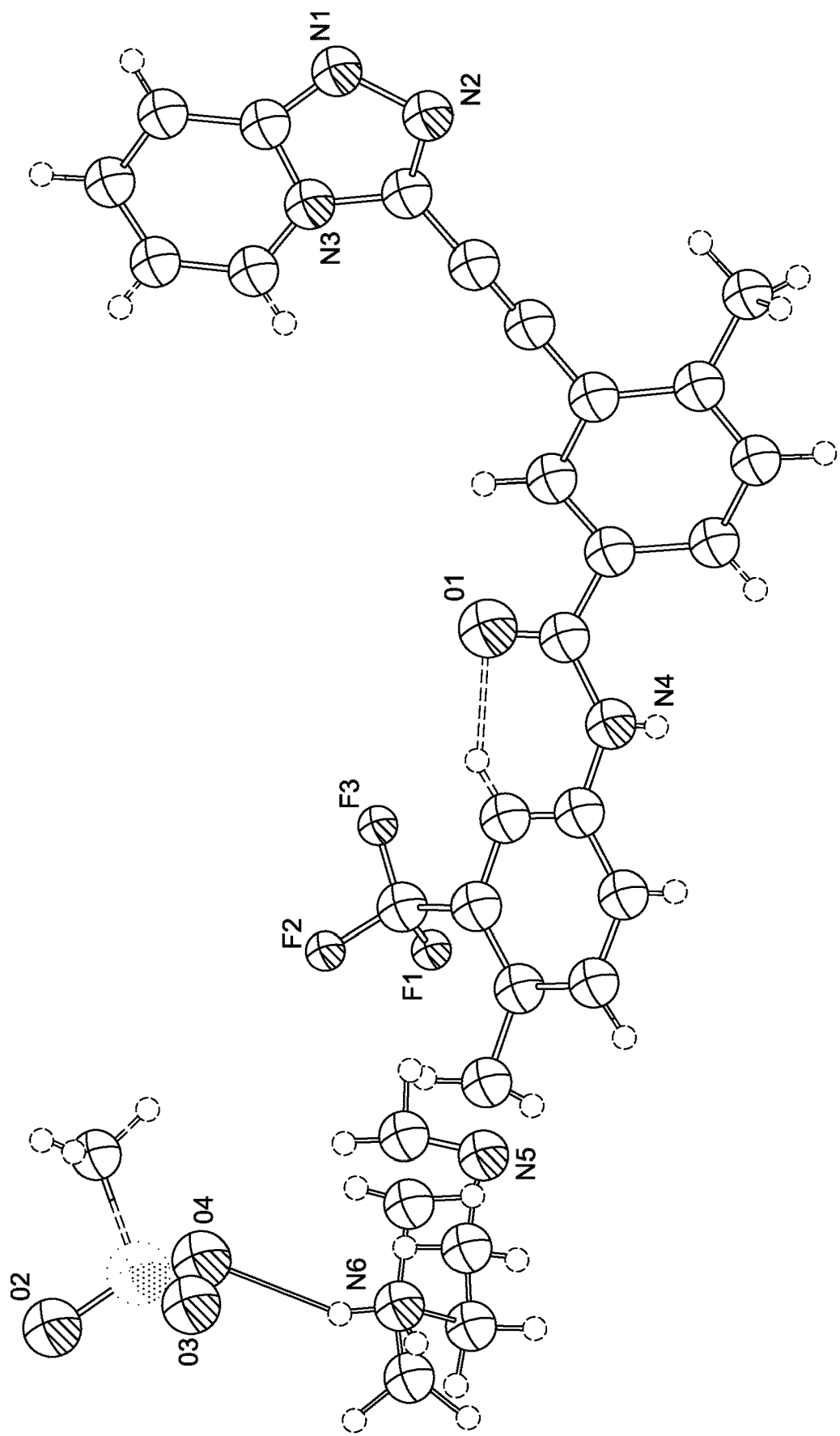
Figure 50B:
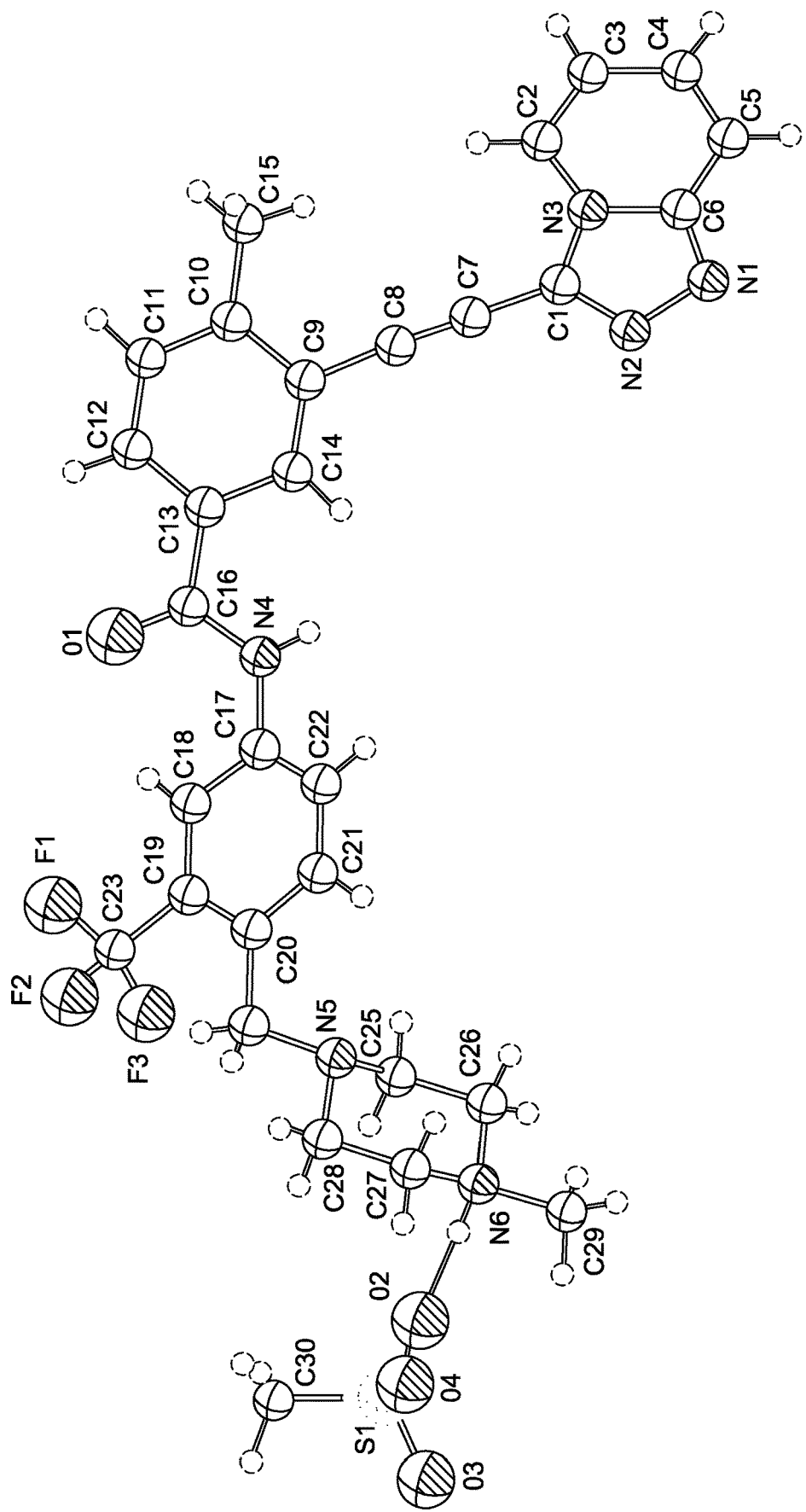

FIGS. 50A-50B. General view of the unit cell of the salt of methanesulfonic acid and 3-(1,2,4-triazolo[4,3-a]pyridine-3-ylethynyl)-4-methyl-N-(4-((4-methylpiperazin-1-yl) methyl)-3-trifluoromethylphenyl)benzamide. FIG. 50A shows the results for Polymorphous modification I; FIG 50B shows the results for Polymorphous modification II.

Figure 51:
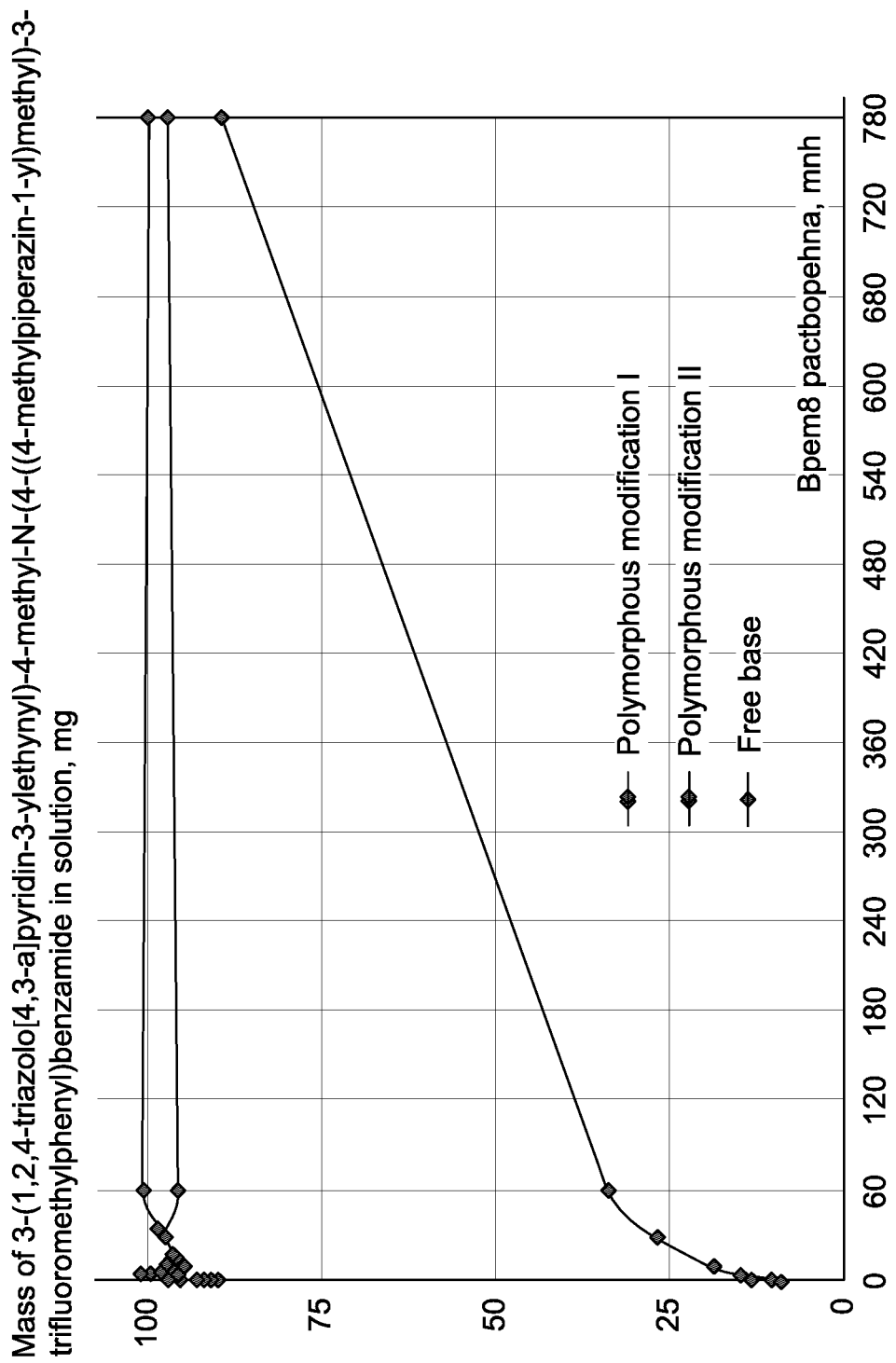

FIG. 51. Plots showing the kinetics of dissolution of free base 3-(1,2,4-triazolo[4,3-a]pyridine-3-ylethynyl)-4-methyl-N-(4-((4-methylpiperazin-1-yl)methyl)-3-trifluoromethylphenyl)benzamide and polymorphous modifications of the salt of methanesulfonic acid and 3-(1,2,4-triazolo[4,3-a]pyridine-3-ylethynyl)-4-methyl-N-(4-((4-methylpiperazin-1-yl)methyl)-3-trifluoromethylphenyl) benzamide.

Figure 52A:
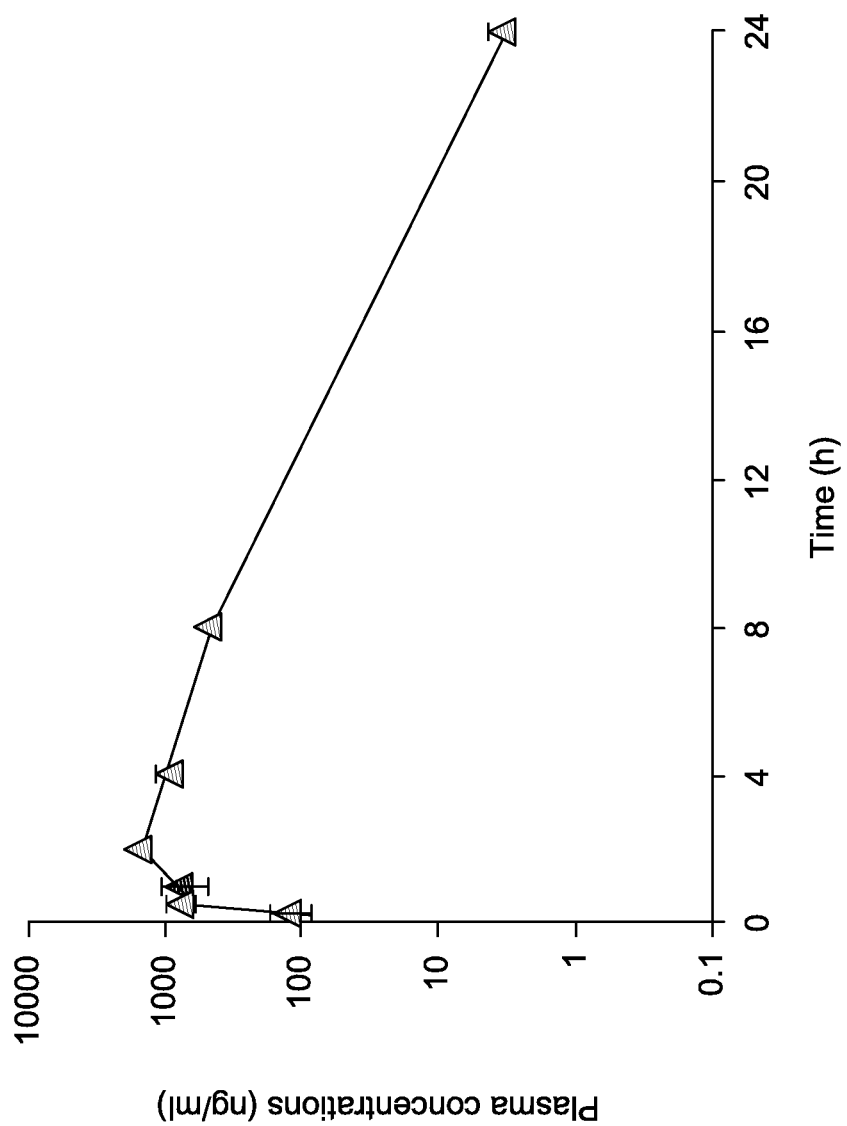
Figure 52B:
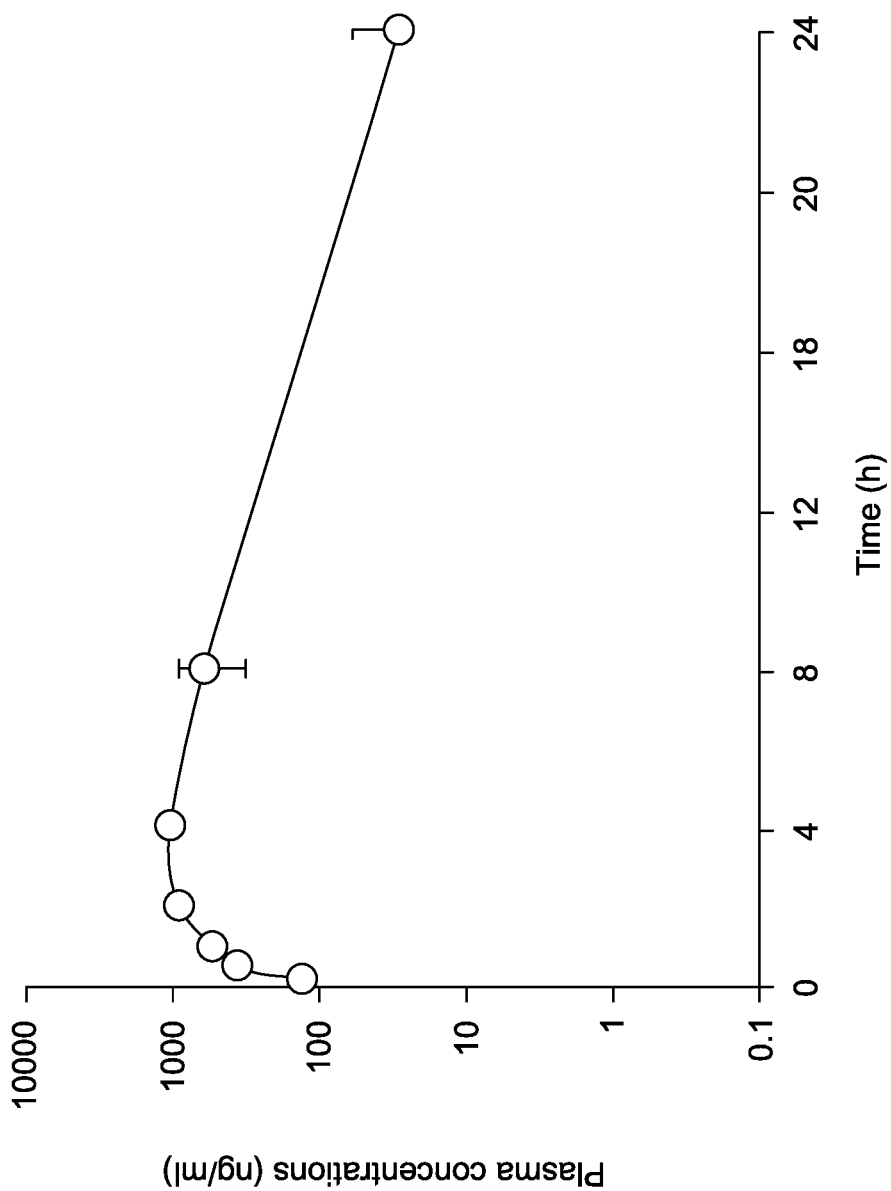

FIGS. 52A-52B. The mean values of the concentration of 3-(1,2,4-triazolo[4,3-a]pyridine-3-ylethynyl)-4-methyl-N-(4-((4-methylpiperazin-1-yl)methyl)-3-trifluoromethylphenyl)benzamide in blood plasma of C57BL/6 mice after a single oral administration. The mean values were determined for each time point on the basis of the individual data obtained from three animals. FIG. 52A shows the results for oral administration of the free base at a dosage of 50 mg/kg; FIG. 52B shows the results for oral administration of the salt of methanesulfonic acid and 3-(1,2,4-triazolo[4,3-a]pyridine-3-ylethynyl)-4-methyl-N-(4-((4-methylpiperazin-1-yl) methyl)-3-trifluoromethylphenyl)benzamide (polymorphous modification I) at a dosage of 59 mg/kg of the salt (equivalent to a dose of 50 mg/kg of the free base).

DETAILED DESCRIPTION

The present disclosure describes a novel salt form of the kinase inhibitor, in particular, a novel salt form of the AbI kinase inhibitor, containing a pharmacologically acceptable counterion, possessing the crystallinity, the high solubility in water, and the constant composition, allowing scaling of production and purification processes, and being useful in terms of clinical application to treat the diseases associated with the impaired activity of different kinases.

The technical result is the development and production of a novel salt form of the kinase inhibitor, in particular, a novel salt form of the AbI kinase inhibitor, including its novel polymorphic modifications (crystalline forms) possessing high solubility in water, high inhibition activity in regard to AbI kinase (and clinically significant mutant forms of this enzyme), high average daily concentration, and a high value of the $AUC_\infty$ parameter (the area under the curve of concentration versus time) in the blood of humans and animals, as well as a favorable safety and efficacy profile for treating diseases associated with impaired activity of protein kinases, in particular, acute lymphoblastic leukemia, chronic myeloid leukemia, hepatocellular carcinoma, non-small cell lung cancer, and gastrointestinal stromal tumors.

The technical result is also the development and production of a novel salt form of the kinase inhibitor which is characterized by easy scaling of production and purification processes, the use of low-toxicity solvents, and the high purity of the final product with a minimal amount of product purification stages.

The indicated technical result is achieved by obtaining the salt of methanesulfonic acid and the base 3-(1,2,4-triazolo[4,3-a]pyridine-3-ylethynyl)-4-methyl-N-(4-((4-methylpiperazin-1-yl)methyl)-3-trifluoromethylphenyl)benzamide

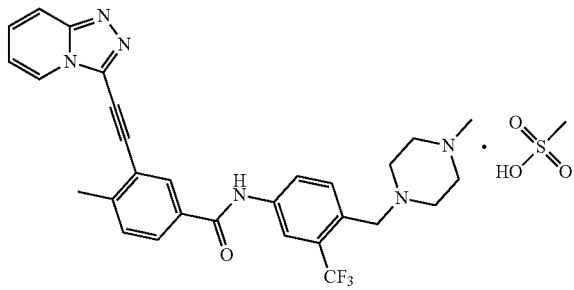

or its hydrate, solvate, as well as polymorphous modifications possessing the ability to inhibit the enzymatic activity of protein kinases, in particular, the AbI kinase.

One of the preferable implementations of the invention is the polymorphous modification of the salt of methanesulfonic acid and the base 3-(1,2,4-triazolo[4,3-a]pyridine-3-ylethynyl)-4-methyl-N-(4-((4-methylpiperazin-1-yl) methyl)-3-trifluoromethylphenyl)benzamide which is the crystalline phase with the parameters of the unit cell obtained by the method of powder X-ray diffraction at 25±5° C. with the use of CuKα1 irradiation at wavelength of 1.5406 Å as follows: a=51.46±0.05 Å; b=7.81±0.05 Å; c=7.63±0.05 Å; β=108.9±0.1°; V=2898.9±0.5 Å³; the space group P2₁/n and characteristic peaks in the Debye X-ray powder pattern with diffraction angle values (2θ) 3.6; 7.2; 11.4; 11.8; 12.5; 13.4; 14.5; 16.2; 16.5; 16.9; 17.2; 17.4; 17.8; 18.1; 18.4; 18.7; 20.8; 21.4; 22.7; 22.8; 23.0; 23.2; 23.4; 24.1; 24.5; 25.4; 25.9; 26.0; 26.2; 26.7; 27.1; 28.4; 33.0; 33.3; and 36.7.

Another preferable implementation of the invention is the polymorphous modification of the salt of methanesulfonic acid and the base 3-(1,2,4-triazolo[4,3-a]pyridine-3-ylethynyl)-4-methyl-N-(4-((4-methylpiperazin-1-yl)methyl)-3-trifluoromethylphenyl)benzamide which is the crystalline phase with the parameters of the unit cell obtained by the method of powder X-ray diffraction at 25±5° C. with the use of CuKα1 irradiation at wavelength of 1.5406 Å as follows: a=13.77±0.05 Å; b=8.09±0.05 Å; and c=30.83±0.05 Å; β=117.8±0.1; V=3036.36±0.5 Å³; the space group P2₁/c and characteristic peaks in the Debye X-ray powder pattern with diffraction angle values (2θ) 7.1; 7.3; 11.6; 11.8; 12.7; 12.9; 13.1; 14.2; 14.6; 16.9; 17.2; 17.4; 17.6; 18.1; 18.3; 19.4; 19.7; 20.8; 21.2; 21.6; 22.0; 22.5; 22.6; 23.2; 23.4; 23.8; 24.9; 25.1; 25.6; 25.9; 26.1; 26.6; 28.3; 28.8; 29.6; and 30.1.

The indicated technical result is also achieved by using the salt or its hydrate, solvate, or the polymorphous modifications according to the invention to obtain a pharmaceutical composition that is useful for preventing and/or treating disorders associated with the kinase activity in humans or animals. In some implementations, the kinase is selected from a group comprising receptor tyrosine kinases, non-receptor tyrosine kinases, and serine/threonine protein kinases, in particular, AbI kinase, c-Src, Yes, Lyn, Lck, EGFR1 (Flt-1), VEGFR2, VEGFR3, PDGFR kinases.

This invention also includes a method for prevention and/or treatment of a disorder associated with kinase activity in the body by introducing a pharmaceutical composition according to the invention into the body. This disorder associated with kinase activity can include an oncological, chronic, inflammatory, and/or the other disease, in particular, acute lymphoblastic leukemia, chronic myeloid leukemia, hepatocellular carcinoma, non-small cell lung cancer, and gastrointestinal stromal tumors. In some implementations, the subject treated can be a human being or an animal. In some implementations, the animal can be a cat, a dog, or a horse.

The indicated technical result is achieved by the method of obtaining the crystalline compounds according to this invention that includes the following stages:

a. Introducing a solution of methanesulfonic acid or its hydrate (in an organic solvent) into a suspension or solution of the base 3-(1,2,4-triazolo[4,3-a]pyridine-3-ylethynyl)-4-methyl-N-(4-((4-methylpiperazin-1-yl)methyl)-3-trifluoromethylphenyl)benzamide in an organic solvent or in a mixture of solvents. The introduction of the solution of methanesulfonic acid or its hydrate can be done at room temperature or with heating or cooling of each component; one can also use the opposite order of mixing the reagents.

b. The crystallization of the obtained salt from the solution.

c. The separation of the salt crystals from the solvent.

In some implementations, the solvent used at stage (a) as a medium for suspending 3-(1,2,4-triazolo[4,3-a]pyridine-3-ylethynyl)-4-methyl-N-(4-((4-methylpiperazin-1-yl) methyl)-3-trifluoromethylphenyl)benzamide can be acetone.

In implementations, the solvent used at stage (a) to prepare the solution of methanesulfonic acid or its hydrate can be ethanol.

In some implementations, an additional recrystallization of the salt can be conducted after stage (c).

In some other implementations, an additional stage of initiating crystal formation is performed in cases when the salt is obtained from solutions. The initiation of crystal formation can be achieved by introducing small amounts of the same salt into the solution or by the other ways.

In particular cases, one can additionally apply a stage of purifying the base of 3-(1,2,4-triazolo[4,3-a]pyridine-3-ylethynyl)-4-methyl-N-(4-((4-methylpiperazin-1-yl)methyl)-3-trifluoromethylphenyl)benzamide by way of transforming the base into a salt with sulfuric, hydrochloric, benzenesulfonic, 4-methyl-benzenesulfonic, 2-methyl-benzenesulfonic, methanesulfonic, citric, phosphoric, trifluoroacetic, 4-nitro-benzenesulfonic, tetrafluoroboric, hexafluorophosphoric, or another acid subsequently using the salt to obtain the base 3-(1,2,4-triazolo[4,3-a]pyridine-3-ylethynyl)-4-methyl-N-(4-((4-methylpiperazin-1-yl)methyl)-3-trifluoromethylphenyl)benzamide that is used to obtain the salt with methanesulfonic acid.

The free base 3-(1,2,4-triazolo[4,3-a]pyridine-3-ylethynyl)-4-methyl-N-(4-((4-methylpiperazin-1-yl)methyl)-3-trifluoromethylphenyl)benzamide is known and described in patent WO/2012/173521.

Definitions (Terms)

Unless defined otherwise, all technical and scientific terms used herein have the same meaning as is commonly understood by one of ordinary skill in the art to which this disclosure belongs, taking into account the context provided by the present disclosure.

For the terms "e.g." and "such as," and grammatical equivalents thereof, the phrase "and without limitation" is understood to follow unless explicitly stated otherwise.

The singular forms "a," "an," and "the" include plural referents unless the context clearly dictates otherwise.

The term "about" means "approximately" (e.g., plus or minus approximately 10% of the indicated value).

The term «° C.», when used with reference to the temperature, means the centigrade scale or the Celsius temperature scale.

The term «IC$_{50}$» means the concentration of the tested compound that is sufficient to achieve the semi-maximal inhibition of kinase activity.

The term «modulation» used in the present document is refers to a change of kinase catalytic activity. In particular, modulation refers to the activation or inhibition of kinase catalytic activity.

The term «polymorphous modification» refers to a solid phase of a substance that possesses several different forms due to the different disposition and/or conformation of molecules in a crystalline lattice. Polymorphous modifications may have different chemical and physical properties. The term «polymorphous modification» includes solvates (i.e., crystalline forms containing the solvent or water), as well as to different non-solvated crystalline forms of the compound.

The term «solvate» is used to describe the molecular complex containing the compound according to the invention and one or more molecules of the pharmaceutically acceptable solvent, for example, ethanol. The term «hydrate» is used when the solvent is water.

The term «powder X-ray diffraction pattern» or «PXRD-pattern» refers to an experimentally observed diffractogram or to parameters derived from it. Usually, powder X-ray diffraction patterns are characterized by the position of the peak (abscissa) and the intensity of the peak (ordinates). The term "peak intensity" refers to the relative intensity of a signal in a given X-ray diffraction pattern. The factors influencing the relative intensity of the peak are (1) the thickness of the sample and (2) the preferred orientation (i.e., the effect arising from non-random orientation of crystalline particles). The term "peak position", used herein, refers to the position of the x-ray reflex measured and observed in powder diffraction experiments. The peaks positions are directly related to the dimensions of the unit cell. The peaks identified by their respective positions are obtained from the diffraction pattern for various polymorphic forms of salt methanesulfonic acid and 3-(1,2,4-triazolo[4,3-a]pyridine-3-ilethynyl)-4-methyl-N-(4-((4-methylpiperazin-1-yl)methyl)-3-trifluoromethylphenyl)benzamide.

The «2-theta value» or «2θ» refers to the peak position (in degrees) which is derived from the experimental X-ray diffraction data and, basically, is the abscissa measurement unit in powder X-ray diffraction. In general, in an X-ray diffraction experiment, an incident beam falls on a sample with an angle of θ (to the normal) and reflects with an angle of 2θ (to the incident beam). It should be noted, that all references to specific values of 2θ for specific polymorph forms in this application assume that 2θ values are measured using a diffractometer of equivalent quality and under the experimental conditions outlined herein. With our diffractometers and the outlined conditions, we estimate the 2θ precision to be ±0.1-0.2 degrees.

The term «aberrant activity» of kinase refers to kinase activity that substantially differs from the basic level of the kinase activity in cells in the absence of pathology. The aberrant activity can be caused by a change in the level of kinase expression, by the impairment of processes leading to kinase activation, by disorder involving the regulation of degradation pathways, or by the other factors.

The term «auxiliary substance» means any pharmaceutically acceptable substance of inorganic or organic origin included in the composition of drug product or used in the drug production process to achieve the required physico-chemical properties of the drug product.

The term «AUC» means a pharmacokinetics parameter characterizing the total concentration of the drug in blood plasma during all times of observation. From a mathematic point of view, AUC is defined as the integral from 0 to ∞ of a plot of concentration of the drug in blood plasma against time (the pharmacokinetics curve) and is equal to the area restricted by the pharmacokinetics curve and the coordinate axes.

The following abbreviations may be used in the present disclosure: A (angstrom); aq. (aqueous); AUC (area under the curve); br (broad); cryst. (crystalline); d (doublet); dd (doublet of doublets); DCM (dichloromethane); DMF (N,N-dimethylformamide); DMSO (dimethyl sulfoxide); DSC (differential scanning calorimetry); eq. (equivalent(s)); Et (ethyl); EtOAc (ethyl acetate); FIG. (figure); g (gram(s)); h (hour(s)); HCl (hydrochloric acid); HPLC (high performance liquid chromatography); Hz (hertz); J (coupling constant); kg (kilogram(s)); L (liter(s)); m (multiplet); M (molar); MHz (megahertz); MS (Mass spectrometry); Me (methyl); MeCN (acetonitrile); MeOH (methanol); mg (milligram(s)); min. (minutes(s)); mL (milliliter(s)); mmol (millimole(s)); MTD (maximum tolerated dose); N (normal); NaHCO$_3$ (sodium bicarbonate); NaOH (sodium hydroxide); Na$_2$SO$_4$ (sodium sulfate); NH$_4$Cl (ammonium chloride); nm (nanometer); nM (nanomolar); NMR (nuclear magnetic resonance spectroscopy); NMT (no more than); Ph. Eur. (European Pharmacopoeia), PPTS (pyridinium p-toluenesulfonate); RP-HPLC (reverse phase high performance liquid chromatography); rt (room temperature); s (singlet); t (triplet or tertiary); tert (tertiary); TGA (thermogravimetric analysis); tt (triplet of triplets); t-Bu (tert-butyl); THF (tetrahydrofuran); μg (microgram(s)); μL (microliter(s)); μM (micromolar); wt % (weight percent), w/v (weight/volume ratio—weight in grams per 100 mL).

The possibility of objective achievement of the technical result by the implementation of invention is confirmed by reliable data shown in examples containing the experimental results obtained in the course of the studies conducted according to the methodology accepted in this field. Features of the invention may be illustrated by figures.

One should understand that examples and all examples included in the patent application are not limiting and shown only to illustrate the present invention.

Therapeutic Applications

The salts and polymorphic modifications thereof described herein can be used in therapy by administering a therapeutically effective amount of the salt according to the invention into the body of a subject in need of treatment. The term "therapeutically effective amount" means such an amount of the compound which causes the biological or medicinal response in the subject of treatment that is being sought by a researcher, veterinarian, medical doctor or other clinician. The precise required amount of the compound can vary from the subject to subject depending on the age, the body weight and the common patient's condition, severity of the disease, the procedure of drug administration, the combination of treatment with the other drugs, etc.

The term "treating" or "treatment" refers to one or more of (1) inhibiting a disease; e.g., inhibiting a disease, condition or disorder in an individual who is experiencing or displaying the pathology or symptomatology of the disease, condition or disorder (i.e., arresting further development of the pathology and/or symptomatology); and (2) ameliorating a disease; e.g., ameliorating a disease, condition or disorder in an individual who is experiencing or displaying the pathology or symptomatology of the disease, condition or disorder (i.e., reversing the pathology and/or symptomatology) such as decreasing the severity of disease. In one embodiment, treating or treatment includes preventing or reducing the risk of developing the disease; e.g., preventing or reducing the risk of developing a disease, condition or disorder in an individual who may be predisposed to the disease, condition or disorder but does not yet experience or display the pathology or symptomatology of the disease.

The terms "individual" or "patient," used interchangeably, refer to (e.g., as a subject of the treatment) any mammal, e.g., mice, rats, other rodents, rabbits, dogs, cats, swine, cattle, sheep, horses, or primates, and most preferably humans.

The phrase "therapeutically effective amount" refers to the amount of active compound or pharmaceutical agent that elicits the biological or medicinal response in a tissue, system, animal, individual or human that is being sought by a researcher, veterinarian, medical doctor or other clinician.

The salt or polymorphic modification thereof according to the invention or the pharmaceutical composition containing the salt or polymorphic modification thereof can be introduced into a patient's body in any amount and by any way effective for treatment or prevention of the disease.

After mixing the salt or polymorphic modification thereof with a suitable pharmaceutically accessible carrier in desirable dosage, pharmaceutical compositions can be introduced into the human body or into animals orally, parenterally, locally, etc.

Administration of the salt or polymorphic modification thereof can be performed once or several times for a day, a week (or for any other time interval), or from time to time. In addition, the compound can be administered every day for a certain time period (for example, for 2-10 days) followed by a time period with no compound administration (for example, for 1-30 days).

In the case, when the salt or polymorphic modification thereof according to the invention is used as a part of the regime of combination therapy, the dose of each component of the combination therapy is administered for the time period required for treatment. The compounds comprising the combination therapy can be administered once (as a dosage of all components) or several times (as individual dosages of the components).

Provided herein are methods of treating a cellular proliferative disorder in a patient. The method includes administering to the patient a therapeutically effective amount of a the crystalline salt and polymorphic forms of 3-(1,2,4-triazolo[4,3-a]pyridine-3-ylethynyl)-4-methyl-N-(4-((4-methylpiperazin-1-yl)methyl)-3-trifluoromethylphenyl)benzamide described in the present disclosure, or any of the embodiments thereof.

A "cellular proliferative disorder" means a disorder wherein cells are made by the body at an atypically accelerated rate, and can include cancer.

Non-limiting examples of cancers include bladder cancer, brain cancer, breast cancer, colorectal cancer, cervical cancer, gastrointestinal cancer, genitourinary cancer, head and neck cancer, lung cancer, ovarian cancer, prostate cancer, renal cancer, skin cancer and testicular cancer.

More particularly, cancers that may be treated by the compound, compositions and methods described herein include, but are not limited to, the following:

1) Nervous system cancers, including, e.g., cancers of the skull, e.g., osteoma, hemangioma, granuloma, xanthoma, and osteitis deformans; cancers of the meninges, e.g., meningioma, meningiosarcoma, and gliomatosis; cancers of the brain, e.g., astrocytoma, medulloblastoma, glioma, ependymoma, germinoma (pinealoma), glioma, glioblastoma, glioblastoma multiform, oligodendroglioma, schwannoma, retinoblastoma, and congenital tumors; and cancers of the spinal cord, e.g., neurofibroma, meningioma, glioma, and sarcoma.

2) Breast cancers, including, e.g., ER+ breast cancer, ER– breast cancer, her2– breast cancer, her2+ breast cancer, stromal tumors such as fibroadenomas, phyllodes tumors and sarcomas and epithelial tumors such as large duct papillomas; carcinomas of the breast including in situ (noninvasive) carcinoma that includes ductal carcinoma in situ (including Paget's disease) and lobular carcinoma in situ, and invasive (infiltrating) carcinoma including, but not limited to, invasive ductal carcinoma, invasive lobular carcinoma, medullary carcinoma, colloid (mucinous) carcinoma, tubular carcinoma, and invasive papillary carcinoma; and miscellaneous malignant neoplasms. Further examples of breast cancers can include luminal A, luminal B, basal A, basal B, and triple negative breast cancer, which is estrogen receptor negative (ER–), progesterone receptor negative, and her2 negative (her2–). In some embodiments, the breast cancer may have a high risk Oncotype score.

3) Cardiac cancers, including, e.g., sarcoma, e.g., angiosarcoma, fibrosarcoma, rhabdomyosarcoma, and liposarcoma; myxoma; rhabdomyoma; fibroma; lipoma and teratoma.

4) Lung cancers, including, e.g., bronchogenic carcinoma, e.g., squamous cell, undifferentiated small cell, undifferentiated large cell, and adenocarcinoma; alveolar and bronchiolar carcinoma; bronchial adenoma; sarcoma; lymphoma; chondromatous hamartoma; and mesothelioma.

5) Gastrointestinal cancer, including, e.g., cancers of the esophagus, e.g., squamous cell carcinoma, adenocarcinoma, leiomyosarcoma, and lymphoma; cancers of the stomach, e.g., carcinoma, lymphoma, and leiomyosarcoma; cancers of the pancreas, e.g., ductal adenocarcinoma, insulinoma, glucagonoma, gastrinoma, carcinoid tumors, and vipoma; cancers of the small bowel, e.g., adenocarcinoma, lymphoma, carcinoid tumors, Kaposi's sarcoma, leiomyoma, hemangioma, lipoma, neurofibroma, and fibroma; cancers of the large bowel, e.g., adenocarcinoma, tubular adenoma, villous adenoma, hamartoma, and leiomyoma.

6) Genitourinary tract cancers, including, e.g., cancers of the kidney, e.g., adenocarcinoma, Wilm's tumor (nephroblastoma), lymphoma, and leukemia; cancers of the bladder and urethra, e.g., squamous cell carcinoma, transitional cell carcinoma, and adenocarcinoma; cancers of the prostate, e.g., adenocarcinoma, and sarcoma; cancer of the testis, e.g., seminoma, teratoma, embryonal carcinoma, teratocarcinoma, choriocarcinoma, sarcoma, interstitial cell carcinoma, fibroma, fibroadenoma, adenomatoid tumors, and lipoma.

7) Liver cancers, including, e.g., hepatoma, e.g., hepatocellular carcinoma; cholangiocarcinoma; hepatoblastoma; angiosarcoma; hepatocellular adenoma; and hemangioma.

8) Bone cancers, including, e.g., osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochrondroma (osteocartilaginous exostoses), benign chondroma, chondroblastoma, chondromyxofibroma, osteoid osteoma and giant cell tumors.

9) Gynecological cancers, including, e.g., cancers of the uterus, e.g., endometrial carcinoma; cancers of the cervix, e.g., cervical carcinoma, and pre tumor cervical dysplasia; cancers of the ovaries, e.g., ovarian carcinoma, including serous cystadenocarcinoma, mucinous cystadenocarcinoma, unclassified carcinoma, granulosa thecal cell tumors, Sertoli Leydig cell tumors, dysgerminoma, and malignant teratoma; cancers of the vulva, e.g., squamous cell carcinoma, intraepithelial carcinoma, adenocarcinoma, fibrosarcoma, and melanoma; cancers of the vagina, e.g., clear cell carcinoma, squamous cell carcinoma, botryoid sarcoma, and embryonal rhabdomyosarcoma; and cancers of the fallopian tubes, e.g., carcinoma.

10) Hematologic cancers, including, e.g., cancers of the blood, e.g., acute myeloid leukemia, chronic myeloid leukemia, acute lymphoblastic leukemia, chronic lymphocytic leukemia, myeloproliferative diseases, multiple myeloma, and myelodysplastic syndrome, Hodgkin's lymphoma, non-Hodgkin's lymphoma (malignant lymphoma) and Waldenström's macroglobulinemia.

11) Skin cancers, including, e.g., malignant melanoma, basal cell carcinoma, squamous cell carcinoma, Kaposi's sarcoma, moles dysplastic nevi, lipoma, angioma, dermatofibroma, keloids, and psoriasis.

12) Adrenal gland cancers, including, e.g., neuroblastoma.

13) Pancreatic cancers, including, e.g., exocrine pancreatic cancers such as adenocarcinomas (M8140/3), adenosquamous carcinomas, signet ring cell carcinomas, hepatoid carcinomas, colloid carcinomas, undifferentiated carcinomas, and undifferentiated carcinomas with osteoclast-like giant cells; and exocrine pancreatic tumors.

Cancers may be solid tumors that may or may not be metastatic. Cancers may also occur, as in leukemia, as a diffuse tissue. Thus, the term "tumor cell" as provided herein, includes a cell afflicted by any one of the above identified disorders.

In some embodiments, the cancer can include acute lymphoblastic leukemia, chronic myeloid leukemia, hepatocellular carcinoma, non-small cell lung cancer, and gastrointestinal stromal tumors.

The crystalline salt and polymorphic forms of 3-(1,2,4-triazolo[4,3-a]pyridine-3-ylethynyl)-4-methyl-N-(4-((4-methylpiperazin-1-yl)methyl)-3-trifluoromethylphenyl)benzamide described in the present disclosure, or any of the embodiments thereof described herein can also be used for the treatment of non-cancer cellular proliferative disorders such as hemangiomatosis in newborns, secondary progressive multiple sclerosis, chronic progressive myelodegenerative disease, neurofibromatosis, ganglioneuromatosis, keloid formation, Paget's disease of the bone, fibrocystic disease of the breast, uterine fibroids, Peyronie's disease, Dupuytren's disease, restenosis, and cirrhosis.

The compound described herein (namely crystalline salt and polymorphic forms of 3-(1,2,4-triazolo[4,3-a]pyridine-3-ylethynyl)-4-methyl-N-(4-((4-methylpiperazin-1-yl) methyl)-3-trifluoromethylphenyl)benzamide described in the present disclosure, or any of the embodiments thereof) may be used in combination with one or more other drugs in the treatment, prevention, control, amelioration, or reduction of risk of diseases or conditions for which compounds described herein or the other drugs may have utility, where the combination of the drugs together are safer or more effective than either drug alone. Such other drug(s) may be administered, by a route and in an amount commonly used therefor, contemporaneously or sequentially with a compound described herein. When a compound as described herein is used contemporaneously with one or more other drugs, a pharmaceutical composition in unit dosage form containing such other drugs and the compound described herein is envisioned. However, the combination therapy may also include therapies in which the compound described herein and one or more other drugs are administered on different overlapping schedules. It is also contemplated that when used in combination with one or more other active ingredients, the compound as described herein and the other active ingredients may be used in lower doses than when each is used singly. Accordingly, the pharmaceutical compositions of the compound described herein include those that contain one or more other active ingredients, in addition to a compound described herein. The above combinations include combinations of a compound described herein not only with one other active compound, but also with two or more other active compounds.

Likewise, compound as described herein may be used in combination with other drugs that are used in the prevention, treatment, control, amelioration, or reduction of risk of the diseases or conditions for which compounds described herein are useful. Such other drugs may be administered, by a route and in an amount commonly used therefor, contemporaneously or sequentially with a compound as described herein. When a compound as described herein is used contemporaneously with one or more other drugs, a pharmaceutical composition containing such other drugs in addition to the compound described herein is envisioned. Accordingly, pharmaceutical compositions can contain one or more other active ingredients, in addition to a compound as described herein, namely crystalline salt and polymorphic forms of 3-(1,2,4-triazolo[4,3-a]pyridine-3-ylethynyl)-4- methyl-N-(4-((4-methylpiperazin-1-yl)methyl)-3-trifluoromethylphenyl)benzamide, or any of the embodiments thereof.

The weight ratio of the compound of the compound described herein to the second active ingredient may be varied and will depend upon the effective dose of each ingredient. Generally, an effective dose of each will be used. Thus, for example, when a compound described herein is combined with another agent, the weight ratio of the compound described herein to the other agent will generally range from about 1000:1 to about 1:1000, including about 200:1 to about 1:200. Combinations of a compound described herein and other active ingredients will generally also be within the aforementioned range, but in each case, an effective dose of each active ingredient should be used. In such combinations the compound described herein and other active agents may be administered separately or in conjunction. In addition, the administration of one element may be prior to, concurrent to, or subsequent to the administration of other agent(s).

The crystalline salt and polymorphic forms of 3-(1,2,4-triazolo[4,3-a]pyridine-3-ylethynyl)-4-methyl-N-(4-((4-methylpiperazin-1-yl)methyl)-3-trifluoromethylphenyl)benzamide, or any of the embodiments thereof described herein can further be used in combination with other methods of treating cancers, for example by chemotherapy, irradiation or surgery. The compounds can be administered in combination with one or more anti-cancer drugs, such as a chemotherapeutics.abarelix, aldesleukin, alemtuzumab, alitretinoin, allopurinol, altretamine, anastrozole, arsenic trioxide, asparaginase, azacitidine, bevacizumab, bexarotene, bleomycin, bortezombi, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculizumab, epirubicin, erlotinib, estramustine, etoposide phosphate, etoposide, exemestane, fentanyl citrate, filgrastim, floxuridine, fludarabine, fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, nofetumomab, oxaliplatin, paclitaxel, pamidronate, panitumumab, pegaspargase, pegfilgrastim, pemetrexed disodium, pentostatin, pipobroman, plicamycin, procarbazine, quinacrine, rasburicase, rituximab, ruxolitinib, sorafenib, streptozocin, sunitinib, sunitinib maleate, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinostat and zoledronate.

Pharmaceutical Compositions

Another aspect of the invention relates to pharmaceutical compositions which contain the salts or polymorphic modifications thereof according to the invention and one or several pharmaceutically acceptable carriers, adjuvants, solvents, and/or excipients, such as those which can be administered along with the salts or polymorphic modifications thereof of this invention. "Pharmaceutically acceptable" means that the carrier, adjuvant, solvent, or excipient does not inhibit the pharmacological activity of the salts or polymorphic modifications thereof described herein, and which are nontoxic in amounts used in the pharmaceutical composition.

The pharmaceutical compositions contain the salts described herein with the pharmaceutically acceptable carriers which can include solvents, diluters, dispersions, suspensions, surfactants, isotonic agents, thickeners, emulsifiers, preservatives, binders, lubricants, etc., which are suitable for the certain dosage form. The materials which can serve as the pharmaceutically acceptable carriers include but are not limited by mono- and oligosaccharides as well as their derivatives; gelatin; talc; excipients, such as cocoa butter and wax for suppositories; vegetable oils, such as peanut butter, cottonseed oil, safflower oil, sesame oil, olive oil, corn oil, and soybean oil; glycols, such as propylene glycol; complex esters, such as ethyl oleate and ethyl laurate; agar; buffer substances, such as magnesium hydroxide and aluminum hydroxide; alginic acid; non-pyrogenic water; isotonic solution; Ringer solution; ethyl alcohol, and phosphate buffer solutions. The pharmaceutical compositions can also include the other nontoxic compatible lubricants, such as sodium lauryl sulfate and magnesium stearate, as well as coloring agents, separative liquids, film-forming agents, sweeteners, flavors, fragrances, preservatives, and antioxidants.

The compositions described herein also include dosage forms, i.e., the pharmaceutical compositions which are optimized for a certain way of introduction into the body in the therapeutically efficient dosage, for example, the introduction by oral, local, pulmonary (for example, as inhalation sprays), intravenous, intranasal, subcutaneous, intramuscular, and infusion administration at an appropriate dosage.

The dosage forms of this invention can contain the pharmaceutical compositions obtained by methods using liposomes, the methods of microencapsulation, the methods for obtaining drug nanoforms, or by the other methods known in pharmaceutics.

To obtain the composition, for example, in the form of a tablet, the active substance is mixed with one or several pharmaceutical excipients, such as gelatin, starch, lactose, magnesium stearate, talc, silica, acacia gum, mannitol, microcrystalline cellulose, hypromellose, or analogous compounds.

The tablets can be coated with sucrose, cellulose derivatives, or other substances suitable for making the coating. The tablets can be obtained by different ways, such as the direct compression, the dry or wet granulation, or hot fusion.

The pharmaceutical composition in the form of a gelatin capsule can be obtained by mixing the active substance with a solvent and filling the soft or solid capsules with the obtained mixture.

For parenteral administration, one can use aqueous suspensions, isotonic saline solutions, or sterile solutions for injections which contain the pharmacologically compatible agents, for example, propylene glycol or butylene glycol.

Examples of Pharmaceutical Compositions

The substances described in this invention can be used to prevent and/or treat diseases in humans or animals as the following formulations ("Substance" means the active ingredient):

| Tablet I | mg/tablet |
|---|---|
| Substance | 50 |
| Lactose Ph. Eur | 223.75 |
| Croscarmellose sodium | 6.0 |
| Corn starch (5% w/v paste) | 15 |
| Polyvinylpyrrolidone | 2.25 |
| Magnesium stearate | 3.0 |

| Tablet II | mg/tablet |
|---|---|
| Substance | 200 |
| Lactose Ph. Eur | 182.75 |
| Croscarmellose sodium | 12.0 |
| Corn starch (5% w/v paste) | 2.25 |
| Magnesium stearate | 3.0 |

| Capsule | mg/capsule |
|---|---|
| Substance | 10 |
| Lactose Ph. Eur | 488.5 |
| Magnesia | 1.5 |

| Aerosol I | mg/mL |
|---|---|
| Substance | 10 |
| Sorbitan trioleate | 13.5 |
| Trichlorofluoromethane | 910.0 |
| Dichlorodifluoromethane | 490.0 |

| Ointment | mL |
|---|---|
| Substance | 40 mg |
| Ethanol | 300 μL |
| Water | 300 μL |
| 1-Dodecylazacycloheptanone | 50 μL |
| Polyethylene glycol | up to 1 mL |

These compositions can be prepared in accordance with the standard pharmaceutical procedures. Tablets (1)-(11) can be covered with the intestine-soluble coat with the use, for example, cellulose acetate phthalate. The aerosol composition (1) can be used in combination with the standard dispensers. Sorbitan monooleate, sorbitan polyoleate, polysorbate 80, polyglycerol oleate, or oleic acid can be used as suspending agents instead of Sorbitan trioleate and soybean lecithin.

EXAMPLES 3-(1,2,4-Triazolo[4,3-a]Pyridine-3-Ylethynyl)-4-Methyl-N-(4-((4-Methylpiperazine-1-Yl)Methyl)-3-Trifluoromethylphenyl)Benzamide Salt Form Investigation Various salt forms of 3-(1,2,4-triazolo[4,3-a]pyridine-3-ylethynyl)-4-methyl-N-(4-((4-methylpiperazine-1-yl)methyl)-3-trifluoromethylphenyl)benzamide were synthesized with the goal of identifying one or more salt forms with the following characteristics: crystallinity, high solubility in water (more than 10 g/L) and fixed composition. In addition, the study sought to identify a salt form whose production would be easily scalable and could carried out in low-toxicity organic solvents.

Various 3-(1,2,4-triazolo[4,3-a]pyridine-3-ylethynyl)-4-methyl-N-(4-((4-methylpiperazine-1-yl)methyl)-3-trifluoromethylphenyl)benzamide salt forms were obtained in polar non-toxic (Classes 2 and 3) organic solvents. Counterions were selected based pharmacological acceptability and acid strength (pKa no higher than 5.0). The minimum acid strength was selected based on the fact that 3-(1,2,4-triazolo[4,3-a]pyridine-3-ylethynyl)-4-methyl-N-(4-((4-methylpiperazine-1-yl)methyl)-3-trifluoromethylphenyl)benzamide is a base with a pKa of about 6.4.

At the first stage the initial base was tested for solubility in selected organic solvents. The maximum selected solvent volume used in this test was 1.25 mL per 1 mg of base. Results of testing solubility of the initial base in various organic solvents are given in Table 1. Low toxicity (Class 3), low-boiling ($T_{boiling}$<100° C.), polar, solvents. in which the base was soluble at no less than 10 mg/mL were selected for further studies.

At the second stage obtaining salts from 100 mg of base of 3-(1,2,4-triazolo[4,3-a]pyridine-3-ylethynyl)-4-methyl-N-(4-((4-methylpiperazine-1-yl)methyl)-3-trifluoromethylphenyl)benzamide and various acids was attempted. For this stage of the investigation, various solvent/acid pairs were selected, in which either the test sample was fully dissolved in the solvent and a precipitate was formed after adding the acid, or the system was homogenous after adding the acid, and a precipitate was formed after cooling the system to the room temperature. In most cases 3-(1,2,4-triazolo[4,3-a]pyridine-3-ylethynyl)-4-methyl-N-(4-((4-methylpiperazine-1-yl)methyl)-3-trifluoromethylphenyl)benzamide salting took place either immediately after adding the acid or after cooling the solution (see FIG. 1). In cases when no precipitate was formed after cooling the solution, methyl tert-butyl ether was added to the salt solutions to initiate crystallization process (see FIG. 2).

TABLE 1

Solubility of 3-(1,2,4-triazolo[4,3-a]pyridine-3-ylethynyl)-4-methyl-N-(4-((4-methylpiperazine-1-yl)methyl)-3-trifluoromethylphenyl)benzamide in various solvents

| Sample | Quantity, mg | Solvent | Solvent volume, mL | Temperature, ° C. | Solubility (+/−) | Solvent toxicity class |
|---|---|---|---|---|---|---|
| HAL-G-194-2 | 4.6 | Water | 4.0* | 50 | − | — |
| HAL-G-194-3 | 4.0 | Methanol | 0.1 | 50 | + | II |
| HAL-G-194-4 | 4.7 | Ethanol | 0.3 | 50 | + | III |
| HAL-G-194-5 | 3.6 | Isopropanol | 0.4 | 50 | + | III |
| HAL-G-194-6 | 3.6 | n-Butanol | 0.2 | 50 | + | III |
| HAL-G-194-7 | 3.5 | Acetonitrile | 4.0* | 50 | − | II |
| HAL-G-194-8 | 3.6 | Tetrahydrofuran | 0.1 | 50 | + | III |
| HAL-G-194-9 | 3.7 | 2-methyltetrahydrofuran | 0.6 | 50 | + | — |
| HAL-G-194-10 | 3.9 | Ethyl acetate | 1.3 | 50 | + | III |

TABLE 1-continued

Solubility of 3-(1,2,4-triazolo[4,3-a]pyridine-3-ylethynyl)-4-methyl-N-(4-((4-methylpiperazine-1-yl)methyl)-3-trifluoromethylphenyl)benzamide in various solvents

| Sample | Quantity, mg | Solvent | Solvent volume, mL | Temperature, °C | Solubility (+/−) | Solvent toxicity class |
|---|---|---|---|---|---|---|
| HAL-G-194-11 | 4.0 | Isopropyl acetate | 4.0 | 50 | − | III |
| HAL-G-194-12 | 3.4 | Acetone | 0.3 | 50 | + | III |
| HAL-G-194-13 | 4.8 | Methyl ethyl ketone | 0.4 | 50 | + | III |
| HAL-G-194-14 | 4.1 | Methyl isobutyl ketone | 0.6 | 50 | + | III |
| HAL-G-194-15 | 3.7 | Dichloromethane | 0.4 | 50 | + | II |
| HAL-G-194-16 | 3.4 | Toluene | 4.0* | 50 | − | II |
| HAL-G-194-17 | 4.7 | Dimethylformamide | 0.1 | RT | + | II |
| HAL-G-194-18 | 3.7 | N-methylpyrrolidone | 0.1 | RT | + | II |
| HAL-G-194-19 | 3.8 | Dimethyl sulfoxide | 0.1 | RT | + | III |
| HAL-G-194-20 | 4.7 | Methyl tert-butyl ether | 4.0* | 50 | − | III |
| HAL-G-194-21 | 3.3 | Heptane | 4.0* | 50 | − | III |
| HAL-G-194-22 | 4.3 | Cyclohexane | 4.0* | 50 | − | II |

RT—room temperature,
*no solution happened.

Crystallinity of all samples obtained was studied using the method of X-ray powder diffraction (to study the crystallinity structure). Diffraction patterns were obtained at a temperature of 25° C. (±5° C.) and relative air humidity of ≈70% using CubiX-Pro XRD X-ray powder diffractometer (anode voltage 45 kV, current 40 mA), with X'Celerator detector. Survey step 0.02° 2θ, angle range 3-45° 2θ. Diffraction patterns obtained were studied in detail using X'Pert HighScore Plus software package.

Studies of the samples' crystallinity using the method of X-ray powder diffraction showed that studied samples HAL-G-194-1, HAL-G-196-1, HAL-G-196-2, HAL-G-196-4, HAL-G-196-5, HAL-G-196-6, HAL-G-196-7, HAL-G-196-8, HAL-G-196-9, HAL-G-196-13, HAL-G-196-16, HAL-G-196-17, HAL-G-196-25, HAL-G-196-28, HAL-G-196-29, HAL-G-196-30, HAL-G-196-3, HAL-G-196-19, HAL-G-196-20, HAL-G-196-21, HAL-G-196-23, HAL-G-196-24, HAL-G-196-26, HAL-G-196-35 represented individual crystalline phases or phase mixtures (see FIGS. 1 and 2). The solubility of such samples was studied using the method of high-performance liquid chromatography (HPLC) (chromatograms were obtained using Agilent 1100 Series apparatus with a Phenomenex Luna column, 5 µM, 4.6×250 mm. Mobile phase (10 mM $KH_2PO_4$ pH=3): acetonitrile volume ratio of 60:40. Flow rate is 1.0 mL/min. Detection was carried out at 254 nm. Runtime is 16 minutes). Samples were also studied using the following methods: polarization microscopy (Leica DMRB Polarized Microscope, resolution of 1600×1200)—to confirm crystallinity, ion chromatography—to confirm anion and cation stoichiometric proportion, differential scanning calorimetry (DSC) and thermogravimetric analysis (TGA)—to confirm composition and study of temperature stability of samples; $^1$H NMR (500 MHz Bruker AVANCE 500.13 MHz, solvent DMSO-$d_6$)—to confirm structure, assess purity and content of organic solvents; gravimetric moisture absorption—to assess hygroscopicity. DSC was carried out using Mettler 822e DSC apparatus. The measuring system was calibrated according to ISO 11357-1 standard based on standard substances phase changes ($C_6H_{12}$; Hg; benzoic acid; Ga; $KNO_3$; In; Sn; Bi; CsCl; purity grade 99.99%). Temperature calibration regular error (determined based on In) is 0.1°. Samples were tested in standard aluminum cells in the artificial air flow at a temperature range of 30-300° C. with heating speed of 10°/min. TG measurements were taken using Mettler 851e SDTA/TGA TG analyzer. The apparatus was calibrated using standard substances melting points (Ag; Al; Bi; In; Sn; purity grade of 99.99%). Weighing error is NMT 0.1% (determined using $CaC_2O_4·2H_2O$ standard). The test was carried out in a standard open aluminum container in the artificial air flow at a temperature range of 30-150° C. with heating speed of 10°/min. To avoid dehydration, the material was not exposed to mechanical treatment before taking measurements.

Study of Physical and Chemical Properties of Free Base of 3-(1,2,4-Triazolo[4,3-a]Pyridine-3-Ylethynyl)-4-Methyl-N-(4-((4-Methylpiperazine-1-Yl) Methyl)-3-Trifluoromethylphenyl)Benzamide (Polymorph Modification I)

Figure 3A:
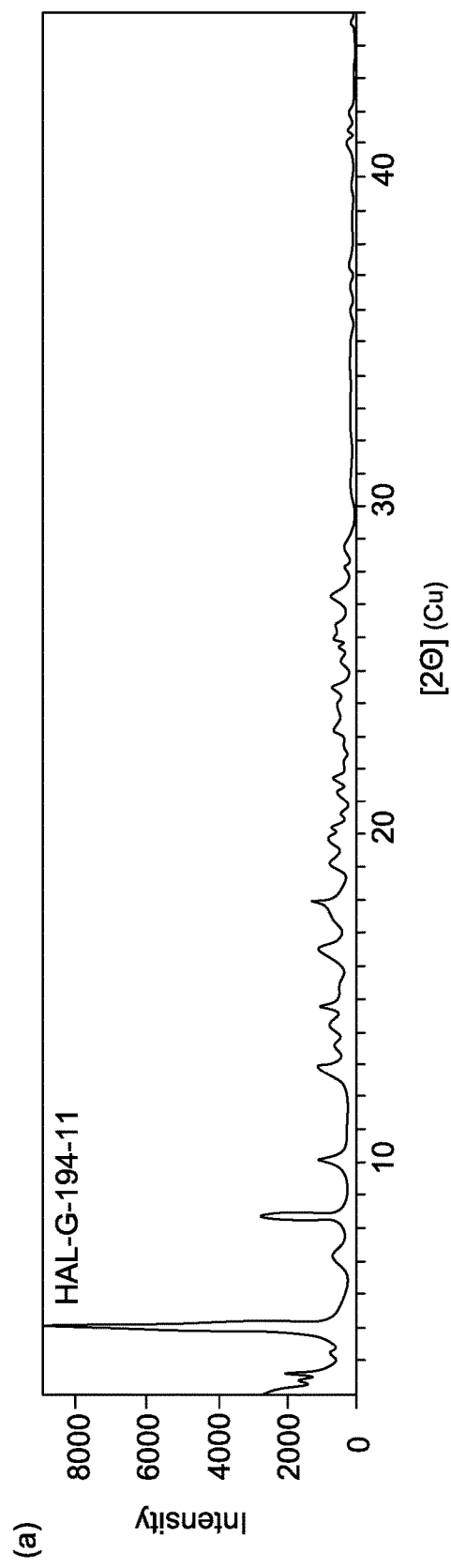
FIGS. 3A-3B. X-ray powder diffraction patterns of free base 3-(1,2,4-triazolo[4,3-a]pyridine-3-ylethynyl)-4-methyl-N-(4-((4-methylpiperazin-1-yl)methyl)-3-trifluoromethylphenyl)benzamide.
Figure 3B:
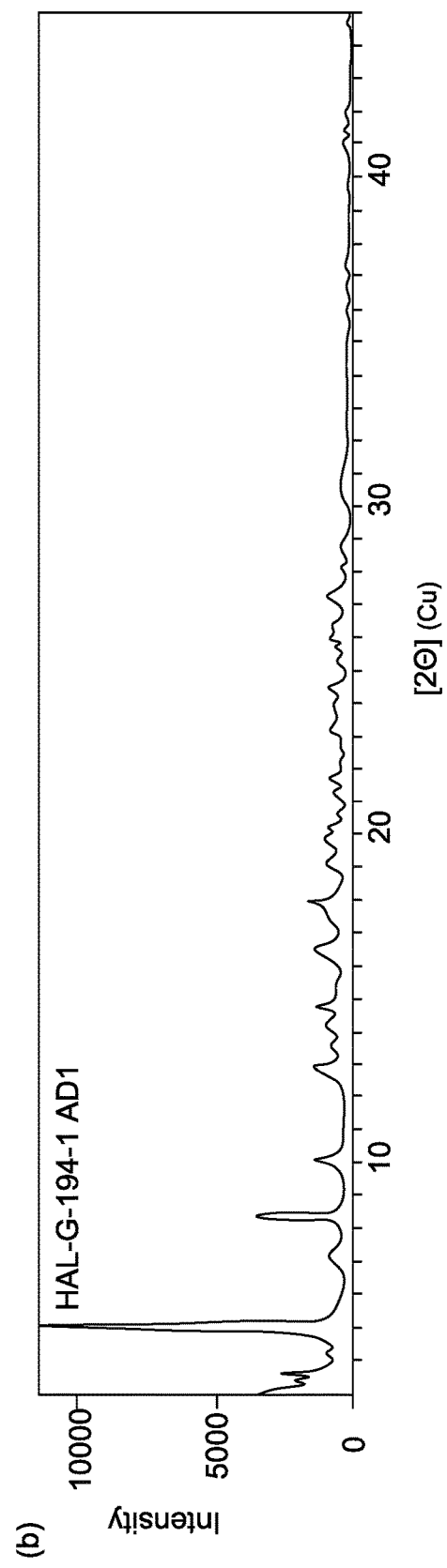
Figure 4:
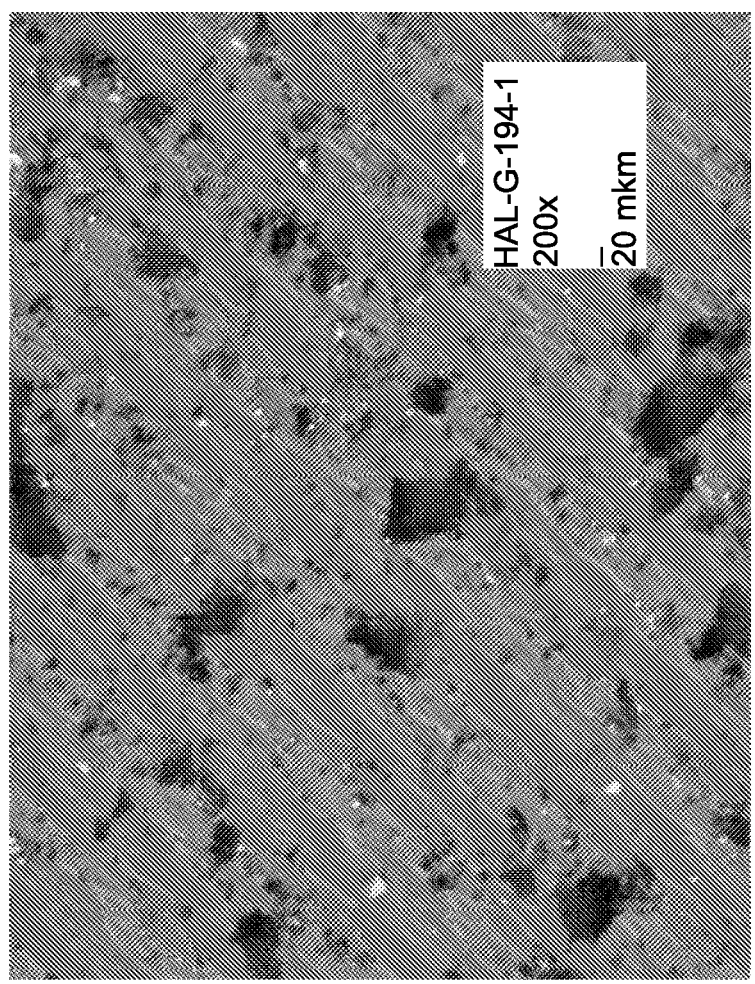
FIG. 4. Photograph of sample crystals of free base 3-(1,2,4-triazolo[4,3-a]pyridine-3-ylethynyl)-4-methyl-N-(4-((4-methylpiperazin-1-yl)methyl)-3-trifluoromethylphenyl)benzamide (sample—HAL-G-194-1, polymorphous modification I) obtained by polarization microscopy.
Figure 5A:
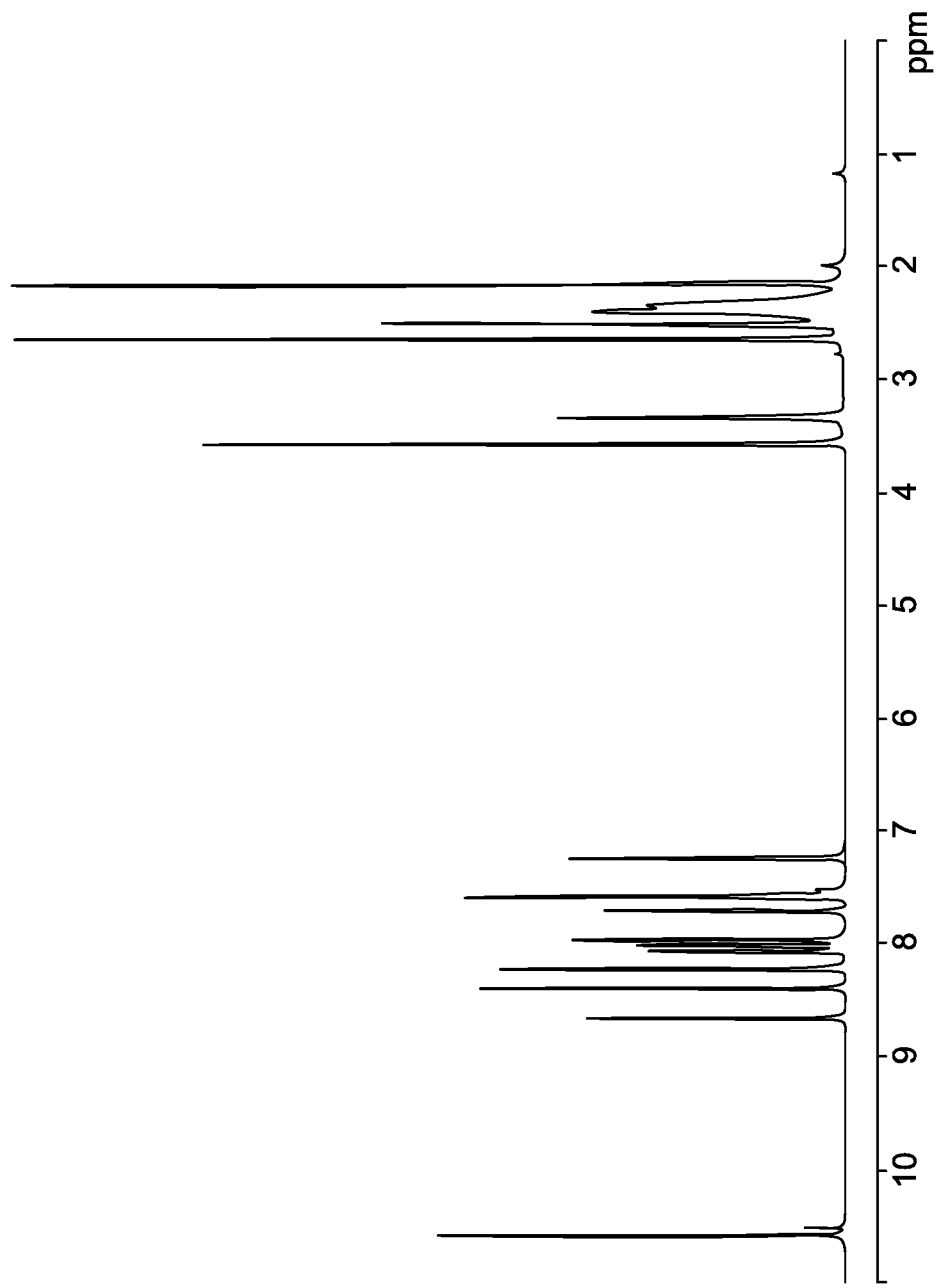
FIGS. 5A-5B. $^1$H nuclear magnetic resonance spectrum of free base 3-(1,2,4-triazolo[4,3-a]pyridine-3-ylethynyl)-4-methyl-N-(4-((4-methylpiperazin-1-yl)methyl)-3-trifluoromethylphenyl)benzamide.
Figure 5B:
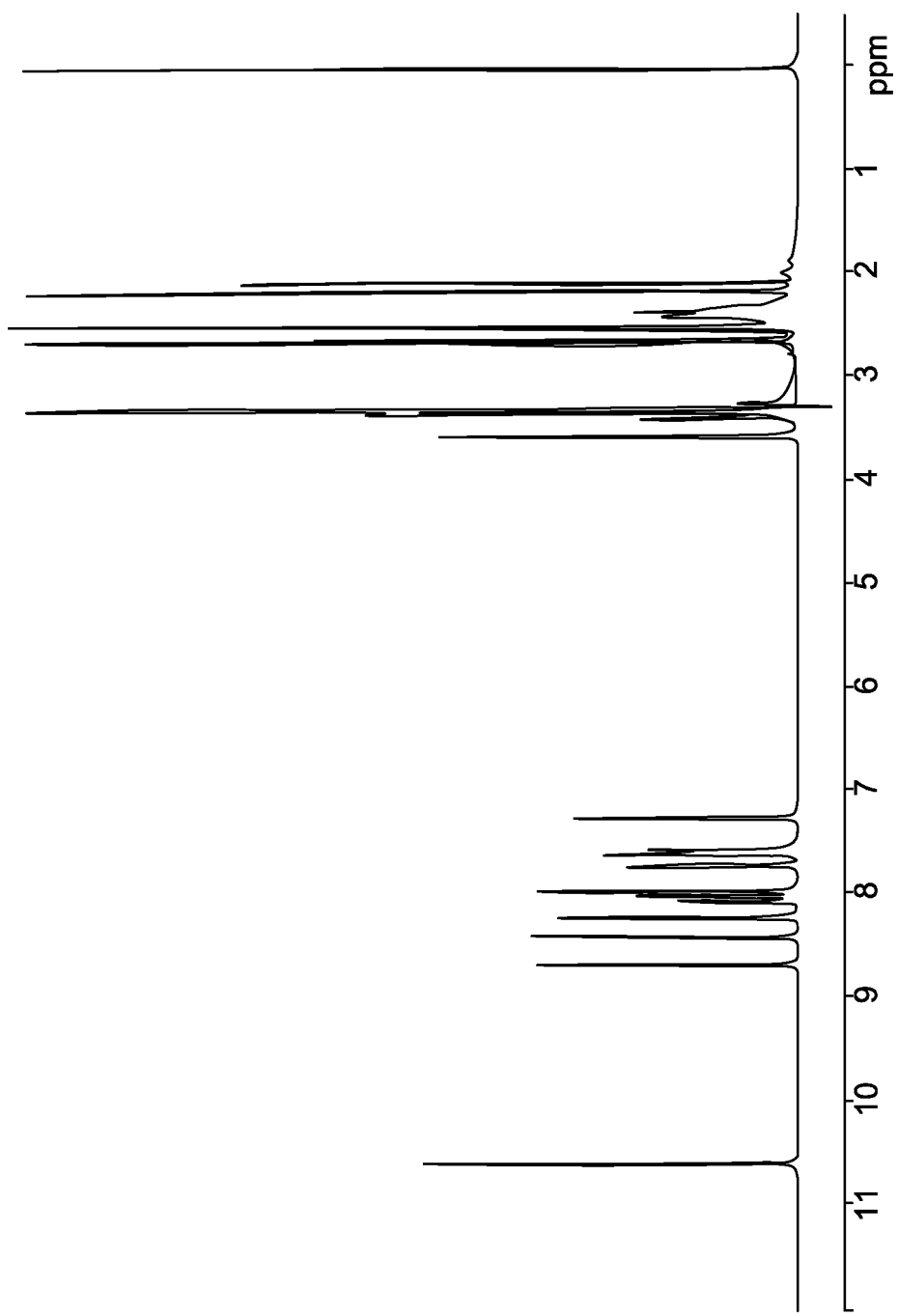

Based on the X-ray powder diffraction data (see FIG. 3), HAL-G-194-1 free base sample is an individual crystalline phase, which was also confirmed by polarization microscopy (see FIG. 4). The structure of the compound was confirmed using $^1$H NMR spectroscopy method (see FIG. 5). The apparent solubility of the free base in deionized water was less than 1 mg/mL (see Table 2).

TABLE 2

Apparent solubility of the free base and various salt forms of 3-(1,2,4-triazolo[4,3-a]pyridine-3-ylethynyl)-4-methyl-N-(4-((4-methylpiperazine-1-yl)methyl)-3-trifluoromethylphenyl)benzamide in water

| Sample | Acid | Crystallinity (form) | Weight, mg | Temperature, °C | Water volume, mL | Apparent solubility, mg/mL |
|---|---|---|---|---|---|---|
| HAL-G-194-1 | (free base) | Form I | 4.6 | RT | 4.0# | <1 |
| HAL-G-196-2 | HCl | Form I | 4.4 | | 0.15 | >29 |
| HAL-G-196-3 | HCl | Form II | 4.3 | | 1.25* | ~3 |
| HAL-G-196-6 | $H_2SO_4$ | Semi-crystalline | 4.5 | | 4.0# | <1 |

TABLE 2-continued

Apparent solubility of the free base and various salt forms of 3-(1,2,4-triazolo[4,3-a]pyridine-3-ylethynyl)-4-methyl-N-(4-((4-methylpiperazine-1-yl)methyl)-3-trifluoromethylphenyl)benzamide in water

| Sample | Acid | Crystallinity (form) | Weight, mg | Temperature, °C. | Water volume, mL | Apparent solubility, mg/mL |
|---|---|---|---|---|---|---|
| HAL-G-196-7 | HBr | Form I | 4.6 | | 1.0* | ~5 |
| HAL-G-196-8 | HBr | Form II | 4.8 | | 4.0# | <1 |
| HAL-G-196-20 | Methanesulfonic acid | Crystalline | 4.6 | | 0.1 | >46 |
| HAL-G-196-24 | 4-methylbenzene sulfonic acid | Crystalline | 4.9 | | 4.0* | ~1 |
| HAL-G-196-29 | Fumaric acid | Crystalline | 4.1 | | 4.0# | <1 |

RT—room temperature,
*muddy solution,
no solution happened.
Equilibrium solubility of a free base in deionized water was approximately $2.3 * 10^{-4}$ mg/mL based on HPLC analysis (see Table 3).

TABLE 3

Equilibrium solubility of the free base and various salt forms of 3-(1,2,4-triazolo[4,3-a]pyridine-3-ylethynyl)-4-methyl-N-(4-((4-methylpiperazine-1-yl)methyl)-3-trifluoromethylphenyl)benzamide in water

| Salt form | Sample code | Weight, mg | Water quantity, mL | Crystallinity initial | Crystallinity in 24 h | pH | Solubility, mg/mL |
|---|---|---|---|---|---|---|---|
| Free base | HAL-G-194-1 | 18.113 | 0.6 | Cryst. | Cryst. | 5.3 | $2.3 \times 10^{-4}$ |
| Hydrochloride | HAL-G-196-3 | 21.939 | 0.6 | Form II | Amorphous | 4.0 | 37.1 |
| Mesylate | HAL-G-196-20 | 19.912 | 0.2 | Cryst. | Dissolution | 3.6 | >100 |
| Tosylate | HAL-G-196-24 | 15.631 | 0.6 | Cryst. | Cryst. | 3.5 | 2.2 |
| Fumarate | HAL-G-196-29 | 18.960 | 0.6 | Cryst. | Cryst. | 4.2 | $7.4 \times 10^{-3}$ |

Figure 6:
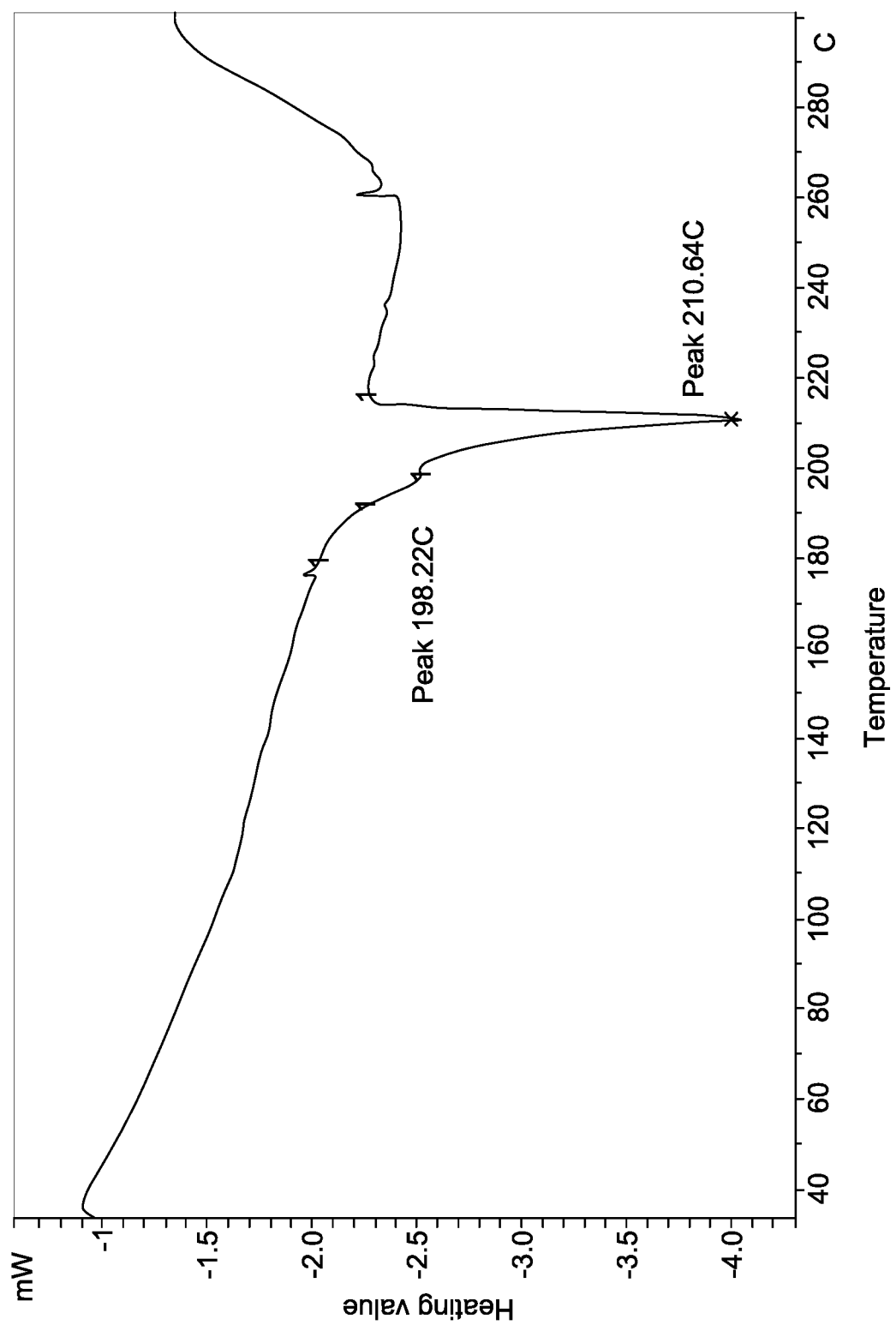
FIG. 6. DSC (differential scanning calorimetry) curve of a sample of free base 3-(1,2,4-triazolo[4,3-a]pyridine-3-ylethynyl)-4-methyl-N-(4-((4-methylpiperazin-1-yl)methyl)-3-trifluoromethylphenyl)benzamide (sample—HAL-G-194-1, polymorphous modification I).
Figure 7:
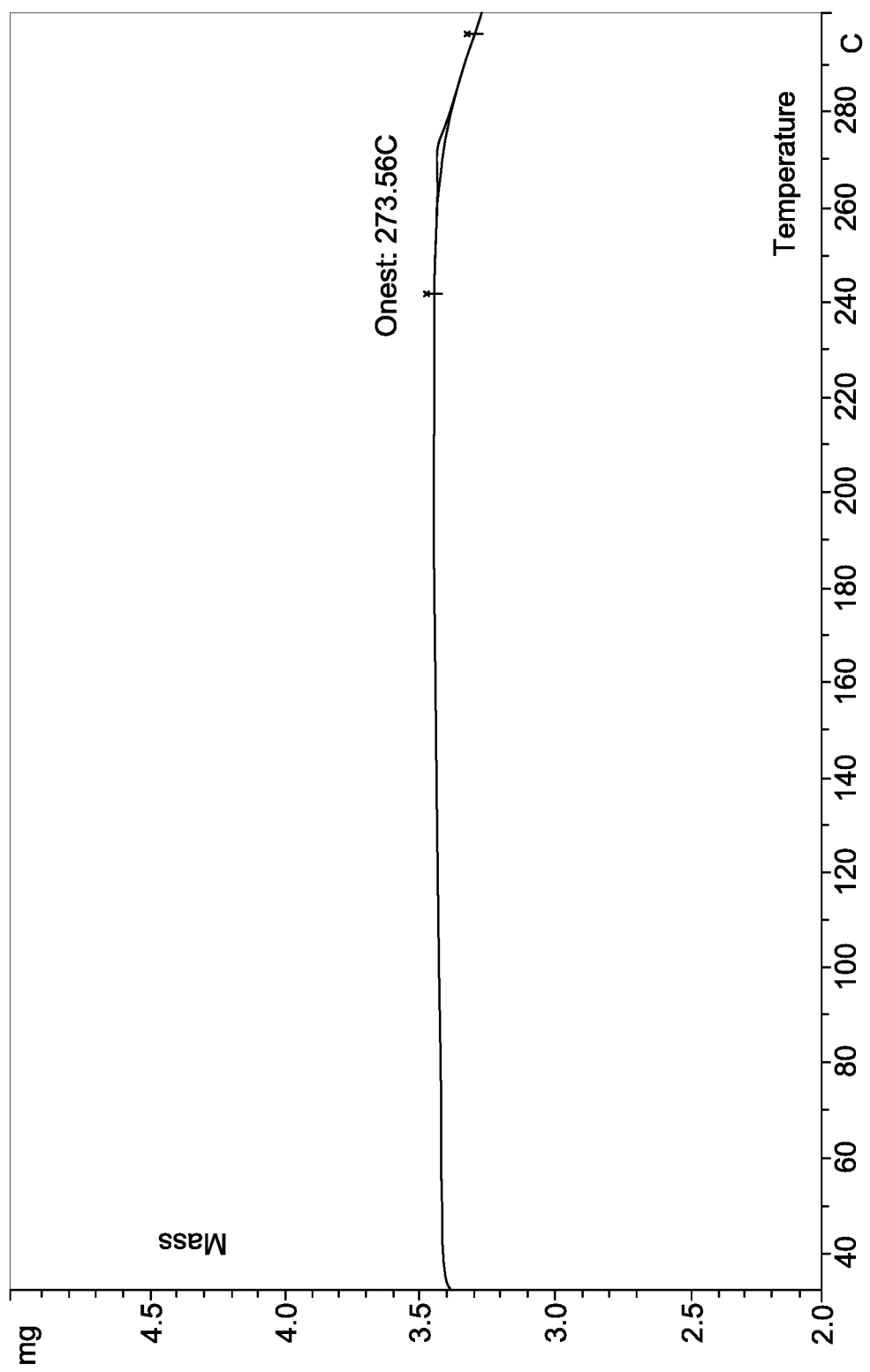
FIG. 7. TGA (thermogravimetric analysis) curve of a sample of free base 3-(1,2,4-triazolo[4,3-a]pyridine-3-ylethynyl)-4-methyl-N-(4-((4-methylpiperazin-1-yl)methyl)-3-trifluoromethylphenyl)benzamide (sample—HAL-G-194-1, polymorphous modification I).
Figure 8:
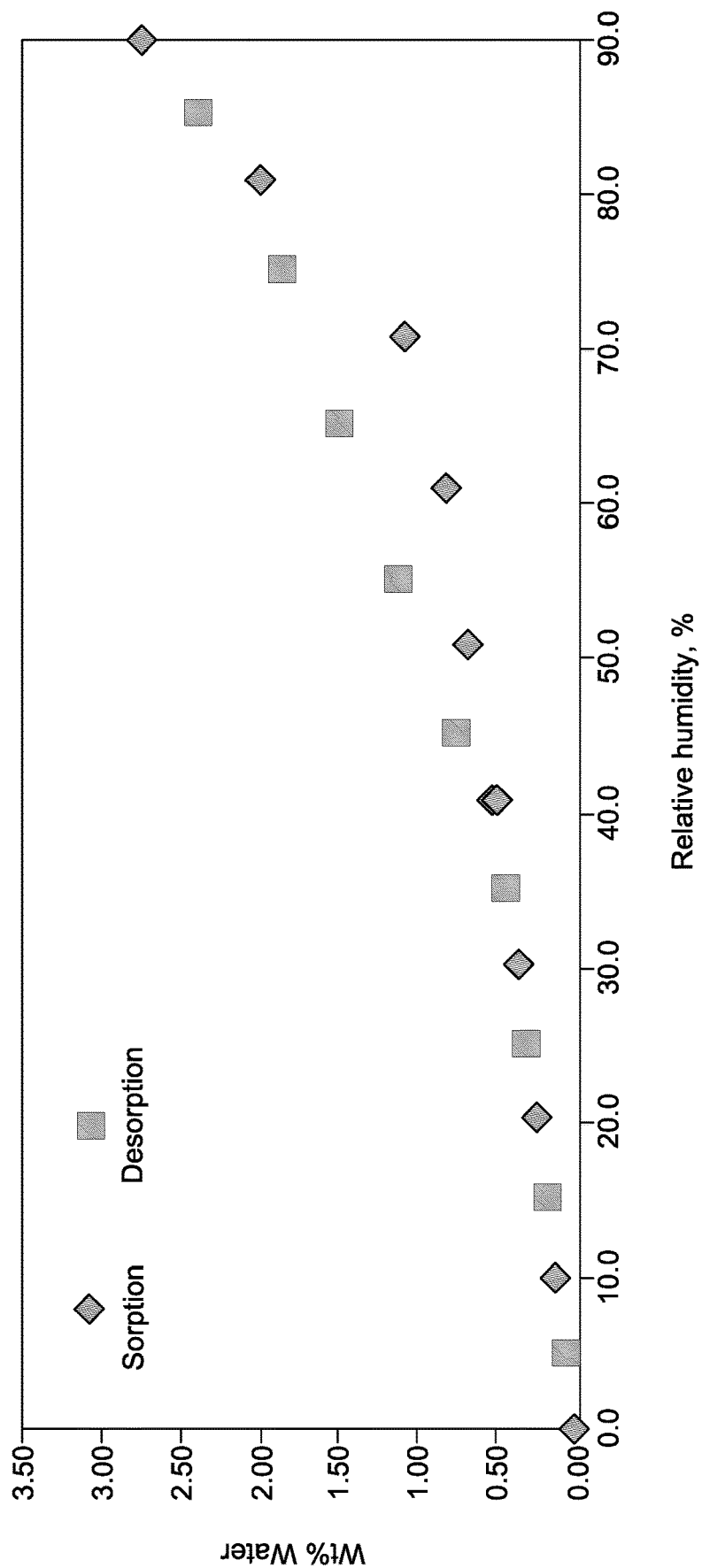
FIG. 8. Plot showing the hygroscopicity of free base 3-(1,2,4-triazolo[4,3-a]pyridine-3-ylethynyl)-4-methyl-N-(4-((4-methylpiperazin-1-yl)methyl)-3-trifluoromethylphenyl)benzamide (sample—HAL-G-194-1, polymorphous modification I) analyzed by gravimetric moisture absorption.

Results of testing samples using DSC and TG methods are given in FIGS. 6 and 7. DSC analysis of free base sample showed that the sample underwent no modifications when heated up to 198° C., the free base melts at 211° C. (see FIG. 6). During TG analysis, no weight loss of the sample was identified (see FIG. 7). A study of the hygroscopicity of the free base of 3-(1,2,4-triazolo[4,3-a]pyridine-3-ylethynyl)-4-methyl-N-(4-((4-methylpiperazine-1-yl)methyl)-3-trifluoromethylphenyl)benzamide showed that at a relative air humidity of 90% the sample absorbed less than three mass percent of water (see FIG. 8). The content of impurities remains constant when the sample is kept during seven days at a temperature of 60° C. (see Table 4).

TABLE 4

Stability of the free base and various salt forms of 3-(1,2,4-triazolo[4,3-a]pyridine-3-ylethynyl)-4-methyl-N-(4-((4-methylpiperazine-1-yl)methyl)-3-trifluoromethylphenyl)benzamide (7 days at T = 60° C.)

| Salt form | Sample code | Weight, mg | Relative peak area, initial, % | Relative peak area, in 7 days, % | Crystallinity initial | Crystallinity in 7 days |
|---|---|---|---|---|---|---|
| Free base | HAL-G-194-1 | 12.7 | 99.7 | 99.7 | Form I | Form I |
| Hydrochloride | HAL-G-196-20 | 10.0 | 99.7 | 99.7 | Cryst. | Cryst. |
| Mesylate | HAL-G-196-24 | 8.8 | 99.8 | 99.9 | Cryst. | Cryst. |
| Tosylate | HAL-G-196-3 | 9.5 | 99.9 | 99.9 | Form II | Form II |
| Fumarate | HAL-G-196-29 | 12.2 | 99.8 | 99.9 | Cryst. | Cryst. |

A study of the stability of the free base polymorph modification of 3-(1,2,4-triazolo[4,3-a]pyridine-3-ylethynyl)-4-methyl-N-(4-((4-methylpiperazine-1-yl)methyl)-3-trifluoromethylphenyl)benzamide suspended in a solvent (acetone) during 6 days showed that crystalline structure of HAL-G-194-1 sample changes (see FIG. 3, Table 5). The structure and purity of the sample received were confirmed using $^1$H NMR spectroscopy (See FIG. 5).

TABLE 5

Stability of the free base polymorph modifications and various salt forms of 3-(1,2,4-triazolo[4,3-a]pyridine-3-ylethynyl)-4-methyl-N-(4-((4-methylpiperazine-1-yl)methyl)-3-trifluoromethylphenyl)benzamide (suspending in acetone for 6 days)

| Salt form | Sample code | Weight, mg | Quantity of acetone, mL | Temperature | Crystallinity initial | in 6 days |
|---|---|---|---|---|---|---|
| Free base | HAL-G-194-1 | 36.5 | 0.3 | Room | Form I | Form II |
| Hydrochloride | HAL-G-200-9 | 22.5 | | | Form II | Form II |
| Mesylate | HAL-G-200-10 | 20.8 | | | Cryst. | Cryst. |
| Tosylate | HAL-G-196-21 | 19.4 | | | Cryst. | Cryst. |
| Fumarate | HAL-G-196-30 | 19.0 | | | Cryst. | Cryst. |

Study of the Physical and Chemical Properties of the Salt of Hydrochloric Acid and 3-(1,2,4-Triazolo[4,3-a]Pyridine-3-Ylethynyl)-4-Methyl-N-(4-((4-Methylpiperazine-1-Yl)Methyl)-3-Trifluoromethylphenyl)Benzamide (Polymorph Modification I)

Figure 9A:
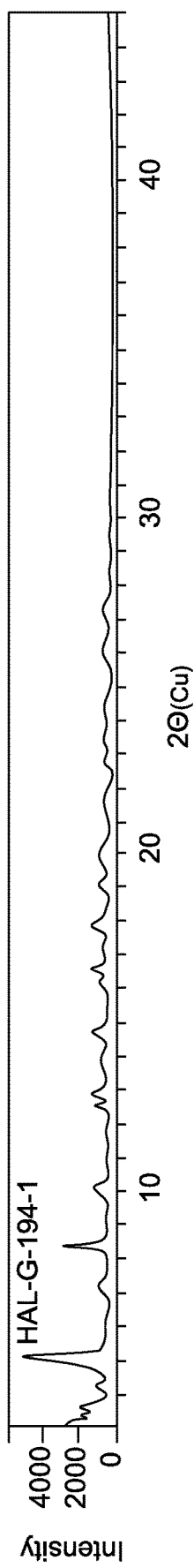
FIG. 9A-9C. X-ray powder diffraction patterns of the salt of hydrochloric acid and free base 3-(1,2,4-triazolo[4,3-a]pyridine-3-ylethynyl)-4-methyl-N-(4-((4-methylpiperazin-1-yl)methyl)-3-trifluoromethylphenyl)benzamide.
Figure 9B:
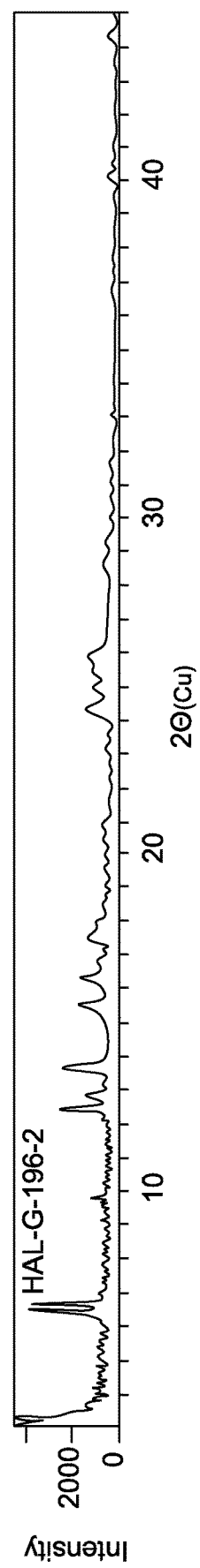
Figure 9C:
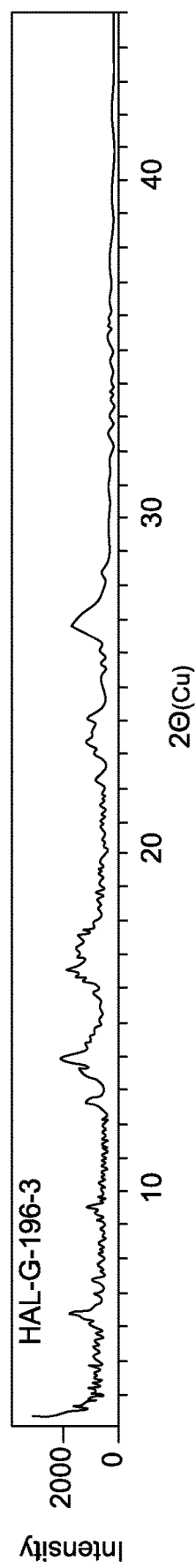
Figure 10A:
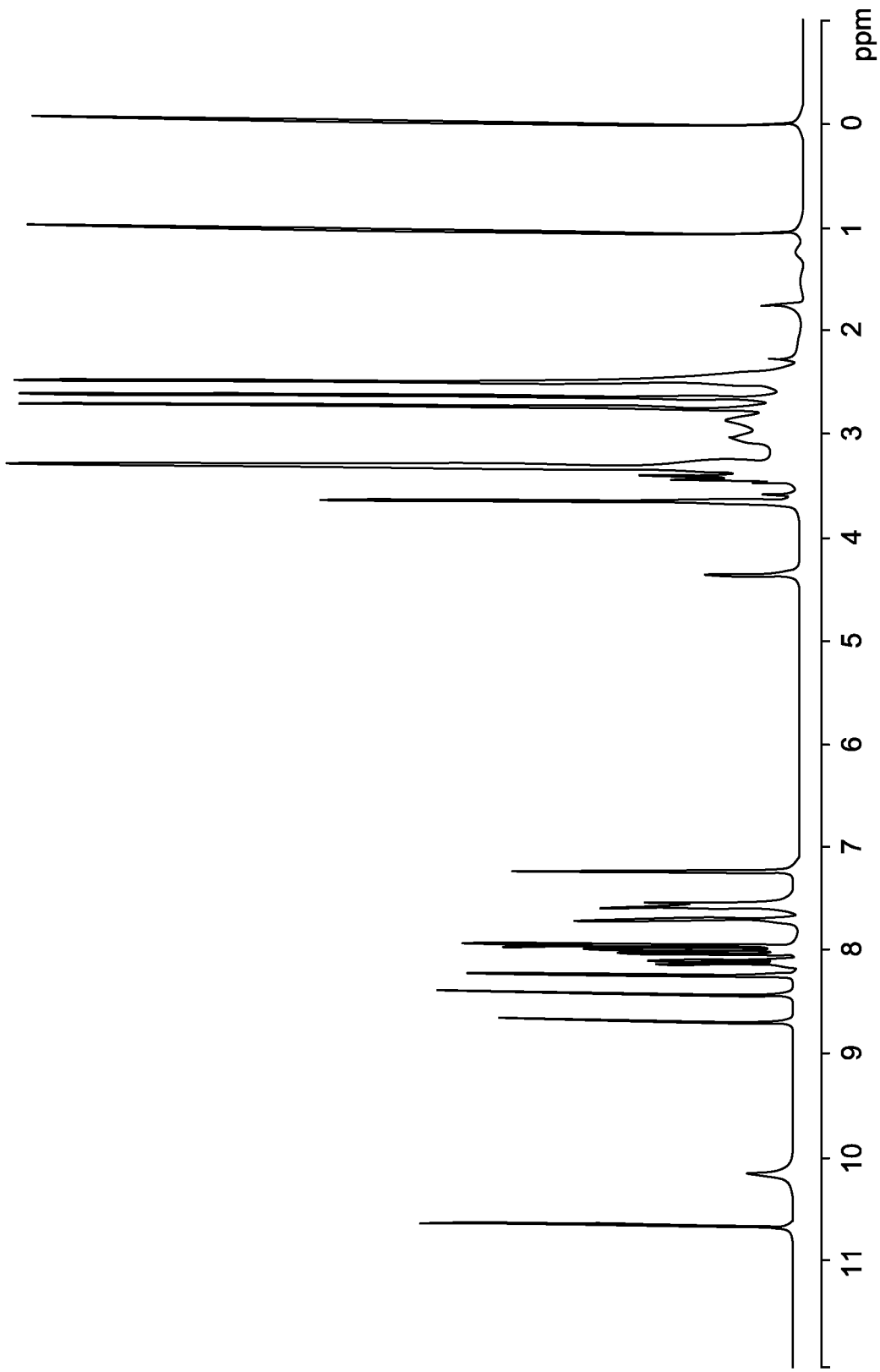
FIGS. 10A-10B. $^1$H nuclear magnetic resonance spectrum of the salt of hydrochloric acid and 3-(1,2,4-triazolo[4,3-a]pyridine-3-ylethynyl)-4-methyl-N-(4-((4-methylpiperazin-1-yl)methyl)-3-trifluoromethylphenyl)benzamide.
Figure 10B:
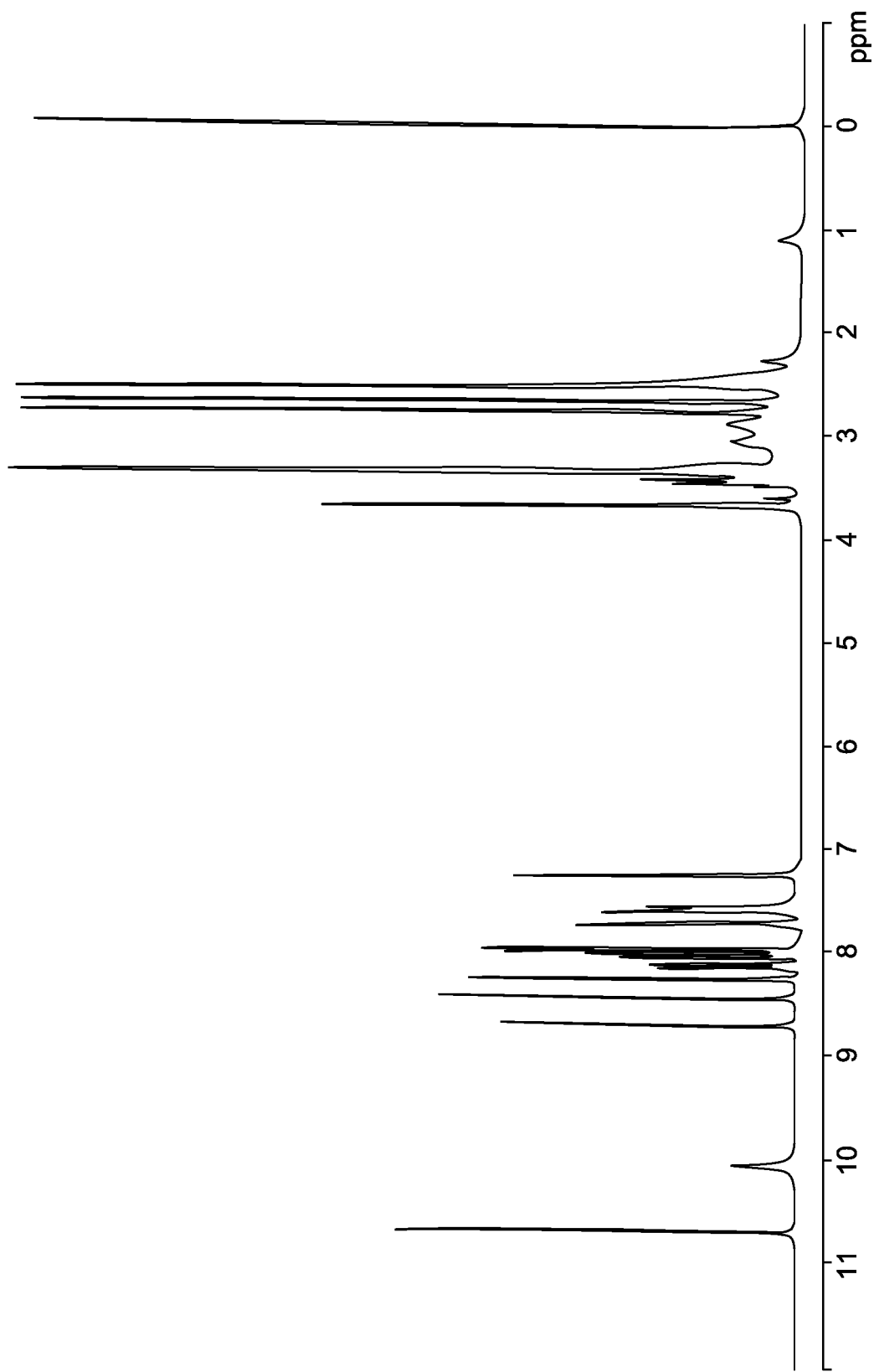
Figure 11:
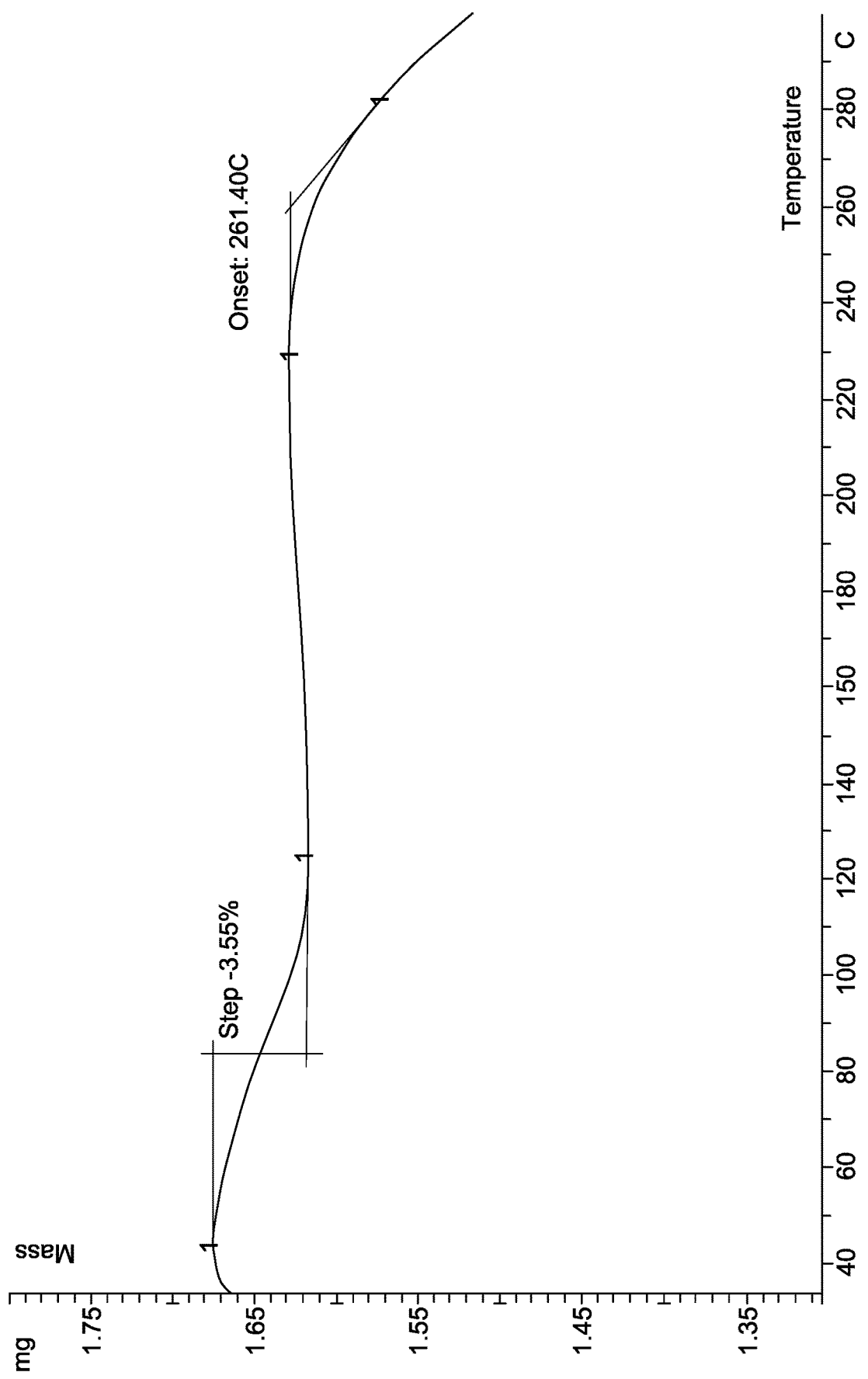
FIG. 11. TGA curve of a sample of the salt of hydrochloric acid and 3-(1,2,4-triazolo[4,3-a]pyridine-3-ylethynyl)-4-methyl-N-(4-((4-methylpiperazin-1-yl)methyl)-3-trifluoromethylphenyl)benzamide (sample—HAL-G-196-2, polymorphous modification I).
Figure 12A:
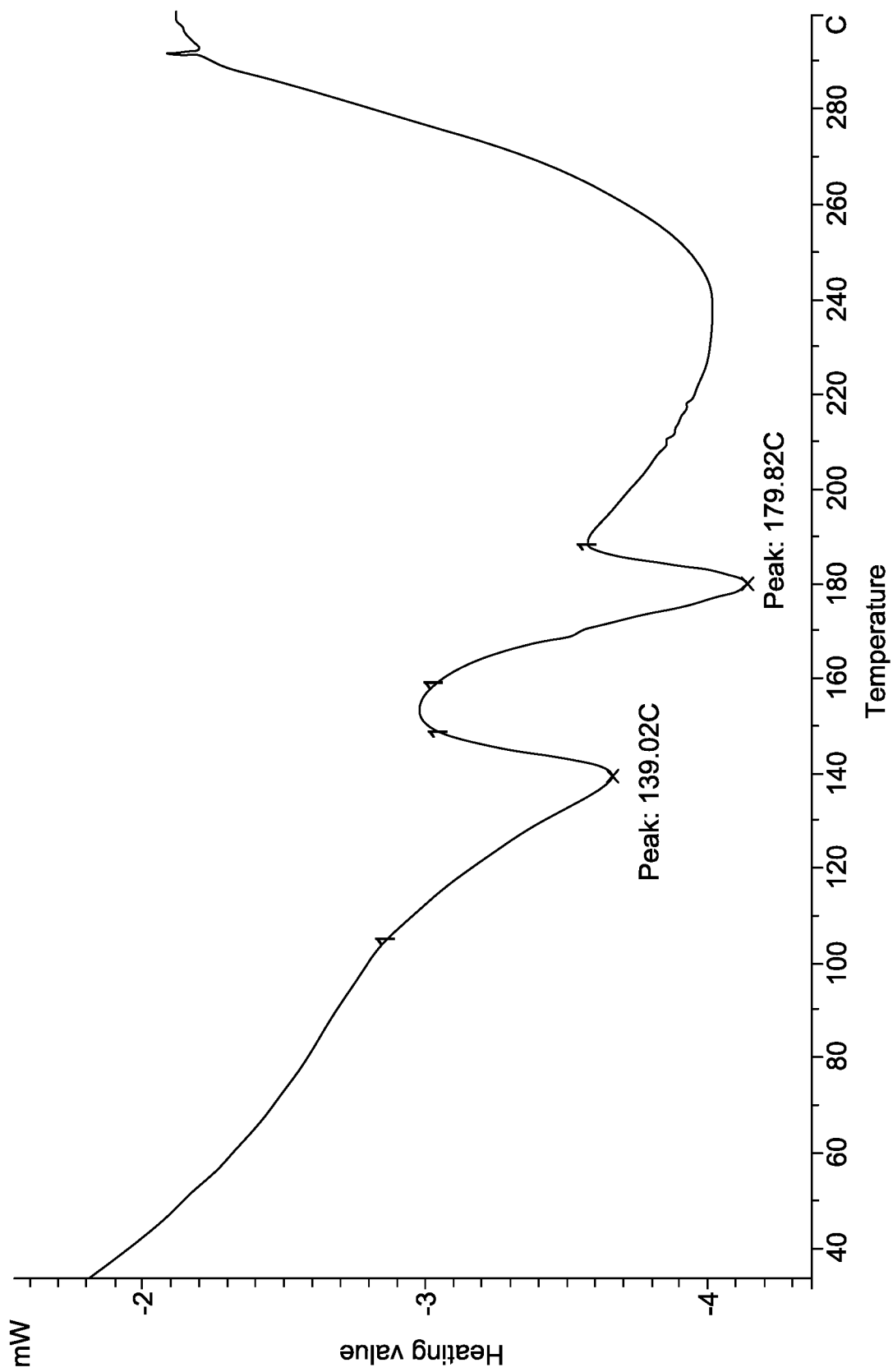
FIGS. 12A-12B. DSC curve of a sample of the salt of hydrochloric acid and 3-(1,2,4-triazolo[4,3-a]pyridine-3-ylethynyl)-4-methyl-N-(4-((4-methylpiperazin-1-yl)methyl)-3-trifluoromethylphenyl)benzamide.
Figure 12B:
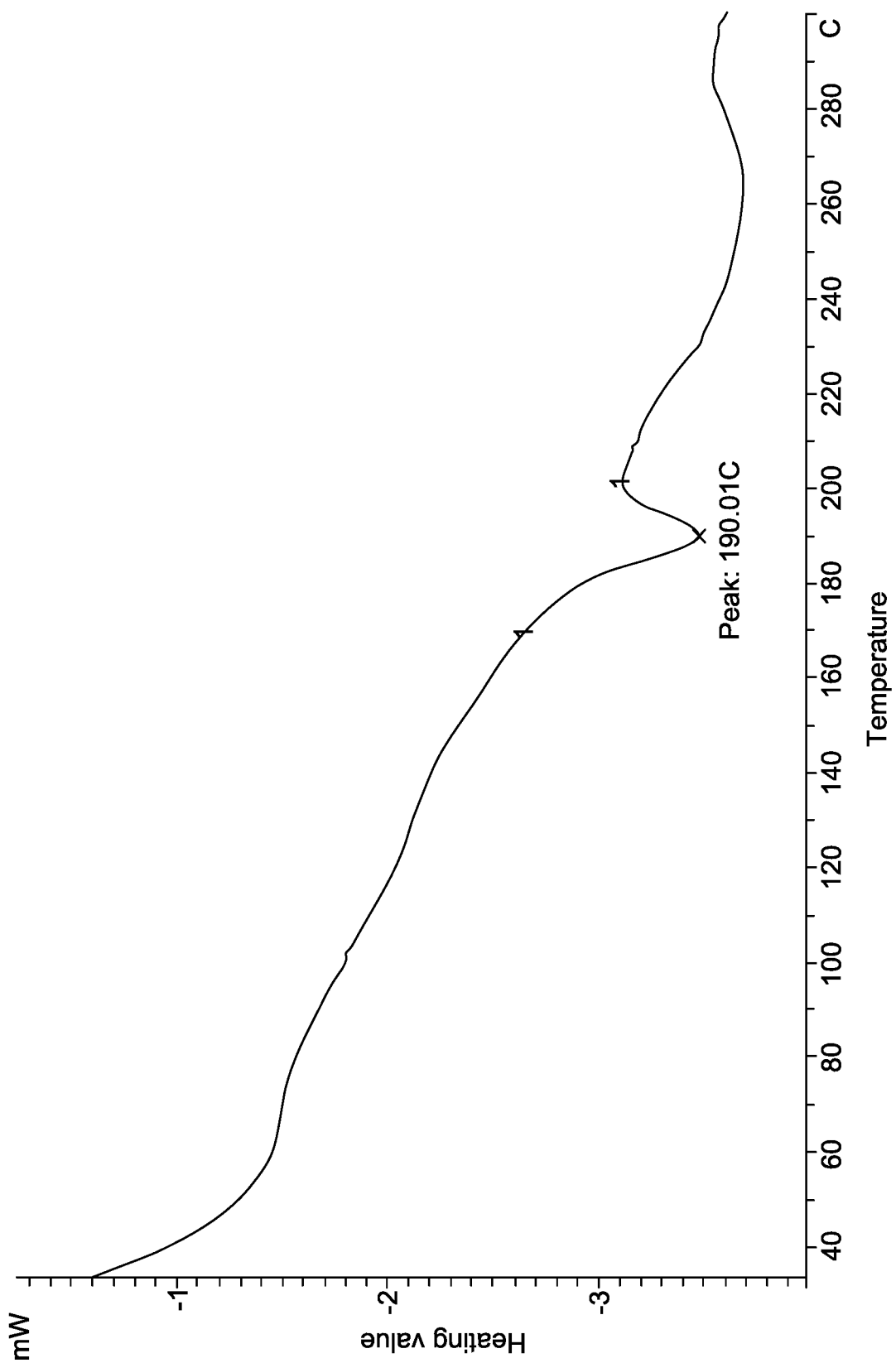
Figure 13:
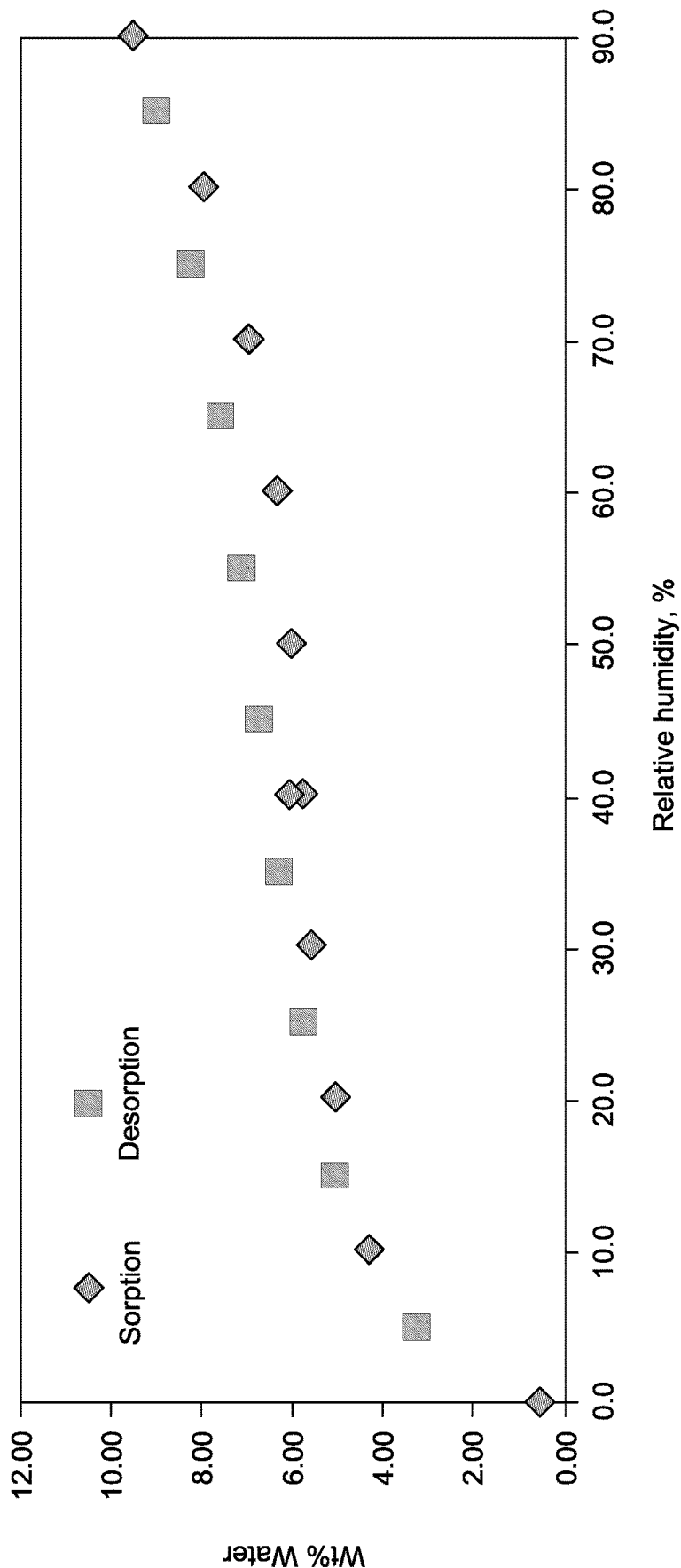
FIG. 13. Plot showing the hygroscopicity of a sample of the salt of hydrochloric acid and 3-(1,2,4-triazolo[4,3-a]pyridine-3-ylethynyl)-4-methyl-N-(4-((4-methylpiperazin-1-yl)methyl)-3-trifluoromethylphenyl)benzamide (sample—HAL-G-196-2, polymorphous modification I) analyzed by gravimetric moisture absorption.

A sample (HAL-G-196-2) of the salt of hydrochloric acid and 3-(1,2,4-triazolo[4,3-a]pyridine-3-ylethynyl)-4-methyl-N-(4-((4-methylpiperazine-1-yl)methyl)-3-trifluoromethylphenyl)benzamide was obtained in tetrahydrofuran (THF). Based on X-ray powder diffraction (see FIG. 9), the salt was identified as an individual crystalline phase. The same crystalline phase was revealed in a sample of the salt of hydrochloric acid and 3-(1,2,4-triazolo[4,3-a]pyridine-3-ylethynyl)-4-methyl-N-(4-((4-methylpiperazine-1-yl)methyl)-3-trifluoromethylphenyl)benzamide prepared in ethanol (HAL-G-196-1 sample). The compound structure was confirmed with 1H NMR spectroscopy (see FIG. 10). It should be noted that the $^1$H NMR spectra of the HAL-G-196-1 and HAL-G-196-2 samples contain signals of residual solvents. The anion and cation stoichiometric proportion was determined using ion chromatography and confirmed formation of a monohydrochloride. DSC analysis (see FIG. 11) resulted in identification of two endothermic transitions— the first one (T=139° C.) corresponds to solvent loss, and second one (T=180° C.) corresponds to sample melting. During TG analysis, a sample weight loss of 3.6% was observed, which was probably caused by loss of residual solvent quantities (see FIG. 12). A study of sample hygroscopicity showed that the HAL-G-196-2 sample probably was a dihydrate, as it desorbed and sorbed water, the volume of which corresponded to a dihydrate (see FIG. 13). Further development was recognized as being unfeasible.

Study of Physical and Chemical Properties of the Sale of Hydrochloric Acid and 3-(1,2,4-Triazolo[4,3-a]Pyridine-3-Ylethynyl)-4-Methyl-N-(4-((4-Methylpiperazine-1-Yl)Methyl)-3-Trifluoromethylphenyl) Benzamide (Polymorph Modification II)

A sample (HAL-G-196-3) of the salt of hydrochloric acid and 3-(1,2,4-triazolo[4,3-a]pyridine-3-ylethynyl)-4-methyl-N-(4-((4-methylpiperazine-1-yl)methyl)-3-trifluoromethylphenyl)benzamide was obtained from acetone media after adding methyl tert-butyl ether (MTBE). Based on X-ray powder diffraction (see FIG. 9), the salt was identified as an individual crystalline phase, which was different from the crystalline phase of HAL-G-196-1 and HAL-G-196-2. The compound structure was confirmed by $^1$H NMR spectroscopy (see FIG. 10). The anion and cation stoichiometric proportion was determined using ion chromatography and confirmed formation of a monohydrochloride. DSC analysis (see FIG. 11) resulted in identification of one endothermic transition (T=190° C.) corresponding to sample melting. During TG analysis, no sample weight loss was observed. The apparent solubility of HAL-G-196-3 sample in deionized water amounted to around 3 mg/mL (see Table 2). Equilibrium solubility of the salt of hydrochloric acid and 3-(1,2,4-triazolo[4,3-a]pyridine-3-ylethynyl)-4-methyl-N-(4-((4-methylpiperazine-1-yl)methyl)-3-trifluoromethylphenyl)benzamide (polymorph modification II) in deionized water was measured at around 37.1 mg/mL by HPLC analysis (see Table 3). A study of sample hygroscopicity showed that the HAL-G-196-3 sample absorbs less than 8 mass percent of water at a relative air humidity of 90% (see FIG. 13). The content of impurities remained constant when the sample was kept for seven days at a temperature of 60° C. (see Table 4). A study of the stability of HAL-G-196-3 sample upon suspending in a solvent (acetone) during 6 days showed that crystalline structure of HAL-G-196-3 sample remained unchanged (see Table 5). Therefore, this form of the salt of hydrochloric acid and 3-(1,2,4-triazolo[4,3-a]pyridine-3-ylethynyl)-4-methyl-N-(4-((4-methylpiperazine-1-yl)methyl)-3-trifluoromethylphenyl)benzamide had physical and chemical properties that met the requirements for further development of the salt form.

Figure 14:
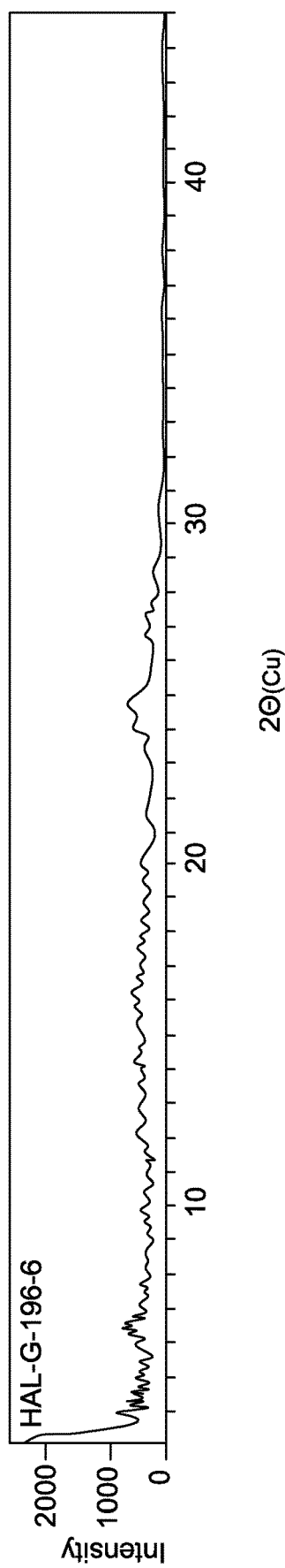
FIG. 14. X-ray powder diffraction pattern of the salt of sulfuric acid and 3-(1,2,4-triazolo[4,3-a]pyridine-3-ylethynyl)-4-methyl-N-(4-((4-methylpiperazin-1-yl)methyl)-3-trifluoromethylphenyl)benzamide (sample—HAL-G-196-6).
Figure 15:
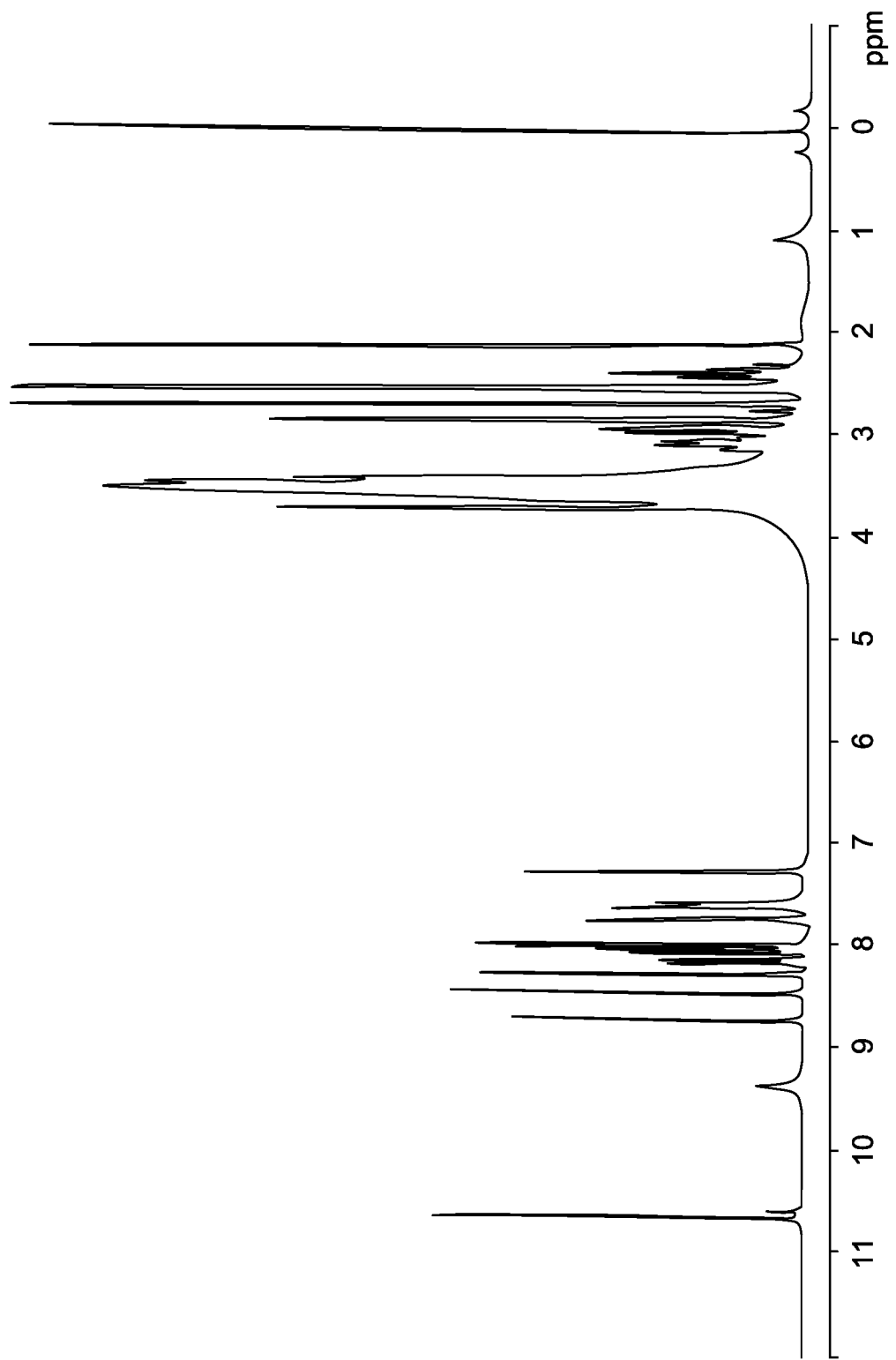
FIG. 15. $^1$H nuclear magnetic resonance spectrum of a sample of the salt of sulfuric acid and 3-(1,2,4-triazolo[4,3-a]pyridine-3-ylethynyl)-4-methyl-N-(4-((4-methylpiperazin-1-yl)methyl)-3-trifluoromethylphenyl)benzamide (sample—HAL-G-196-6).
Figure 16:
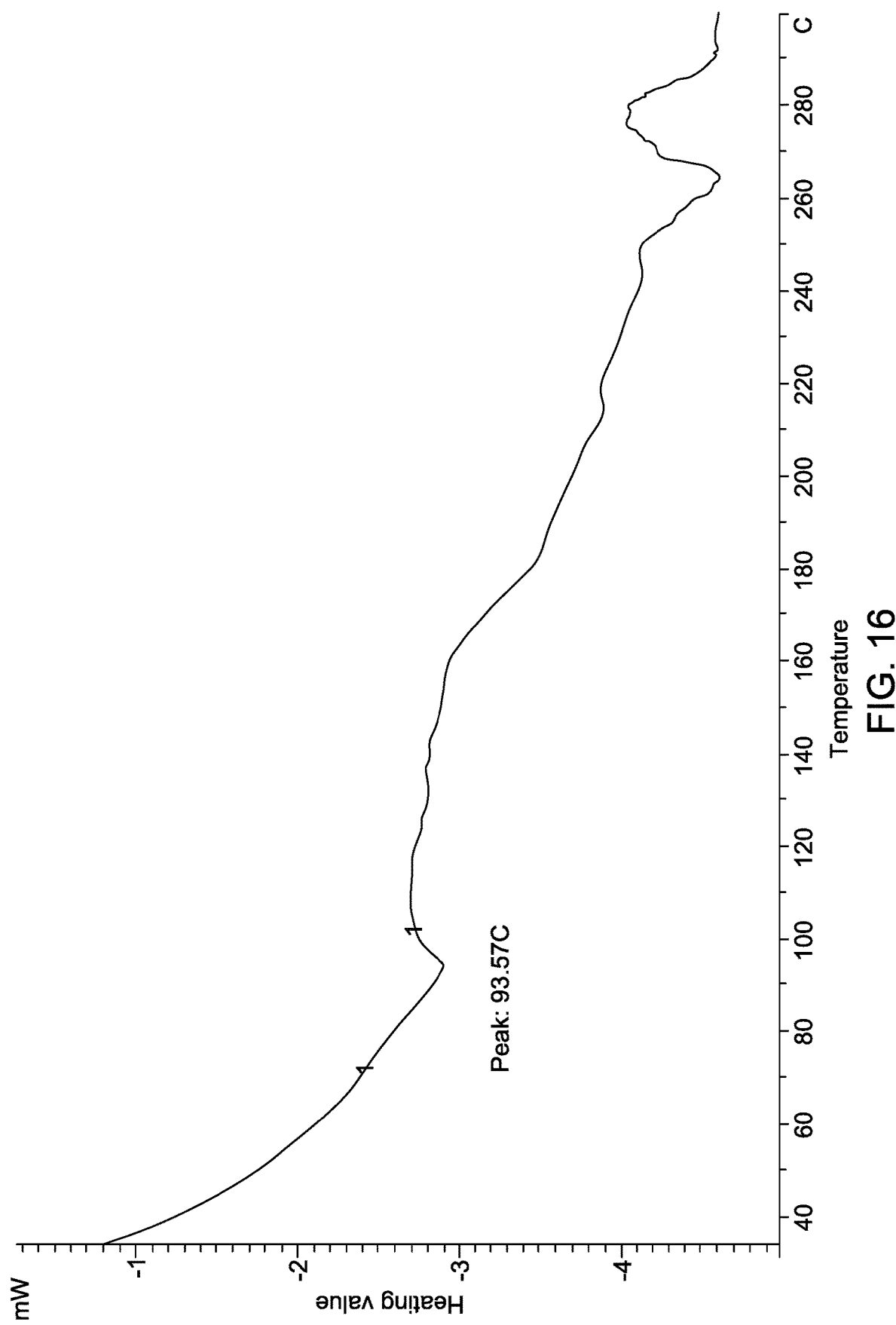
FIG. 16. DSC curve of a sample of the salt of sulfuric acid and 3-(1,2,4-triazolo[4,3-a]pyridine-3-ylethynyl)-4-methyl-N-(4-((4-methylpiperazin-1-yl)methyl)-3-trifluoromethylphenyl)benzamide (sample—HAL-G-196-6).

Study of Physical and Chemical Properties of a Salt of Sulfuric Acid and 3-(1,2,4-Triazolo[4,3-a]Pyridine-3-Ylethynyl)-4-Methyl-N-(4-((4-Methylpiperazine-1-Yl)Methyl)-3-Trifluoromethylphenyl)Benzamide A sample (HAL-G-196-6) of a salt of sulfuric acid and 3-(1,2,4-triazolo[4,3-a]pyridine-3-ylethynyl)-4-methyl-N-(4-((4-methylpiperazine-1-yl)methyl)-3-trifluoromethylphenyl)benzamide was obtained in acetone media. Based on X-ray powder diffraction (see FIG. 14), the sample was found to contain a combination of crystalline phases, as the diffusion nature of peaks and inability to establish and describe diffraction patterns using phase reflections with one unit cell demonstrated presence of several crystalline phases and, probably, significant share of amorphous phase in the test sample. The compound structure was confirmed by $^1$H NMR spectroscopy (see FIG. 15). It should be mentioned that $^1$H NMR spectrum of HAL-G-196-6 sample contains signals of the residual solvent. The anion and cation stoichiometric proportion was determined using ion chromatography, which confirmed formation of a monosulfate salt. DSC analysis (see FIG. 16) resulted in the identification of one endothermic transition, which probably corresponded to solvent loss. The absence of an express endothermic transition corresponding to substance melting demonstrated that there was a substantial proportion of amorphous phase in the test sample. The apparent solubility of the salt of sulfuric acid and 3-(1,2,4-triazolo[4,3-a]pyridine-3-ylethynyl)-4-methyl-N-(4-((4-methylpiperazine-1-yl)methyl)-3-trifluoromethylphenyl)benzamide in deionized water was around 1 mg/mL (see Table 2). Further development was recognized as being unfeasible due to low solubility of this salt.

Study of Physical and Chemical Properties of a Salt of Hydrogen Bromide and 3-(1,2,4-Triazolo[4,3-a]Pyridine-3-Ylethynyl)-4-Methyl-N-(4-((4-Methylpiperazine-1-Yl)Methyl)-3-Trifluoromethylphenyl)Benzamide (Polymorph Modification I)

Figure 17A:
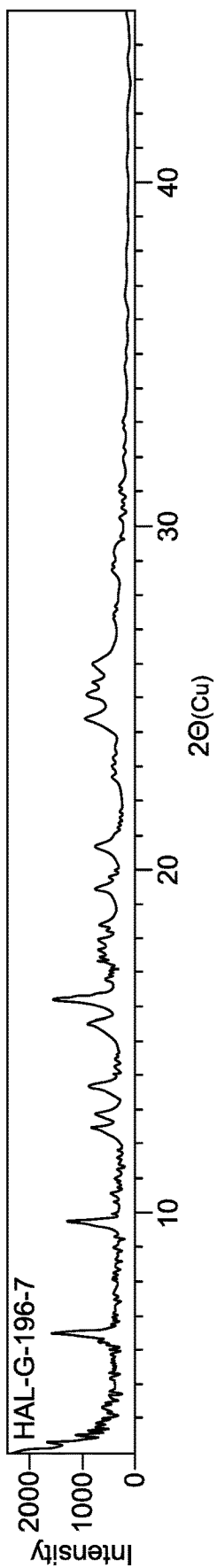
FIGS. 17A-17B. The X-ray powder diffraction pattern of the salt of hydrobromic acid and 3-(1,2,4-triazolo[4,3-a]pyridine-3-ylethynyl)-4-methyl-N-(4-((4-methylpiperazin-1-yl)methyl)-3-trifluoromethylphenyl)benzamide.
Figure 17B:
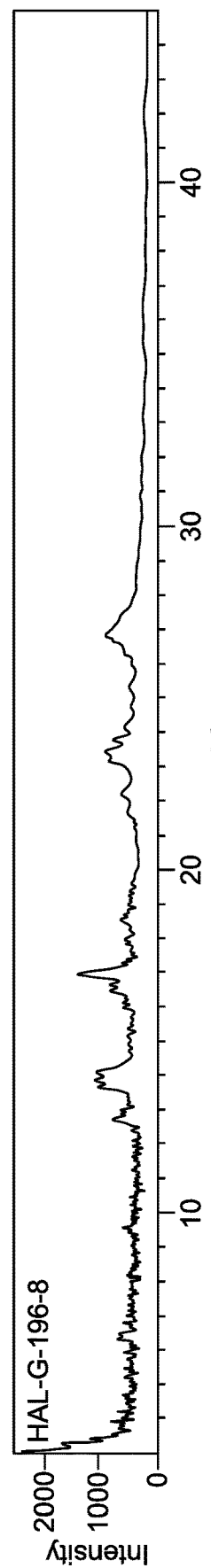
Figure 18A:
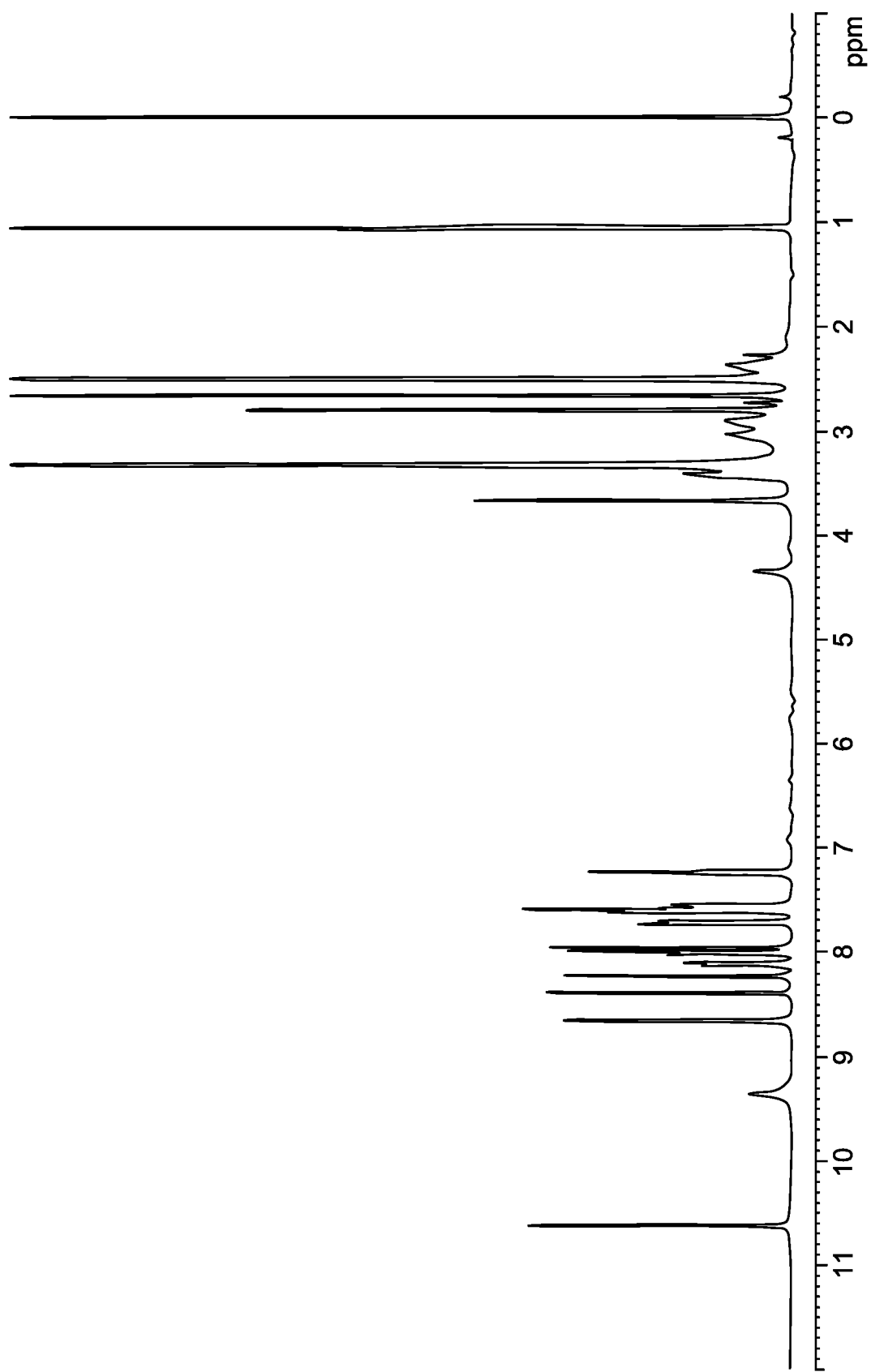
FIGS. 18A-18B. $^1$H nuclear magnetic resonance spectrum of samples of the salt of hydrobromic acid and 3-(1,2,4-triazolo[4,3-a]pyridine-3-ylethynyl)-4-methyl-N-(4-((4-methylpiperazin-1-yl)methyl)-3-trifluoromethylphenyl)benzamide.
Figure 18B:
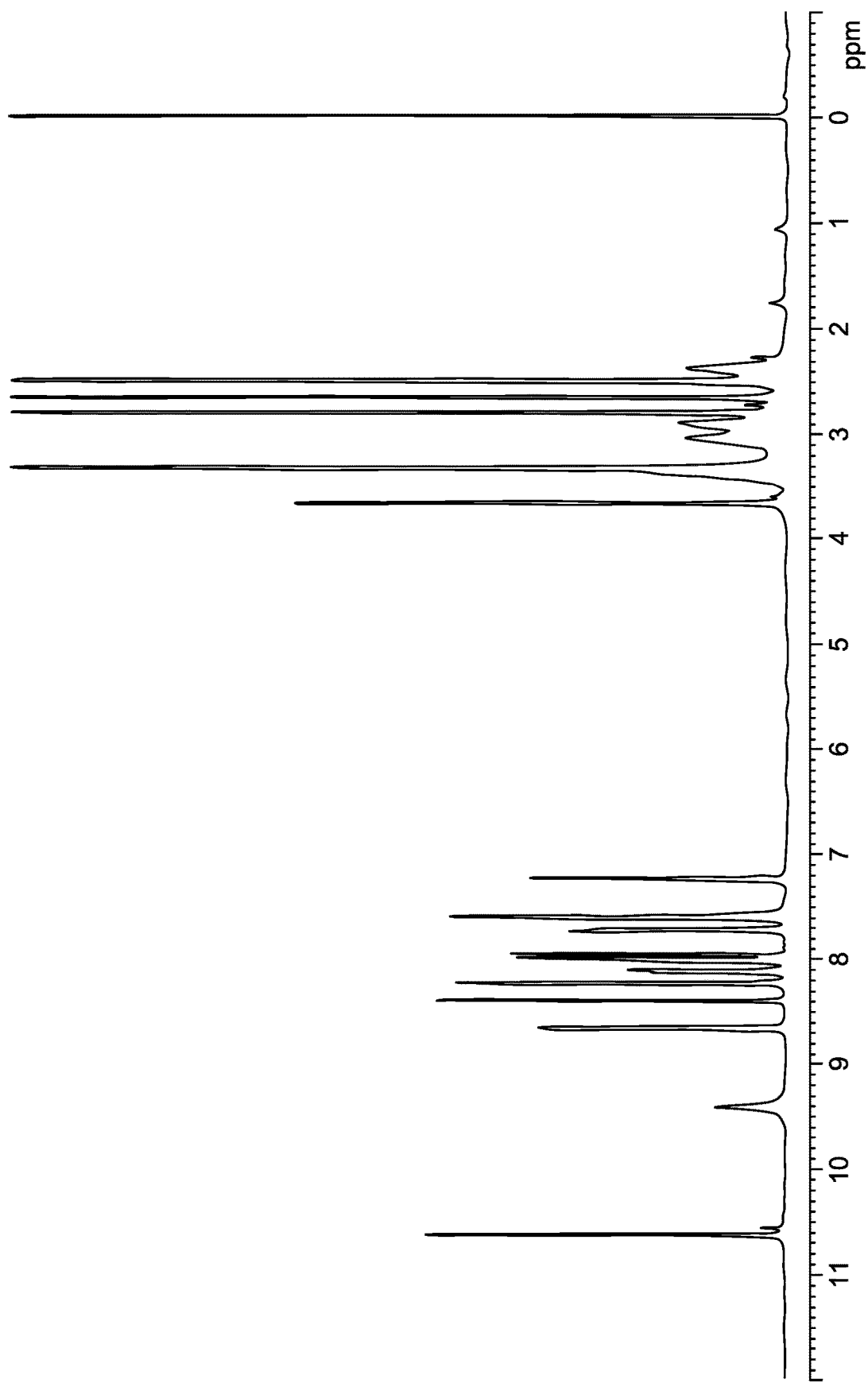
Figure 19A:
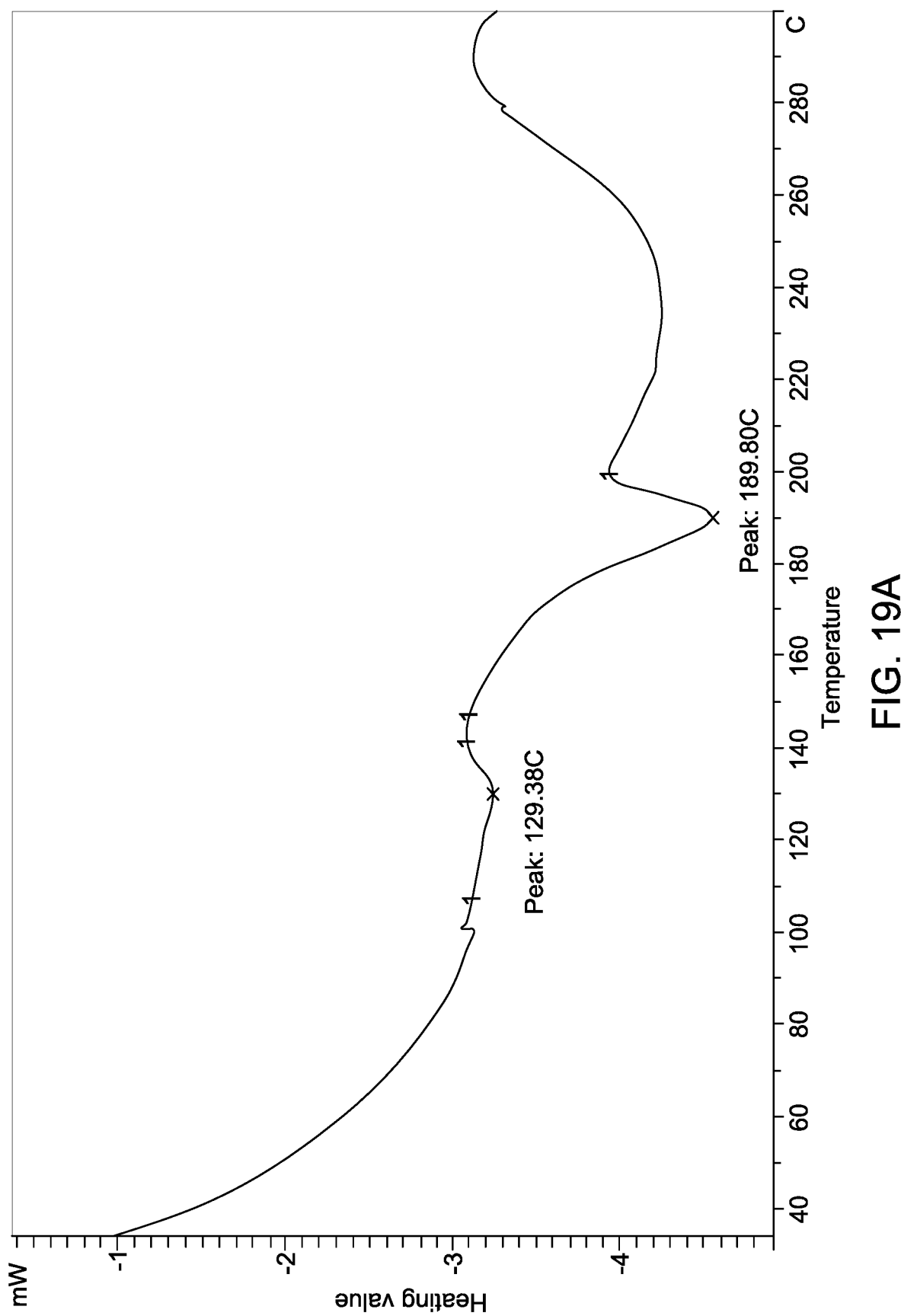
FIGS. 19A-19B. DSC curve of samples of the salt of hydrobromic acid and 3-(1,2,4-triazolo[4,3-a]pyridine-3-ylethynyl)-4-methyl-N-(4-((4-methylpiperazin-1-yl)methyl)-3-trifluoromethylphenyl)benzamide.
Figure 19B:
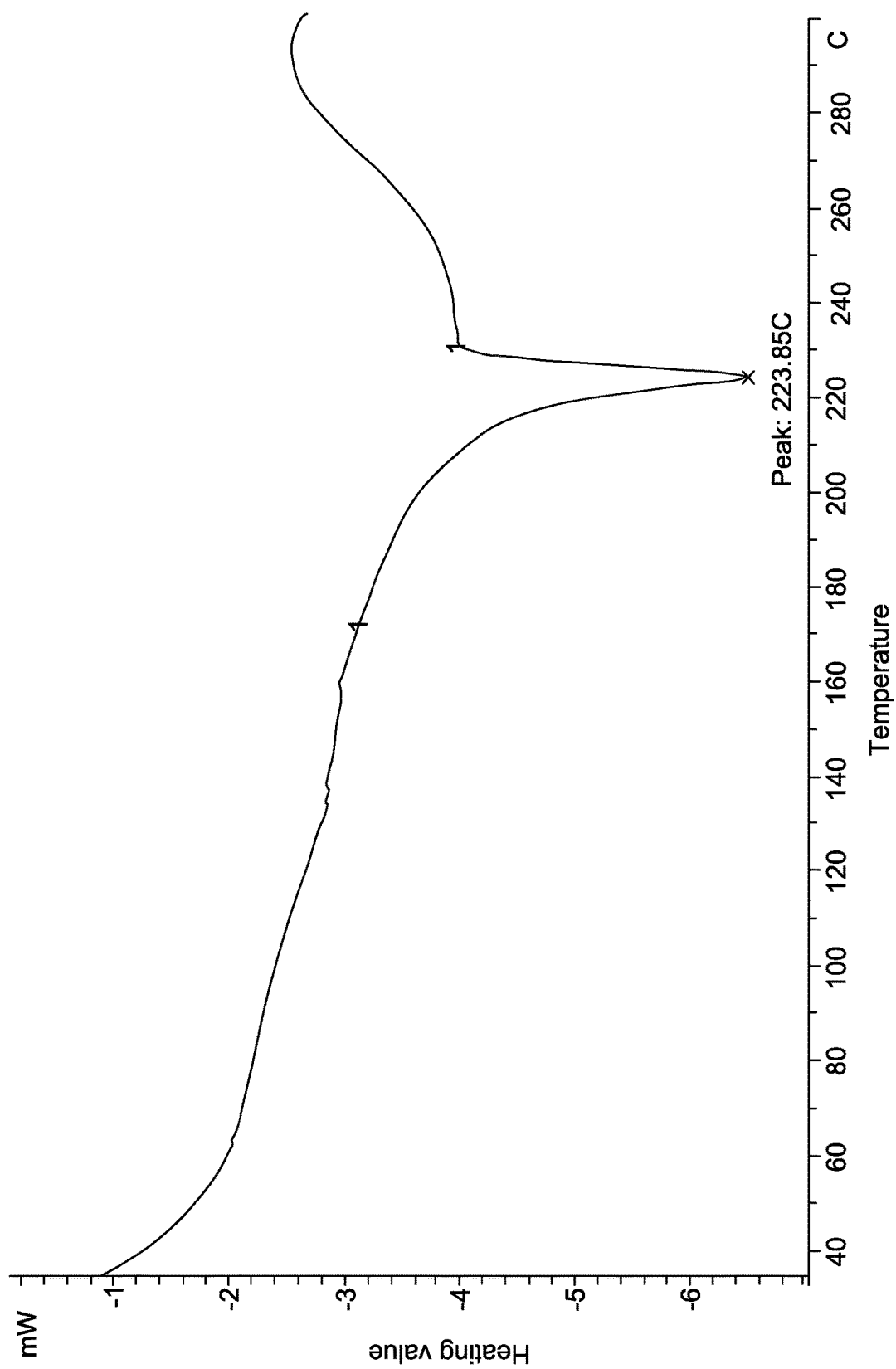
Figure 20:
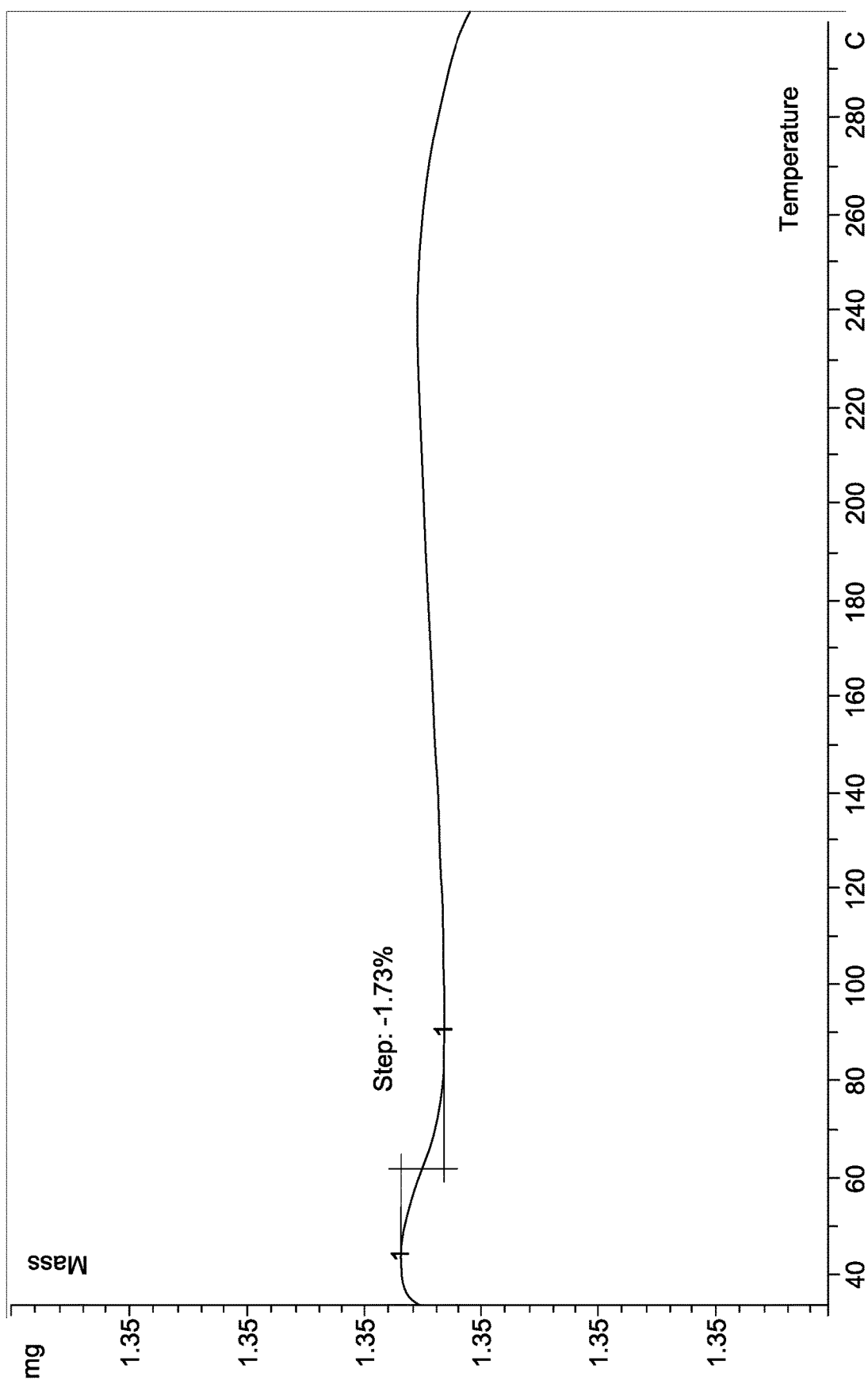
FIG. 20. TGA curve of samples of the salt of hydrobromic acid and 3-(1,2,4-triazolo[4,3-a]pyridine-3-ylethynyl)-4-methyl-N-(4-((4-methylpiperazin-1-yl)methyl)-3-trifluoromethylphenyl)benzamide (sample—HAL-G-196-7, polymorphous modification I).

A sample (HAL-G-196-7) of a salt of hydrogen bromide and 3-(1,2,4-triazolo[4,3-a]pyridine-3-ylethynyl)-4-methyl-N-(4-((4-methylpiperazine-1-yl)methyl)-3-trifluoromethylphenyl)benzamide was obtained via crystallization from an ethanol medium. Based on X-ray powder diffraction (see FIG. 17) the salt was identified as being an individual crystalline phase. The compound structure was confirmed by $^1$H NMR spectroscopy (see FIG. 18). The $^1$H NMR spectrum of HAL-G-196-7 sample contains signals of the residual solvent. The anion and cation stoichiometric proportion was determined using ion chromatography which confirmed formation of a monohydrobromide. DSC analysis (see FIG. 19) resulted in identification of two endothermic transitions—the first one (T=129° C.) corresponds to solvent loss, while the second one (T=190° C.) corresponds to sample melting. During TG analysis, a sample weight loss of 1.7% was observed, which was probably caused by loss of residual solvent quantities (see FIG. 20). The apparent solubility of the salt of hydrobromic acid and 3-(1,2,4-triazolo[4,3-a]pyridine-3-ylethynyl)-4-methyl-N-(4-((4-methylpiperazine-1-yl)methyl)-3-trifluoromethylphenyl)benzamide in deionized water was around 5 mg/mL (see Table 2). A study of sample hygroscopicity showed that at a relative air humidity of 90% the sample absorbed more than ten mass percent of water and thawed in the air. Further development was recognized as being unfeasible due to the high hygroscopicity of this salt form.

Study of Physical and Chemical Properties of a Salt of Hydrogen Bromide and 3-(1,2,4-Triazolo[4,3-a]Pyridine-3-Ylethynyl)-4-Methyl-N-(4-((4-Methylpiperazine-1-Yl)Methyl)-3-Trifluoromethylphenyl)Benzamide (Polymorph Modification II)

A sample (HAL-G-196-8) of a salt of hydrogen bromide and 3-(1,2,4-triazolo[4,3-a]pyridine-3-ylethynyl)-4-methyl-N-(4-((4-methylpiperazine-1-yl)methyl)-3-trifluoromethylphenyl)benzamide obtained via crystallization from a tetrahydrofuran (THF) medium. Based on X-ray powder diffraction (see FIG. 17) the salt was identified as being an individual crystalline phase. The same crystalline phase was obtained when a salt of hydrogen bromide and 3-(1,2,4-triazolo[4,3-a]pyridine-3-ylethynyl)-4-methyl-N-(4-((4-methylpiperazine-1-yl)methyl)-3-trifluoromethylphenyl)benzamide was crystallized from acetone (HAL-G-196-9 sample). The compound structure was confirmed by $^1$H NMR spectroscopy (see FIG. 18). The $^1$H NMR spectra of both HAL-G-196-8 and HAL-G-196-9 contain signals of residual solvents. The anion and cation stoichiometric proportion in the samples HAL-G-196-8 and HAL-G-196-9 was determined using ion chromatography confirmed formation of a monohydrobromide. DSC analysis (see FIG. 19) resulted in identification of one endothermic transition (T=224° C.), which corresponded to sample melting. TG analysis revealed no weight loss of the sample. The apparent solubility of the salt of hydrogen bromide and 3-(1,2,4-triazolo[4,3-a]pyridine-3-ylethynyl)-4-methyl-N-(4-((4-methylpiperazine-1-yl)methyl)-3-trifluoromethylphenyl)benzamide in deionized water was less than 1 mg/mL (see Table 2). Further development was recognized as being unfeasible due to low solubility of this salt.

Figure 23:
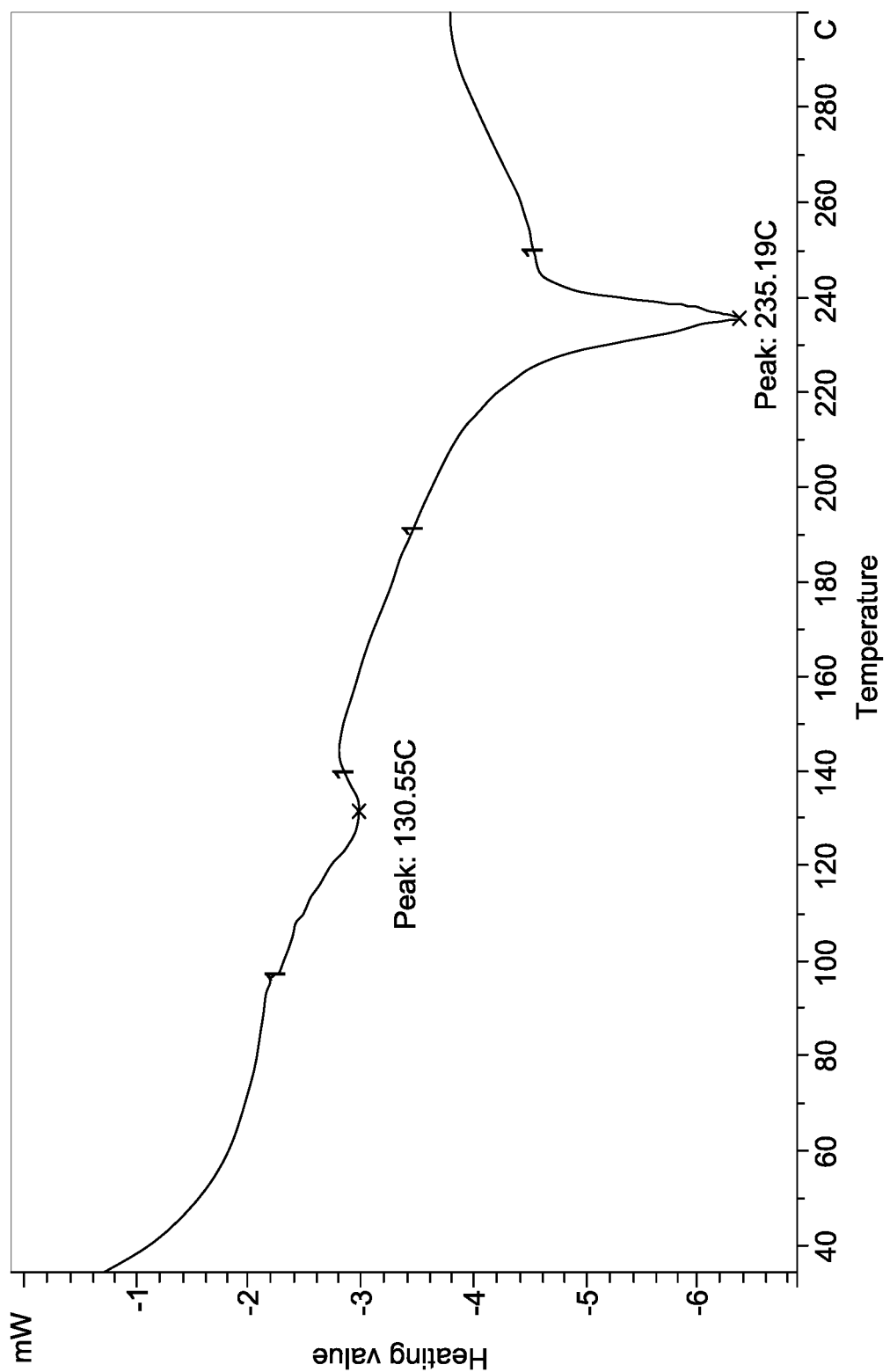
FIG. 23. DSC curve of a sample of the salt of phosphoric acid and 3-(1,2,4-triazolo[4,3-a]pyridine-3-ylethynyl)-4-methyl-N-(4-((4-methylpiperazin-1-yl)methyl)-3-trifluoromethylphenyl)benzamide (sample—HAL-G-196-13).
Figure 24:
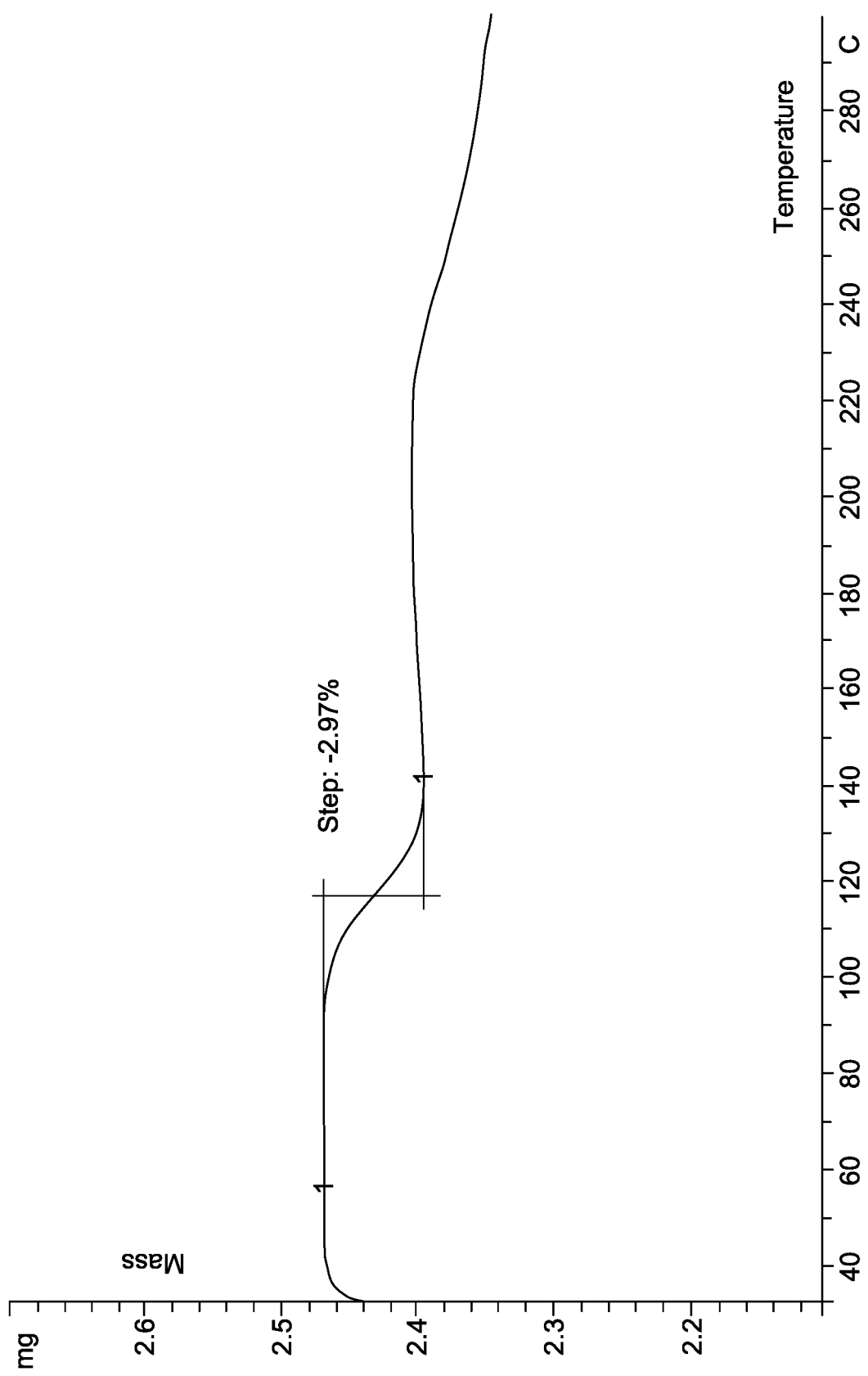
FIG. 24. TGA curve of a sample of the salt of phosphoric acid and 3-(1,2,4-triazolo[4,3-a]pyridine-3-ylethynyl)-4-methyl-N-(4-((4-methylpiperazin-1-yl)methyl)-3-trifluoromethylphenyl)benzamide (sample—HAL-G-196-13).

Study of Physical and Chemical Properties of a Salt of Phosphoric Acid and 3-(1,2,4-Triazolo[4,3-a]Pyridine-3-Ylethynyl)-4-Methyl-N-(4-((4-Methylpiperazine-1-Yl)Methyl)-3-Trifluoromethylphenyl)Benzamide A sample (HAL-G-196-13) of a salt of phosphoric acid and 3-(1,2,4-triazolo[4,3-a]pyridine-3-ylethynyl)-4-methyl-N-(4-((4-methylpiperazine-1-yl)methyl)-3-trifluoromethylphenyl)benzamide was obtained via crystallization from an ethanol medium. Based on X-ray powder diffraction (see FIG. 21), the salt was identified as an individual crystalline phase. The compound structure was confirmed by $^1$H NMR spectroscopy (see FIG. 22). The $^1$H NMR spectrum of the HAL-G-196-13 sample contains signals of residual solvent. The anion and cation stoichiometric proportion determined using ion chromatography confirmed formation of dihydrophosphate salt. DSC analysis (see FIG. 23) resulted in identification of two endothermic transitions—a first one (T=131° C.) corresponding to solvent loss, and a second one (T=235° C.) corresponding to sample melting. During TG analysis, a sample weight loss of 3% was observed, which was probably caused by loss of residual solvent quantities (see FIG. 24). The HAL-G-196-13 sample was identified as probably being a solvate containing ethanol in the crystalline structure, which was confirmed by X-ray powder diffraction data (see FIG. 21). Further development was recognized as being unfeasible due to high solvent content in the crystalline structure of this salt.

Figure 26:
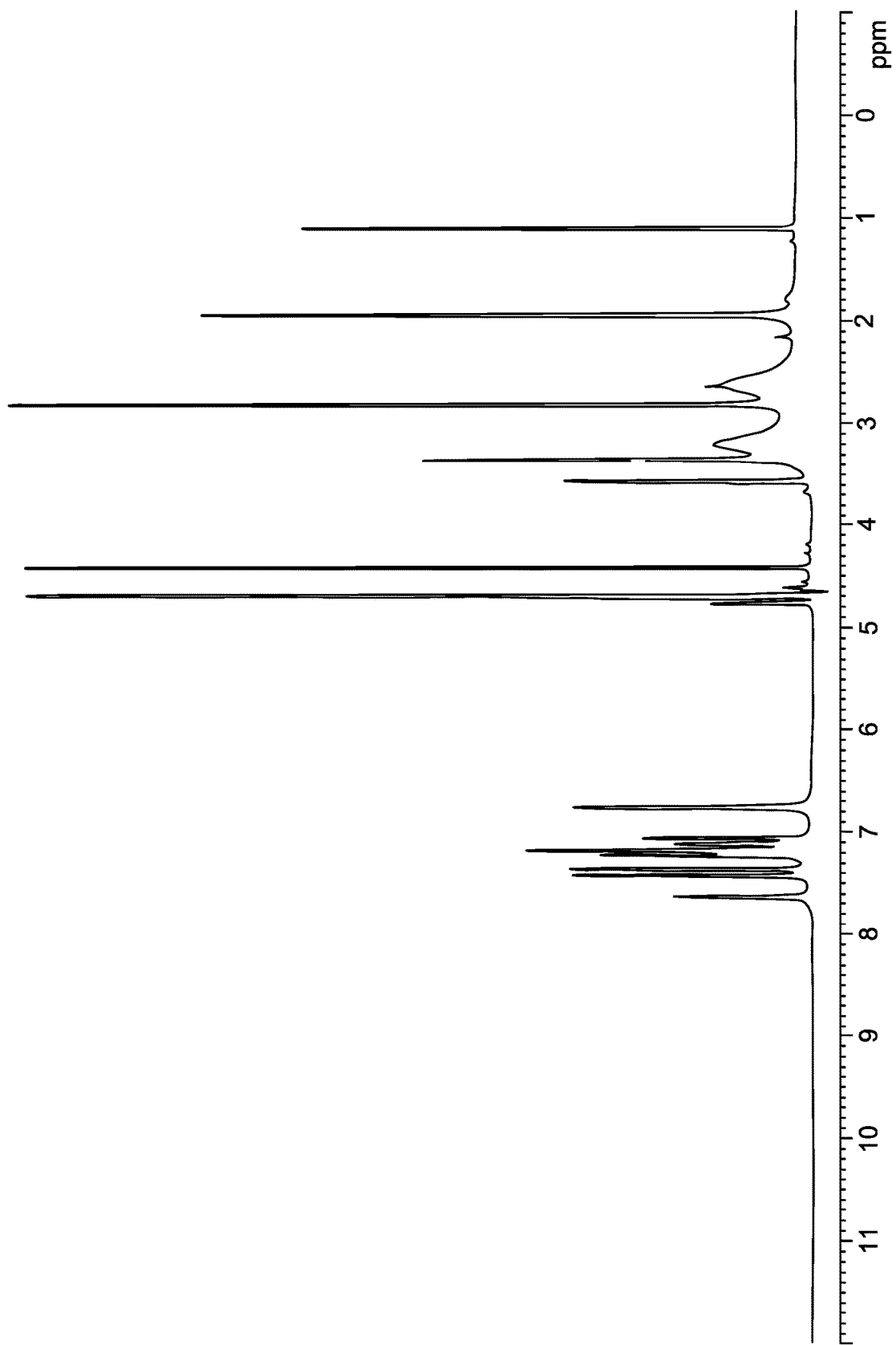
FIG. 26. $^1$H nuclear magnetic resonance spectrum of a sample of the salt of tartaric acid and 3-(1,2,4-triazolo[4,3-a]pyridine-3-ylethynyl)-4-methyl-N-(4-((4-methylpiperazin-1-yl)methyl)-3-trifluoromethylphenyl)benzamide (sample—HAL-G-196-16).

Study of Physical and Chemical Properties of a Salt of Tartaric Acid and 3-(1,2,4-Triazolo[4,3-a]Pyridine-3-Ylethynyl)-4-Methyl-N-(4-((4-Methylpiperazine-1-Yl)Methyl)-3-Trifluoromethylphenyl)Benzamide A sample (HAL-G-196-16) of a salt of tartaric acid and 3-(1,2,4-triazolo[4,3-a]pyridine-3-ylethynyl)-4-methyl-N-(4-((4-methylpiperazine-1-yl)methyl)-3-trifluoromethylphenyl)benzamide was obtained via crystallization from an ethanol medium. Based on X-ray powder diffraction (see FIG. 25), the salt was identified as an individual crystalline phase. The same crystalline phase was obtained when a salt of tartaric acid and 3-(1,2,4-triazolo[4,3-a]pyridine-3-ylethynyl)-4-methyl-N-(4-((4-methylpiperazine-1-yl)methyl)-3-trifluoromethylphenyl)benzam was crystallized from a THF medium (HAL-G-196-17 sample). The compound structure was confirmed by $^1$H NMR spectroscopy (see FIG. 26). The $^1$H NMR spectrum of HAL-G-196-8 and HAL-G-196-9 samples contained signals of residual solvents. The anion and cation stoichiometric proportion in the HAL-G-

196-16 and HAL-G-196-17 samples determined using ion chromatography confirmed formation of a monotartrate for each sample. DSC analysis (see FIG. 27) resulted in identification of one endothermic transition (T=161° C.) corresponding to solvent loss and sample melting. During TG analysis of HAL-G-196-16 sample, a weight loss of 0.8% at a temperature range of 30-100° C. and then an additional weight loss of 0.7% at a temperature range of 130-170° C. were observed, which was probably due to partial degradation of the sample (see FIG. 28). The HAL-G-196-16 sample was identified as probably being a solvate containing ethanol in the crystalline structure, which was confirmed by X-ray powder diffraction data (see FIG. 25). Further development recognized as being unfeasible due to the high solvent content in the crystalline structure of this salt.

Figure 29A:
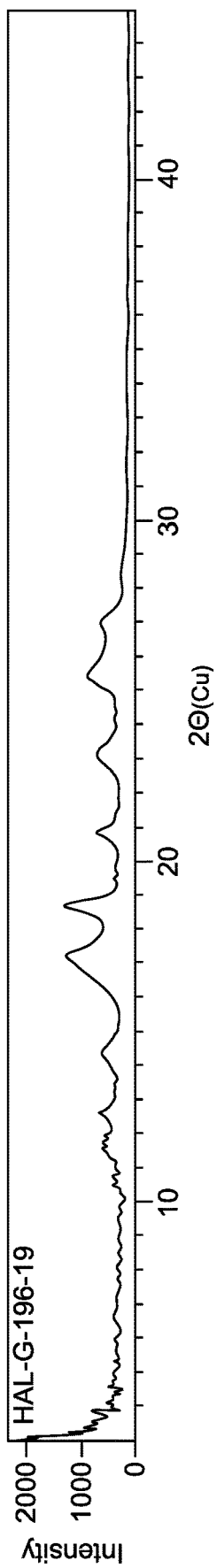
FIGS. 29A-29C. X-ray powder diffraction patterns of the salt of methanesulfonic acid and 3-(1,2,4-triazolo[4,3-a]pyridine-3-ylethynyl)-4-methyl-N-(4-((4-methylpiperazin-1-yl)methyl)-3-trifluoromethylphenyl)benzamide.
Figure 29B:
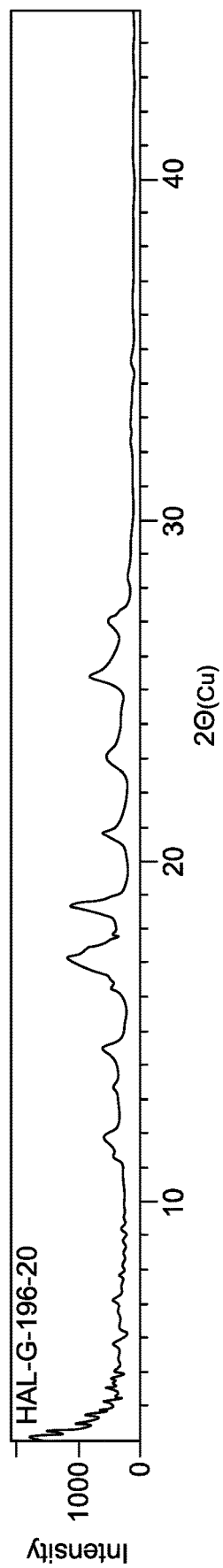
Figure 29C:
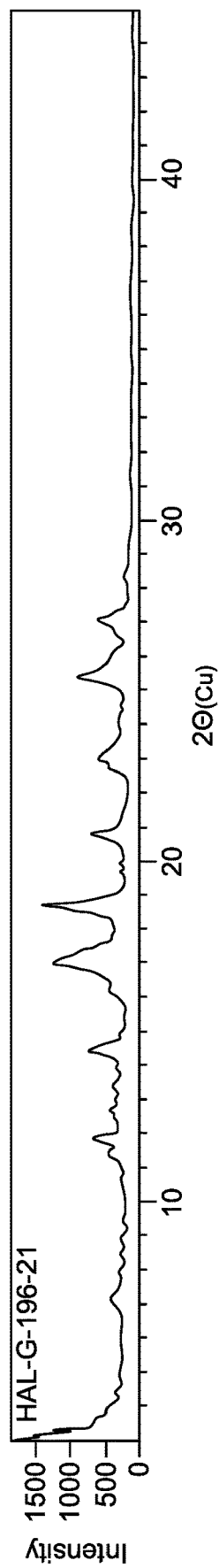
Figure 30:
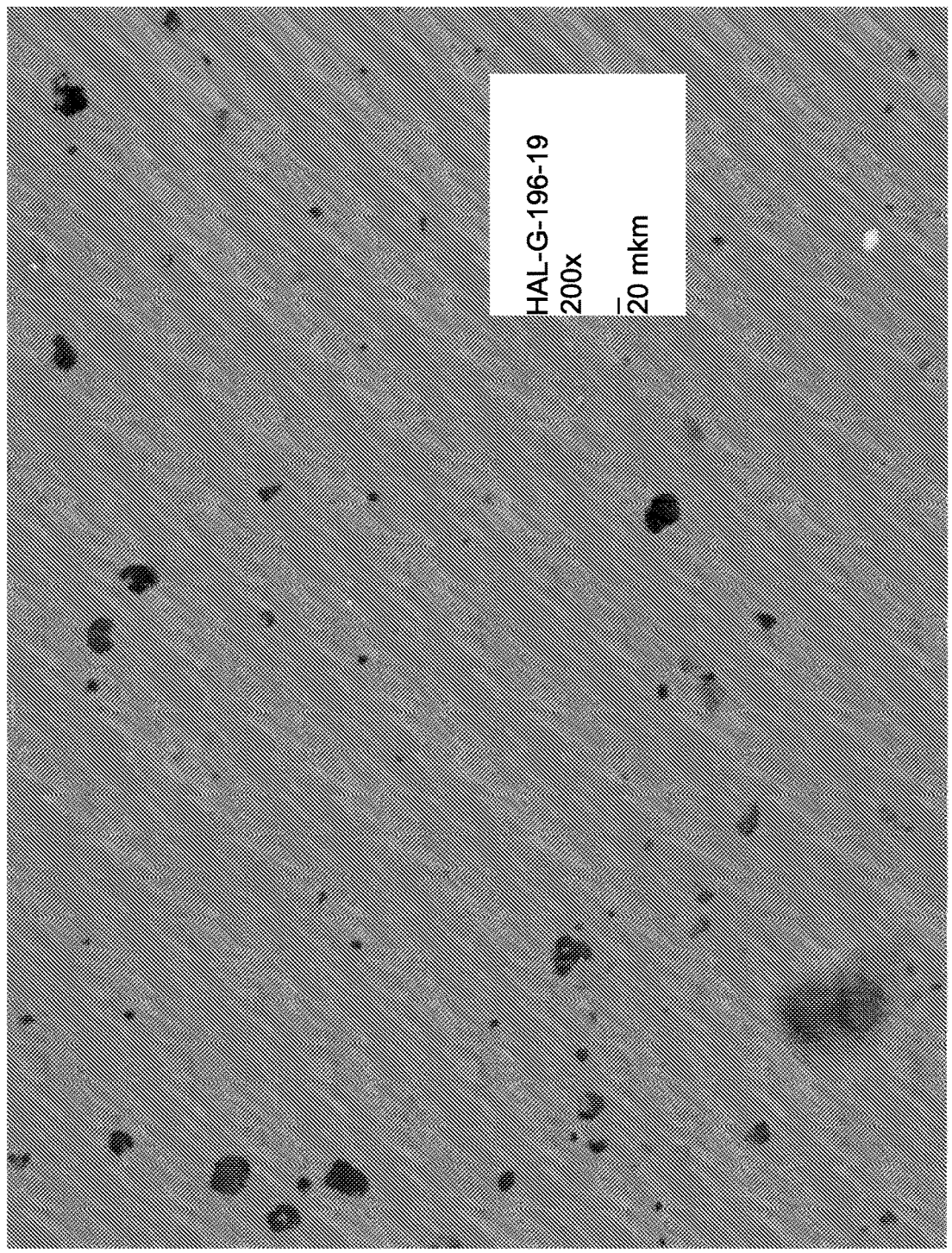
FIG. 30. Photograph of sample crystals of the salt of methanesulfonic acid and 3-(1,2,4-triazolo[4,3-a]pyridine-3-ylethynyl)-4-methyl-N-(4-((4-methylpiperazin-1-yl)methyl)-3-trifluoromethylphenyl)benzamide (sample—HAL-G-196-21) obtained by polarization microscopy.
Figure 31:
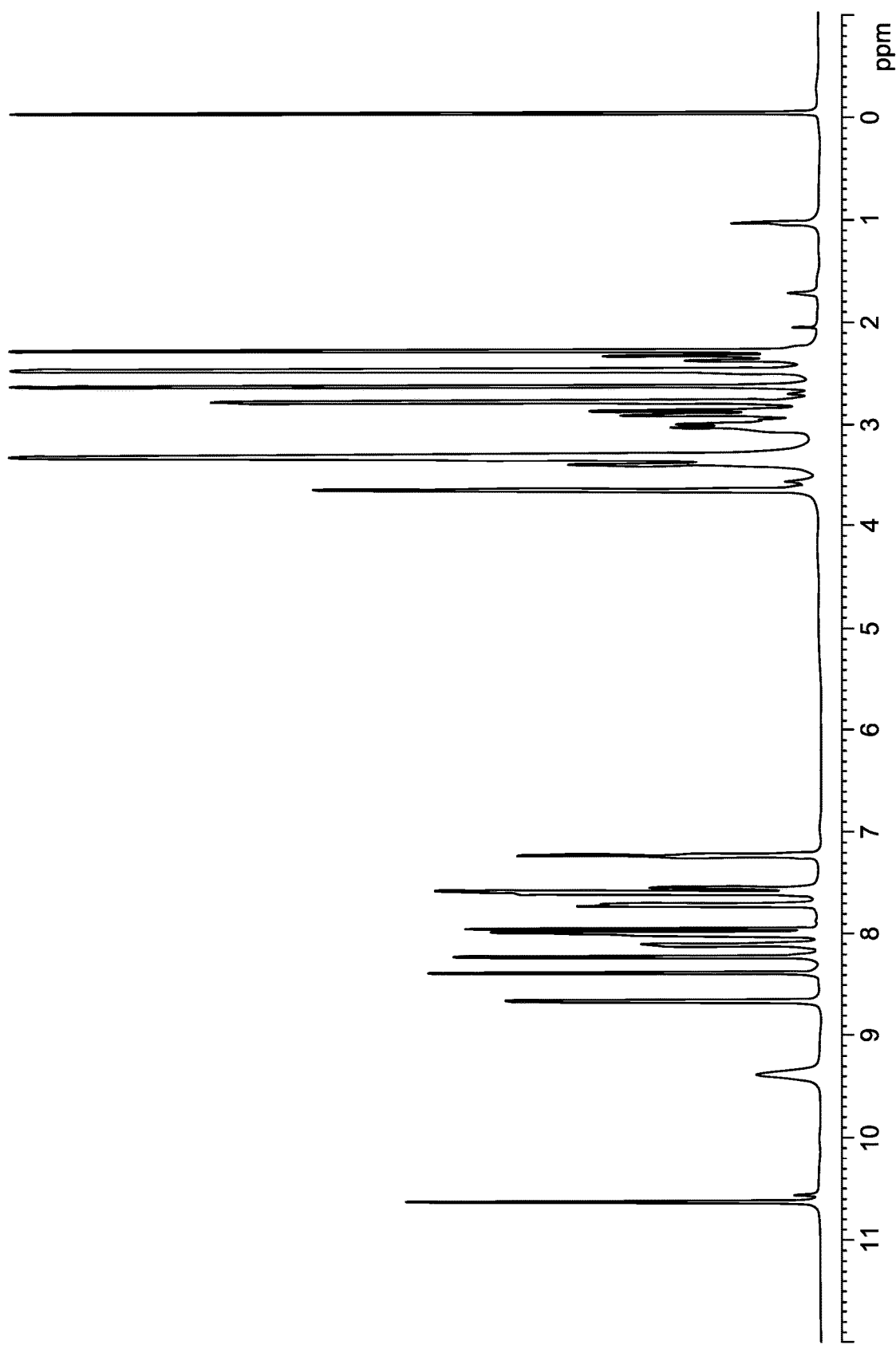
FIG. 31. $^1$H nuclear magnetic resonance spectrum of a sample of the salt of methanesulfonic acid and 3-(1,2,4-triazolo[4,3-a]pyridine-3-ylethynyl)-4-methyl-N-(4-((4- methylpiperazin-1-yl)methyl)-3-trifluoromethylphenyl)benzamide (sample—HAL-G-196-19).

Study of Physical and Chemical Properties a Salt of Methanesulfonic Acid and 3-(1,2,4-Triazolo[4,3-a]Pyridine-3-Ylethynyl)-4-Methyl-N-(4-((4-Methylpiperazine-1-Yl)Methyl)-3-Trifluoromethylphenyl)Benzamide A sample (HAL-G-196-21) of a salt of methanesulfonic acid salt and 3-(1,2,4-triazolo[4,3-a]pyridine-3-ylethynyl)-4-methyl-N-(4-((4-methylpiperazine-1-yl)methyl)-3-trifluoromethylphenyl)benzamide was obtained via crystallization from an acetone medium. Based on X-ray powder diffraction (see FIG. 29), the salt was identified as an individual crystalline phase, which was also confirmed by polarization microscopy (see FIG. 30). The same crystalline phase was obtained when a salt of methanesulfonic acid salt and 3-(1,2,4-triazolo[4,3-a]pyridine-3-ylethynyl)-4-methyl-N-(4-((4-methylpiperazine-1-yl)methyl)-3-trifluoromethylphenyl)benzamide was crystallized from a THF medium (HAL-G-196-20 sample) and an ethanol medium (HAL-G-196-19 sample). The compound structure was confirmed by $^1$H NMR spectroscopy (see FIG. 31). The anion and cation stoichiometric proportion in the HAL-G-196-19, HAL-G-196-20 and HAL-G-196-21 samples was determined using ion chromatography and confirmed formation of a monomesylate for each sample. DSC analysis of these samples (see FIG. 32) resulted in identification of one endothermic transition (T=220° C.) corresponding to sample melting. During TG analysis, no sample weight loss was observed. A study of the hygroscopicity of sample of the salt of methanesulfonic acid and 3-(1,2,4-triazolo[4,3-a]pyridine-3-ylethynyl)-4-methyl-N-(4-((4-methylpiperazine-1-yl)methyl)-3-trifluoromethylphenyl)benzamide showed that, at a relative air humidity of 90%, the sample absorbed less than two mass percent of water. The apparent solubility of the salt of methanesulfonic acid and 3-(1,2,4-triazolo[4,3-a]pyridine-3-ylethynyl)-4-methyl-N-(4-((4-methylpiperazine-1-yl)methyl)-3-trifluoromethylphenyl)benzamide in deionized water was more than 46 mg/mL (see Table 2). The equilibrium solubility of the methanesulfonic acid salt of 3-(1,2,4-triazolo[4,3-a]pyridine-3-ylethynyl)-4-methyl-N-(4-((4-methylpiperazine-1-yl)methyl)-3-trifluoromethylphenyl)benzamide in deionized water was more than 100 mg/mL according to data obtained by HPLC analysis (see Table 3). The content of impurities remained constant when the sample was kept during seven days at a temperature of 60° C. (see Table 4). A study of the stability of the methanesulfonic acid salt of 3-(1,2,4-triazolo[4,3-a]pyridine-3-ylethynyl)-4-methyl-N-(4-((4-methylpiperazine-1-yl)methyl)-3-trifluoromethylphenyl)benzamide treated with a solvent (acetone) during 6 days showed that crystalline structure of the sample remained unchanged (see Table 5). Therefore, the salt of methanesulfonic acid and 3-(1,2,4-triazolo[4,3-a]pyridine-3-ylethynyl)-4-methyl-N-(4-((4-methylpiperazine-1-yl)methyl)-3-trifluoromethylphenyl)benzamide had physical and chemical properties that met the requirements for further development as a salt form.

Study of Physical and Chemical Properties of a Salt of 4-Methylbenzene Sulfonic Acid and 3-(1,2,4-Triazolo[4,3-a]Pyridine-3-Ylethynyl)-4-Methyl-N-(4-((4-Methylpiperazine-1-Yl)Methyl)-3-Trifluoromethylphenyl)Benzamide A sample (HAL-G-196-24) of a salt of 4-methylbenzene sulfonic acid and 3-(1,2,4-triazolo[4,3-a]pyridine-3-ylethynyl)-4-methyl-N-(4-((4-methylpiperazine-1-yl)methyl)-3-trifluoromethylphenyl)benzamide was obtained via crystallization from an acetone medium. Based on X-ray powder diffraction (see FIG. 33) the salt was identified as an individual crystalline phase, which was also confirmed by polarization microscopy (see FIG. 34). The same crystalline phase was obtained when a salt of 4-methylbenzene sulfonic acid and 3-(1,2,4-triazolo[4,3-a]pyridine-3-ylethynyl)-4-methyl-N-(4-((4-methylpiperazine-1-yl)methyl)-3-trifluoromethylphenyl)benzamide was obtained via crystallization from a THF medium (HAL-G-196-23 sample). The compound structure was confirmed by $^1$H NMR spectroscopy (see FIG. 35). The anion and cation stoichiometric proportion in the HAL-G-196-23 and HAL-G-196-24 samples was determined using ion chromatography and confirmed formation of a monotosylate for each sample. DSC analysis of HAL-G-196-24 sample (see FIG. 36) resulted in identification of one endothermic transition (T=184° C.) corresponding to sample melting. During TG analysis, no sample weight loss was observed. A study of sample hygroscopicity showed that at a relative air humidity of 90%, the HAL-G-196-24 sample absorbed less than four mass percent of water (see FIG. 37). The apparent solubility of the salt of 4-methylbenzene sulfonic acid and 3-(1,2,4-triazolo[4,3-a]pyridine-3-ylethynyl)-4-methyl-N-(4-((4-methylpiperazine-1-yl)methyl)-3-trifluoromethylphenyl)benzamide in deionized water was less than 1 mg/mL (see Table 2). The equilibrium solubility of the salt of 4-methylbenzene sulfonic acid and 3-(1,2,4-triazolo[4,3-a]pyridine-3-ylethynyl)-4-methyl-N-(4-((4-methylpiperazine-1-yl)methyl)-3-trifluoromethylphenyl)benzamide in deionized water was 2.2 mg/mL according to data obtained by HPLC analysis (see Table 3). The content of impurities remained constant when the sample was kept during seven days at a temperature of 60° C. (see Table 4). A study of the stability of the salt of 4-methylbenzene sulfonic acid and 3-(1,2,4-triazolo[4,3-a]pyridine-3-ylethynyl)-4-methyl-N-(4-((4-methylpiperazine-1-yl)methyl)-3-trifluoromethylphenyl)benzamide treated with a solvent (acetone) during 6 days showed that crystalline structure of the sample remained unchanged (see Table 5). Therefore, the salt of 4-methylbenzene sulfonic acid and 3-(1,2,4-triazolo[4,3-a]pyridine-3-ylethynyl)-4-methyl-N-(4-((4-methylpiperazine-1-yl)methyl)-3-trifluoromethylphenyl)benzamide had physical and chemical properties met the requirements for further development as a salt form.

Study of Physical and Chemical Properties of a Malic Acid and 3-(1,2,4-Triazolo[4,3-a]Pyridine-3-Ylethynyl)-4-Methyl-N-(4-((4-Methylpiperazine-1-Yl)Methyl)-3-Trifluoromethylphenyl)Benzamide A sample (HAL-G-196-25) of a salt of malic acid and 3-(1,2,4-triazolo[4,3-a]pyridine-3-ylethynyl)-4-methyl-N-

(4-((4-methylpiperazine-1-yl)methyl)-3-trifluoromethylphenyl)benzamide was obtained via crystallization from an ethanol medium. Based on X-ray powder diffraction (see FIG. 38) the salt was identified as an individual crystalline phase. The same crystalline phase of salt of malic acid and 3-(1,2,4-triazolo[4,3-a]pyridine-3-ylethynyl)-4-methyl-N-(4-((4-methylpiperazine-1-yl)methyl)-3-trifluoromethylphenyl)benzamide was obtained via crystallization from a THF medium (HAL-G-196-26 sample). The compound structure was confirmed by $^1$H NMR spectroscopy (see FIG. 39). The anion and cation stoichiometric proportion in the samples HAL-G-196-19, HAL-G-196-25 and HAL-G-196-26 determined using ion chromatography confirmed formation of a monomalate salt for each sample. The $^1$H NMR spectrum of the HAL-G-196-25 sample contains signals of the residual solvent. DSC analysis (see FIG. 40) resulted in identification of two endothermic transitions—the first one (T=128° C.) corresponds to solvent loss and sample melting, the second (T=205° C.) corresponds to subsequent sample degradation. During TG analysis, a sample weight loss of 2% at a temperature range of 80-130° C. was observed, which was probably due to the loss of residual solvent during salt melting (see FIG. 41). Subsequent weight loss is probably associated with degradation of the sample melted. Based on the studies performed it was understood that the HAL-G-196-25 sample was a solvate. Further development was recognized as unfeasible due to the high solvent content of the crystalline structure of this salt.

Study of Physical and Chemical Properties of a Salt of Fumaric Acid and 3-(1,2,4-Triazolo[4,3-a]Pyridine-3-Ylethynyl)-4-Methyl-N-(4-((4-Methylpiperazine-1-Yl)Methyl)-3-Trifluoromethylphenyl)Benzamide (Monofumarate)

A sample (HAL-G-196-28) of a salt of fumaric acid and 3-(1,2,4-triazolo[4,3-a]pyridine-3-ylethynyl)-4-methyl-N-(4-((4-methylpiperazine-1-yl)methyl)-3-trifluoromethylphenyl)benzamide was obtained from an ethanol medium. Based on X-ray powder diffraction (see FIG. 42) the salt was identified as being an individual crystalline phase. The compound structure was confirmed by $^1$H NMR spectroscopy (see FIG. 43). The anion and cation stoichiometric proportion in the HAL-G-196-28 sample determined using ion chromatography confirmed formation of a monofumarate. The $^1$H NMR spectrum of the HAL-G-196-28 sample contains residual solvent signals. DSC analysis (see FIG. 44) resulted in identification of one endothermic transition (T=148° C.) corresponding to solvent loss and salt melting, which is probably accompanied by partial sample degradation. During TG analysis, a sample weight loss of 3.5% at a temperature range of 95-170° C. was observed, which was probably caused by the loss of residual solvent during salt melting (see FIG. 45). Based on the studies performed it was understood that the HAL-G-196-28 sample was a solvate. Further development was recognized as being unfeasible due to the high solvent content in the crystalline structure of this salt.

Study of Physical and Chemical Properties of a Salt of Fumaric Acid and 3-(1,2,4-Triazolo[4,3-a]Pyridine-3-Ylethynyl)-4-Methyl-N-(4-((4-Methylpiperazine-1-Yl)Methyl)-3-Trifluoromethylphenyl)Benzamide (Hemifumarate)

A sample (HAL-G-196-29) of a salt of fumaric acid and 3-(1,2,4-triazolo[4,3-a]pyridine-3-ylethynyl)-4-methyl-N-(4-((4-methylpiperazine-1-yl)methyl)-3-trifluoromethylphenyl)benzamide was obtained via crystallization from a THF medium. Based on X-ray powder diffraction (see FIG. 42) the salt was identified as an individual crystalline phase, which was also confirmed with polarization microscopy (see FIG. 46). The same crystalline phase was identified in samples of a salt of fumaric acid and 3-(1,2,4-triazolo[4,3-a]pyridine-3-ylethynyl)-4-methyl-N-(4-((4-methylpiperazine-1-yl)methyl)-3-trifluoromethylphenyl)benzamide obtained via crystallization from an acetone medium (HAL-G-196-30 sample). The compound structure was confirmed by $^1$H NMR spectroscopy (see FIG. 43). The anion and cation stoichiometric proportion in the HAL-G-196-29 and HAL-G-196-30 samples determined using ion chromatography confirmed formation of a hemifumarate. DSC analysis of HAL-G-196-29 sample (see FIG. 44) resulted in identification of one endothermic transition (T=244° C.) corresponding to solvent loss and sample melting. During TG analysis, a sample weight loss of 1% was observed, which was probably caused by the loss of residual solvent quantities (see FIG. 45). A study of sample hygroscopicity for the salt of fumaric acid and 3-(1,2,4-triazolo[4,3-a]pyridine-3-ylethynyl)-4-methyl-N-(4-((4-methylpiperazine-1-yl)methyl)-3-trifluoromethylphenyl)benzamide showed that at a relative air humidity of 90% the sample absorbed less than four mass percent of water. The apparent solubility of the salt of fumaric acid and 3-(1,2,4-triazolo[4,3-a]pyridine-3-ylethynyl)-4-methyl-N-(4-((4-methylpiperazine-1-yl)methyl)-3-trifluoromethylphenyl)benzamide in deionized water was less than 1 mg/mL (see Table 2). The equilibrium solubility of the salt of fumaric acid and 3-(1,2,4-triazolo[4,3-a]pyridine-3-ylethynyl)-4-methyl-N-(4-((4-methylpiperazine-1-yl)methyl)-3-trifluoromethylphenyl)benzamide in deionized water was $7.4 \times 10^{-3}$ mg/mL according to data obtained by HPLC analysis (see Table 3). The content of impurities remained constant when the sample was kept during seven days at a temperature of 60° C. (see Table 4). A study of the stability of the salt of fumaric acid and 3-(1,2,4-triazolo[4,3-a]pyridine-3-ylethynyl)-4-methyl-N-(4-((4-methylpiperazine-1-yl)methyl)-3-trifluoromethylphenyl)benzamide when treated with a solvent (acetone) during 6 days showed that the crystalline structure of the sample remained unchanged (see Table 5). Therefore, the hemifumarate salt of fumaric acid and 3-(1,2,4-triazolo[4,3-a]pyridine-3-ylethynyl)-4-methyl-N-(4-((4-methylpiperazine-1-yl)methyl)-3-trifluoromethylphenyl)benzamide had physical and chemical properties that met the requirements for further development as a salt form.

Results of Salt Form Identification for 3-(1,2,4-Triazolo[4,3-a]Pyridine-3-Ylethynyl)-4-Methyl-N-(4-((4-Methylpiperazine-1-Yl)Methyl)-3-Trifluoromethylphenyl)Benzamide To sum up, during the course of the investigation to identify salt forms of 3-(1,2,4-triazolo[4,3-a]pyridine-3-ylethynyl)-4-methyl-N-(4-((4-methylpiperazine-1-yl)methyl)-3-trifluoromethylphenyl)benzamide, more than 50 samples of various salt forms, containing 12 counter-ions and obtained with 4 different solvents, were studied. The studies conducted showed that salts of four acids (hydrochloric acid, methanesulfonic acid, 4-methylbenzene sulfonic acid and fumaric acid) had favorable physical and chemical properties, i.e. crystallinity, high solubility in water compared to a free base, as well as high purity upon preparation and temperature stability. In addition, these salts may be manufactured using low-toxicity organic solvents and easily scalable method and contain a pharmacologically acceptable anion.

However, the salts identified surprisingly showed significant differences in terms of their solubility in water: e.g., the solubility of the fumaric acid salt ($7.4 \times 10^{-3}$ mg/mL) was comparable to the free base solubility ($2.3 \times 10^{-4}$ mg/mL); whereas the solubility of the 4-methylbenzene sulfonic acid (2.4 mg/mL), muriatic acid (37.1 mg/mL) and methanesulfonic acid (more than 100 mg/mL) salts had a solubility that was 10,000-fold greater than the solubility of 3-(1,2,4-triazolo[4,3-a]pyridine-3-ylethynyl)-4-methyl-N-(4-((4-methylpiperazine-1-yl)methyl)-3-trifluoromethylphenyl)benzamide in the form of a free base. However, only the methanesulfonic acid salt may be obtained via crystallization from acetone or ethanol without addition of methyl tert-butyl ether or additional cooling of the solution below room temperature.

Thus, the preferable crystalline salt form of 3-(1,2,4-triazolo[4,3-a]pyridine-3-ylethynyl)-4-methyl-N-(4-((4-methylpiperazine-1-yl)methyl)-3-trifluoromethylphenyl)benzamide, which may be obtained in low-toxic organic solvents using an easily scalable method and which contains a pharmacologically acceptable anion having crystallinity and is high solubility in water, was identified as the methanesulfonic acid salt of 3-(1,2,4-triazolo[4,3-a]pyridine-3-ylethynyl)-4-methyl-N-(4-((4-methylpiperazine-1-yl)methyl)-3-trifluoromethylphenyl)benzamide.

Obtaining and Description of Polymorphous Modifications of Methanesulfonic Acid Salt and 3-(1,2,4-Triazolo[4,3-a]Pyridine-3-Ylethynyl)-4-Methyl-N-(4-((4-Methylpiperazine-1-Yl)Methyl)-3-Trifluoromethylphenyl)Benzamide Examples For the purpose of further study of the methanesulfonic acid salt of 3-(1,2,4-triazolo[4,3-a]pyridine-3-ylethynyl)-4-methyl-N-(4-((4-methylpiperazine-1-yl)methyl)-3-trifluoromethylphenyl)benzamide, the method of its preparation has been developed. During method development it was found that the methanesulfonic acid salt of 3-(1,2,4-triazolo[4,3-a]pyridine-3-ylethynyl)-4-methyl-N-(4-((4-methylpiperazine-1-yl)methyl)-3-trifluoromethylphenyl)benzamide could exist in two polymorphous modifications. Differences in formation these phases we revealed can be summarized by saying that in some cases, when the methanesulfonic acid salt of 3-(1,2,4-triazolo[4,3-a]pyridine-3-ylethynyl)-4-methyl-N-(4-((4-methylpiperazine-1-yl)methyl)-3-trifluoromethylphenyl)benzamide was prepared in acetone, a precipitate did not form spontaneously. Upon crystallization of the salt out of a more concentrated solution it was found that a combination of phases or any individual phase may be formed. X-ray powder diffraction method was applied to both polymorphous modifications to study structure crystallinity. Diffraction patterns of samples of the methanesulfonic acid salt of 3-(1,2,4-triazolo[4,3-a]pyridine-3-ylethynyl)-4-methyl-N-(4-((4-methylpiperazine-1-yl)methyl)-3-trifluoromethylphenyl)benzamide samples were obtained at 25° C. (±5° C.) and relative air humidity of ≈70% using X-ray powder diffractometer Bruker D8 Advance in Bragg-Brentano geometry (anode voltage of 40 kV, currency of 40 mA) equipped with nickel filter (radiation CuKα1, wave length=1.5406 Å) and position-sensitive detector LynxEye, survey step of 0.02° 2θ, angle range of 4-65° 2θ. Diffraction patterns obtained were studied in detail using Bruker TOPAS5 software package.

Synthesis of the Methanesulfonic Acid Salt of 3-(1,2,4-Triazolo[4,3-a]Pyridine-3-Ylethynyl)-4-Methyl-N-(4-((4-Methylpiperazine-1-Yl)Methyl)-3-Trifluoromethylphenyl)Benzamide (Polymorphous Modification I)

A suspension of 3-(1,2,4-triazolo[4,3-a]pyridine-3-ylethynyl)-4-methyl-N-(4-((4-methylpiperazine-1-yl)methyl)-3-trifluoromethylphenyl)benzamide (53.2 g, 0.10 mol) in acetone (1,050 mL, in the amount of 20 mL per gram) was heated to boiling and boiled for 10 minutes with vigorous stirring. Then, while continuing to heat and stir the mixture, a freshly prepared (immediately before adding) solution of methanesulfonic acid (10.1 g, 0.105 mol) in 200 mL of ethanol (quantity of ethanol is calculated in a way that concentration of the solution obtained was 0.5 mol/L) was added in a single portion. The resulting reaction mixture was boiled for 15 minutes, then cooled to 20° C. at the rate of approximately 10° C./hour, then left to stand for 12 hours at a temperature of +10° C. to allow crystallization and formation of a precipitate. The precipitate was collected by filtration, washed with acetone (3×150 mL) and dried to constant mass in a cabinet at a temperature of 60° C. Yield: 85-90%.

NMR $^1$H (500 MHz, DMSO-$d_6$) spectrum: 2.36-2.45 (m, 1H, $H_{piperazine}$), 2.41 (C, 3H, Me), 2.67 (C, 3H, Me), 2.86 (C, 3H, Me), 2.94 (d, J=11.2 Hz, 1H, $H_{piperazine}$), 3.08 (t, J=10.7 Hz, 1H, $H_{piperazine}$), 2.94 (d, J=10.7 Hz, 1H, $H_{piperazine}$), 4.06 (C, 2H, $CH_{2(benzyl)}$), 7.24 (t, J=6.8 Hz, 1H, $H_{(arom.)}$), 7.53-7.63 (m, 2H, $H_{(arom.)}$), 7.73 (d, J=8.6 Hz, 1H, $H_{(arom.)}$), 7.96 (d, J=9.2 Hz, 1H, $H_{(arom.)}$), 8.03 (dd, $J_1$=8.6 Hz, $J_2$=1.6 Hz, 1H, $H_{(arom.)}$), 8.12 (d, J=8.6 Hz, 1H, $H_{(arom.)}$), 8.25 (C, 1H, $H_{(arom.)}$), 8.40 (C, 1H, $H_{(arom.)}$), 8.65 (d, J=6.8 1H, $H_{(arom.)}$), 10.60 (c, 1H, $NH_{amide}$).

Mass-spectrum, m/z: 533.2263

NMR $^1$H and $^{13}$C spectra of the methanesulfonic acid salt of 3-(1,2,4-triazolo[4,3-a]pyridine-3-ylethynyl)-4-methyl-N-(4-((4-methylpiperazine-1-yl)methyl)-3-trifluoromethylphenyl)benzamide (polymorphous modification I) are given in FIG. 47.

Synthesis of Methanesulfonic Acid Salt and 3-(1,2,4-Triazolo[4,3-a]Pyridine-3-Ylethynyl)-4-Methyl-N-(4-((4-Methylpiperazine-1-Yl)Methyl)-3-Trifluoromethylphenyl)Benzamide (Polymorphous Modification II)

A suspension of 3-(1,2,4-triazolo[4,3-a]pyridine-3-ylethynyl)-4-methyl-N-(4-((4-methylpiperazine-1-yl)methyl)-3-trifluoromethylphenyl)benzamide (17.73 g, 0.033 mol) in 350 mL of acetone was heated to boiling and boiled for 10 minutes with vigorous stirring. Then, while continuing to heat and stir the mixture, a freshly prepared (immediately before adding) solution of methanesulfonic acid (3.36 g, 0.035 mol) in 70 mL of ethanol was added. The reaction mixture was boiled for 15 minutes, then cooled to 20° C.; no precipitate formed. The solution was evaporated at low pressure to the half of the initial volume and allowed to stand for 24 hours at a temperature of 20-25° C. The precipitate that formed was collected by filtration, washed through with acetone (3×150 mL) and dried to constant mass in a cabinet at a temperature of 45° C. Yield: 85-90%.

NMR $^1$H (500 MHz, DMSO-d$_6$) spectrum: 2.35-2.43 (m, 1H, H$_{piperazine}$), 2.41 (c, 3H, Me), 2.66 (c, 3H, Me), 2.87 (c, 3H, Me), 2.95 (d, J=11.3 Hz, 1H, H$_{piperazine}$), 3.10 (t, J=10.5 Hz, 1H, H$_{piperazine}$), 2.94 (d, J=10.5 Hz, 1H, H$_{piperazine}$), 4.05 (c, 2H, CH$_{2(benzyl)}$), 7.26 (t, J=6.9 Hz, 1H, H$_{(arom.)}$), 7.52-7.61 (m, 2H, H$_{(arom.)}$), 7.73 (d, J=8.6 Hz, 1H, H$_{(arom.)}$), 7.96 (д, J=9.1 Hz, 1H, H$_{(arom.)}$), 8.03 (dd, J$_1$=8.6 Hz, J$_2$=1.6 Hz, 1H, H$_{(arom.)}$), 8.12 (d, J=8.6 Hz, 1H, H$_{(arom.)}$), 8.27 (C, 1H, H$_{(arom.)}$), 8.41 (C, 1H, H$_{(arom.)}$), 8.65 (d, J=6.9 1H, H$_{(arom.)}$) 10.62 (C, 1H, NH$_{amide}$).

Mass-spectrum, m/z: 533.2268.

NMR $^1$H and $^{13}$C spectra of the methanesulfonic acid salt of 3-(1,2,4-triazolo[4,3-a]pyridine-3-ylethynyl)-4-methyl-N-(4-((4-methylpiperazine-1-yl)methyl)-3-trifluoromethylphenyl)benzamide (polymorphous modification I) are given in FIG. 48.

Study of Crystallinity of Methanesulfonic Acid Salt and 3-(1,2,4-Triazolo[4,3-a]Pyridine-3-Ylethynyl)-4-Methyl-N-(4-((4-Methylpiperazine-1-Yl)Methyl)-3-Trifluoromethylphenyl)Benzamide (Polymorphous Modification I)

The methanesulfonic acid salt of 3-(1,2,4-triazolo[4,3-a]pyridine-3-ylethynyl)-4-methyl-N-(4-((4-methylpiperazine-1-yl)methyl)-3-trifluoromethylphenyl)benzamide (polymorphous modification I) was an individual crystalline phase with the following unit cell parameters: a=51.46±0.05 Å; b=7.81±0.05 Å and c=7.63±0.05 Å, β=108.9±0.1°, V=2898.9±0.5 Å$^3$. P2$_1$/n space group. The volume of the independent part corresponded to one formula unit (see FIG. 49A). Positions and intensities of characteristic, visually distinguishable peaks on a Debye powder diagram of the sample are given in Table 6. The general appearance of the independent part of the unit cell of methanesulfonic acid salt and 3-(1,2,4-triazolo[4,3-a]pyridine-3-ylethynyl)-4-methyl-N-(4-((4-methylpiperazine-1-yl)methyl)-3-trifluoromethylphenyl)benzamide in polymorphous modification I, are given in FIG. 50A.

TABLE 6

Positions and intensities of characteristic, visually distinguishable peaks on a Debye powder diagram of a sample of methanesulfonic acid salt and 3-(1,2,4-triazolo[4,3-a]pyridine-3-ylethynyl)-4-methyl-N-(4-((4-methylpiperazine-1-yl)methyl)-3-trifluoromethylphenyl)benzamide (polymorphous modification I).

| Peak position (2θ) | Relative intensity | Peak position (2θ) | Relative intensity | Peak position (2θ) | Relative intensity |
|---|---|---|---|---|---|
| 1 | 2 | 3 | 4 | 5 | 6 |
| 3.6 | 10.9 | 25.4 | 68.6 | 40.2 | 3.7 |
| 7.2 | 8.0 | 25.9 | 17.9 | 40.5 | 1.2 |
| 10.8 | 4.6 | 26.0 | 14.0 | 40.9 | 0.7 |
| 11.4 | 9.0 | 26.2 | 11.3 | 41.9 | 3.8 |
| 11.8 | 19.3 | 26.4 | 4.2 | 42.2 | 2.2 |
| 12.5 | 8.9 | 26.7 | 14.3 | 42.4 | 2.3 |
| 12.9 | 1.3 | 27.1 | 41.9 | 42.7 | 1.5 |
| 13.4 | 7.3 | 28.0 | 2.1 | 44.0 | 0.6 |
| 14.5 | 42.8 | 28.0 | 2.1 | 44.5 | 1.8 |
| 14.9 | 4.4 | 28.4 | 7.2 | 45.8 | 1.7 |
| 16.2 | 19.2 | 29.2 | 3.2 | 46.9 | 2.4 |
| 16.5 | 9.9 | 30.0 | 2.6 | 47.2 | 1.4 |
| 16.9 | 66.7 | 30.4 | 1.7 | 47.6 | 1.4 |
| 17.2 | 42.2 | 31.4 | 3.3 | 47.9 | 1.3 |
| 17.4 | 30.3 | 31.6 | 1.6 | 48.3 | 2.6 |
| 17.8 | 7.3 | 32.1 | 2.8 | 48.8 | 1.8 |
| 18.1 | 6.3 | 32.5 | 1.5 | 49.4 | 1.1 |
| 18.4 | 13.0 | 33.0 | 5.4 | 50.3 | 1.7 |

TABLE 6-continued

Positions and intensities of characteristic, visually distinguishable peaks on a Debye powder diagram of a sample of methanesulfonic acid salt and 3-(1,2,4-triazolo[4,3-a]pyridine-3-ylethynyl)-4-methyl-N-(4-((4-methylpiperazine-1-yl)methyl)-3-trifluoromethylphenyl)benzamide (polymorphous modification I).

| Peak position (2θ) | Relative intensity | Peak position (2θ) | Relative intensity | Peak position (2θ) | Relative intensity |
|---|---|---|---|---|---|
| 18.7 | 100.0 | 33.3 | 5.4 | 51.1 | 0.9 |
| 19.3 | 1.4 | 33.6 | 1.8 | 51.4 | 2.0 |
| 19.7 | 4.2 | 34.2 | 1.9 | 52.2 | 0.9 |
| 20.3 | 2.8 | 34.5 | 2.4 | 52.5 | 1.3 |
| 20.8 | 49.7 | 34.9 | 1.3 | 53.5 | 1.2 |
| 21.4 | 9.4 | 35.4 | 4.7 | 53.9 | 1.5 |
| 21.8 | 1.6 | 35.8 | 0.9 | 54.4 | 0.6 |
| 22.7 | 17.3 | 36.1 | 1.8 | 54.8 | 0.9 |
| 22.8 | 14.4 | 36.3 | 3.5 | 55.0 | 0.8 |
| 23.0 | 25.4 | 36.7 | 5.7 | 55.4 | 1.0 |
| 23.2 | 17.0 | 37.1 | 3.5 | 55.9 | 1.2 |
| 23.4 | 12.3 | 37.9 | 0.6 | 56.2 | 0.8 |
| 23.6 | 4.2 | 38.4 | 2.5 | 56.4 | 0.9 |
| 23.8 | 2.5 | 38.7 | 1.1 | 57.2 | 1.3 |
| 24.1 | 11.3 | 38.9 | 1.8 | 59.4 | 0.9 |
| 24.5 | 7.9 | 39.4 | 1.6 | | |

Intensities are peak heights (with a background adjustment). Positions correspond to maxima on the diffraction pattern, not to reflection positions.

Ancillary Tests of Crystallinity of Salt Methanesulfonic Acid and 3-(1,2,4-Triazolo[4,3-a]Pyridine-3-Ilethynyl)-4-Methyl-N-(4-((4-Methylpiperazin-1-Yl)Methyl)-3-Trifluoromethylphenyl)Benzamide (Polymorphic Modification I)

It is well known that purity of samples, the size of crystallites, presence of micro-stresses in the studies sample and a range of other factors can produce significant influence on positions and intensity of characteristic, visually distinctive peaks in the Debye powder diagram of the studied samples. For specification of the type of Debye powder diagram, in particular, for specification of the position and intensity of characteristic, visually distinctive peaks, ancillary tests were carried out on the samples of salt methanesulfonic acid and 3-(1,2,4-triazolo[4,3-a]pyridine-3-ilethynyl)-4-methyl-N-(4-((4-methylpiperazin-1-yl)methyl)-3-trifluoromethylphenyl)benzamide (polymorphic modification I). Receipt of Debye powder diagrams was performed with the use of different geometry of survey: x-ray transmittance and Bragg-Brentano's geometry. Positions and intensity of characteristic, visually distinctive peaks in the Debye powder diagram of the sample are presented in the table 7 and 8.

TABLE 7

Positions and intensities of characteristic, visually distinctive peaks in the Debye powder diagram of the sample of salt methanesulfonic acid and 3-(1,2,4-triazolo[4,3-a]pyridine-3-ilethynyl)-4-methyl-N-(4-((4-methylpiperazin-1-yl)methyl)-3-trifluoromethylphenyl)benzamide (sample No. 2, polymorphic modification I).

| Transmittance λ = 1.540596 Å | | Bragg-Brentano λ = 1.5418 Å | |
|---|---|---|---|
| Peak position (2θ) | Relative intensity, % | Peak position (2θ) | Relative intensity, % |
| 3.6 | 8.1 | | |
| 7.2 | 6.1 | 7.3 | 9.4 |
| 10.8 | 4.3 | 10.9 | 6.7 |

TABLE 7-continued

Positions and intensities of characteristic, visually distinctive peaks in the Debye powder diagram of the sample of salt methanesulfonic acid and 3-(1,2,4-triazolo[4,3-a]pyridine-3-ilethynyl)-4-methyl-N-(4-((4-methylpiperazin-1-yl)methyl)-3-trifluoromethylphenyl)benzamide (sample No. 2, polymorphic modification I).

| Transmittance λ = 1.540596 Å | | Bragg-Brentano λ = 1.5418 Å | |
|---|---|---|---|
| Peak position (2θ) | Relative intensity, % | Peak position (2θ) | Relative intensity, % |
| 11.4 | 10 | 11.5 | 7.6 |
| 11.6 | 6.9 | 11.7 | 3 |
| 11.8 | 18 | 11.9 | 15 |
| 12.5 | 10.1 | 12.6 | 8.6 |
| 13.4 | 5.9 | 13.5 | 6.1 |
| 14.5 | 40 | 14.5 | 50.7 |
| 14.9 | 3.9 | 15 | 4.4 |
| 16.2 | 20.4 | 16.2 | 15.9 |
| 16.5 | 12.4 | 16.6 | 8.7 |
| 16.6 | 15 | 16.7 | 11.6 |
| 16.9 | 67.4 | 17.0 | 79.3 |
| 17.2 | 43.9 | 17.2 | 41.8 |
| 17.4 | 28.7 | 17.5 | 33.5 |
| 18.4 | 13.3 | 18.5 | 13.2 |
| 18.7 | 100 | 18.8 | 100 |
| 19.7 | 4.0 | 19.8 | 4.6 |
| 20.8 | 49.5 | 20.9 | 52 |
| 21.4 | 8.8 | 21.5 | 11.6 |
| 22.7 | 20.0 | 22.8 | 18.2 |
| 23.0 | 25.6 | 23.0 | 24.5 |
| 23.2 | 19.7 | 23.3 | 20.3 |
| 23.4 | 12.6 | 23.5 | 16.1 |
| 24.1 | 11.5 | 24.2 | 11.4 |
| 24.5 | 8.2 | 24.6 | 9.2 |
| 25.4 | 77.3 | 25.5 | 78.6 |
| 25.9 | 21.0 | 26.0 | 20.1 |
| 26.0 | 14.8 | 26.1 | 17.6 |
| 26.7 | 15.3 | 26.8 | 16.7 |
| 27.1 | 46.8 | 27.2 | 51.3 |
| 28.4 | 8.9 | 28.5 | 8.8 |
| 29.2 | 3.4 | 29.3 | 4.3 |
| 31.4 | 3.2 | 31.4 | 3.6 |
| 32.9 | 6.0 | 33.0 | 6.9 |
| 33.4 | 6.0 | 33.4 | 5.4 |
| 35.4 | 4.8 | 35.5 | 4.7 |
| 36.7 | 6.3 | 36.8 | 8.1 |
| 40.2 | 4.2 | 40.3 | 4.1 |

Intensities are the heights (background corrected) of the peaks. Positions correspond to the maximum values on the X-ray diffraction pattern, not to estimated positions of reflections.

As it is obvious from the data provided in the table 7, use of various survey geometries does not influence much on the positions and intensity of peaks in the Debye powder diagram.

Small size of crystallites and presence of micro-stresses in the sample PF114-56-MsOH leads to strong widening of the lines and distortion of its X-ray diffraction pattern in contrast to the sample No. 2 (see table 8). Besides, X-ray diffraction pattern of the sample No. 3 shows the peak of impurity, the volumetric ratio of which (assessed according to the ratio between intensities of impurities' peaks and the major phase) amounts to 5%.

TABLE 8

Positions and intensities of characteristic, visually distinctive peaks in the Debye powder diagram of the sample of salt methanesulfonic acid and 3-(1,2,4-triazolo[4,3-a]pyridine-3-ilethynyl)-4-methyl-N-(4-((4-methylpiperazin-1-yl)methyl)-3-trifluoromethylphenyl)benzamide (sample No. 3, polymorphic modification I).

| Transmittance λ = 1.540596 Å | | Bragg-Brentano λ = 1.5418 Å | |
|---|---|---|---|
| Peak position (2θ) | Relative intensity, % | Peak position (2θ) | Relative intensity, % |
| 7.2 | 6.0 | 7.3 | 4.1 |
| 9.0 | 4.2 | 10.9 | 4.3 |
| 9.7 | 2.8 | 11.5 | 7.3 |
| 10.8 | 4.3 | 12.0 | 13.0 |
| 11.4 | 9.4 | 12.6 | 8.7 |
| 11.8 | 14.4 | 13.5 | 4.8 |
| 12.5 | 10.5 | 14.6 | 40.0 |
| 13.4 | 5.4 | 15.0 | 3.9 |
| 14.4 | 41.2 | 16.3 | 16.0 |
| 16.1 | 23.0 | 17.0 | 67.6 |
| 16.9 | 70.7 | 17.3 | 37.4 |
| 17.1 | 41.1 | 15.5 | 28.4 |
| 17.4 | 31.2 | 18.5 | 11.0 |
| 18.7 | 100.0 | 18.8 | 100.0 |
| 20.8 | 52.7 | 20.9 | 52.9 |
| 21.4 | 11.2 | 21.5 | 10.3 |
| 22.9 | 23.5 | 23.1 | 25.7 |
| 23.2 | 19.5 | 23.3 | 20.2 |
| 24.1 | 10.7 | 24.2 | 9.9 |
| 24.5 | 10.2 | 24.6 | 8.7 |
| 25.4 | 72.5 | 25.5 | 78.0 |
| 27.0 | 48.2 | 27.2 | 57.2 |

Intensities are the heights (background corrected) of the peaks. Positions correspond to the maximum values on the X-ray diffraction pattern, not to estimated positions of reflections.

Comparison of X-ray diffraction patterns of different samples allowed to determine peaks characteristic for all samples and analyze possible variations in the positions and intensities of peaks (see table 9).

TABLE 9

Positions and intensities of characteristic, visually distinctive peaks in the Debye powder diagram of the sample of salt methanesulfonic acid and 3-(1,2,4-triazolo[4,3-a]pyridine-3-ilethynyl)-4-methyl-N-(4-((4-methylpiperazin-1-yl)methyl)-3-trifluoromethylphenyl)benzamide (polymorphic modification I).

| Peak position (2θ) | | | Relative intensity, % | | |
|---|---|---|---|---|---|
| Average value | Minimum | Maximum | Average value | Minimum | Maximum |
| 18.7 | 18.7 | 18.8 | 100.0 | 100.0 | 100.0 |
| 25.4 | 25.4 | 25.5 | 75.0 | 68.6 | 78.6 |
| 16.9 | 16.9 | 17.0 | 70.3 | 66.7 | 79.3 |
| 20.8 | 20.8 | 20.9 | 51.4 | 49.5 | 52.9 |
| 27.1 | 27.0 | 27.2 | 49.1 | 41.9 | 57.2 |
| 14.5 | 14.4 | 14.6 | 42.9 | 40.0 | 50.7 |
| 17.2 | 17.1 | 17.3 | 41.3 | 37.4 | 43.9 |
| 17.4 | 17.4 | 17.5 | 30.4 | 28.4 | 33.5 |
| 23.2 | 23.1 | 23.3 | 20.4 | 17.0 | 25.7 |
| 16.2 | 16.1 | 16.3 | 18.9 | 15.9 | 23.0 |
| 11.9 | 11.8 | 12.0 | 15.9 | 13.0 | 19.3 |
| 24.1 | 24.1 | 24.2 | 11.0 | 9.9 | 11.5 |
| 21.4 | 21.4 | 21.5 | 10.3 | 8.8 | 11.6 |
| 12.5 | 12.5 | 12.6 | 9.3 | 8.6 | 10.5 |
| 24.6 | 24.5 | 24.6 | 8.8 | 7.9 | 10.2 |
| 7.2 | 7.2 | 7.3 | 6.9 | 4.1 | 9.4 |
| 13.4 | 13.4 | 13.5 | 5.9 | 4.8 | 7.3 |

Intensities are the heights (background corrected) of the peaks. Positions correspond to the maximum values on the X-ray diffraction pattern, not to estimated positions of reflections.

The most informative region of the X-ray powder diffraction patterns is the low-angle region of 2θ. In this region the position of reflections significantly differ, while upon enlargement of diffraction angles, the number of peaks increases and their overlapping becomes material. Angles region which can be considered representative depends on the values of the unit cell parameters of the studied compound; for researched organic compounds with 5-50 A cell parameters, the interlayer distance range 3-30 Å can be considered as the representative region. In such case, the diffraction angles range will be equal to 3-25° 2θ. Therefore, for characterization of salt methanesulfonic acid and 3-(1, 2,4-triazolo[4,3-a]pyridine-3-ilethynyl)-4-methyl-N-(4-((4-methylpiperazin-1-yl)methyl)-3-trifluoromethylphenyl)benzamide in polymorphic modification I, it is possible to use peaks at diffraction angles (2θ) 14.5, 16.9, 17.2, 17.4, 18.7, 20.8, 23.2 with relative intensity 20% and higher.

As one can see from the data provided in the table 9, all peaks at diffraction angles (2θ) 14.5, 16.9, 17.2, 18.7, 20.8 have relative intensities higher than 20%. However, the intensities of such peaks can vary essentially depending on the survey method, purity of samples, size of salt crystals, effects of sample texturing and a range of other parameters. Due to this reason, in the X-ray diffraction pattern of salt methanesulfonic acid and 3-(1,2,4-triazolo[4,3-a]pyridine-3-ilethynyl)-4-methyl-N-(4-((4-methylpiperazin-1-yl)methyl)-3-trifluoromethylphenyl)benzamide in polymorphic modification I some peaks at diffraction angles (2θ) 14.5, 16.9, 17.2, 17.4, 18.7, 20.8, 23.2 can gave the intensity below 20%. Therefore, for characterization of salt methanesulfonic acid and 3-(1,2,4-triazolo[4,3-a]pyridine-3-ilethynyl)-4-methyl-N-(4-((4-methylpiperazin-1-yl)methyl)-3-trifluoromethylphenyl)benzamide in polymorphic modification I, it is possible to use two, three or four peaks with relative intensity 20% or higher at diffraction angles (2θ) selected from 14.5, 16.9, 17.2, 17.4, 18.7, 20.8, 23.2.

It is obvious from analysis of peaks of X-ray diffraction pattern obtained in the process of surveying different samples of salt methanesulfonic acid and 3-(1,2,4-triazolo[4,3-a]pyridine-3-ilethynyl)-4-methyl-N-(4-((4-methylpiperazin-1-yl)methyl)-3-trifluoromethylphenyl)benzamide (polymorphic modification I), that the peak at diffraction angle (2θ) 18.7 is in all cases the peak having maximum relative intensity. Therefore, for characterization of salt methanesulfonic acid and 3-(1,2,4-triazolo[4,3-a]pyridine-3-ilethynyl)-4-methyl-N-(4-((4-methylpiperazin-1-yl)methyl)-3-trifluoromethylphenyl)benzamide in polymorphic modification I, it is possible to use the peak at diffraction angle (2θ) 18.7 having maximum relative intensity. It is important to note that X-ray diffraction pattern characterization in terms of position of the most intense peak cannot be always reliable, since, depending on sample texturing, the most intensive one can be another peak, which was observed for polymorphic modification II (see below) during survey by instruments with different geometry.

Taking into account the above-specified observations, for characterization of salt methanesulfonic acid and 3-(1,2,4-triazolo[4,3-a]pyridine-3-ilethynyl)-4-methyl-N-(4-((4-methylpiperazin-1-yl)methyl)-3-trifluoromethylphenyl)benzamide in polymorphic modification I, it is possible to use a full set of peaks at diffraction angles (2θ) presented in the table 9: 7.2, 11.9, 12.5, 13.4, 14.5, 16.2, 16.9, 17.2, 17.4, 18.7, 20.8, 21.4, 23.2, 24.1, 24.6, 25.4, 27.1.

Effects of sample texturing, changes of the size of crystallites and ordering can have strong influence in peaks intensity. Due to this, the number of observed peaks can be notable lower. Widely used rules of representative sampling search were not found. The United States Pharmacopeia of 1995 mentions requirements to characterization of X-ray powder diffraction patterns. To describe an X-ray diffraction pattern, it is necessary to select 10 the most intense peaks, and their position shall be determined with accuracy to ±0.20° 2θ. Along with that, deviation of sampling peaks' relative intensity shall not exceed 20%. Due to the fact that peaks intensities can significantly vary, we believe it is reasonable for characterization of salt methanesulfonic acid and 3-(1,2,4-triazolo[4,3-a]pyridine-3-ilethynyl)-4-methyl-N-(4-((4-methylpiperazin-1-yl)methyl)-3-trifluoromethylphenyl)benzamide in polymorphic modification I to use from 5 to 10 the most intense peaks at diffraction angles (2θ) selected from: 7.2, 11.9, 12.5, 13.4, 14.5, 16.2, 16.9, 17.2, 17.4, 18.7, 20.8, 21.4, 23.2, 24.1, 24.6, 25.4, 27.1.

Study of the Crystallinity of the Salt Methanesulfonic Acid of 3-(1,2,4-Triazolo[4,3-a]Pyridine-3-Yl-ethynyl)-4-Methyl-N-(4-((4-Methylpiperazine-1-Yl) Methyl)-3-Trifluoromethylphenyl)Benzamide (Polymorphous Modification II)

The crystallinity of a sample of the methanesulfonic acid salt of 3-(1,2,4-triazolo[4,3-a]pyridine-3-ylethynyl)-4-methyl-N-(4-((4-methylpiperazine-1-yl)methyl)-3-trifluoromethylphenyl)benzamide (polymorphous modification II) was studied using X-ray powder diffraction. The results showed that the sample was an individual crystalline phase with the following unit cell parameters: a=13.77±0.05 Å; b=8.09±0.05 Å and c=30.83±0.05 Å, β=117.8±0.1, V=3036.36±0.5 Å$^3$ and P2$_1$/c space group (see FIG. 49B). Positions and intensities of characteristic, visually distinguishable peaks on salt sample Debye powder diagram are given in Table 10. The general appearance of the independent part of the unit cell of methanesulfonic acid salt and 3-(1,2,4-triazolo[4,3-a]pyridine-3-ylethynyl)-4-methyl-N-(4-((4-methylpiperazine-1-yl)methyl)-3-trifluoromethylphenyl)benzamide in polymorphous modification II are given in FIG. 50B.

TABLE 10

Positions and intensities of characteristic, visually distinguishable peaks on Debye powder diagram of a sample of 3-(1,2,4-triazolo[4,3-a]pyridine-3-ylethynyl)-4-methyl-N-(4-((4-methylpiperazine-1-yl)methyl)-3-trifluoromethylphenyl)benzamide methanesulfonic acid salt (polymorphous modification II).

| Peak position (2θ) | Relative intensity | Peak position (2θ) | Relative intensity | Peak position (2θ) | Relative intensity |
|---|---|---|---|---|---|
| 1 | 2 | 3 | 4 | 5 | 6 |
| 6.5 | 1.8 | 29.6 | 8.3 | 43.1 | 2.9 |
| 7.1 | 8.4 | 29.7 | 4.1 | 43.5 | 1.3 |
| 7.3 | 8.3 | 30.1 | 10.3 | 43.8 | 1.2 |
| 11.4 | 4.6 | 30.4 | 2.9 | 44.0 | 1.0 |
| 11.6 | 11.1 | 30.9 | 1.1 | 44.2 | 0.9 |
| 11.8 | 19.1 | 31.1 | 2.2 | 44.6 | 0.9 |
| 12.7 | 10.7 | 31.3 | 1.2 | 45.0 | 1.9 |
| 12.9 | 9.3 | 31.8 | 0.7 | 45.4 | 1.4 |
| 13.1 | 12.7 | 31.9 | 0.6 | 45.6 | 1.3 |
| 14.2 | 20.2 | 32.1 | 4.2 | 45.7 | 1.6 |
| 14.3 | 4.4 | 32.4 | 3.3 | 45.8 | 1.7 |
| 14.6 | 22.2 | 32.5 | 1.8 | 46.1 | 2.0 |
| 15.9 | 0.6 | 32.8 | 1.2 | 46.4 | 1.0 |
| 16.9 | 17.0 | 33.0 | 0.9 | 46.8 | 1.3 |
| 17.2 | 19.7 | 33.6 | 1.9 | 47.0 | 1.5 |
| 17.4 | 63.5 | 33.8 | 0.8 | 47.4 | 1.9 |
| 17.6 | 32.6 | 34.2 | 1.4 | 47.6 | 1.4 |
| 18.1 | 19.7 | 34.4 | 1.5 | 47.8 | 0.7 |
| 18.3 | 10.4 | 34.5 | 2.3 | 48.1 | 1.7 |

TABLE 10-continued

Positions and intensities of characteristic, visually distinguishable peaks on Debye powder diagram of a sample of 3-(1,2,4-triazolo[4,3-a]pyridine-3-ylethynyl)-4-methyl-N-(4-((4-methylpiperazine-1-yl)methyl)-3-trifluoromethylphenyl)benzamide methanesulfonic acid salt (polymorphous modification II).

| Peak position (2θ) | Relative intensity | Peak position (2θ) | Relative intensity | Peak position (2θ) | Relative intensity |
|---|---|---|---|---|---|
| 18.5 | 4.5 | 34.8 | 3.4 | 48.3 | 1.1 |
| 19.4 | 29.9 | 35.0 | 3.3 | 48.6 | 1.0 |
| 19.7 | 32.9 | 35.2 | 1.2 | 48.9 | 1.5 |
| 20.6 | 3.6 | 35.4 | 0.8 | 49.2 | 0.9 |
| 20.8 | 7.8 | 35.7 | 2.6 | 49.4 | 0.7 |
| 21.2 | 100.0 | 35.8 | 3.5 | 49.6 | 1.5 |
| 21.6 | 12.0 | 36.2 | 0.8 | 49.9 | 0.4 |
| 22.0 | 40.8 | 36.5 | 4.0 | 50.1 | 0.5 |
| 22.3 | 1.3 | 37.0 | 3.1 | 50.3 | 0.6 |
| 22.5 | 10.6 | 37.1 | 1.6 | 50.6 | 0.6 |
| 22.6 | 31.6 | 37.2 | 1.3 | 51.0 | 0.4 |
| 22.9 | 4.2 | 37.4 | 1.2 | 51.5 | 0.8 |
| 23.2 | 21.5 | 37.6 | 1.3 | 51.8 | 0.5 |
| 23.4 | 8.3 | 37.9 | 1.8 | 52.1 | 0.6 |
| 23.5 | 2.0 | 38.1 | 0.5 | 52.7 | 1.5 |
| 23.6 | 2.0 | 38.4 | 0.9 | 53.0 | 1.2 |
| 23.8 | 12.1 | 38.7 | 1.8 | 53.4 | 1.0 |
| 24.1 | 2.0 | 38.9 | 1.0 | 53.5 | 1.1 |
| 24.6 | 2.0 | 39.4 | 1.8 | 53.6 | 1.2 |
| 24.9 | 9.3 | 39.7 | 1.8 | 53.9 | 1.0 |
| 25.1 | 7.0 | 39.8 | 1.5 | 54.2 | 1.4 |
| 25.4 | 3.4 | 40.1 | 1.8 | 54.5 | 1.2 |
| 25.6 | 8.0 | 40.3 | 0.4 | 54.7 | 1.3 |
| 25.9 | 26.7 | 40.6 | 0.8 | 54.9 | 1.1 |
| 26.1 | 18.8 | 40.7 | 1.2 | 55.2 | 1.3 |
| 26.4 | 1.8 | 41.0 | 0.9 | 55.8 | 0.6 |
| 26.6 | 14.5 | 41.2 | 1.7 | 56.3 | 0.6 |
| 26.9 | 2.1 | 41.3 | 1.7 | 56.5 | 0.8 |
| 27.3 | 0.7 | 41.6 | 0.6 | 56.7 | 0.7 |
| 27.4 | 1.7 | 41.9 | 1.0 | 57.0 | 0.6 |
| 28.3 | 5.8 | 41.9 | 1.0 | 57.5 | 0.4 |
| 28.7 | 2.1 | 42.1 | 0.4 | 57.8 | 0.4 |
| 28.8 | 9.3 | 42.5 | 2.4 | 58.1 | 0.4 |
| 29.0 | 1.1 | 42.8 | 3.3 | | |

Intensities are peak heights (with a background adjustment). Positions correspond to maximums on the diffraction pattern, not to reflections positions.

Ancillary Tests of Crystallinity of Salt Methanesulfonic Acid and 3-(1,2,4-Triazolo[4,3-a]Pyridine-3-Ilethynyl)-4-Methyl-N-(4-((4-Methylpiperazin-1-Yl)Methyl)-3-Trifluoromethylphenyl)Benzamide (Polymorphic Modification II)

For specification of positions and intensity of characteristic, visually distinctive peaks in the Debye powder diagram of methanesulfonic acid salt and 3-(1,2,4-triazolo[4,3-a]pyridine-3-ilethynyl)-4-methyl-N-(4-((4-methylpiperazin-1-yl)methyl)-3-trifluoromethylphenyl)benzamide (polymorphic modification II), ancillary tests of salt crystallinity were carried by methods of X-ray diffraction analysis. Receipt of Debye powder diagrams was performed with the use of different geometry of survey: x-ray transmittance and Bragg-Brentano's geometry. Positions and intensity of characteristic, visually distinctive peaks in the Debye powder diagram of the sample are presented in the table 11 and 12.

TABLE 11

Positions and intensities of characteristic, visually distinctive peaks in the Debye powder diagram of the sample of salt methanesulfonic acid and 3-(1,2,4-triazolo[4,3-a]pyridine-3-ilethynyl)-4-methyl-N-(4-((4-methylpiperazin-1-yl)methyl)-3-trifluoromethylphenyl)benzamide (sample PF114-19-1-MsOH, polymorphic modification II).

| Transmittance λ = 1.540596 Å | | Bragg-Brentano λ = 1.5418 Å | |
|---|---|---|---|
| Peak position (2θ) | Relative intensity, % | Peak position (2θ) | Relative intensity, % |
| | | 6.6 | 2.5 |
| 7.1 | 5.0 | 7.4 | 10.0 |
| 7.2 | 1.3 | | |
| 11.4 | 3.9 | | |
| 11.5 | 6.2 | 11.6 | 5.9 |
| 11.8 | 2.5 | 11.9 | 51.8 |
| 12.6 | 6.1 | 12.9 | 7.0 |
| 12.9 | 4.1 | | |
| 13.1 | 8.7 | | |
| 12.1 | 3.2 | | |
| 14.2 | 19.3 | 14.4 | 6.5 |
| 14.5 | 4.0 | 14.7 | 47.8 |
| 16.9 | 9.4 | | |
| 17.2 | 15.2 | 17.1 | 8.9 |
| | | 17.5 | 54.4 |
| 17.4 | 29.3 | 17.7 | 100.0 |
| 17.6 | 5.1 | | |
| 18.1 | 11.7 | 18.2 | 12.7 |
| 18.1 | 16.4 | 18.4 | 12.3 |
| | | 19.5 | 12.3 |
| 19.4 | 30.7 | 19.8 | 53.7 |
| | | 20.9 | 8.6 |
| 21.2 | 100.0 | 21.3 | 43.7 |
| | | 21.7 | 18.9 |
| 21.9 | 57.9 | 22.1 | 15.1 |
| 22.5 | 6.0 | | |
| 22.6 | 12.0 | 22.7 | 30.0 |
| 22.9 | 4.8 | | |
| 23.1 | 23.1 | | |
| 23.8 | 14.4 | | |
| 24.9 | 11.3 | | |
| 25.1 | 6.0 | | |
| 25.6 | 6.9 | | |
| 25.9 | 12.1 | | |
| 26.1 | 9.3 | 26.0 | 34.4 |
| | | 26.2 | 24.7 |
| 26.6 | 9.4 | | |
| 28.3 | 3.3 | | |
| 28.6 | 2.6 | | |
| 28.8 | 7.0 | | |
| 29.6 | 4.1 | | |
| 29.7 | 3.3 | | |
| 30.1 | 10.6 | | |

Intensities are the heights (background corrected) of the peaks. Positions correspond to the maximum values on the X-ray diffraction pattern, not to estimated positions of reflections.

Due to strong texturing of X-ray diffraction pattern sample, readings taken on instruments with different geometry, much differ. Moreover, survey in Bragg-Brentano's geometry lead to essential change of peaks intensity. Thus, upon surveying in the transmittance geometry, the peak at diffraction angle (2θ) 21.2 is the peak having maximum relative intensity, while upon surveying in Bragg-Brentano's geometry the intensity of such peak amounted from 43.7% up to maximum value.

TABLE 12

Positions and intensities of characteristic, visually
distinctive peaks in the Debye powder diagram of the
sample of salt methanesulfonic acid and 3-(1,2,4-triazolo[4,3-
a]pyridine-3-ilethynyl)-4-methyl-N-(4-((4-methylpiperazin-
1-yl)methyl)-3-trifluoromethylphenyl)benzamide (sample
A819419, polymorphic modification II).

| Peak position (2θ) | Relative intensity, % |
|---|---|
| 6.7 | 1.2 |
| 7.5 | 15.5 |
| 12.0 | 65.6 |
| 13.1 | 9.4 |
| 14.8 | 52.9 |
| 17.3 | 11.2 |
| 17.8 | 85.8 |
| 17.9 | 100 |
| 18.5 | 18.6 |
| 19.9 | 52.8 |
| 21.5 | 42.3 |
| 21.8 | 16.9 |
| 22.2 | 14.9 |
| 22.8 | 26.4 |
| 23.5 | 12.8 |
| 24.1 | 6.2 |
| 25.3 | 4.8 |
| 26.2 | 35.8 |

Intensities are the heights (background corrected) of the peaks. Positions correspond to the maximum values on the X-ray diffraction pattern, not to estimated positions of reflections.

The instrument from which data on the sample A819419 were obtained, has a high "zero error" equal to 0.25° 2θ. X-ray diffraction pattern shows strong widening of the lines, however, since the instrument's contribution into widening is not known, it is impossible to access the size of crystallites exactly.

Comparison of X-ray diffraction patterns of different samples allowed to determine peaks characteristic for all samples and analyze possible variations in the positions and intensities of peaks (see table 13).
11.8; 14.6; 17.2; 17.4; 17.6; 19.7; 21.2; 22.0 and 22.6.

TABLE 13

Positions and intensities of characteristic, visually
distinctive peaks in the Debye powder diagram of the
sample of salt methanesulfonic acid and 3-(1,2,4-triazolo[4,3-
a]pyridine-3-ilethynyl)-4-methyl-N-(4-((4-methylpiperazin-
1-yl)methyl)-3-trifluoromethylphenyl)benzamide (polymorphic
modification II).

| Peak position (2θ) | | | Relative intensity, % | | |
|---|---|---|---|---|---|
| Average value | Minimum | Maximum | Average value | Minimum | Maximum |
| 21.2 | 21.2 | 21.5 | 71.5 | 42.3 | 100.0 |
| 17.4 | 17.4 | 17.8 | 67.9 | 54.4 | 85.8 |
| 17.6 | 17.4 | 17.9 | 65.5 | 29.3 | 100.0 |
| 19.7 | 19.4 | 19.9 | 41.8 | 29.9 | 53.7 |
| 11.8 | 11.8 | 12.0 | 34.7 | 2.5 | 65.6 |
| 22.0 | 21.9 | 22.2 | 32.2 | 14.9 | 57.9 |
| 14.6 | 14.5 | 14.8 | 31.7 | 4.0 | 52.9 |
| 22.6 | 22.6 | 22.8 | 25.0 | 12.0 | 31.6 |
| 26.1 | 26.0 | 26.2 | 24.6 | 9.3 | 35.8 |
| 17.2 | 17.1 | 17.3 | 13.8 | 8.9 | 19.7 |
| 7.3 | 7.1 | 7.5 | 9.7 | 5.0 | 15.5 |

Intensities are the heights (background corrected) of the peaks. Positions correspond to the maximum values on the X-ray diffraction pattern, not to estimated positions of reflections.
11.9, 14.7, 17.2, 17.4, 17.6, 19.7, 21.2, 22.0, 22.6 and 26.1

The most intensive peaks of polymorphic modification II are characteristic for the following angle values: 11.8; 14.6; 17.2; 17.4; 17.6; 19.7; 21.2; 22.0 and 22.7. These peaks shall be present on the X-ray diffraction pattern and their relative intensity shall be higher than 10%. Decrease of permitted intensity is determined by the fact that such modification is prone to texturing, therefore the range of peaks' relative intensity is wider than in case of polymorphic modification I. Thus, for characterization of salt methanesulfonic acid and 3-(1,2,4-triazolo[4,3-a]pyridine-3-ilethynyl)-4-methyl-N-(4-((4-methylpiperazin-1-yl)methyl)-3-trifluoromethylphenyl)benzamide in polymorphic modification II, it is possible to use peaks at diffraction angles (2θ) 11.8; 14.6; 17.2; 17.4; 17.6; 19.7; 21.2; 22.0 and 22.7 with relative intensity 10% or higher.

As one can see from the data provided in the table 13, all peaks at diffraction angles (2θ) 11.8; 14.6; 17.2; 17.4; 17.6; 19.7; 21.2; 22.0 and 22.7 have relative intensities higher than 10%. However, the intensities of such peaks can vary essentially depending on the survey method, purity of samples, size of salt crystals, effects of sample texturing and a range of other parameters. Due to this reason, in the X-ray diffraction pattern of salt methanesulfonic acid and 3-(1,2,4-triazolo[4,3-a]pyridine-3-ilethynyl)-4-methyl-N-(4-((4-methylpiperazin-1-yl)methyl)-3-trifluoromethylphenyl)benzamide in polymorphic modification II, some peaks at diffraction angles (2θ) 11.8; 14.6; 17.2; 17.4; 17.6; 19.7; 21.2; 22.0 and 22.7 can have relative intensities below 10%. Therefore, for characterization of salt methanesulfonic acid and 3-(1,2,4-triazolo[4,3-a]pyridine-3-ilethynyl)-4-methyl-N-(4-((4-methylpiperazin-1-yl)methyl)-3-trifluoromethylphenyl)benzamide in polymorphic modification II, it is possible to use three, four, five or six peaks with relative intensity 20% or higher at diffraction angles (2θ) selected from 11.8; 14.6; 17.2; 17.4; 17.6; 19.7; 21.2; 22.0 and 22.7

It is obvious from analysis of peaks of X-ray diffraction pattern obtained in the process of surveying different samples of salt methanesulfonic acid and 3-(1,2,4-triazolo[4,3-a]pyridine-3-ilethynyl)-4-methyl-N-(4-((4-methylpiperazin-1-yl)methyl)-3-trifluoromethylphenyl)benzamide (polymorphic modification II), that, depending on the survey parameters, maximum relative intensity can belong to the peak at diffraction angle (2θ) 21.3 or peak at diffraction angle (2θ) 17.6. Therefore, for characterization of methanesulfonic acid salt and 3-(1,2,4-triazolo[4,3-a]pyridine-3-ilethynyl)-4-methyl-N-(4-((4-methylpiperazin-1-yl)methyl)-3-trifluoromethylphenyl)benzamide in polymorphic modification II, it is possible to use the peak having maximum relative intensity, at diffraction angle (2θ) selected from 17.6 or 21.2.

Taking into account the above-specified observations, for characterization of salt methanesulfonic acid and 3-(1,2,4-triazolo[4,3-a]pyridine-3-ilethynyl)-4-methyl-N-(4-((4-methylpiperazin-1-yl)methyl)-3-trifluoromethylphenyl)benzamide in polymorphic modification II, it is possible to use a full set of peaks at diffraction angles (2θ) presented in the table 13: 7.3, 11.8, 14.6, 17.2, 17.4, 17.6, 19.7, 21.2, 22.0, 22.7, 26.1.

Due to the fact that peaks intensities can significantly vary, we believe it is reasonable for characterization of salt methanesulfonic acid and 3-(1,2,4-triazolo[4,3-a]pyridine-3-ilethynyl)-4-methyl-N-(4-((4-methylpiperazin-1-yl)methyl)-3-trifluoromethylphenyl)benzamide in polymorphic modification I to use from 4 to 8 peaks at diffraction angles (2θ) selected from: 7.3, 11.8, 14.6, 17.2, 17.4, 17.6, 19.7, 21.2, 22.0, 22.7, 26.1

Study of the Dissolution Kinetics of 3-(1,2,4-Triazolo[4,3-a]Pyridine-3-Ylethynyl)-4-Methyl-N-(4-((4-Methylpiperazine-1-Yl)Methyl)-3-Trifluoromethylphenyl)Benzamide Free Base and the Polymorphous Modifications of 3-(1,2,4-Triazolo[4,3-a]Pyridine-3-Ylethynyl)-4-Methyl-N-(4-((4-Methylpiperazine-1-Yl)Methyl)-3-Trifluoromethylphenyl)Benzamide Methanesulfonic Acid Salt During further studies of the polymorphous modifications of the methanesulfonic acid salt of 3-(1,2,4-triazolo[4,3-a]pyridine-3-ylethynyl)-4-methyl-N-(4-((4-methylpiperazine-1-yl)methyl)-3-trifluoromethylphenyl)benzamide, the kinetics of dissolution of the free base and the two methanesulfonic acid salt form polymorphous modifications was studied. Dissolution kinetics studies were performed using USP Apparatus 1 Basket Method (USP40, General Chapter <711>. Dissolution), dissolution media volume—700 mL, temperature—37±1° C. paddle stirrers' rotation rate—100 rpm. The test sample dissolution rate was calculated as an average of six repeats. Distilled water was used as the dissolution medium for the polymorphous modifications of 3-(1,2,4-triazolo[4,3-a]pyridine-3-ylethynyl)-4-methyl-N-(4-((4-methylpiperazine-1-yl)methyl)-3-trifluoromethylphenyl)benzamide methanesulfonic acid salt and, and a solution of 12.2 mL of methanesulfonic acid in 500 mL of water was used as the dissolution medium for the free base. Test portions containing 100 mg of 3-(1,2,4-triazolo[4,3-a]pyridine-3-ylethynyl)-4-methyl-N-(4-((4-methylpiperazine-1-yl)methyl)-3-trifluoromethylphenyl)benzamide or 118 mg of 3-(1,2,4-triazolo[4,3-a]pyridine-3-ylethynyl)-4-methyl-N-(4-((4-methylpiperazine-1-yl)methyl)-3-trifluoromethylphenyl)benzamide methanesulfonic acid salt (100 mg calculated as free base) were used for dissolution. In 780 minutes (13 hours) after the beginning of the test, pH of prepared solutions was measured. The pH of the solution used for testing dissolution of the free base was more acidic (pH 4.02) compared to that of the solutions used for testing the dissolution of the polymorphous modifications of 3-(1,2,4-triazolo[4,3-a]pyridine-3-ylethynyl)-4-methyl-N-(4-((4-methylpiperazine-1-yl)methyl)-3-trifluoromethylphenyl)benzamide methanesulfonic acid salt (pH 5.04—for polymorphous modification I and pH 4.95—for polymorphous modification II).

The results of the dissolution kinetics studies results are shown in FIG. 51. According to the data presented, 95% of 3-(1,2,4-triazolo[4,3-a]pyridine-3-ylethynyl)-4-methyl-N-(4-((4-methylpiperazine-1-yl)methyl)-3-trifluoromethylphenyl)benzamide contained in the samples of the methanesulfonic acid salt of 3-(1,2,4-triazolo[4,3-a]pyridine-3-ylethynyl)-4-methyl-N-(4-((4-methylpiperazine-1-yl)methyl)-3-trifluoromethylphenyl)benzamide transferred to the solution in less than one minute, and full dissolution of the salt occurs within less than 4 minutes. In contrast, less than 90% of the free base dissolved in the solution containing 12.2 mL of methanesulfonic acid, even over a dissolution period of 780 minutes (13 hours).

Therefore, the studies conducted on the synthesis and crystalline structure determination of the methanesulfonic acid salt of 3-(1,2,4-triazolo[4,3-a]pyridine-3-ylethynyl)-4-methyl-N-(4-((4-methylpiperazine-1-yl)methyl)-3-trifluoromethylphenyl)benzamide showed that this compound may exist at least in two polymorphous modifications. Each of the polymorphous modifications may be obtained in low-toxic organic solvents using an easily scalable method, contains a pharmacologically acceptable anion, has crystallinity, and high solubility in water. The cation chemical structures in both polymorphous modifications match and correspond to 3-(1,2,4-triazolo[4,3-a]pyridine-3-ylethynyl)-4-methyl-N-(4-((4-methylpiperazine-1-yl)methyl)-3-trifluoromethylphenyl)benzamide cation, both compounds are methanesulfonic acid salts and contain protonated form of 3-(1,2,4-triazolo[4,3-a]pyridine-3-ylethynyl)-4-methyl-N-(4-((4-methylpiperazine-1-yl)methyl)-3-trifluoromethylphenyl)benzamide and mesylate-anion. 3-(1,2,4-triazolo[4,3-a]pyridine-3-ylethynyl)-4-methyl-N-(4-((4-methylpiperazine-1-yl)methyl)-3-trifluoromethylphenyl)benzamide in both polymorphous modifications is protonated on the nitrogen atom of the piperazine ring carrying a methyl group. Both polymorphous modifications do not contain solvent molecules. The differences in the structures of the polymorphous modifications are mainly associated with the mutual position of the aromatic heterocycle compared with the rest of a molecule (see FIG. 50).

Study of the Pharmacokinetic Characteristics of Free Base and Methanesulfonic Acid Salt of 3-(1,2,4-Triazolo[4,3-a]Pyridine-3-Ylethynyl)-4-Methyl-N-(4-((4-Methylpiperazine-1-Yl)Methyl)-3-Trifluoromethylphenyl)Benzamide To analyze applicability of 3-(1,2,4-triazolo[4,3-a]pyridine-3-ylethynyl)-4-methyl-N-(4-((4-methylpiperazine-1-yl)methyl)-3-trifluoromethylphenyl)benzamide salt form as a drug, a study of its pharmacokinetic characteristics has been conducted.

The pharmacokinetics of 3-(1,2,4-triazolo[4,3-a]pyridine-3-ylethynyl)-4-methyl-N-(4-((4-methylpiperazine-1-yl)methyl)-3-trifluoromethylphenyl)benzamide were studied after a single administration of a free base at a dose of 50 mg/kg and a single administration of the methanesulfonic acid salt of 3-(1,2,4-triazolo[4,3-a]pyridine-3-ylethynyl)-4-methyl-N-(4-((4-methylpiperazine-1-yl)methyl)-3-trifluoromethylphenyl)benzamide (polymorphous modification I) at a dose of 59 mg/kg (equivalent to 50 mg/kg calculated as a free base) to C57BL/6 line mice. The results of the study are given in FIG. 52 and in Tables 14 and 15.

TABLE 14

Main pharmacokinetic parameters of 3-(1,2,4-triazolo[4,3-a]pyridine-3-ylethynyl)-4-methyl-N-(4-((4-methylpiperazine-1-yl)methyl)-3-trifluoromethylphenyl)benzamide when the free base is administered to C57BL/6 line mice at a dose of 50 mg/kg.

| $T_{1/2}$ (h) | $T_{max}$ (h) | $C_{max}$ (ng/mL) | $AUC_{0-24}$ (ngh/mL) | $AUC_{0-24}/24$ (ng/mL) | $AUC_{0-\infty}$ (ngh/mL) |
|---|---|---|---|---|---|
| 2.4 | 2 | 1,490 | 10,856 | 452 | 10,868 |

Average values are determined for each time point based on individual data obtained from three animals.

TABLE 15

Main pharmacokinetic parameters of 3-(1,2,4-triazolo[4,3-a]pyridine-3-ylethynyl)-4-methyl-N-(4-((4-methylpiperazine-1-yl)methyl)-3-trifluoromethylphenyl)benzamide when the methanesulfonic acid salt of 3-(1,2,4-triazolo[4,3-a]pyridine-3-ylethynyl)-4-methyl-N-(4-((4-methylpiperazine-1-yl)methyl)-3-trifluoromethylphenyl)benzamide (polymorphous modification I)* is administered to C57BL/6 line mice at a dose of 59 mg/kg (equivalent to 50 mg/kg calculated as a free base).

| $T_{1/2}$ (h) | $T_{max}$ (h) | $C_{max}$ (ng/mL) | $AUC_{0-24}$ (ngh/mL) | $AUC_{0-24}/24$ (ng/mL) | $AUC_{0-\infty}$ (ng · h/mL) |
|---|---|---|---|---|---|
| 3.8 | 4 | 1,099 | 11,933 | 497 | 12,103 |

Average values are determined for each time point based on individual data obtained from three animals.
Note:
No statistically true differences in all pharmacokinetic parameters studied were revealed after administration of the salt form as polymorphous modification II ($p < 0.05$).

The pharmacokinetic studies lead to unexpected results, where following administration of the free base, maximum 3-(1,2,4-triazolo[4,3-a]pyridine-3-ylethynyl)-4-methyl-N-(4-((4-methylpiperazine-1-yl)methyl)-3-trifluoromethylphenyl)benzamide animal plasma concentration ($C_{max}$=1,490 ng/mL) exceeded maximum concentration ($C_{max}$=1,099 ng/mL) identified after administration of the salt form by more than one third. Moreover, despite the fact that the salt form had much higher dissolution rate than that of the free base, the maximum concentration achievement time ($T_{max}$) for the salt form was twice as long as that for the free base. Despite the lesser 3-(1,2,4-triazolo[4,3-a]pyridine-3-ylethynyl)-4-methyl-N-(4-((4-methylpiperazine-1-yl)methyl)-3-trifluoromethylphenyl)benzamide maximum plasma concentration following oral administration of the salt form, administration of the salt form provides a higher substance concentration average ($AUC_t/t$). These results are unexpected in light of the solubility difference between the free base and salt form since maximum ($C_{max}$) and average ($AUC_t/t$) animal plasma concentrations typically correlate with the solubility of a salt form used for substance administration while the time to maximum plasma concentration ($T_{max}$) typically correlates inversely with the dissolution rate of the salt forms used.

Therefore, the studies of the pharmacokinetic parameters of the free base and methanesulfonic acid salt of 3-(1,2,4-triazolo[4,3-a]pyridine-3-ylethynyl)-4-methyl-N-(4-((4-methylpiperazine-1-yl)methyl)-3-trifluoromethylphenyl)benzamide provide unexpected results in which significant differences in their pharmacokinetic profiles were observed, but not in a manner that could be explained based on the differences in dissolution kinetics. The differences in pharmacokinetic properties may lead to changes in the therapeutic efficacy, administration safety and/or other properties of a drug candidate. For further assessment of usability of the developed 3-(1,2,4-triazolo[4,3-a]pyridine-3-ylethynyl)-4-methyl-N-(4-((4-methylpiperazine-1-yl)methyl)-3-trifluoromethylphenyl)benzamide salt form, studies of the acute toxicity and efficacy of the free base and methanesulfonic acid salt form of 3-(1,2,4-triazolo[4,3-a]pyridine-3-ylethynyl)-4-methyl-N-(4-((4-methylpiperazine-1-yl)methyl)-3-trifluoromethylphenyl)benzamide were conducted.

Studies of Safety of a Free Base and Methanesulfonic Acid Salt and 3-(1,2,4-Triazolo[4,3-a]Pyridine-3-Ylethynyl)-4-Methyl-N-(4-((4-Methylpiperazine-1-Yl)Methyl)-3-Trifluoromethylphenyl)Benzamide in Compounds Acute Toxicity Study Experiments To study safety of the free base and methanesulfonic acid salt of 3-(1,2,4-triazolo[4,3-a]pyridine-3-ylethynyl)-4-methyl-N-(4-((4-methylpiperazine-1-yl)methyl)-3-trifluoromethylphenyl)benzamide, acute toxicity studies were conducted.

The acute toxicity of the free base of 3-(1,2,4-triazolo[4,3-a]pyridine-3-ylethynyl)-4-methyl-N-(4-((4-methylpiperazine-1-yl)methyl)-3-trifluoromethylphenyl)benzamide and its salt with methanesulfonic acid were studied on CD-1 line mice males at the age of 2-3 months using oral route of administration. For each drug dose study a group of six animals was used. The study included control groups with the same animal headcount, which received equivalent solvent doses of a 0.5% water solution of methylcellulose. The follow-up period was 28 days. Lab mouse survivability analysis allowed carrying out Bliss analysis and determining the lethal doses of the studied drugs. The results of the acute toxicity studies and the calculated half-lethal doses for the free base and methanesulfonic acid salt are given in Table 16.

TABLE 16

Lethal doses of 3-(1,2,4-triazolo[4,3-a]pyridine-3-ylethynyl)-4-methyl-N-(4-((4-methyl piperazine-1-yl)methyl)-3-trif luoromethylphenyl)benzamide when orally administered in the form of a free base and methanesulfonic acid salt to male mice.

| | Dose without observable effects, mg/kg | $LD_{10}$, mg/kg | $LD_{50}$, mg/kg | $LD_{90}$, mg/kg |
|---|---|---|---|---|
| 3-(1,2,4-triazolo[4,3-a]pyridine-3-ylethynyl)-4-methyl-N-(4-((4-methylpiperazine-1-yl)methyl)-3-trifluoromethylphenyl)benzamide free base | 160 | 504 | 677 ± 55 | 850 |
| Methanesulfonic acid salt and 3-(1,2,4-triazolo[4,3-a]pyridine-3-ylethynyl)-4-methyl-N-(4-((4-methylpiperazine-1-yl)methyl)-3-trifluoromethylphenyl)benzamide | 400 (338*) | 600 (508*) | 1,400 ± 200 (1,186 ± 169*) | 2,200 (1,864*) |

*Doses in brackets are calculated as a free base

The data given above show that the semi-lethal doses ($LD_{50}$ are doses, which lead to the death of half of animals from the test group) for the methanesulfonic acid salt of 3-(1,2,4-triazolo[4,3-a]pyridine-3-ylethynyl)-4-methyl-N-(4-((4-methylpiperazine-1-yl)methyl)-3-trifluoromethylphenyl)benzamide were about twice as high as the lethal doses for the free base. A similar more pronounced effect was observed for doses which lead to the death of 90% of animals from the test group (see Table 16). Administration of 3-(1,2,4-triazolo[4,3-a]pyridine-3-ylethynyl)-4-methyl-N-(4-((4-methylpiperazine-1-yl)methyl)-3-trifluoromethylphenyl)benzamide both as free base and salt form caused similar signs of animal intoxication: dyspnea, hypodynamia, tumbled fur, diarrhea, bloating, in some animals—focal alopecia; however, when the substance was administered in the form of methanesulfonic acid salt and 3-(1,2,4-triazolo[4,3-a]pyridine-3-ylethynyl)-4-methyl-N-(4-((4-methylpiperazine-1-yl)methyl)-3-trifluoromethylphenyl)benzamide, the dose not leading to the development of such effects, was twice higher.

Thus, the safety study for the free base and methanesulfonic acid salt of 3-(1,2,4-triazolo[4,3-a]pyridine-3-ylethynyl)-4-methyl-N-(4-((4-methylpiperazine-1-yl)methyl)-3-trifluoromethylphenyl)benzamide provided unexpected results showing that the salt form was characterized by significantly higher safety, which was shown by the higher 3-(1,2,4-triazolo[4,3-a]pyridine-3-ylethynyl)-4-methyl-N-(4-((4-methylpiperazine-1-yl)methyl)-3-trifluoromethylphenyl)benzamide dose (calculated as a free base), which upon administration by lab animals' organisms caused no observable effects, as well as by almost two-fold increase in the semi-lethal dose ($LD_{50}$) of the salt form compared to the free base. The favorable safety profile of the methanesulfonic acid salt of 3-(1,2,4-triazolo[4,3-a]pyridine-3-ylethynyl)-4-methyl-N-(4-((4-methylpiperazine-1-yl)methyl)-3-trifluoromethylphenyl)benzamide make this salt form more attractive as a drug candidate compared to its free base.

Study of the Efficacy of the Free Base and Methanesulfonic Acid Salt of 3-(1,2,4-Triazolo[4,3-a]Pyridine-3-Ylethynyl)-4-Methyl-N-(4-((4-Methylpiperazine-1-Yl)Methyl)-3-Trifluoromethylphenyl)Benzamide Using BCR/ABL-Induced Chronic Myelogenous Leukemia Model To assess the efficacy of the free base and methanesulfonic acid salt of 3-(1,2,4-triazolo[4,3-a]pyridine-3-ylethynyl)-4-methyl-N-(4-((4-methylpiperazine-1-yl)methyl)-3-trifluoromethylphenyl)benzamide for treating chronic myelogenous leukemia (CML) studies of the compounds' activity on the BCR/ABL-induced CML-like disease in mice were conducted. In the study C57BL/6N line mice were used. The subject animals received a sub lethal dose of radiation followed by intravenous transplantation of donor Sca1+ marrow cells, expressing p185-T315I$^{BCR/ABL}$ due to retroviral transduction. Treatment was started on the 11$^{th}$ day after transplantation of cells expressing p185-T315I$^{BCR/ABL}$.

The efficacy of therapy with 3-(1,2,4-triazolo[4,3-a]pyridine-3-ylethynyl)-4-methyl-N-(4-((4-methylpiperazine-1-yl)methyl)-3-trifluoromethylphenyl)benzamide administered orally as a free base and methanesulfonic acid salt was studied. The results of the study of the effect of oral administration of 3-(1,2,4-triazolo[4,3-a]pyridine-3-ylethynyl)-4-methyl-N-(4-((4-methylpiperazine-1-yl)methyl)-3-trifluoromethylphenyl)benzamide free base (at a dose of 50 mg/kg), methanesulfonic acid salt and 3-(1,2,4-triazolo[4,3-a]pyridine-3-ylethynyl)-4-methyl-N-(4-((4-methylpiperazine-1-yl)methyl)-3-trifluoromethylphenyl)benzamide (at doses 8.5; 21; 34 and 50 mg/kg calculated as a free base) on average survival of the treated animals are given in Table 17.

As the data presented show, administration of 3-(1,2,4-triazolo[4,3-a]pyridine-3-ylethynyl)-4-methyl-N-(4-((4-methylpiperazine-1-yl)methyl)-3-trifluoromethylphenyl)benzamide both as free base and salt form lead to an increase in the average survival of the treated animals. For animals treated with the methanesulfonic acid salt of 3-(1,2,4-triazolo[4,3-a]pyridine-3-ylethynyl)-4-methyl-N-(4-((4-methylpiperazine-1-yl)methyl)-3-trifluoromethylphenyl)benzamide, s dependence of mice average life on the dose of the salt form administered is observed. Administration of the methanesulfonic acid salt of 3-(1,2,4-triazolo[4,3-a]pyridine-3-ylethynyl)-4-methyl-N-(4-((4-methylpiperazine-1-yl)methyl)-3-trifluoromethylphenyl)benzamide at a dose of 40 mg/kg (equivalent to 34 mg/kg calculated as a free base) has the same therapeutic effect as administration of 50 mg/kg of a free base. Administration of methanesulfonic acid salt and 3-(1,2,4-triazolo[4,3-a]pyridine-3-ylethynyl)-4-methyl-N-(4-((4-methylpiperazine-1-yl)methyl)-3-trifluoromethylphenyl)benzamide at a dose of 59 mg/kg (equivalent to 50 mg/kg calculated as a free base) ensure almost two-fold increase of animals' lives compared to the control group. The salt form efficacy by this indicator is greater than that of a free base.

TABLE 17

Effect of the free base and methanesulfonic acid salt of 3-(1,2,4-triazolo[4,3-a]pyridine-3-ylethynyl)-4-methyl-N-(4-((4-methylpiperazine-1-yl)methyl)-3-trifluoromethylphenyl)benzamide on average survival of lab animals in a BCR/ABL-induced chronic myelogenous leukemia model

| Studied substance | Dose, mg/kg | Average life, days |
|---|---|---|
| Control (solvent) | 0 | 55.0 ± 6.3 |
| 3-(1,2,4-triazolo[4,3-a]pyridine-3-ylethynyl)-4-methyl-N-(4-((4-methylpiperazine-1-yl)methyl)-3-trifluoromethylphenyl)benzamide free base | 50 | 93.0 ± 6.1 |
| Methanesulfonic acid salt of 3-(1,2,4-triazolo[4,3-a]pyridine-3-ylethynyl)-4-methyl-N-(4-((4-methylpiperazine-1-yl)methyl)-3-trifluoromethylphenyl)benzamide | 10 (8.5) | 65.5 ± 6.7 |
| | 25 (21) | 73.9 ± 7.1 |
| | 40 (34) | 90.3 ± 6.9 |
| | 59 (50) | 104.5 ± 5.2 |

*Values in brackets are calculated as a free base

Therefore, studies the efficacy of the free base and methanesulfonic acid salt of 3-(1,2,4-triazolo[4,3-a]pyridine-3-ylethynyl)-4-methyl-N-(4-((4-methylpiperazine-1-yl)methyl)-3-trifluoromethylphenyl)benzamide gave unexpected results showing that administration of the salt form was more effective, which was manifested in longer average survival of animals in the group which received the salt form as compared to the group, which received the equivalent dose of a free base. Therefore, the higher efficacy of methanesulfonic acid salt and 3-(1,2,4-triazolo[4,3-a]pyridine-3-ylethynyl)-4-methyl-N-(4-((4-methylpiperazine-1-yl)methyl)-3-trifluoromethylphenyl)benzamide makes this salt form more attractive as a drug candidate compared to a free base.

Study of the Biological Activity of the Methanesulfonic Acid Salt of 3-(1,2,4-Triazolo[4,3-a]Pyridine-3-Ylethynyl)-4-Methyl-N-(4-((4-Methylpiperazine-1-Yl)Methyl)-3-Trifluoromethylphenyl)Benzamide The biological activity of the methanesulfonic acid salt of 3-(1,2,4-triazolo[4,3-a]pyridine-3-ylethynyl)-4-methyl-N-(4-((4-methylpiperazine-1-yl)methyl)-3-trifluoromethylphenyl)benzamide, as well as of its crystalline forms, which are the subject of this disclosure, has been studied in various experiments.

Study of the Effect of the Methanesulfonic Acid Salt of 3-(1,2,4-Triazolo[4,3-a]Pyridine-3-Ylethynyl)-4-Methyl-N-(4-((4-Methylpiperazine-1-Yl)Methyl)-3-Trifluoromethylphenyl)Benzamide on Human Kinase Enzyme Activity The methanesulfonic acid salt of 3-(1,2,4-triazolo[4,3-a]pyridine-3-ylethynyl)-4-methyl-N-(4-((4-methylpiperazine-1-yl)methyl)-3-trifluoromethylphenyl)benzamide at the nanomolar range of concentrations inhibit Bcr-AbI tyrosine kinase, inactivating clinically significant mutant forms of this enzyme. The results of Bcr-AbI kinases inhibition experiments are summed up in Table 18. Half-maximal inhibitory concentration ($IC_{50}$) of wild-type Bcr-AbI by the methanesulfonic acid salt of 3-(1,2,4-triazolo[4,3-a]pyridine-3-ylethynyl)-4-methyl-N-(4-((4-methylpiperazine-1-yl)methyl)-3-trifluoromethylphenyl)benzamide ranged from 0.49-3.1 nM (based on the results of 3 independent experiments). The $IC_{50}$ for Bcr-AbI with T315I mutation ranged from 0.78-21 nM (based on the results of 3 independent experiments).

TABLE 18

Effect of the methanesulfonic acid salt of 3-(1,2,4-triazolo[4,3-a]pyridine-3-ylethynyl)-4-methyl-N-(4-((4-methylpiperazine-1-yl)methyl)-3-trifluoromethylphenyl)benzamide on Bcr-AbI tyrosine kinase enzyme activity, including clinically significant mutant forms of this enzyme.

| Kinase | IC50, nM |
| --- | --- |
| Bcr-Abl | 0.49-3.1* |
| Bcr-Abl (T315I) | 0.78-21* |
| Bcr-Abl (E255K) | 9.5 |
| Bcr-Abl (F317I) | 2.0 |
| Bcr-Abl (G250E) | 7.4 |
| Bcr-Abl (H396P) | 1.0 |
| Bcr-Abl (M351T) | 2.8 |
| Bcr-Abl (Q252H) | 12 |
| Bcr-Abl (Y253F) | 4.1 |

At a concentration of 100 nM, the methanesulfonic acid salt of 3-(1,2,4-triazolo[4,3-a]pyridine-3-ylethynyl)-4-methyl-N-(4-((4-methylpiperazine-1-yl)methyl)-3-trifluoromethylphenyl)benzamide significantly (more than 50% inhibition) inhibited activity of each of the following human tyrosine kinases (out of 337 kinases that were tested): ABL1, ABL2/ARG, BLK, DDR1, DDR2, EPHA2, EPHA8, EPHB2, FGR, FLT4/VEGFR3, FMS, FRK/PTK5, FYN, HCK, KDR/VEGFR2, LCK, LYN, LYN B, P38a/MAPK14, PDGFRa, PDGFRb, RAF1, RET, RIPK3, ZAK/MLTK, where more than 90% of activity was inhibited for the following kinases: ABL1, ABL2/ARG, DDR1, DDR2, FMS, FRK/PTK5, LCK, LYN, LYN B, PDGFRa, RET.

Study of the Cytotoxicity of the Methanesulfonic Acid Salt of 3-(1,2,4-Triazolo[4,3-a]Pyridine-3-Ylethynyl)-4-Methyl-N-(4-((4-Methylpiperazine-1-Yl)Methyl)-3-Trifluoromethylphenyl)Benzamide with Respect to Various Tumor Cell Lines The methanesulfonic acid salt of 3-(1,2,4-triazolo[4,3-a]pyridine-3-ylethynyl)-4-methyl-N-(4-((4-methylpiperazine-1-yl)methyl)-3-trifluoromethylphenyl)benzamide showed cytotoxicity against immature lymphoid cells in Philadelphia chromosome positive (Ph+) chronic myeloid leukemia (CML) and Ph+ acute lymphoblastic leukemia (ALL) models, including T315I mutation cells. During the experiment, the drug showed toxicity against the human tumor cell lines K562 ($IC_{50}$ 8 nM), KCL-22 ($IC_{50}$ 9 nM), and BV-173 ($IC_{50}$ 5 nM) (representing a Ph+ CML model), as well as the Tom-1 ($IC_{50}$ 5 nM), SupB15 ($IC_{50}$ 50 nM) cell lines (representing Ph+ ALL model).

The methanesulfonic acid salt of 3-(1,2,4-triazolo[4,3-a]pyridine-3-ylethynyl)-4-methyl-N-(4-((4-methylpiperazine-1-yl)methyl)-3-trifluoromethylphenyl)benzamide also showed toxicity with respect to model tumor cell lines obtained by retroviral transduction of the murine hematopoietic BaF3 line BCR-ABL gene or its mutant forms [1]: BaF3/BCR-ABL ($IC_{50}$ 5 nM), BaF3/BCR-ABL Y253F ($IC_{50}$ 25 nM), BaF3/BCR-ABL E255K ($IC_{50}$ 25 nM), BaF3/BCR-ABL F317L ($IC_{50}$ 250 nM), and BaF3/BCR-ABL T315I ($IC_{50}$ 75 nM).

The methanesulfonic acid salt of 3-(1,2,4-triazolo[4,3-a]pyridine-3-ylethynyl)-4-methyl-N-(4-((4-methylpiperazine-1-yl)methyl)-3-trifluoromethylphenyl)benzamide also showed cytotoxicity with respect to human tumor cell lines, including, but not limited to, an acute lymphoblastic leukemia line (CCRF-CEM), a breast cancer line (MDA-MB-468), an ovarian cancer line (SKOV-3), and lymphoma lines (SR, EL4).

Study of the Efficacy of Methanesulfonic Acid Salt of 3-(1,2,4-Triazolo[4,3-a]Pyridine-3-Ylethynyl)-4-Methyl-N-(4-((4-Methylpiperazine-1-Yl)Methyl)-3-Trifluoromethylphenyl)Benzamide in a Xenograft Chronic Leukemia Model During a study using a xenograft model with thymus-deprived mice with subcutaneous implantation of K562 line cells, the effects of oral administration of the methanesulfonic acid salt of 3-(1,2,4-triazolo[4,3-a]pyridine-3-ylethynyl)-4-methyl-N-(4-((4-methylpiperazine-1-yl)methyl)-3-trifluoromethylphenyl)benzamide at doses of 25 and 40 mg/kg (21 and 34 mg/kg calculated as a free base, correspondingly) per day on the tumor size were assessed. The therapy was started after the size of the tumor had reached 500 mm³, therapy duration was 14 days, the follow-up period was 240 days. Administration of the methanesulfonic acid salt of 3-(1,2,4-triazolo[4,3-a]pyridine-3-ylethynyl)-4-methyl-N-(4-((4-methylpiperazine-1-yl)methyl)-3-trifluoromethylphenyl)benzamide at a dose of 25 mg/kg (21 calculated as a free base) per day led to the decrease of the tumor size to an immeasurable size with subsequent proliferation after the $35^{th}$ day of follow-up. Administration of the drug at a dose of 40 mg/kg (34 calculated as a free base) per day led to elimination of the tumor without relapse during all 240 days of follow-up in all mice.

Study of the Efficacy of the Methanesulfonic Acid Salt of 3-(1,2,4-Triazolo[4,3-a]Pyridine-3-Ylethynyl)-4-Methyl-N-(4-((4-Methylpiperazine-1-Yl)Methyl)-3-Trifluoromethylphenyl)Benzamide in an Acute Leukemia Model The efficacy of the methanesulfonic acid salt of 3-(1,2,4-triazolo[4,3-a]pyridine-3-ylethynyl)-4-methyl-N-(4-((4-methylpiperazine-1-yl)methyl)-3-trifluoromethylphenyl)benzamide was assessed in an acute leukemia mouse model. To induce the pathology, marrow cells obtained from C57BL/6N line mice with induced acute leukemia were used. Cells were injected to the tail vein of an animal following administration of a sub lethal dose of radiation. Therapy was initiated on the $5^{th}$ day after pathology induction and continued for 2 weeks. The study results showed that oral administration of the methanesulfonic acid salt of 3-(1,2,4-triazolo[4,3-a]pyridine-3-ylethynyl)-4-methyl-N-(4-((4-methylpiperazine-1-yl)methyl)-3-trifluoromethylphenyl)benzamide at a dose of 40 mg/kg (equivalent to 34 mg/kg calculated as a free base) lead to the increase of average lives in animals by more than 25% compared to the control group that received no therapy.

Study of the Efficacy of the Methanesulfonic Acid Salt and 3-(1,2,4-Triazolo[4,3-a]Pyridine-3-Ylethynyl)-4-Methyl-N-(4-((4-Methylpiperazine-1-Yl) Methyl)-3-Trifluoromethylphenyl)Benzamide in an Intestinal Solid Tumor Model The efficacy of the methanesulfonic acid salt and 3-(1,2,4-triazolo[4,3-a]pyridine-3-ylethynyl)-4-methyl-N-(4-((4-methylpiperazine-1-yl)methyl)-3-trifluoromethylphenyl) benzamide was studied in an intestinal solid tumor model. To induce pathology, HCT116 line cells were used. Cells in the amount of 200 μL ($2.5 \times 10^7$ cells/mL) were subcutaneously injected to the right side of thymus-deprived female mice (SCID). After the tumor had reached the size of 200 mm$^3$ all mice were randomized by tumor size and distributed between a control group and a therapeutic group. Oral administration of the methanesulfonic acid salt of 3-(1,2,4-triazolo[4,3-a]pyridine-3-ylethynyl)-4-methyl-N-(4-((4-methylpiperazine-1-yl)methyl)-3-trifluoromethylphenyl) benzamide at a dose of 25 mg/kg (equivalent to 21 mg/kg calculated as a free base) was started on the next day following randomization and continued for 20 days. To determine the efficacy of tumor growth inhibition upon completion of treatment (20 days), the average size ratio was calculated between the therapeutic/control groups (% T/C). The results of the study showed that administration of the drug at a dose of 25 mg/kg led to almost complete tumor non-dissemination (T/C<35%)

Study of the Efficacy of the Methanesulfonic Acid Salt of 3-(1,2,4-Triazolo[4,3-a]Pyridine-3-Ylethynyl)-4-Methyl-N-(4-((4-Methylpiperazine-1-Yl) Methyl)-3-Trifluoromethylphenyl)Benzamide in a Model of Non-Small Cell Lung Carcinoma Thymus-deprived male mice were used in the studies. A549 ($1 \times 10^7$ cells) were injected with 0.2 mL of matrigel solution (BD Pharmingen) into the left leg of a mouse under ketamine/xylazine anesthesia. In a week after the injections, mice were distributed between therapeutic and control groups that were randomized by tumor size. Oral administration of the methanesulfonic acid salt of 3-(1,2,4-triazolo[4,3-a]pyridine-3-ylethynyl)-4-methyl-N-(4-((4-methylpiperazine-1-yl)methyl)-3-trifluoromethylphenyl)benzamide at a dose of 25 mg/kg (equivalent to 21 mg/kg calculated as the free base) was started on the next day after randomization and continued for 20 days. To determine the efficacy of tumor growth inhibition, the average size ratio was calculated for the therapeutic/control groups (% T/C). The results of the study showed that administration of the drug at a dose of 25 mg/kg led to almost complete tumor non-dissemination (T/C<35%)

Detailed Study of the Pharmacokinetics of the Methanesulfonic Acid Salt of 3-(1,2,4-Triazolo[4,3-a]Pyridine-3-Ylethynyl)-4-Methyl-N-(4-((4-Methylpiperazine-1-Yl)Methyl)-3-Trifluoromethylphenyl) Benzamide During a study of the pharmacokinetics of the methanesulfonic acid salt and 3-(1,2,4-triazolo[4,3-a]pyridine-3-ylethynyl)-4-methyl-N-(4-((4-methylpiperazine-1-yl)methyl)-3-trifluoromethylphenyl)benzamide in rats and dogs, it was found that the bioavailability of the drug following oral administration was quite high: bioavailability in dogs F=45.9%-66.1% at a dose range of 2 to 22 mg/kg (2 to 19 mg/kg calculated as a free base), in rats F=13.8%-59.5% at a dose range of 5 to 80 mg/kg (4.2 to 68 mg/kg calculated as a free base).

The methanesulfonic acid salt of 3-(1,2,4-triazolo[4,3-a]pyridine-3-ylethynyl)-4-methyl-N-(4-((4-methylpiperazine-1-yl)methyl)-3-trifluoromethylphenyl)benzamide was absorbed over a period of 2-4 hours following oral administration to mice at a dose range 5 to 50 mg/kg, reaching corresponding maximum concentrations from 82 ng/mL to 1,099 ng/mL.

The area under the concentration-time curve (AUC) changed linearly throughout the whole dose range from 5 mg/kg to 50 mg/kg from 372 ng*h/mL to 12,104 ng*h/mL. Following oral administration of the drug as the methanesulfonate salt to rats at a dose range from 5 to 80 mg/kg, the drug reached corresponding maximum concentrations from 72 ng/mL to 1,250 ng/within for 2.3-5.3 hours. The AUC changed linearly throughout the whole dose range from 5 mg/kg to 80 mg/kg from 430 ng*h/mL to 21,124 ng*h/mL.

3-(1,2,4-Triazolo[4,3-a]pyridine-3-ylethynyl)-4-methyl-N-(4-((4-methylpiperazine-1-yl)methyl)-3-trifluoromethylphenyl)benzamide was absorbed relatively slowly from the gastrointestinal tract after oral administration of the methanesulfonic acid salt of 3-(1,2,4-triazolo[4,3-a]pyridine-3-ylethynyl)-4-methyl-N-(4-((4-methylpiperazine-1-yl) methyl)-3-trifluoromethylphenyl)benzamide to dogs at a dose range from 2 to 45 mg/kg, reaching a maximum plasma concentration at a range from 31.8 to 224 ng/ml after 3-8.5 hours. The AUC changed linearly throughout the whole dose range from 2 mg/kg to 22 mg/kg from 420 ng*h/ml to 5,480 ng*h/ml, and did not change during subsequent dose escalation to 45 mg/kg (5,173 ng*h/ml).

The 3-(1,2,4-triazolo[4,3-a]pyridine-3-ylethynyl)-4-methyl-N-(4-((4-methylpiperazine-1-yl)methyl)-3-trifluoromethylphenyl)benzamide is eliminated quite slowly from the systemic blood flow; the half-life period is about 7 hours in dogs, and about 3 hours in rats and mice. Clearance following intravenous administration is quite high: 2.12 L/h/kg for dogs, 1.61 L/h/kg for rats. A large apparent volume of distribution (Vd=14.1 L/kg for dogs, 6.16 L/kg for rats) indicates extensive drug distribution in tissues.

The study of drug distribution in rat tissues revealed high concentrations of the substance in the lungs (approximately 71-fold higher than blood plasma), spleen (45-fold higher than plasma), kidneys (34-fold higher than plasma), bone marrow (27-fold higher than plasma), liver (21-fold higher than plasma). The concentration of 3-(1,2,4-triazolo[4,3-a]pyridine-3-ylethynyl)-4-methyl-N-(4-((4-methylpiperazine-1-yl)methyl)-3-trifluoromethylphenyl)benzamide exposure in brain amounted to approximately 20% from blood plasma exposure.

3-(1,2,4-Triazolo[4,3-a]pyridine-3-ylethynyl)-4-methyl-N-(4-((4-methylpiperazine-1-yl)methyl)-3-trifluoromethylphenyl)benzamide metabolism involves participation of cytochrome P450 isoform CYP3A4 but does not involve the following cytochrome P450 isoforms: CYP1A2, 2B6, 2C8, 2C9, 2C19, 2D6, according to the study using cytochrome enzyme drugs. A study of the metabolism of 3-(1,2,4-triazolo[4,3-a]pyridine-3-ylethynyl)-4-methyl-N-(4-((4-methylpiperazine-1-yl)methyl)-3-trifluoromethylphenyl) benzamide in hepatocytes if rats, dogs and humans revealed formation of similar metabolite profiles, among which two glutathione conjugates, an N-desmethyl-derivative, and an N-oxide, were identified. In the blood plasma of rats and dogs a carboxylic acid product resulting from the hydrolysis to the amide bond of 3-(1,2,4-triazolo[4,3-a]pyridine-3-ylethynyl)-4-methyl-N-(4-((4-methylpiperazine-1-yl)methyl)-3-trifluoromethylphenyl)benzamide was identified. Quantitative determination of such metabolites in animal plasma showed that the area under the concentration-time curve for the metabolites never exceeds 10% that of the exposure of 3-(1,2,4-triazolo[4,3-a]pyridine-3-ylethynyl)-4-methyl-N-(4-((4-methylpiperazine-1-yl) methyl)-3-trifluoromethylphenyl)benzamide itself.

Studies of the Safety of the Methanesulfonic Acid Salt of 3-(1,2,4-Triazolo[4,3-a]Pyridine-3-Ylethynyl)-4-Methyl-N-(4-((4-Methylpiperazine-1-Yl) Methyl)-3-Trifluoromethylphenyl)Benzamide 3-(1,2,4-triazolo[4,3-a]pyridine-3-ylethynyl)-4-methyl-N-(4-((4-methylpiperazine-1-yl)methyl)-3-trifluoromethylphenyl)benzamide drug (in the form of the mesylate salt) was the subject of expanded pre-clinical safety evaluation trials, including a study of the effect of the drug on the ion hERG channel, evaluation of drug toxicity after single and repeated administration, and studies of the compounds allergenic capacity and immune toxicity.

3-(1,2,4-Triazolo[4,3-a]pyridine-3-ylethynyl)-4-methyl-N-(4-((4-methylpiperazine-1-yl)methyl)-3-trifluoromethylphenyl)benzamide drug (0.1-10 μM) in the form of the mesylate salt inhibited potassium hERG channel with an $IC_{50}$ value of 7.8 μM.

The results of acute toxicity studies showed that the $LD_{10}$ of the methanesulfonic acid salt of 3-(1,2,4-triazolo[4,3-a]pyridine-3-ylethynyl)-4-methyl-N-(4-((4-methylpiperazine-1-yl)methyl)-3-trifluoromethylphenyl)benzamide for mice was 800 mg/kg (equivalent to 678 mg/kg calculated as the free base), and for rats was 2,000 mg/kg (equivalent to 1,695 mg/kg calculated as a free base). The MTD of the drug at a single administration to dogs was 45 mg/kg (38 mg/kg calculated as a free base).

Pursuant to the data of 2 separate studies, the MTD of the methanesulfonic acid salt and 3-(1,2,4-triazolo[4,3-a]pyridine-3-ylethynyl)-4-methyl-N-(4-((4-methylpiperazine-1-yl)methyl)-3-trifluoromethylphenyl)benzamide for rats at a daily intragastric administration during 28 days amounted to 50-73 mg/kg (42-62 mg/kg calculated as a free base), which corresponded to $C_{max}$ 661±289 ng/mL and $AUC_{24}$ 8,596±2,209 ng*h/mL on Day 28 (for dose of 50 mg/kg).

To identify allergenic properties, the following methods were used: evaluation of anaphylactogenic activity using Guinea pig general systemic anaphylaxis and active cutaneous anaphylaxis models; evaluation of immediate-type hypersensitivity (ITH) reaction and delayed-type hypersensitivity (DTH) reaction in Guinea pigs following epicutaneous and conjunctival drug application; evaluation of DTH reaction in mice; study of the inflammation reaction to A concanavalin in mice; measuring of eosinophil blood count, evaluation of the effect on phagocyte neutrophil activity (Nitro Blue-Tetrazolium Test (NBT)), and leukocyte specific lysis reaction scenario using a Guinea pig model with subcutaneous administration of the drug. The methanesulfonic acid salt of 3-(1,2,4-triazolo[4,3-a]pyridine-3-ylethynyl)-4-methyl-N-(4-((4-methylpiperazine-1-yl)methyl)-3-trifluoromethylphenyl)benzamide did not display any detectable allergenic activity any of the models studied.

The studies of the immune toxic effect of the methanesulfonic acid salt of 3-(1,2,4-triazolo[4,3-a]pyridine-3-ylethynyl)-4-methyl-N-(4-((4-methylpiperazine-1-yl)methyl)-3-trifluoromethylphenyl)benzamide showed that a single intragastric administration of the drug to mice had no effect on the hemagglutinin and hemolysin level in the blood of test animals compared to control groups. Intragastric administration (21 days) of the drug to mice had no effect on the hemagglutinin and hemolysin levels in the blood, no effect in the delayed-type hypersensitivity test, no effect in the rosette test and did not change the phagocytic activity of neutrophils separated from blood. Therefore, the studies conducted showed that the methanesulfonic acid salt of 3-(1,2,4-triazolo[4,3-a]pyridine-3-ylethynyl)-4-methyl-N-(4-((4-methylpiperazine-1-yl)methyl)-3-trifluoromethylphenyl)benzamide had no toxic immune effect.

The results of gene toxicity testing using the Ames test, the test of induced somatic mosaicism in *Drosophila melanogaster* and the metaphase chromosome aberration assay with murine marrow cells showed that the methanesulfonic acid salt of 3-(1,2,4-triazolo[4,3-a]pyridine-3-ylethynyl)-4-methyl-N-(4-((4-methylpiperazine-1-yl)methyl)-3-trifluoromethylphenyl)benzamide had no genotoxic effects in any of the models at all doses (concentrations) tested.

The invention claimed is:

1. A salt of methanesulfonic acid and 3-(1,2,4-triazolo[4,3-a]pyridine-3-ylethynyl)-4-methyl-N-(4-((4-methylpiperazin-1-yl)methyl)-3-trifluoromethylphenyl)benzamide.

2. The salt according to claim 1 that is 3-(1,2,4-triazolo[4,3-a]pyridine-3-ylethynyl)-4-methyl-N-(4-((4-methylpiperazin-1-yl)methyl)-3-trifluoromethylphenyl)benzamide monomesylate salt.

3. The salt according to claim 2, wherein the salt is crystalline 3-(1,2,4-triazolo[4,3-a]pyridine-3-ylethynyl)-4-methyl-N-(4-((4-methylpiperazin-1-yl)methyl)-3-trifluoromethylphenyl)benzamide monomesylate salt.

Figure 27:
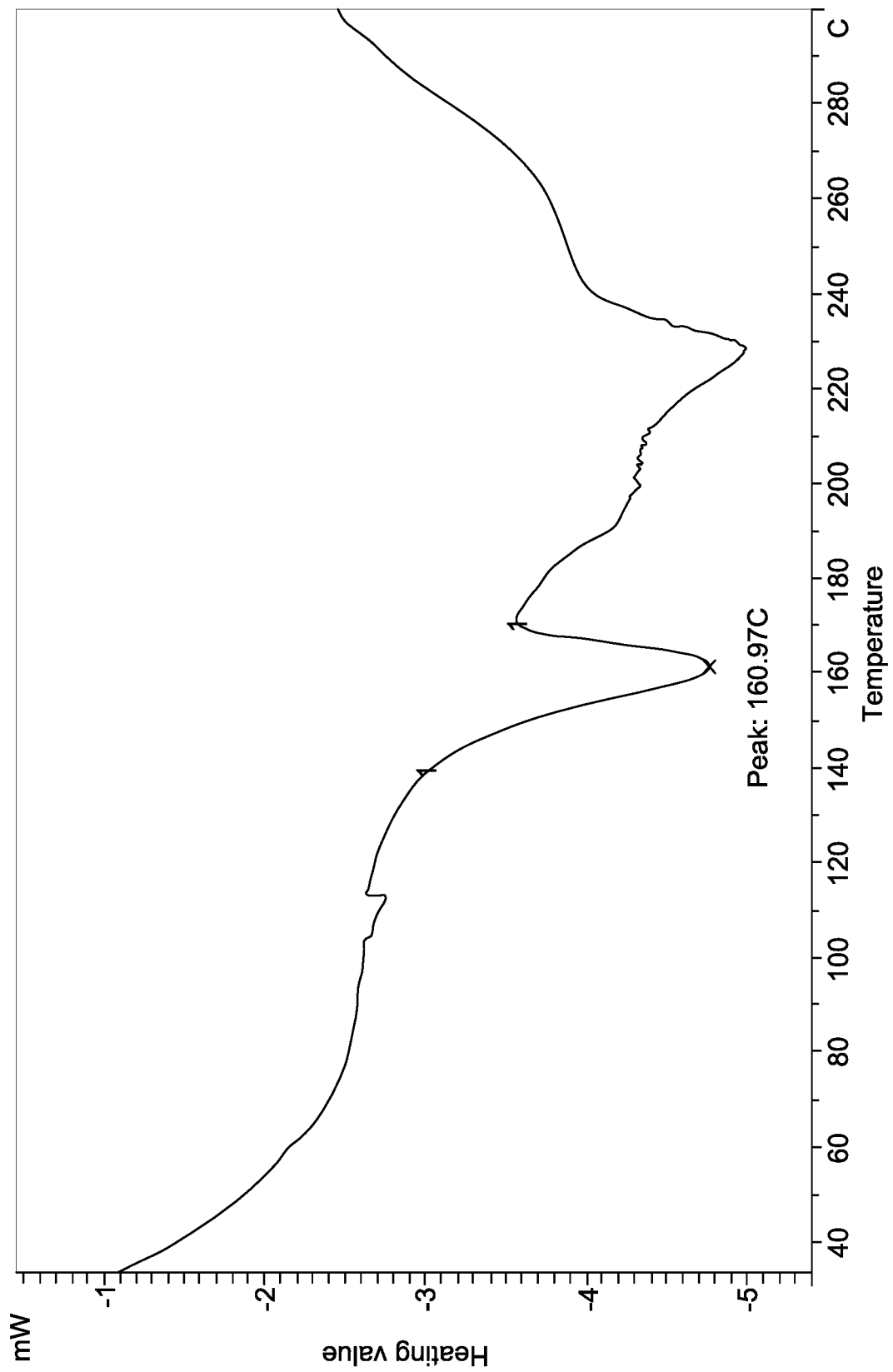
FIG. 27. DSC curve of a sample of the salt of tartaric acid and 3-(1,2,4-triazolo[4,3-a]pyridine-3-ylethynyl)-4-methyl-N-(4-((4-methylpiperazin-1-yl)methyl)-3-trifluoromethylphenyl)benzamide (sample—HAL-G-196-16).
Figure 28:
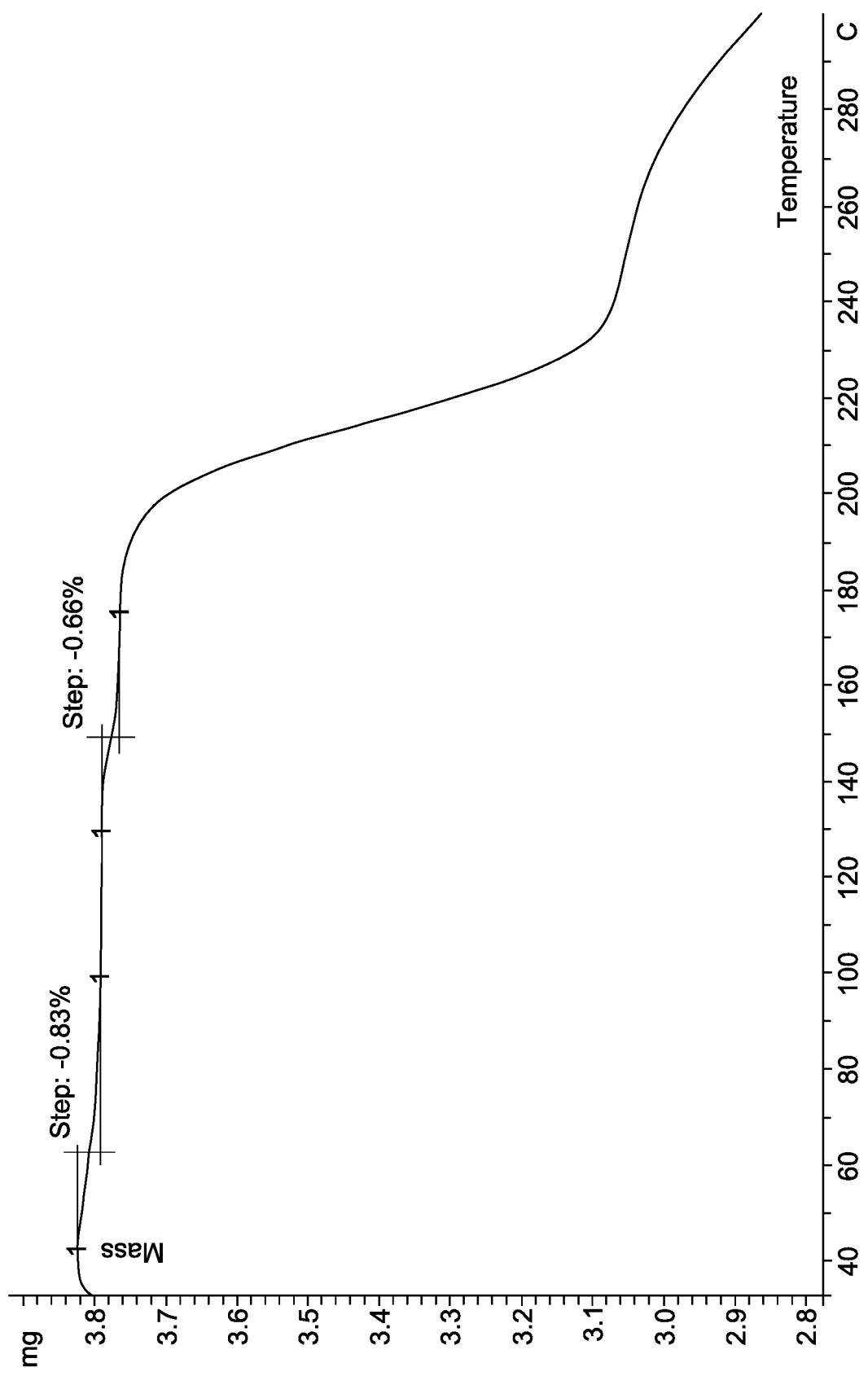
FIG. 28. TGA curve of a sample of the salt of tartaric acid and 3-(1,2,4-triazolo[4,3-a]pyridine-3-ylethynyl)-4-methyl-N-(4-((4-methylpiperazin-1-yl)methyl)-3-trifluoromethylphenyl)benzamide (sample—HAL-G-196-16).

4. The salt according to claim 3, wherein the salt is characterized by an X-ray powder diffraction pattern obtained at 25±5° C. using CuKα radiation substantially as shown in FIG. 27.

5. The salt according to claim 3, wherein the salt is characterized by a DSC curve having an endothermic transition at 220° C.

6. The salt according to claim 3 wherein the salt is 3-(1,2,4-triazolo[4,3-a]pyridine-3-ylethynyl)-4-methyl-N-(4-((4-methylpiperazin-1-yl)methyl)-3-trifluoromethylphenyl)benzamide monomesylate salt, polymorphic modification I.

7. The salt according to claim 3, wherein the salt is characterized by a monoclinic crystal lattice with space group $P2_1/n$.

8. The salt according to claim 7, wherein the salt is characterized by a monoclinic crystal lattice with a unit cell having parameters a=51.46±0.05 Å; b=7.81±0.05 Å; c=7.63±0.05 Å; and β=108.9±0.1°, as determined by X-ray powder diffraction at 25±5° C. using CuKα radiation.

9. The salt according to claim 8, wherein the salt is characterized by a monoclinic crystal lattice with a unit cell volume V=2,898.9±0.5 Å$^3$, as determined by X-ray powder diffraction at 25±5° C. using CuKα radiation.

10. The salt according to claim 3, wherein the salt is characterized by an X-ray powder diffraction pattern obtained at 25±5° C. using CuKα radiation comprising at least one peak with a relative intensity of about 20% or higher at diffraction angles (2θ) selected from 16.9; 17.2; 18.7 and/or 20.8.

11. The salt according to claim 10, wherein the salt is characterized by an X-ray powder diffraction pattern obtained at 25±5° C. using CuKα radiation having peaks at diffraction angles (2θ) 16.9; 17.2; 18.7 and 20.8, each with a relative intensity of about 20% or greater.

12. The salt according to claim 3, wherein the salt is characterized by an X-ray powder diffraction pattern obtained at 25±5° C. using CuKα radiation having a peak at diffraction angle (2θ) 18.7 as the peak with highest relative intensity.

13. The salt according to claim 3, wherein the salt is characterized by an X-ray powder diffraction pattern obtained at 25±5° C. using CuKα radiation and having at least three peaks at diffraction angles (2θ) selected from: 3.6; 7.2; 11.4; 11.8; 12.5; 13.4; 14.5; 16.2; 16.5; 16.9; 17.2; 17.4; 17.8; 18.1; 18.4; 18.7; 20.8; 21.4; 22.7; 22.8; 23.0; 23.2; 23.4; 24.1; 24.5; 25.4; 25.9; 26.0; 26.2; 26.7; 27.1; 28.4; 33.0; 33.3 and 36.7.

14. The salt according to claim 13, wherein the salt is characterized by an X-ray powder diffraction pattern obtained at 25±5° C. using CuKα radiation having peaks at the following diffraction angles (2θ) as characteristic peaks: 3.6; 7.2; 11.4; 11.8; 12.5; 13.4; 14.5; 16.2; 16.5; 16.9; 17.2; 17.4; 17.8; 18.1; 18.4; 18.7; 20.8; 21.4; 22.7; 22.8; 23.0; 23.2; 23.4; 24.1; 24.5; 25.4; 25.9; 26.0; 26.2; 26.7; 27.1; 28.4; 33.0; 33.3 and 36.7.

15. The salt according to claim 3, wherein the salt is characterized by an X-ray powder diffraction pattern obtained at 25±5° C. using CuKα radiation having at least three peaks at diffraction angles (2θ) selected from: 1.8; 14.5; 16.2; 16.9; 17.2; 17.4; 18.7; 20.8 and 23.0.

16. The salt according to claim 15, wherein the salt is characterized by an X-ray powder diffraction pattern obtained at 25±5° C. using CuKα radiation having peaks at the following diffraction angles (2θ) as characteristic peaks: 11.8; 14.5; 16.2; 16.9; 17.2; 17.4; 18.7; 20.8 and 23.0.

17. The salt according to claim 3, wherein the salt is characterized by an X-ray powder diffraction pattern obtained at 25±5° C. using CuKα radiation having at least three peaks at diffraction angles (2θ) selected from: 14.5; 16.9; 17.2; 17.4; 18.7 and 20.8.

18. The salt according to claim 17, wherein the salt is characterized by an X-ray powder diffraction pattern obtained at 25±5° C. using CuKα radiation and having peaks at the following diffraction angles (2θ) as characteristic peaks: 14.5; 16.9; 17.2; 17.4; 18.7 and 20.8.

19. The salt according to claim 3, wherein the salt is characterized by an X-ray powder diffraction pattern obtained at 25±5° C. using CuKα radiation substantially as shown in FIG. 47A.

20. The salt according to claim 3, wherein the salt is characterized by an X-ray powder diffraction pattern obtained at 25±5° C. using CuKα radiation containing a set of peaks substantially as shown in Table 8.

21. The salt according to claim 3, wherein the salt is 3-(1,2,4-triazolo[4,3-a]pyridine-3-ylethynyl)-4-methyl-N-(4-((4-methylpiperazin-1-yl)methyl)-3-trifluoromethylphenyl)benzamide monomesylate salt, polymorphic modification II.

22. The salt according to claim 3, wherein the salt is characterized by a monoclinic crystal lattice with space group P2₁/c.

23. The salt according to claim 22, wherein the salt is characterized by a monoclinic crystal lattice with a unit cell having parameters a=13.77±0.05 Å; b=8.09±0.05 Å and c=30.83±0.05 Å, and β=117.8±0.1, as determined by X-ray powder diffraction at 25±5° C. using CuKα radiation.

24. The salt according to claim 23, wherein the salt is characterized by a monoclinic crystal lattice with a unit cell volume V=3,036.36±0.5 Å³, as determined by X-ray powder diffraction at 25±5° C. using CuKα1 radiation.

25. The salt according to claim 3, wherein the salt is characterized by an X-ray powder diffraction pattern obtained at 25±5° C. using CuKα radiation and having at least one peak with a relative intensity of about 20% or higher at diffraction angles (2θ) selected from: 17.4; 17.6; 19.4; 19.7; 21.2; 22.0 and 22.6.

26. The salt according to claim 25, wherein the salt is characterized by an X-ray powder diffraction pattern obtained at 25±5° C. using CuKα radiation and containing a peak at diffraction angle (2θ) 21.2 as the peak with highest relative intensity.

27. The salt according to claim 3, wherein the salt is characterized by an X-ray powder diffraction pattern obtained at 25±5° C. using CuKα radiation having at least three peaks at diffraction angles (2θ) selected from: 7.1; 7.3; 11.6; 11.8; 12.7; 12.9; 13.1; 14.2; 14.6; 16.9; 17.2; 17.4; 17.6; 18.1; 18.3; 19.4; 19.7; 20.8; 21.2; 21.6; 22.0; 22.5; 22.6; 23.2; 23.4; 23.8; 24.9; 25.1; 25.6; 25.9; 26.1; 26.6; 28.3; 28.8; 29.6 and 30.1.

28. The salt according to claim 27, wherein the salt is characterized by an X-ray powder diffraction pattern obtained at 25±5° C. using CuKα radiation having peaks at the following diffraction angles (2θ) as characteristic peaks: 7.1; 7.3; 11.6; 11.8; 12.7; 12.9; 13.1; 14.2; 14.6; 16.9; 17.2; 17.4; 17.6; 18.1; 18.3; 19.4; 19.7; 20.8; 21.2; 21.6; 22.0; 22.5; 22.6; 23.2; 23.4; 23.8; 24.9; 25.1; 25.6; 25.9; 26.1; 26.6; 28.3; 28.8; 29.6 and 30.1.

29. The salt according to claim 3, wherein the salt is characterized by an X-ray powder diffraction pattern obtained at 25±5° C. using CuKα radiation having at least three peaks at diffraction angles (2θ) selected from: 17.4; 17.6; 19.4; 19.7; 21.2; 22.0; 22.6 and 25.9.

30. The salt according to claim 29, wherein the salt is characterized by an X-ray powder diffraction pattern obtained at 25±5° C. using CuKα radiation having at least three peaks at the following diffraction angles (2θ) as characteristic peaks: 17.4; 17.6; 19.4; 19.7; 21.2; 22.0; 22.6 and 25.9.

31. The salt according to claim 3, wherein the salt is characterized by an X-ray powder diffraction pattern obtained at 25±5° C. using CuKα radiation having at least three peaks at diffraction angles (2θ) selected from: 17.4; 17.6; 19.7; 21.2; 22.0 and 22.6.

32. The salt according to claim 31, wherein the salt is characterized by an X-ray powder diffraction pattern obtained at 25±5° C. using CuKα radiation and having at least three peaks at the following diffraction angles (2θ) as characteristic peaks: 17.4; 17.6; 19.7; 21.2; 22.0 and 22.6.

33. The salt according to claim 1, that is substantially isolated.

34. A composition containing a salt according to claim 1 and at least one pharmaceutically acceptable carrier and/or excipient.

35. A method of preparing crystalline 3-(1,2,4-triazolo[4,3-a]pyridine-3-ylethynyl)-4-methyl-N-(4-((4-methylpiperazin-1-yl)methyl)-3-trifluoromethylphenyl)benzamide monomesylate salt according to claim 3, comprising:
(1) reacting 3-(1,2,4-triazolo[4,3-a]pyridine-3-ylethynyl)-4-methyl-N-(4-((4-methylpiperazin-1-yl)methyl)-3-trifluoromethylphenyl)benzamide and methanesulfonic acid to form 3-(1,2,4-triazolo[4,3-a]pyridine-3-ylethynyl)-4-methyl-N-(4-((4-methylpiperazin-1-yl)methyl)-3-trifluoromethylphenyl)benzamide monomesylate salt; and (2) cooling a solution of 3-(1,2,4-triazolo[4,3-a]pyridine-3-ylethynyl)-4-methyl-N-(4((4-methylpiperazin-1-yl)methyl)-3-trifluoromethylphenyl)benzamide monomesylate salt dissolved in a mixture of acetone:ethanol in an approximate ratio of 5:1 v/v to a temperature of about 10° C. to obtain the crystalline salt.

36. Crystalline 3-(1,2,4-triazolo[4,3-a]pyridine-3-ylethynyl)-4-methyl-N-(4-(4-methylpiperazin-1-yl)methyl)-3-trifluoromethylphenyl)benzamide monomesylate salt obtained by the method according to claim 35.

37. A method of preparing crystalline 3-(1,2,4-triazolo[4,3-a]pyridine-3-ylethynyl)-4-methyl-N-(4-((4-methylpiperazin-1-yl)methyl)-3-trifluoromethylphenyl)benzamide monomesylate salt according to claim 3, comprising:
   (1) reacting 3-(1,2,4-triazolo[4,3-a]pyridine-3-ylethynyl)-4-methyl-N-(4((4-methylpiperazin-1-yl)methyl)-3-trifluoromethylphenyl)benzamide and methanesulfonic acid to form 3-(1,2,4-triazolo[4,3-a]pyridine-3-ylethynyl)-4-methyl-N-(4-((4-methylpiperazin-1-yl)methyl)-3-trifluoromethylphenyl)benzamide monomesylate salt; and
   (2) concentrating a solution of 3-(1,2,4-triazolo[4,3-a]pyridine-3-ylethynyl)-4-methyl-N-(4((4-methylpiperazin-1-yl)methyl)-3-trifluoromethylphenyl)benzamide monomesylate salt dissolved in a mixture of acetone:ethanol in an approximate ratio of 5:1 v/v and subsequently cooling the solution to a temperature of about 20-25° C. to form the crystalline salt.

38. Crystalline 3-(1,2,4-triazolo[4,3-a]pyridine-3-ylethynyl)-4-methyl-N-(4-((4-methylpiperazin-1-yl)methyl)-3-trifluoromethylphenyl)benzamide monomesylate salt obtained by the method according to claim 37.

39. A method for treating oncological disease in a subject having said disease, comprising administering to the subject an effective amount of the salt according to claim 1.

40. The method according to claim 39, wherein the oncological disease is acute lymphoblastic leukemia, chronic myeloid leukemia, hepatocellular carcinoma, non-small cell lung cancer or gastrointestinal stromal tumor.

41. The method according to claim 39, wherein the oncological disease is chronic myeloid leukemia, chronic leukemia, acute leukemia, intestinal solid tumor, or non-small cell lung carcinoma.

* * * * *